(12) United States Patent
Deng et al.

(10) Patent No.: US 7,696,223 B2
(45) Date of Patent: Apr. 13, 2010

(54) PYRROLO- AND THIAZOLO-PYRIDINE COMPOUNDS, AND METHODS OF USE THEREOF

(75) Inventors: Shaojiang Deng, San Mateo, CA (US); Min Wu, Sunnyvale, CA (US); Eric D. Turtle, Belmont, CA (US); Wen-Bin Ho, Los Altos, CA (US); Michael P. Arend, Foster City, CA (US); Heng Cheng, Foster City, CA (US); Lee A. Flippin, Woodside, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

(21) Appl. No.: 11/696,549

(22) Filed: Apr. 4, 2007

(65) Prior Publication Data

US 2008/0004309 A1 Jan. 3, 2008

Related U.S. Application Data

(60) Provisional application No. 60/789,310, filed on Apr. 4, 2006.

(51) Int. Cl.
*A61K 31/435* (2006.01)
*C07D 471/02* (2006.01)

(52) U.S. Cl. ............... 514/301; 546/113; 546/114

(58) Field of Classification Search ............... None
See application file for complete search history.

(56) References Cited

U.S. PATENT DOCUMENTS

| 3,989,704 | A | 11/1976 | Houlihan et al. |
|---|---|---|---|
| 4,036,964 | A | 7/1977 | Buckle et al. |
| 4,260,611 | A | 4/1981 | Bartmann et al. |
| 4,559,403 | A | 12/1985 | Bruderer et al. |
| 4,584,379 | A | 4/1986 | Wagner |
| 4,673,682 | A | 6/1987 | Konz et al. |
| 4,822,800 | A | 4/1989 | Faltico et al. |
| 4,952,588 | A | 8/1990 | Glamkowski et al. |
| 4,966,906 | A | 10/1990 | Glamkowski et al. |
| 5,620,995 | A | 4/1997 | Weidmann et al. |
| 5,658,933 | A | 8/1997 | Weidmann et al. |
| 5,719,164 | A | 2/1998 | Weidmann et al. |
| 6,093,730 | A | 7/2000 | Weidmann et al. |
| 6,319,931 | B1 | 11/2001 | Kroemer et al. |
| 6,358,973 | B1 | 3/2002 | Napoletano et al. |
| 6,358,976 | B1 | 3/2002 | Wityak et al. |
| 6,369,053 | B1 | 4/2002 | Yuan et al. |
| 6,762,318 | B2 | 7/2004 | Kodra et al. |
| 6,777,425 | B2 | 8/2004 | Burli et al. |
| 6,903,114 | B2 | 6/2005 | Backstrom et al. |
| 7,208,601 | B2 | 4/2007 | Majalli et al. |
| 7,248,053 | B2 | 7/2007 | Houldsworth |
| 7,294,457 | B2 | 11/2007 | Kukolj et al. |
| 7,323,475 | B2 | 1/2008 | Arend et al. |
| 2003/0153503 | A1 | 8/2003 | Klaus et al. |
| 2003/0176317 | A1 | 9/2003 | Guenzler-Pukall et al. |
| 2004/0204356 | A1 | 10/2004 | Guenzler-Pukall et al. |
| 2004/0235082 | A1 | 11/2004 | Fourney et al. |
| 2005/0020487 | A1 | 1/2005 | Klaus et al. |
| 2006/0035965 | A1 | 2/2006 | Dalton et al. |
| 2006/0094717 | A1* | 5/2006 | Regueiro-Ren et al. .... 514/234.2 |
| 2006/0178316 | A1 | 8/2006 | Klaus et al. |
| 2006/0183695 | A1 | 8/2006 | Klaus et al. |
| 2006/0199836 | A1* | 9/2006 | Turtle et al. ............... 514/301 |
| 2006/0217416 | A1 | 9/2006 | Arend et al. |
| 2006/0251638 | A1 | 11/2006 | Guenzler-Pukall |
| 2006/0258660 | A1 | 11/2006 | Guenzler-Pukall et al. |
| 2006/0270699 | A1 | 11/2006 | Guenzler-Pukall et al. |
| 2006/0276477 | A1 | 12/2006 | Klaus et al. |
| 2007/0004627 | A1 | 1/2007 | Seeley et al. |
| 2007/0155784 | A1 | 7/2007 | Arend et al. |
| 2007/0185159 | A1 | 8/2007 | Arend et al. |
| 2007/0292433 | A1 | 12/2007 | Seeley et al. |
| 2007/0293575 | A1 | 12/2007 | Seeley et al. |
| 2007/0298104 | A1 | 12/2007 | Arend et al. |
| 2008/0004309 | A1 | 1/2008 | Deng et al. |
| 2008/0090854 | A1* | 4/2008 | Hachtel et al. ............... 514/274 |

FOREIGN PATENT DOCUMENTS

| CA | 2134866 | 5/1995 |
|---|---|---|
| CA | A-H11-302257 | 11/1999 |
| EP | 532466 | 3/1993 |
| EP | 0650960 | 9/1994 |
| EP | 0650961 | 10/1994 |
| EP | 626178 | 11/1994 |
| EP | 706795 | 4/1996 |
| EP | 0911340 | 4/1999 |
| EP | 1 676 834 A1 | 7/2006 |
| JP | A-H07-224039 | 8/1995 |
| JP | A-H07-228571 | 8/1995 |

(Continued)

OTHER PUBLICATIONS

Safadi et al., 1993, Pharmaceutical Research, 10, 1350-1355.*
Kris et al., 1996, Advanced Drug Review, 19, 287-310.*
Samara et al., 1995, Biopharmaceutics & Drug Disposition, 1, 201-210, 1995.*
Jaakkola et al. (2001), "Targeting of HIF-alpha to the von Hippel-Lindau ubiquitylation complex by $O_2$-regulated prolyl hydroxylation," Science 292 (5516):468-472.
Jiang et al., (1996) J Biol Chem 271:17771-17778.
Iliopoulus et al., (1996) Proc Natl Acad Sci USA, 93:10595-10599.
Maxwell et al., (1999) Nature 399:271-275.
Sutter et al., (2000) Proc Natl Acad Sci USA 97:4748-4753.
Cockman et al., (2000) J Biol Chem 275:25733-25741.
Tanimoto et al., (2000) EMBO J 19:4298-4309.
Majamaa et al. (1984) Eur J Biochem 138:239-245.
Majamaa et al. (1985) Biochem J 229:127-133.
Kivirikko and Myllyharju (1998) Matrix Biol 16:357-368.
Bickel et al. (1998) Hepatology 28:404-411.
Friedman et al. (2000) Proc Natl Acad Sci USA 97:4736-4741.
Franklin et al., (2000) Biochem J 353:333-338.

(Continued)

*Primary Examiner*—Brian-Yong S Kwon
(74) *Attorney, Agent, or Firm*—Swiss Tanner, P.C.

(57) ABSTRACT

The present invention relates to novel compounds capable of modulating the stability and/or activity of hypoxia inducible factor (HIF).

32 Claims, No Drawings

FOREIGN PATENT DOCUMENTS

| | | |
|---|---|---|
| WO | WO 96/18616 | 6/1996 |
| WO | WO 98/50343 | 11/1998 |
| WO | WO 98/50346 | 11/1998 |
| WO | WO 01/58892 | 8/2001 |
| WO | WO 02/070510 | 9/2002 |
| WO | WO 02/074981 | 9/2002 |
| WO | WO 02/100832 | 12/2002 |
| WO | WO 02/101073 | 12/2002 |
| WO | WO 03/007945 | 1/2003 |
| WO | WO 03/010141 | 2/2003 |
| WO | WO 03/014377 | 2/2003 |
| WO | WO 03/049686 | 6/2003 |
| WO | WO 03/053997 | 7/2003 |
| WO | WO 03/080566 | 10/2003 |
| WO | WO 2004/108681 | 12/2004 |
| WO | WO 2005/09962 | 2/2005 |
| WO | WO 2005/014533 | 2/2005 |
| WO | WO 2006/094292 | 9/2006 |

OTHER PUBLICATIONS

U.S. Appl. No. 11/495,118, filed Jul. 28, 2006, Guenzler-Pukall et al.
U.S. Appl. No. 11/406,484, filed Apr. 17, 2006, Klaus et al.
U.S. Appl. No. 12/015,275, filed Jan. 16, 2008, Arend et al.
Sato et al. "Stability and Physicochemical Properties of Viracept Tablets" *Antibiotics and Chemotherapy* 14(9):1589-1592 (1998)—English Translation Not Available.
Franklin, et al. "Approaches to the design of anti-fibrotic drugs" Biochem. Soc. Trans. 19(4): 812-815 (1991).
Ivan, et al. "HlFα Targeted for VHL-Mediated Destruction by Proline Hydroxylation: Implications for O2 Sensing", *Science*, 292:464-468, 2001.
Lando, et al. "Oxygen-dependent regulation of hypoxia-inducible factors by prolyl and asparaginyl hydroxylation", *Eur.J. Biochem*, 270:781-790 (2003).
Richard, et al, "Nonhypoxic Pathway Mediates the Induction of Hypoxia-inducible Factor lα in Vascular Smooth Muscle Cells", *J. Biol. Chm*, 275:26765-26771 (2000).
Sandau, et al. "Induction of Hypoxia-Inducible-Factor 1 by Nitric Oxide Is Mediated via the PI 3K Pathway" *Biochem. Biophys. Res. Commun.*, 278:263-267(2000).
Safran, et al. "HIF hydroxylation and the mammalian oxygen-sensing pathway" *J. Clin. Invest*. 111(6):779-783 (2003).
Sodhi, et al. "MAPK and AKT Act Cooperatively but Independently on Hypoxia Inducible Factor-lα in *ras*V12 Unpregulation of VEGF" *Biochem.Biophys. Res.Commun.*, 287:292-300 (2001).
Tacchini, et al. "Hepatocyte growth factor signaling stimulates hypoxia inducible factor-1 (HIF-1) activity in HepG2 hepatoma cells" *Carcinogenesis*, 22:1363-1371 (2001).

* cited by examiner

US 7,696,223 B2

PYRROLO- AND THIAZOLO-PYRIDINE COMPOUNDS, AND METHODS OF USE THEREOF

CROSS-REFERENCE TO RELATED APPLICATION

This application claims priority benefit under 35 U.S.C. § 119(e) of U.S. Provisional Application Ser. No. 60/789,310, filed Apr. 4, 2006, which is hereby incorporated by reference in its entirety.

BACKGROUND OF THE INVENTION

1. Field of the Invention

The present invention relates to novel compounds capable of modulating the stability and/or activity of hypoxia inducible factor (HIF).

2. State of the Art

Hypoxia inducible factor (HIF) is a basic helix-loop-helix (bHLH) PAS (Per/Arnt/Sim) transcriptional activator that mediates changes in gene expression in response to changes in cellular oxygen concentration. HIF is a heterodimer containing an oxygen-regulated α-subunit (HIFα), and a constitutively expressed β-subunit (HIFβ), also known as aryl hydrocarbon receptor nuclear transporter (ARNT). In oxygenated (normoxic) cells, HIFα subunits are rapidly degraded by a mechanism that involves ubiquitination by the von Hippel-Lindau tumor suppressor (pVHL) E3 ligase complex. Under hypoxic conditions, HIFα is not degraded, and an active HIFα/β complex accumulates in the nucleus, and activates the expression of several genes including glycolytic enzymes, glucose transporters, erythropoietin (EPO), and vascular endothelial growth factor (VEGF). (Jiang et al. (1996) J Biol Chem 271:17771-17778; Iliopoulus et al. (1996) Proc Natl Acad Sci USA, 93:10595-10599; Maxwell et al. (1999) Nature 399:271-275; Sutter et al. (2000) Proc Natl Acad Sci USA 97:4748-4753; Cockman et al. (2000) J Biol Chem 275:25733-25741; and Tanimoto et al. (2000) EMBO J 19:4298-4309.)

Levels of HIFα are elevated in most cells in response to hypoxia, and HIFα is induced in vivo when animals are subjected to anemia or hypoxia. HIFα levels rise within a few hours after the onset of hypoxia, and induce numerous beneficial cellular processes including cytoprotective effects, enhanced erythropoiesis, and physiological adaptation to ischemic or hypoxic states. Induction of HIFα is potentially beneficial in conditions such as myocardial acute ischemia, and early infarction, pulmonary hypertension, inflammation, and anemia.

HIFα levels are also increased by a number of factors that mimic hypoxia, including iron chelators such as desferrioxamine (DFO), and divalent metal salts such as $CoCl_2$. Additionally, compounds originally identified as inhibitors of procollagen prolyl hydroxylase enzymes have been found to stabilize HIFα. Examples of such compounds can be found, e.g., in Majamaa et al. (1984) Eur J Biochem 138:239-245; Majamaa et al. (1985) Biochem J 229:127-133; Kivirikko, and Myllyharju (1998) Matrix Biol 16:357-368; Bickel et al. (1998) Hepatology 28:404-411; Friedman et al. (2000) Proc Natl Acad Sci USA 97:4736-4741; Franklin (1991) Biochem Soc Trans 19): 812-815; and Franklin et al. (2001) Biochem J 353:333-338. Additionally, compounds that stabilize HIFα have been described in, e.g., International Publication Nos. WO 03/049686, WO 02/074981, WO 03/080566, and WO 2004/108681.

There remains a need for compounds that are effective in the prevention of disorders associated with HIF, including anemia, and tissue damage caused by ischemia that occurs due to, e.g., atherosclerosis, diabetes, and pulmonary disorders such as pulmonary embolism, and the like. Compounds that modulate HIF and can thus be used to treat and prevent HIF-associated disorders including conditions involving anemia, ischemia, and hypoxia are provided herein.

SUMMARY OF THE INVENTION

The present invention is directed to novel compounds, and methods of using the compounds to modulate the stability and/or activity of hypoxia inducible factor (HIF).

In one aspect, there are provided compounds represented by formula I:

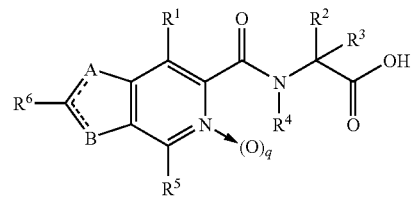

wherein:

q is 0 or 1;

A and B are independently selected from the group consisting =C($R^7$)—, —N($R^8$)—, =N—, and —S— with the proviso that one of the following is present:
A is =C($R^7$)— and B is —N($R^8$)—;
A is —S— and B is =N—;
A =N— and B is —S—; or
A is —N($R^8$)— and B is =C($R^7$)—;

one of -A≐C($R^6$)— or —B≐C($R^6$)— is a double bond and the other is a single bond;

$R^1$ is selected from the group consisting of hydroxyl, alkoxy, substituted alkoxy, acyloxy, cycloalkoxy, substituted cycloalkoxy, aryloxy, substituted aryloxy, heteroaryloxy, substituted heteroaryloxy, heterocyclyloxy, substituted heterocyclyloxy, mercapto, thioether, substituted alkylthio, arylsulfanyl, heteroarylsulfanyl, amino, substituted amino, acylamino and aminoacyl;

$R^2$ is selected from the group consisting of hydrogen, deuterium, and methyl;

$R^3$ is selected from the group consisting of hydrogen, deuterium, alkyl, and substituted alkyl;

$R^4$ is selected from the group consisting of hydrogen, alkyl, and substituted alkyl;

$R^5$ is selected from the group consisting of hydrogen, halo, cyano, hydroxyl, alkyl, substituted alkyl, cycloalkyl, substituted cycloalkyl, alkenyl, substituted alkenyl, alkynyl, substituted alkynyl, alkoxy, substituted alkoxy, cycloalkoxy, substituted cycloalkoxy, aryl, substituted aryl, aryloxy, substituted aryloxy, heteroaryl, substituted heteroaryl, heterocyclyl, substituted heterocyclyl, heterocyclyloxy, substituted heterocyclyloxy, heteroaryloxy, substituted heteroaryloxy, acyl, aminoacyl, nitro, amino, substituted amino, acylamino, sulfanyl, sulfonyl, thioether, arylthio, and substituted arylthio;

$R^6$ and $R^7$ are each independently selected from the group consisting of hydrogen, halo, cyano, hydroxyl, alkyl, substituted alkyl, cycloalkyl, substituted cycloalkyl, alkenyl, substituted alkenyl, alkynyl, substituted alkynyl, alkoxy, substituted alkoxy, cycloalkoxy, substituted cycloalkoxy, aryl, substituted aryl, aryloxy, substituted aryloxy, heteroaryl, substituted heteroaryl, heterocyclyl, substituted heterocyclyl, heterocyclyloxy, substituted heterocyclyloxy, heteroaryloxy, substituted heteroaryloxy, acyl, aminoacyl, nitro, amino, substituted amino, acylamino, sulfanyl, sulfonyl, thioether, arylthio, and substituted arylthio;

or where when A or B is $=C(R^7)-$, then $R^6$ and $R^7$ together with the carbon atoms bound thereto join to form a cycloalkenyl, substituted cycloalkenyl, aryl, substituted aryl, heteroaryl, or substituted heteroaryl; and $R^8$ is selected from the group consisting of hydrogen, hydroxyl, alkyl, substituted alkyl, alkenyl, substituted alkenyl, alkynyl, substituted alkynyl, aryl, substituted aryl, heteroaryl, and substituted heteroaryl;

or pharmaceutically acceptable salts, single stereoisomers, mixtures of stereoisomers, esters, or prodrugs thereof.

The invention also provides pharmaceutical compositions comprising one or more compounds of Formula I and a pharmaceutically acceptable excipient. In some embodiments, the composition further comprises at least one additional therapeutic agent. In some embodiments, the agent is selected from the group consisting of vitamin $B_{12}$, folic acid, ferrous sulfate, recombinant human erythropoietin, and an erythropoiesis stimulating agent (ESA).

The invention is also directed to methods of treating, pretreating, or delaying onset of a condition mediated at least in part by hypoxia inducible factor (HIF) and/or erythropoietin (EPO), comprising administering to a patient, a therapeutically effective amount of a compound of Formula I.

DETAILED DESCRIPTION OF THE INVENTION

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

1. Compounds of the Invention

As stated above, the invention is directed to compounds of formula I:

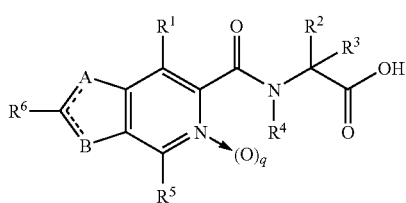

I wherein:
q is 0 or 1;
A and B are independently selected from the group consisting
$=C(R^7)-$, $-N(R^8)-$, $=N-$, and
$-S-$ with the proviso that one of the following is present:
A is $=C(R^7)-$ and B is $-N(R^8)-$;
A is $-S-$ and B is $=N-$;
A $=N-$ and B is $-S-$; or A is $-N(R^8)-$ and B is $=C(R^7)-$;
one of $-A=C(R^6)-$ or $-B=C(R^6)-$ is a double bond and the other is a single bond;

$R^1$ is selected from the group consisting of hydroxyl, alkoxy, substituted alkoxy, acyloxy, cycloalkoxy, substituted cycloalkoxy, aryloxy, substituted aryloxy, heteroaryloxy, substituted heteroaryloxy, heterocyclyloxy, substituted heterocyclyloxy, mercapto, thioether, substituted alkylthio, arylsulfanyl, heteroarylsulfanyl, amino, substituted amino, acylamino, and aminoacyl;

$R^2$ is selected from the group consisting of hydrogen, deuterium, and methyl;

$R^3$ is selected from the group consisting of hydrogen, deuterium, alkyl, and substituted alkyl;

$R^4$ is selected from the group consisting of hydrogen, alkyl, and substituted alkyl;

$R^5$ is selected from the group consisting of hydrogen, halo, cyano, hydroxyl, alkyl, substituted alkyl, cycloalkyl, substituted cycloalkyl, alkenyl, substituted alkenyl, alkynyl, substituted alkynyl, alkoxy, substituted alkoxy, cycloalkoxy, substituted cycloalkoxy, aryl, substituted aryl, aryloxy, substituted aryloxy, heteroaryl, substituted heteroaryl, heterocyclyl, substituted heterocyclyl, heterocyclyloxy, substituted heterocyclyloxy, heteroaryloxy, substituted heteroaryloxy, acyl, aminoacyl, nitro, amino, substituted amino, acylamino, sulfanyl, sulfonyl, thioether, arylthio, and substituted arylthio;

$R^6$ and $R^7$ are each independently selected from the group consisting of hydrogen, halo, cyano, hydroxyl, alkyl, substituted alkyl, cycloalkyl, substituted cycloalkyl, alkenyl, substituted alkenyl, alkynyl, substituted alkynyl, alkoxy, substituted alkoxy, cycloalkoxy, substituted cycloalkoxy, aryl, substituted aryl, aryloxy, substituted aryloxy, heteroaryl, substituted heteroaryl, heterocyclyl, substituted heterocyclyl, heterocyclyloxy, substituted heterocyclyloxy, heteroaryloxy, substituted heteroaryloxy, acyl, aminoacyl, nitro, amino, substituted amino, acylamino, sulfanyl, sulfonyl, thioether, arylthio, and substituted arylthio;

or where when A or B is $=C(R^7)-$, then $R^6$ and $R^7$ together with the carbon atoms bound thereto join to form a cycloalkenyl, substituted cycloalkenyl, aryl, substituted aryl, heteroaryl, or substituted heteroaryl; and $R^8$ is selected from the group consisting of hydrogen, hydroxyl, alkyl, substituted alkyl, alkenyl, substituted alkenyl, alkynyl, substituted alkynyl, aryl, substituted aryl, heteroaryl, and substituted heteroaryl;

or pharmaceutically acceptable salts, single stereoisomers, mixtures of stereoisomers, esters, or prodrugs thereof.

Compounds contemplated by this invention include compounds of the following structures:

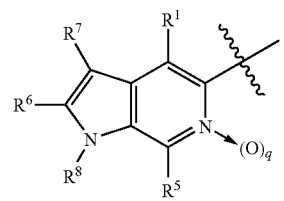

IA

-continued

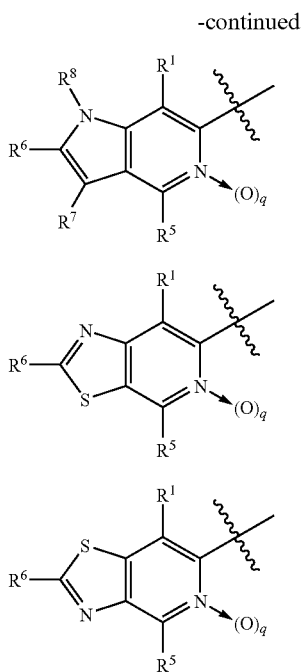

In some embodiments, q is 0.

In some embodiments, $R^1$ is hydroxyl. In particular embodiments wherein $R^1$ is hydroxyl, $R^2$, $R^3$, and $R^4$ are all hydrogen. In other embodiments wherein $R^1$ is hydroxyl, $R^2$ is methyl and $R^3$ and $R^4$ are hydrogen.

In some embodiments, $R^5$ is selected from the group consisting of hydrogen, alkyl, cyano, halo, and aryl. In particular embodiments, $R^5$ is selected from hydrogen, cyano, methyl, ethyl, propyl, butyl, chloro, and phenyl. In still particular embodiments, $R^5$ is cyano.

In some embodiments, $R^5$ is selected from the group consisting of hydrogen, cyano, alkyl, substituted alkyl, substituted alkenyl, alkynyl, aryl, substituted aryl, heteroaryl, heterocyclyl, and acyl. In particular embodiments, $R^5$ is selected from the group consisting of hydrogen, cyano, acetyl, methyl, ethyl, propyl, butyl, benzyl, phenethyl, ethynyl, styryl, isopropyl-sulfonylmethyl, phenyl, 4-cyanophenyl, furan-2-yl, thiazol-2-yl, and piperidin-1-yl.

In some embodiments, $R^6$ is selected from the group consisting of hydrogen, halo, cyano, alkyl, aryl, substituted aryl, aryloxy, substituted amino, heteroaryl, and substituted heteroaryl. In particular embodiments, $R^6$ is selected from the group consisting of hydrogen, chloro, bromo, cyano, methyl, propyl, t-butyl, phenyl, 4-chlorophenyl, and 4-fluorophenyl. In other particular embodiments, $R^6$ is selected from the group consisting of methyl, tert-butyl, phenyl, 4-cyanophenyl, 4-t-butyl-phenyl, trifluoromethylphenyl, 3-chloro-4-fluorophenyl, 4-chlorophenyl, 4-fluorophenyl, 2-methoxyphenyl, 3-methoxyphenyl, 4-methoxyphenyl, biphenyl-4-yl, 4-phenoxyphenyl, phenoxy, naphthalene-2-yl, 2,3-dihydro-benzo[1,4]dioxin-6-yl, 2,3-dihydro-benzofuran-5-yl, dibenzofuran-4-yl, pyridin-2-yl, pyridin-3-yl, 6-chloro-pyridin-3-yl, 5-bromo-pyridin-3-yl, 6-butoxy-pyridin-3-yl, quinolin-3-yl, 6-phenylsulfanyl-pyridin-3-yl, pyrimidin-5-yl, thiophen-2-yl, benzo[b]thiophen-2-yl, benzo[b]thiophen-3-yl, furan-2-yl, benzofuran-2-yl, 1-benzyl-1H-pyrazol-4-yl, and 2-benzyl-2H-pyrazol-3-yl.

In some embodiments, A is $=C(R^7)—$, and $R^7$ is selected from the group consisting of hydrogen, halo, cyano, alkyl, aryl, and substituted aryl. In particular embodiments wherein A is $=C(R^7)—$, $R^7$ is selected from the group consisting of hydrogen, chloro, bromo, cyano, methyl, propyl, t-butyl, and phenyl.

In some embodiments, B is $—N(R^8)—$, and $R^8$ is selected from the group consisting of alkyl, substituted alkyl, aryl, and substituted aryl. In particular embodiments, B is $—N(R^8)—$ and $R^8$ is selected from hydrogen, methyl, n-propyl, t-butyl, 3-methylbutyl, 1-cyclohexylmethyl, phenethyl, (R)-1-phenylethyl, (S)-1-phenylethyl, phenyl, 4-methoxyphenyl, 4-fluorophenyl, benzyl, 2-fluorobenzyl, 3-fluorobenzyl, 4-fluorobenzyl, 3,4-difluorobenzyl, 2-methoxybenzyl, 3-methoxybenzyl, 4-methoxybenzyl, and benzo[1,3]-dioxol-5-ylmethyl.

In some embodiments when A is $=C(R^7)—$, $R^6$ and $R^7$ together with the carbon atoms bound thereto join to form an aryl group. In some embodiments, the aryl group is phenyl.

Each of the various embodiments above also relate to the pharmaceutically acceptable salts, single stereoisomers, mixtures of stereoisomers, esters, or prodrugs thereof of compound of formula I.

In one embodiment, the present invention relates to compounds of formula I wherein
A is $=C(R^7)—$;
B is $—N(R^8)—$;
$R^1$ is hydroxyl;
$R^2$, $R^3$, and $R^4$ are hydrogen;
$R^5$ is selected from the group consisting of hydrogen, halo, cyano, alkyl, and aryl;
$R^6$ is selected from the group consisting of hydrogen, halo, cyano, alkyl, aryl, substituted aryl, aryloxy, substituted amino, heteroaryl, and substituted heteroaryl;
$R^7$ is selected from the group consisting of hydrogen, halo, cyano, alkyl, aryl, and substituted aryl; and
$R^8$ is selected from the group consisting of alkyl, substituted alkyl, aryl, and substituted aryl;
or pharmaceutically acceptable salts, single stereoisomers, mixtures of stereoisomers, esters, or prodrugs thereof.

In another embodiment, the present invention relates to compounds of formula I wherein
A is $=C(R^7)—$;
B is $—N(R^8)—$;
$R^1$ is hydroxyl;
$R^2$, $R^3$, and $R^4$ are hydrogen;
$R^5$ is selected from the group consisting of hydrogen, halo, cyano, alkyl, and aryl;
$R^8$ is selected from aryl or substituted aryl; and
$R^6$ and $R^7$, together with the carbons to which they are attached, form an aryl or substituted aryl group;
or pharmaceutically acceptable salts, single stereoisomers, mixtures of stereoisomers, esters, or prodrugs thereof.

In a particular embodiment, the present invention relates to compounds of formula I wherein
A is $=C(R^7)—$;
B is $—N(R^8)—$;
$R^1$ is hydroxyl;
$R^2$, $R^3$, and $R^4$ are hydrogen;
$R^5$ is hydrogen, cyano, methyl, or phenyl;
$R^8$ is selected from methyl or phenyl; and
$R^6$ and $R^7$, together with the carbons to which they are attached, form an aryl or substituted aryl group;
or pharmaceutically acceptable salts, single stereoisomers, mixtures of stereoisomers, esters, or prodrugs thereof.

In a particular embodiment, the present invention relates to compounds of formula I wherein
A is $=C(R^7)—$;
B is $—N(R^8)—$;

$R^1$ is hydroxyl;
$R^2$, $R^3$, and $R^4$ are hydrogen;
$R^5$ is selected from the group consisting of hydrogen, chloro, cyano, methyl, ethyl, and phenyl;
$R^6$ is selected from the group consisting of hydrogen, chloro, bromo, cyano, methyl, propyl, t-butyl, phenyl, 4-chlorophenyl, and 4-fluorophenyl;
$R^7$ is selected from the group consisting of hydrogen, chloro, bromo, cyano, methyl, propyl, t-butyl, and phenyl; and
$R^8$ is selected from the group consisting of hydrogen, methyl, 3-methyl-butyl, 1-cyclohexylmethyl, phenethyl, (R)-1-phenylethyl, (S)-1-phenylethyl, phenyl, 4-methoxyphenyl, 4-fluorophenyl, benzyl, 2-fluorobenzyl, 3-fluorobenzyl, 4-fluorobenzyl, 3,4-difluorobenzyl, 2-methoxybenzyl, 3-methoxybenzyl, 4-methoxybenzyl, and benzo[1,3]-dioxol-5-ylmethyl;
or pharmaceutically acceptable salts, single stereoisomers, mixtures of stereoisomers, esters, or prodrugs thereof.

In a particular embodiment, the present invention relates to compounds of formula I wherein
A is $=C(R^7)—$;
B is $—N(R^8)—$;
$R^1$ is hydroxyl;
$R^2$, $R^3$, and $R^4$ are hydrogen;
$R^5$ is cyano;
$R^6$ is selected from hydrogen, chloro, or bromo;
$R^7$ is selected from the group consisting of hydrogen, methyl, chloro, bromo, and phenyl; and
$R^8$ is selected from the group consisting of phenethyl, (R)-1-phenylethyl, (S)-1-phenylethyl, phenyl, 4-methoxyphenyl, 4-fluorophenyl, benzyl, 2-fluorobenzyl, 4-fluorobenzyl, 2-methoxybenzyl, and 4-methoxybenzyl;
or pharmaceutically acceptable salts, single stereoisomers, mixtures of stereoisomers, esters, or prodrugs thereof.

In another embodiment, the present invention relates to compounds of formula I wherein
A is $—S—$;
B is $=N—$;
$R^1$ is hydroxyl;
$R^2$, $R^3$, and $R^4$ are hydrogen;
$R^5$ is selected from the group consisting of hydrogen, cyano, alkyl, substituted alkyl, substituted alkenyl, alkynyl, aryl, substituted aryl, heteroaryl, heterocyclyl, and acyl; and
$R^6$ is selected from the group consisting of hydrogen, alkyl, aryl, substituted aryl, aryloxy, substituted amino, heteroaryl, and substituted heteroaryl;
or pharmaceutically acceptable salts, single stereoisomers, mixtures of stereoisomers, esters, or prodrugs thereof.

In a particular embodiment, the present invention relates to compounds of formula I wherein
A is $—S—$;
B is $=N—$;
$R^1$ is hydroxyl;
$R^2$, $R^3$, and $R^4$ are hydrogen or methyl;
$R^5$ is selected from the group consisting of hydrogen, cyano, acetyl, methyl, ethyl, propyl, butyl, phenethyl, ethynyl, styryl, isopropyl-sulfonylmethyl, phenyl, 4-cyanophenyl, furan-2-yl, thiazol-2-yl, and piperidin-1-yl; and
$R^6$ is selected from the group consisting of methyl, tert-butyl, phenyl, 4-cyanophenyl, 4-t-butylphenyl, trifluoromethylphenyl, 3-chloro-4-fluorophenyl, 4-chlorophenyl, 4-fluorophenyl, 2-methoxyphenyl, 3-methoxyphenyl, 4-methoxyphenyl, biphenyl-4-yl, 4-phenoxyphenyl, phenoxy, naphthalene-2-yl, 2,3-dihydro-benzo[1,4]dioxin-6-yl, 2,3-dihydro-benzofuran-5-yl, dibenzofuran-4-yl, pyridin-2-yl, pyridin-3-yl, 6-chloro-pyridin-3-yl, 5-bromo-pyridin-3-yl, 6-butoxy-pyridin-3-yl, quinolin-3-yl, 6-phenylsulfanyl-pyridin-3-yl, pyrimidin-5-yl, thiophen-2-yl, benzo[b]thiophen-2-yl, benzo[b]thiophen-3-yl, furan-2-yl, benzofuran-2-yl, 1-benzyl-1H-pyrazol-4-yl, and 2-benzyl-2H-pyrazol-3-yl;
or pharmaceutically acceptable salts, single stereoisomers, mixtures of stereoisomers, esters, or prodrugs thereof.

In some particular embodiments, the present invention relates to compounds of formula I wherein
A is $—S—$;
B is $=N—$;
$R^1$ is hydroxyl;
$R^2$, $R^3$, and $R^4$ are hydrogen;
$R^5$ is selected from the group consisting of hydrogen, methyl, ethyl, butyl, and phenyl; and
$R^6$ is phenyl;
or pharmaceutically acceptable salts, single stereoisomers, mixtures of stereoisomers, esters, or prodrugs thereof.

In another embodiment, the invention relates to compounds of formula I wherein
A is $=N—$;
B is $—S—$;
$R^1$ is hydroxyl;
$R^2$, $R^3$, and $R^4$ are hydrogen;
$R^5$ is selected from the group consisting of hydrogen, alkyl, and aryl; and
$R^6$ is selected from hydrogen, alkyl, aryl, substituted aryl, aryloxy, substituted amino, heteroaryl, and substituted heteroaryl;
or pharmaceutically acceptable salts, single stereoisomers, mixtures of stereoisomers, esters, or prodrugs thereof.

In a particular embodiment, the invention relates to compounds of formula I wherein
A is $=N—$;
B is $—S—$;
$R^1$ is hydroxyl;
$R^2$, $R^3$, and $R^4$ are hydrogen;
$R^5$ is selected from the group consisting of hydrogen, methyl, benzyl, phenyl, and 4-morpholin-4-ylphenyl; and
$R^6$ is phenyl;
or pharmaceutically acceptable salts, single stereoisomers, mixtures of stereoisomers, esters, or prodrugs thereof.

In another embodiment, the invention relates to compounds of formula I wherein
A is $—N(R^8)—$;
B is $=C(R^7)—$;
$R^1$ is hydroxyl;
$R^2$, $R^3$, and $R^4$ are hydrogen;
$R^5$ is selected from hydrogen, cyano, and alkyl;
$R^6$ and $R^7$ are selected from hydrogen or halogen;
or $R^6$ and $R^7$, together with the carbons to which they are attached, form an aryl or substituted aryl group; and
$R^8$ is selected from the group consisting of hydrogen, alkyl, substituted alky, and aryl;
or pharmaceutically acceptable salts, single stereoisomers, mixtures of stereoisomers, esters, or prodrugs thereof.

Compounds included within the scope of this invention include, for example, [(2-bromo-4-hydroxy-1-phenyl-1H-pyrrolo[2,3-c]pyridine-5-carbonyl)-amino]-acetic acid, [(4-hydroxy-1-phenyl-1H-pyrrolo[2,3-c]pyridine-5-carbonyl)-amino]-acetic acid, [(2,3-dibromo-4-hydroxy-1-phenyl-1H-pyrrolo[2,3-c]pyridine-5-carbonyl)-amino]-acetic acid, {[3- bromo-2-(4-fluoro-phenyl)-4-hydroxy-1-phenyl-1H-pyrrolo[2,3-c]pyridine-5-carbonyl]-amino}-acetic acid, [(1-benzyl-2,3,-dibromo-4-hydroxy-1H-pyrrolo[2,3-c]pyridine-5-carbonyl]-amino]-acetic acid, {[2-(4-fluoro-phenyl)-4-hydroxy-1-phenyl-1H-pyrrolo[2,3-c]pyridine-5-carbonyl]-amino}-acetic acid, [(1-benzyl-4-hydroxy-1H-pyrrolo[2,3-c]pyridine-5-carbonyl)-amino]-acetic acid, {[3-bromo-1,2-bis-(4-fluoro-phenyl)-4-hydroxy-1H-pyrrolo[2,3-c]pyridine-5-carbonyl]-amino}-acetic acid, {[1,2-bis-(4-fluoro-phenyl)-4-hydroxy-1H-pyrrolo[2,3-c]pyridine-5-carbonyl]-amino}-acetic acid, {[3-chloro-1,2-bis-(4-fluoro-phenyl)-4-hydroxy-1H-pyrrolo[2,3-c]pyridine-5-carbonyl]-amino}-acetic acid, {[3-bromo-2-(4-fluoro-phenyl)-4-hydroxy-1-(4-methoxy-phenyl)-1H-pyrrolo[2,3-c]pyridine-5-carbonyl]-amino}-acetic acid, {[2-(4-fluoro-phenyl)-4-hydroxy-1-(4-methoxy-phenyl)-1H-pyrrolo[2,3-c]pyridine-5-carbonyl]-amino}-acetic acid, {[2-bromo-1-(4-fluoro-phenyl)-4-hydroxy-3-phenyl-1H-pyrrolo[2,3-c]pyridine-5-carbonyl]-amino}-acetic acid, {[1-(4-fluoro-phenyl)-4-hydroxy-3-phenyl-1H-pyrrolo[2,3-c]pyridine-5-carbonyl]-amino}-acetic acid, {[7-chloro-1-(4-fluoro-phenyl)-4-hydroxy-3-phenyl-1H-pyrrolo[2,3-c]pyridine-5-carbonyl]-amino}-acetic acid, {[7-methyl-1-(4-fluoro-phenyl)-4-hydroxy-3-phenyl-1H-pyrrolo[2,3-c]pyridine-5-carbonyl]-amino}-acetic acid, {[3-bromo-2-tert-butyl-1-(4-fluoro-phenyl)-4-hydroxy-1H-pyrrolo[2,3-c]pyridine-5-carbonyl]-amino}-acetic acid, {[2-tert-butyl-1-(4-fluoro-phenyl)-4-hydroxy-1H-pyrrolo[2,3-c]pyridine-5-carbonyl]-amino}-acetic acid, [(1-benzyl-4-hydroxy-2,3-dimethyl-1H-pyrrolo[2,3-c]pyridine-5-carbonyl)-amino]-acetic acid, [(2,3-dibromo-4-hydroxy-1-methyl-1H-pyrrolo[2,3-c]pyridine-5-carbonyl)-amino]-acetic acid, [(4-hydroxy-1,2,3-trimethyl-1H-pyrrolo[2,3-c]pyridine-5-carbonyl)-amino]-acetic acid, {[2-bromo-3-tert-butyl-1-(4-fluoro-phenyl)-4-hydroxy-1H-pyrrolo[2,3-c]pyridine-5-carbonyl]-amino}-acetic acid, {[3-tert-butyl-1-(4-fluoro-phenyl)-4-hydroxy-1H-pyrrolo[2,3-c]pyridine-5-carbonyl]-amino}-acetic acid, [(1-benzyl-4-hydroxy-2,3-dipropyl-1H-pyrrolo[2,3-c]pyridine-5-carbonyl)-amino]-acetic acid, [(1-benzyl-3,7-dichloro-4-hydroxy-1H-pyrrolo[2,3-c]pyridine-5-carbonyl)-amino]-acetic acid, [(4-hydroxy-9-phenyl-9h-beta-carboline-3-carbonyl)-amino]-acetic acid, [(4-hydroxy-1-methyl-9-phenyl-9h-beta-carboline-3-carbonyl)-amino]-acetic acid, [(4-hydroxy-1,9-diphenyl-9h-beta-carboline-3-carbonyl)-amino]-acetic acid, [(1-benzyl-3-chloro-4-hydroxy-7-methyl-1H-pyrrolo[2,3-c]pyridine-5-carbonyl)-amino]-acetic acid, [(1-benzyl-3-chloro-4-hydroxy-7-phenyl-1H-pyrrolo[2,3-c]pyridine-5-carbonyl)-amino]-acetic acid, [(1-benzyl-3-chloro-7-ethyl-4-hydroxy-1H-pyrrolo[2,3-c]pyridine-5-carbonyl)-amino]-acetic acid, {[2-(4-fluoro-phenyl)-4-hydroxy-1,3-diphenyl-1H-pyrrolo[2,3-c]pyridine-5-carbonyl]-amino}-acetic acid, [(3-chloro-4-hydroxy-1-phenyl-1H-pyrrolo[2,3-c]pyridine-5-carbonyl)-amino]-acetic acid, [(3-chloro-4-hydroxy-7-methyl-1-phenyl-1H-pyrrolo[2,3-c]pyridine-5-carbonyl)-amino]-acetic acid, {[1-(benzo[1,3]dioxol-5-ylmethyl)-3-bromo-2-(4-chloro-phenyl)-4-hydroxy-1H-pyrrolo[2,3-c]pyridine-5-carbonyl]-amino}-acetic acid, {[3-bromo-2-(4-chloro-phenyl)-4-hydroxy-1-phenyl-1H-pyrrolo[2,3-c]pyridine-5-carbonyl]-amino}-acetic acid, [(1-(benzo[1,3]dioxol-5-ylmethyl)-4-hydroxy-2-phenyl-1H-pyrrolo[2,3-c]pyridine-5-carbonyl)-amino]-acetic acid, {[1-(benzo[1,3]dioxol-5-ylmethyl)-2-(4-chloro-phenyl)-4-hydroxy-1H-pyrrolo[2,3-c]pyridine-5-carbonyl]-amino}-acetic acid, {[1-benzo[1,3]dioxol-5-ylmethyl)-2-(4-chloro-phenyl)-4-hydroxy-3-methyl-1H-pyrrolo[2,3-c]pyridine-5-carbonyl]-amino}-acetic acid, [(4-hydroxy-1,2-diphenyl-1H-pyrrolo[2,3-c]pyridine-5-carbonyl)-amino]-acetic acid, {[2-(4-chloro-phenyl)-4-hydroxy-3-methyl-1-phenyl-1H-pyrrolo[2,3-c]pyridine-5-carbonyl]-amino}-acetic acid, [(7-hydroxy-2-phenyl-thiazolo[4,5-c]pyridine-6-carbonyl)-amino]-acetic acid, [(7-hydroxy-2,4-diphenyl-thiazolo[4,5-c]pyridine-6-carbonyl)-amino]-acetic acid, [(7-hydroxy-4-methyl-2-phenyl-thiazolo[4,5-c]pyridine-6-carbonyl)-amino]-acetic acid, (S)-2-[(7-hydroxy-4-methyl-2-phenyl-thiazolo[4,5-c]pyridine-6-carbonyl)-amino]-propionic acid, {[7-hydroxy-2-(4-trifluoromethyl-phenyl)-thiazolo[4,5-c]pyridine-6-carbonyl]-amino}-acetic acid, {[2-(4-chloro-phenyl)-7-hydroxy-thiazolo[4,5-c]pyridine-6-carbonyl]-amino}-acetic acid, {[7-hydroxy-2-(4-methoxy-phenyl)-thiazolo[4,5-c]pyridine-6-carbonyl]-amino}-acetic acid, {[2-(4-fluoro-phenyl)-7-hydroxy-thiazolo[4,5-c]pyridine-6-carbonyl]-amino}-acetic acid, [(4-ethyl-7-hydroxy-2-phenyl-thiazolo[4,5-c]pyridine-6-carbonyl)-amino]-acetic acid, [(7-hydroxy-2-phenoxy-thiazolo[4,5-c]pyridine-6-carbonyl)-amino]-acetic acid, {[7-hydroxy-2-(methyl-phenyl-amino)-thiazolo[4,5-c]pyridine-6-carbonyl]-amino}-acetic acid, {[7-hydroxy-2-(phenylamino)-thiazolo[4,5-c]pyridine-6-carbonyl]-amino}-acetic acid, [(7-hydroxy-2-phenyl-thiazolo[5,4-c]pyridine-6-carbonyl)-amino]-acetic acid, {[2-(5-bromo-pyridin-3-yl)-7-hydroxy-thiazolo[4,5-c]pyridine-6-carbonyl]-amino}-acetic acid, [(7-hydroxy-2-pyridin-3-yl-thiazolo[4,5-c]pyridine-6-carbonyl)-amino]-acetic acid, [(4-butyl-7-hydroxy-2-phenyl-thiazolo[4,5-c]pyridine-6-carbonyl)-amino]-acetic acid, [(7-hydroxy-2-pyridin-2-yl-thiazolo[4,5-c]pyridine-6-carbonyl)-amino]-acetic acid, {[2-(4-fluoro-phenyl)-7-hydroxy-4-methyl-thiazolo[4,5-c]pyridine-6-carbonyl]-amino}-acetic acid, [(7-hydroxy-2-phenyl-4-propyl-thiazolo[4,5-c]pyridine-6-carbonyl)-amino]-acetic acid, {[7-hydroxy-2-(4-phenoxy-phenyl)-thiazolo[4,5-c]pyridine-6-carbonyl]-amino}-acetic acid, [(4-cyano-7-hydroxy-2-phenyl-thiazolo[4,5-c]pyridine-6-carbonyl)-amino]-acetic acid, [(7-hydroxy-4-isobutyl-2-phenyl-thiazolo[4,5-c]pyridine-6-carbonyl)-amino]-acetic acid, {[7-hydroxy-2-(3-methoxy-phenyl)-thiazolo[4,5-c]pyridine-6-carbonyl]-amino}-acetic acid, [(4-furan-2-yl-7-hydroxy-2-phenyl-thiazolo[4,5-c]pyridine-6-carbonyl)-amino]-acetic acid, [(7-hydroxy-2-phenyl-4-thiazol-2-yl-thiazolo[4,5-c]pyridine-6-carbonyl)-amino]-acetic acid, {[7-hydroxy-2-(2-methoxy-phenyl)-thiazolo[4,5-c]pyridine-6-carbonyl]-amino}-acetic acid, [(7-hydroxy-4-methyl-2-phenyl-thiazolo[5,4-c]pyridine-6-carbonyl)-amino]-acetic acid, {[2-(4-cyano-phenyl)-7-hydroxy-thiazolo[4,5-c]pyridine-6-carbonyl]-amino}-acetic acid, [(7-hydroxy-2,4-diphenyl-thiazolo[5,4-c]pyridine-6-carbonyl)-amino]-acetic acid, {[2-(3-chloro-4-fluoro-phenyl)-7-hydroxy-thiazolo[4,5-c]pyridine-6-carbonyl]-amino}-acetic acid, [(4-benzyl-7-hydroxy-2-phenyl-thiazolo[5,4-c]pyridine-6-carbonyl)-amino]-acetic acid, {[7-hydroxy-4-(4-morpholin-4-yl-phenyl)-2-phenyl-thiazolo[5,4-c]pyridine-6-carbonyl]-amino}-acetic acid, {[4-(4-cyano-phenyl)-7-hydroxy-2-phenyl-thiazolo[4,5-c]pyridine-6-carbonyl]-amino}-acetic acid, {[4-cyano-2-(4-fluoro-phenyl)-7-hydroxy-thiazolo[4,5-c]pyridine-6-carbonyl]-amino}-acetic acid, {[4-cyano-7-hydroxy-2-(3-methoxy-phenyl)-thiazolo[4,5-c]pyridine-6-carbonyl]-amino}-acetic acid, [(4-cyano-7-hydroxy-2-phenyl-thiazolo[5,4-c]pyridine-6-carbonyl)-amino]-acetic acid, [(4-ethynyl-7-hydroxy-2-phenyl-thiazolo[4,5-c]pyridine-6-carbonyl)-amino]-acetic acid, [(4-acetyl-7-hydroxy-2-phenyl-thiazolo[4,5-c]pyridine-6-carbonyl)-amino]-acetic acid, [(7-hydroxy-2-phenyl-4-piperidin-1-yl-thiazolo[4,5-c]pyridine-6-carbonyl)-amino]-acetic acid, {[2-(4-tert-butyl-phenyl)-7-hydroxy-thiazolo[4,5-c]pyridine-6-carbonyl]-amino}-acetic acid, {[2-(2,3-dihydro-benzo[1,4]dioxin-6- yl)-7-hydroxy-thiazolo[4,5-c]pyridine-6-carbonyl]-amino}-acetic acid, [(2-benzo[b]thiophen-3-yl-7-hydroxy-thiazolo[4,5-c]pyridine-6-carbonyl)-amino]-acetic acid, [(2-biphenyl-4-yl-7-hydroxy-thiazolo[4,5-c]pyridine-6-carbonyl)-amino]-acetic acid, [(2-benzo[b]thiophen-2-yl-7-hydroxy-thiazolo[4,5-c]pyridine-6-carbonyl)-amino]-acetic acid, [(7-hydroxy-2-quinolin-3-yl-thiazolo[4,5-c]pyridine-6-carbonyl)-amino]-acetic acid, [(2-benzofuran-2-yl-7-hydroxy-thiazolo[4,5-c]pyridine-6-carbonyl)-amino]-acetic acid, [(2-dibenzofuran-4-yl-7-hydroxy-thiazolo[4,5-c]pyridine-6-carbonyl)-amino]-acetic acid, {[2-(2,3-dihydro-benzofuran-5-yl)-7-hydroxy-thiazolo[4,5-c]pyridine-6-carbonyl]-amino}-acetic acid, [(7-hydroxy-2-pyrimidin-5-yl-thiazolo[4,5-c]pyridine-6-carbonyl)-amino]-acetic acid, {[2-(1-benzyl-1H-pyrazol-4-yl)-7-hydroxy-thiazolo[4,5-c]pyridine-6-carbonyl]-amino}-acetic acid, {[2-(6-chloro-pyridin-3-yl)-7-hydroxy-thiazolo[4,5-c]pyridine-6-carbonyl]-amino}-acetic acid, {[2-(6-butoxy-pyridin-3-yl)-7-hydroxy-thiazolo[4,5-c]pyridine-6-carbonyl]-amino}-acetic acid, {[7-hydroxy-2-(6-phenylsulfanyl-pyridin-3-yl)-thiazolo[4,5-c]pyridine-6-carbonyl]-amino}-acetic acid, {[2-(1-benzyl-1H-pyrazol-4-yl)4-cyano-7-hydroxy-thiazolo[4,5-c]pyridine-6-carbonyl]-amino}-acetic acid, {[2,3-dichloro-7-cyano-4-hydroxy-1-(3-methyl-butyl)-1H-pyrrolo[2,3-c]pyridine-5-carbonyl]-amino}-acetic acid, {[7-cyano-4-hydroxy-1-(3-methyl-butyl)-1H-pyrrolo[2,3-c]pyridine-5-carbonyl]-amino}-acetic acid, {[3-chloro-7-cyano-4-hydroxy-1-(3-methyl-butyl)-1H-pyrrolo[2,3-c]pyridine-5-carbonyl]-amino}-acetic acid, {[2,3-dichloro-7-cyano-1-cyclohexylmethyl-4-hydroxy-1H-pyrrolo[2,3-c]pyridine-5-carbonyl]-amino}-acetic acid, {[7-cyano-4-hydroxy-1-cyclohexylmethyl-1H-pyrrolo[2,3-c]pyridine-5-carbonyl]-amino}-acetic acid, [(1-benzyl-3-chloro-4-hydroxy-1H-pyrrolo[2,3-c]pyridine-5-carbonyl)-amino]-acetic acid, [(4-hydroxy-9-methyl-9H-beta-carboline-3-carbonyl)-amino]-acetic acid, [(4-hydroxy-1,9-dimethyl-9H-beta-carboline-3-carbonyl)-amino]-acetic acid, [(4-hydroxy-9-methyl-1-phenyl-9H-beta-carboline-3-carbonyl)-amino]-acetic acid, [(1-cyano-4-hydroxy-9-methyl-9H-beta-carboline-3-carbonyl)-amino]-acetic acid, {[3-bromo-7-cyano-2-(4-fluoro-phenyl)-4-hydroxy-1-phenyl-1H-pyrrolo[2,3-c]pyridine-5-carbonyl]-amino}-acetic acid, {[7-cyano-2-(4-fluoro-phenyl)-4-hydroxy-1-phenyl-1H-pyrrolo[2,3-c]pyridine-5-carbonyl]-amino}-acetic acid, [(4-hydroxy-5-phenyl-5H-pyrido[4,3-b]indole-3-carbonyl)-amino]-acetic acid, [(1-cyano-4-hydroxy-5-phenyl-5H-pyrido[4,3-b]indole-3-carbonyl)-amino]-acetic acid, [(4-hydroxy-1-methyl-5-phenyl-5H-pyrido[4,3-b]indole-3-carbonyl)-amino]-acetic acid, [(1-benzyl-3-chloro-7-cyano-4-hydroxy-1H-pyrrolo[2,3-c]pyridine-5-carbonyl)-amino]-acetic acid, {[3-cyano-2-(4-fluoro-phenyl)-4-hydroxy-1-phenyl-1H-pyrrolo[2,3-c]pyridine-5-carbonyl]-amino}-acetic acid, {[3-cyano-2-(4-fluoro-phenyl)-4-hydroxy-7-methyl-1-phenyl-1H-pyrrolo[2,3-c]pyridine-5-carbonyl]-amino}-acetic acid, {[3,7-dicyano-2-(4-fluoro-phenyl)-4-hydroxy-1-phenyl-1H-pyrrolo[2,3-c]pyridine-5-carbonyl]-amino}-acetic acid, [(7-cyano-4-hydroxy-1-phenyl-1H-pyrrolo[2,3-c]pyridine-5-carbonyl)-amino]-acetic acid, [(3-chloro-7-cyano-4-hydroxy-1-phenyl-1H-pyrrolo[2,3-c]pyridine-5-carbonyl)-amino]-acetic acid, {[2,3-dibromo-1-(4-fluoro-benzyl)-4-hydroxy-1H-pyrrolo[2,3-c]pyridine-5-carbonyl]-amino}-acetic acid, [(4-hydroxy-1-phenethyl-1H-pyrrolo[2,3-c]pyridine-5-carbonyl)-amino]-acetic acid, {[2,3-dibromo-7-cyano-1-(4-fluoro-benzyl)-4-hydroxy-1H-pyrrolo[2,3-c]pyridine-5-carbonyl]-amino}-acetic acid, [(3-bromo-7-cyano-4-hydroxy-1-phenyl-1H-pyrrolo[2,3-c]pyridine-5-carbonyl)-amino]-acetic acid, {[7-cyano-1-(4-fluoro-benzyl)-4-hydroxy-1H-pyrrolo[2,3-c]pyridine-5-carbonyl]-amino}-acetic acid, [(3-chloro-7-cyano-4-hydroxy-1-phenethyl-1H-pyrrolo[2,3-c]pyridine-5-carbonyl)-amino]-acetic acid, {[2,3-dibromo-4-hydroxy-1-(1(S)-phenyl-ethyl)-1H-pyrrolo[2,3-c]pyridine-5-carbonyl]-amino}-acetic acid, {[3-chloro-7-cyano-1-(4-fluoro-benzyl)-4-hydroxy-1H-pyrrolo[2,3-c]pyridine-5-carbonyl]-amino}-acetic acid, [(1-benzyl-2,3-dichloro-7-cyano-4-hydroxy-1H-pyrrolo[2,3-c]pyridine-5-carbonyl)-amino]-acetic acid, {[4-hydroxy-1-(1S-phenyl-ethyl)-1H-pyrrolo[2,3-c]pyridine-5-carbonyl]-amino}-acetic acid, [(2,3-dichloro-7-cyano-4-hydroxy-1-phenyl-1H-pyrrolo[2,3-c]pyridine-5-carbonyl)-amino]-acetic acid, [(2,3-dichloro-7-cyano-4-hydroxy-1-phenethyl-1H-pyrrolo[2,3-c]pyridine-5-carbonyl)-amino]-acetic acid, {[2,3-dichloro-7-cyano-4-hydroxy-1-(1S-phenyl-ethyl)-1H-pyrrolo[2,3-c]pyridine-5-carbonyl]-amino}-acetic acid, [(1-benzyl-3-bromo-7-cyano-4-hydroxy-1H-pyrrolo[2,3-c]pyridine-5-carbonyl)-amino]-acetic acid, {[4-hydroxy-1-(1R-phenyl-ethyl)-1H-pyrrolo[2,3-c]pyridine-5-carbonyl]-amino}-acetic acid, {[4-hydroxy-1-(4-methoxy-benzyl)-1H-pyrrolo[2,3-c]pyridine-5-carbonyl]-amino}-acetic acid, {[7-cyano-4-hydroxy-1-(4-methoxy-benzyl)-1H-pyrrolo[2,3-c]pyridine-5-carbonyl]-amino}-acetic acid, [(1-benzyl-7-cyano-4-hydroxy-3-methyl-1H-pyrrolo[2,3-c]pyridine-5-carbonyl)-amino]-acetic acid, {[2,3-dichloro-7-cyano-4-hydroxy-1-(4-methoxy-benzyl)-1H-pyrrolo[2,3-c]pyridine-5-carbonyl]-amino}-acetic acid, {[2,3-dichloro-7-cyano-4-hydroxy-1-(1R-phenyl-ethyl)-1H-pyrrolo[2,3-c]pyridine-5-carbonyl]-amino}-acetic acid, {[3-chloro-7-cyano-4-hydroxy-1-(4-methoxy-benzyl)-1H-pyrrolo[2,3-c]pyridine-5-carbonyl]-amino}-acetic acid, {[7-cyano-4-hydroxy-1-(4-methoxy-phenyl)-1H-pyrrolo[2,3-c]pyridine-5-carbonyl]-amino}-acetic acid, {[2,3-dichloro-7-cyano-4-hydroxy-1-(4-methoxy-phenyl)-1H-pyrrolo[2,3-c]pyridine-5-carbonyl]-amino}-acetic acid, {[3-chloro-7-cyano-4-hydroxy-1-(4-methoxy-phenyl)-1H-pyrrolo[2,3-c]pyridine-5-carbonyl]-amino}-acetic acid, {[1-(4-fluoro-benzyl)-4-hydroxy-2,3-dimethyl-1H-pyrrolo[2,3-c]pyridine-5-carbonyl]-amino}-acetic acid, {[7-cyano-1-(4-fluoro-phenyl)-4-hydroxy-1H-pyrrolo[2,3-c]pyridine-5-carbonyl]-amino}-acetic acid, {[2,3-dichloro-7-cyano-4-hydroxy-1-(4-fluoro-phenyl)-1H-pyrrolo[2,3-c]pyridine-5-carbonyl]-amino}-acetic acid, {[3-chloro-7-cyano-4-hydroxy-1-(4-fluoro-phenyl)-1H-pyrrolo[2,3-c]pyridine-5-carbonyl]-amino}-acetic acid, {[1-(4-fluoro-benzyl)-4-hydroxy-1H-pyrrolo[2,3-c]pyridine-5-carbonyl]-amino}-acetic acid, [(2-cyano-4-hydroxy-1-phenyl-1H-pyrrolo[2,3-c]pyridine-5-carbonyl)-amino]-acetic acid, {[1-(2-fluoro-benzyl)-4-hydroxy-1H-pyrrolo[2,3-c]pyridine-5-carbonyl]-amino}-acetic acid, {[4-hydroxy-1-(2-methoxy-benzyl)-1H-pyrrolo[2,3-c]pyridine-5-carbonyl]-amino}-acetic acid, {[4-hydroxy-1-(3-methoxy-benzyl)-1H-pyrrolo[2,3-c]pyridine-5-carbonyl]-amino}-acetic acid, {[7-cyano-1-(4-fluoro-phenyl)-4-hydroxy-3-phenyl-1H-pyrrolo[2,3-c]pyridine-5-carbonyl]-amino}-acetic acid, {[7-cyano-1-(2-fluoro-benzyl)-4-hydroxy-1H-pyrrolo[2,3-c]pyridine-5-carbonyl]-amino}-acetic acid, {[7-cyano-1-(2-methoxy-benzyl)-4-hydroxy-1H-pyrrolo[2,3-c]pyridine-5-carbonyl]-amino}-acetic acid, {[7-cyano-1-(3-methoxy-benzyl)-4-hydroxy-1H-pyrrolo[2,3-c]pyridine-5-carbonyl]-amino}-acetic acid, {[2-cyano-1-(3-fluoro-benzyl)-4-hydroxy-1H-pyrrolo[2,3-c]pyridine-5-carbonyl]-amino}-acetic acid, {[2,3-dichloro-7-cyano-1-(2-fluoro-benzyl)-4-hydroxy-1H-pyrrolo[2,3-c]pyridine-5-carbonyl]-amino}-acetic acid, {[1-(3-fluoro-benzyl)-4-hydroxy-1H-pyrrolo[2,3-c]pyridine-5-carbonyl]-amino}-acetic acid, {[3-chloro-7-cyano-1-(2-fluoro-benzyl)-4-hydroxy-1H-pyrrolo

[2,3-c]pyridine-5-carbonyl]-amino}-acetic acid, {[3-chloro-7-cyano-4-hydroxy-1-(3-methoxy-benzyl)-1H-pyrrolo[2,3-c]pyridine-5-carbonyl]-amino}-acetic acid, {[7-cyano-1-(3-fluoro-benzyl)-4-hydroxy-1H-pyrrolo[2,3-c]pyridine-5-carbonyl]-amino}acetic acid, {[7-cyano-1-(3,4-difluoro-benzyl)-4-hydroxy-1H-pyrrolo[2,3-c]pyridine-5-carbonyl]-amino}-acetic acid, {[3-chloro-7-cyano-1-(3,4-difluoro-benzyl)-4-hydroxy-1H-pyrrolo[2,3-c]pyridine-5-carbonyl]-amino}-acetic acid, {[2,3-dichloro-7-cyano-1-(3-fluoro-benzyl)-4-hydroxy-1H-pyrrolo[2,3-c]pyridine-5-carbonyl]-amino}-acetic acid, {[3-chloro-7-cyano-1-(3-fluoro-benzyl)-4-hydroxy-1H-pyrrolo[2,3-c]pyridine-5-carbonyl]-amino}-acetic acid, {[2,3-dichloro-7-cyano-1-(3,4-difluoro-benzyl)-4-hydroxy-1H-pyrrolo[2,3-c]pyridine-5-carbonyl]-amino}-acetic acid, [(1-benzyl-2,3-dichloro-7-hydroxy-1H-pyrrolo[3,2-c]pyridine-6-carbonyl)-amino]-acetic acid, [(2-tert-butyl-7-hydroxy-thiazolo[4,5-c]pyridine-6-carbonyl)-amino]-acetic acid, [(2-tert-butyl-7-hydroxy-4-methyl-thiazolo[4,5-c]pyridine-6-carbonyl)-amino]-acetic acid, [(2-tert-butyl-4-cyano-7-hydroxy-thiazolo[4,5-c]pyridine-6-carbonyl)-amino]-acetic acid, [(4-butyl-2-tert-butyl-7-hydroxy-thiazolo[4,5-c]pyridine-6-carbonyl)-amino]-acetic acid, [(2-tert-butyl-7-hydroxy-4-((E)-styryl)-thiazolo[4,5-c]pyridine-6-carbonyl)-amino]-acetic acid, [(2-tert-butyl-7-hydroxy-4-phenyl-thiazolo[4,5-c]pyridine-6-carbonyl)-amino]-acetic acid, [(2-tert-butyl-7-hydroxy-4-phenethyl-thiazolo[4,5-c]pyridine-6-carbonyl)-amino]-acetic acid, [(2-tert-butyl-7-hydroxy-4-isopropylsulfanylmethyl-thiazolo[4,5-c]pyridine-6-carbonyl)-amino]-acetic acid, [(7-hydroxy-2-methyl-4-phenyl-thiazolo[4,5-c]pyridine-6-carbonyl)-amino]-acetic acid, [(7-hydroxy-2-methyl-thiazolo[4,5-c]pyridine-6-carbonyl)-amino]-acetic acid, [(7-hydroxy-2-naphthalen-2-yl-thiazolo[4,5-c]pyridine-6-carbonyl)-amino]-acetic acid, [(7-hydroxy-2-thiophen-2-yl-thiazolo[4,5-c]pyridine-6-carbonyl)-amino]-acetic acid, and [(2-furan-2-yl-7-hydroxy-thiazolo[4,5-c]pyridine-6-carbonyl)-amino]-acetic acid.

2. Compositions and Methods of the Invention

The invention provides for use of a compound of formula I for the manufacture of a medicament for use in treating various conditions or disorders as described herein. In one embodiment, a pharmaceutical composition is provided comprising a pharmaceutically acceptable excipient or carrier, and a therapeutically effective amount of at least one compound of formula I.

The medicament or composition can further comprise at least one additional therapeutic agent selected from the group including, but not limited to, vitamin $B_{12}$, ferrous sulfate, folic acid, and/or recombinant erythropoietin or an erythropoiesis stimulating agent (ESA).

The compounds of the present invention, or medicaments or compositions comprising the compounds, can be used to modulate the stability and/or activity of HIF, and thereby activate HIF-regulated gene expression. The compound, or composition or medicament thereof, can be used in methods to treat, pretreat, or delay progression or onset of conditions associated with HIF including, but not limited to, anemic, ischemic, and hypoxic conditions. In various embodiments, the compound is administered immediately following a condition producing acute ischemia, e.g., myocardial infarction, pulmonary embolism, intestinal infarction, ischemic stroke, and renal ischemic-reperfusion injury. In another embodiment, the compound, or composition or medicament thereof, is administered to a patient diagnosed with a condition associated with the development of chronic ischemia, e.g., cardiac cirrhosis, macular degeneration, pulmonary embolism, acute respiratory failure, neonatal respiratory distress syndrome, and congestive heart failure. In yet another embodiment, the compound, or composition or medicament thereof, is administered immediately after a trauma or injury. In other embodiments, the compound, or composition or medicament thereof, can be administered to a subject based on predisposing conditions, e.g., hypertension, diabetes, occlusive arterial disease, chronic venous insufficiency, Raynaud's disease, chronic skin ulcers, cirrhosis, congestive heart failure, and systemic sclerosis. In still other embodiments, compounds may be administered to pretreat a subject to decrease or prevent the development of tissue damage associated with ischemia or hypoxia.

The compounds of the present invention, or compositions or medicaments thereof, can also be used to increase endogenous erythropoietin (EPO). The compounds, or composition or medicament thereof, can be administered to prevent, pretreat, or treat EPO-associated conditions, including, e.g., conditions associated with anemia and neurological disorders. In one embodiment, the compounds of the present invention, or compositions or medicaments thereof, can be used to treat, pretreat, or delay onset of anemia. Conditions associated with anemia include disorders such as acute or chronic kidney disease, diabetes, cancer, ulcers, infection with virus, e.g., HIV, bacteria, or parasites; inflammation, etc. Anemic conditions can further include those associated with procedures or treatments including, e.g., radiation therapy, chemotherapy, dialysis, and surgery. Disorders associated with anemia additionally include abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

The invention is also directed to use of a compound, or composition or medicament thereof, to treat, pretreat, or delay onset of a condition associated with a disorder selected from the group consisting of anemic disorders; neurological disorders and/or injuries including cases of stroke, trauma, epilepsy, and neurodegenerative disease; cardiac ischemia including, but not limited to, myocardial infarction and congestive heart failure; liver ischemia including, but not limited to, cardiac cirrhosis; renal ischemia including, but not limited to, acute kidney failure and chronic kidney failure; peripheral vascular disorders, ulcers, burns, and chronic wounds; pulmonary embolism; and ischemic-reperfusion injury.

The invention is also directed to a method of inhibiting the activity of at least one hydroxylase enzyme which modifies the alpha subunit of hypoxia inducible factor. The HIF hydroxylase enzyme may be an asparaginyl hydroxylase such as Factor Inhibiting HIF (FIH); and/or a prolyl hydroxylase including, but not limited to, the group consisting of EGLN1, EGLN2, and EGLN3. The method comprises contacting the enzyme with an inhibiting effective amount of one or more compounds selected from the group comprising compounds of formula I.

3. Definitions

It must be noted that as used herein, and in the appended claims, the singular forms "a," "an,", and "the" include plural references unless the context clearly dictates otherwise.

Unless defined otherwise, all technical, and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology, and pharmacology, within the skill of the art. Such techniques are explained fully in the literature. (See, e.g., Gennaro, A. R., ed. (1990) Remington's Pharmaceutical Sciences, 18$^{th}$ ed., Mack Publishing Co.; Colowick, S. et al., eds., Methods In Enzymology, Academic Press, Inc.; D. M. Weir, and C. C. Blackwell, eds. (1986) Handbook of Experimental Immunology, Vols. I-IV, Blackwell Scientific Publications; Maniatis, T. et al., eds. (1989) Molecular Cloning: A Laboratory Manual, 2$^{nd}$ edition, Vols. I-III, Cold Spring Harbor Laboratory Press; Ausubel, F. M. et al., eds. (1999) Short Protocols in Molecular Biology, 4$^{th}$ edition, John Wiley & Sons; Ream et al., eds. (1998) Molecular Biology Techniques: An Intensive Laboratory Course, Academic Press; Newton & Graham eds. (1997) PCR (Introduction to Biotechniques Series), 2nd ed., Springer Verlag).

The term "HIFα" refers to the alpha subunit of hypoxia inducible factor protein. HIFα may be any human or other mammalian protein, or fragment thereof, including, but not limited to, human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130, and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and bovine HIF-1α (Genbank Accession No. BAA78675). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234).

A fragment of HIFα includes any fragment retaining at least one functional or structural characteristic of HIFα. Fragments of HIFα include, e.g., the regions defined by human HIF-1α from amino acids 401 to 603 (Huang et al., supra), amino acid 531 to 575 (Jiang et al. (1997) J Biol. Chem 272:19253-19260), amino acid 556 to 575 (Tanimoto et al., supra), amino acid 557 to 571 (Srinivas et al. (1999) Biochem Biophys Res. Commun 260:557-561), and amino acid 556 to 575 (Ivan, and Kaelin (2001) Science 292:464-468). Further, HIFα fragments include any fragment containing at least one occurrence of the motif LXXLAP, e.g., as occurs in the human HIF-1α native sequence from $L_{397}$ to $P_{402}$, and from $L_{559}$ to $P_{564}$.

The term "HIF PH" refers to any enzyme capable of hydroxylating a proline residue in the HIF protein. Preferably, the proline residue hydroxylated by HIF PH includes the proline found within the motif LXXLAP. HIF PH includes members of the Egl-Nine (EGLN) gene family described by Taylor (2001, Gene 275:125-132), and characterized by Aravind, and Koonin (2001, Genome Biol 2: RESEARCH 0007), Epstein et al. (2001, Cell 107:43-54), and Bruick and McKnight (2001, Science 294:1337-1340). HIF PH2, as used in assays described herein, may be selected from human EGLN1 (hEGLN1, GenBank Accession No. AAG33965; Dupuy et al. (2000) Genomics 69:348-54), mouse EGLN1 (GenBank Accession No. CAC42515), and rat EGLN1 (GenBank Accession No. P59722). Alternatively, another HIF PH may be used in the assay. Such HIF PH enzymes include, but are not limited to, human EGLN2 isoform 1 (GenBank Accession No. CAC42510; Taylor, supra), human EGLN2 isoform 3 (GenBank Accession No. NP_542770), mouse EGLN2 (GenBank Accession No. CAC42516), and rat EGLN2 (GenBank Accession No. AAO46039); human EGLN3 (GenBank Accession No. CAC42511; Taylor, supra), mouse EGLN3 (GenBank Accession No. CAC42517), and rat EGLN3 (SM-20) (GenBank Accession No. AAA19321). In other embodiments of the present invention, EGLN may include *Caenorhabditis elegans* EGL-9 (GenBank Accession No. AAD56365) and *Drosophila melanogaster* CG1114 gene product (GenBank Accession No. AAF52050). HIF PH also includes any fragment of the foregoing full-length proteins that retain at least one structural or functional characteristic.

The term "anemia" as used herein refers to any abnormality in hemoglobin or erythrocytes that leads to reduced oxygen levels in the blood. Anemia can be associated with abnormal production, processing, or performance of erythrocytes and/or hemoglobin. The term anemia refers to any reduction in the number of red blood cells and/or level of hemoglobin in blood relative to normal blood levels.

Anemia can arise due to conditions such as acute or chronic kidney disease, infections, inflammation, cancer, irradiation, toxins, diabetes, and surgery. Infections may be due to, e.g., virus, bacteria, and/or parasites, etc. Inflammation may be due to infection or autoimmune disorders, such as rheumatoid arthritis, etc. Anemia can also be associated with blood loss due to, e.g., stomach ulcer, duodenal ulcer, hemorrhoids, cancer of the stomach or large intestine, trauma, injury, surgical procedures, etc. Anemia is further associated with radiation therapy, chemotherapy, and kidney dialysis. Anemia is also associated with HIV-infected patients undergoing treatment with azidothymidine (zidovudine) or other reverse transcriptase inhibitors, and can develop in cancer patients undergoing chemotherapy, e.g., with cyclic cisplatin- or non-cisplatin-containing chemotherapeutics. Aplastic anemia and myelodysplastic syndromes are diseases associated with bone marrow failure that result in decreased production of erythrocytes. Further, anemia can result from defective or abnormal hemoglobin or erythrocytes, such as in disorders including microcytic anemia, hypochromic anemia, etc. Anemia can result from disorders in iron transport, processing, and utilization, see, e.g., sideroblastic anemia, etc.

The terms "disorders," "diseases," and "conditions" are used inclusively and refer to any condition deviating from normal.

The terms "anemic conditions" and "anemic disorders" refer to any condition, disease, or disorder associated with anemia. Such disorders include, but are not limited to, those disorders listed above. Anemic disorders further include, but are not limited to, aplastic anemia, autoimmune hemolytic anemia, bone marrow transplantation, Churg-Strauss syndrome, Diamond Blackfan anemia, Fanconi's anemia, Felty syndrome, graft versus host disease, hematopoietic stem cell transplantation, hemolytic uremic syndrome, myelodysplastic syndrome, nocturnal paroxysmal hemoglobinuria, osteomyelofibrosis, pancytopenia, pure red-cell aplasia, purpura Schoenlein-Henoch, sideroblastic anemia, refractory anemia with excess of blasts, rheumatoid arthritis, Shwachman syndrome, sickle cell disease, thalassemia major, thalassemia minor, thrombocytopenic purpura, etc.

The term "erythropoietin-associated conditions" is used inclusively and refers to any condition associated with below normal, abnormal, or inappropriate modulation of erythropoietin. Erythropoietin-associated conditions include any condition wherein an increase in EPO level would provide therapeutic benefit. Levels of erythropoietin associated with such conditions can be determined by any measure accepted and utilized by those of skill in the art. Erythropoietin-associated conditions include anemic conditions such as those described above.

Erythropoietin-associated conditions further include neurological disorders and/or injuries, including cases of stroke, trauma, epilepsy, neurodegenerative disease and the like, wherein erythropoietin may provide a neuroprotective effect. Neurodegenerative diseases contemplated by the invention include Alzheimer's disease, Parkinson's disease, Huntington's disease, and the like.

The term "erythropoietin" refers to any recombinant or naturally occurring erythropoietin or erythropoiesis stimulating protein (ESP) or ESA or EPO including, e.g., human erythropoietin (GenBank Accession No. AAA52400; Lin et al. (1985) Proc Nat'l Acad. Sci USA 82:7580-7584), EPO-ETIN human recombinant erythropoietin (Amgen, Inc., Thousand Oaks Calif.), ARANESP human recombinant erythropoietin (Amgen), PROCRIT human recombinant erythropoietin (Ortho Biotech Products, L.P., Raritan N.J.), glycosylated erythropoietin such as those described in U.S. Pat. No. 6,930,086 (which is incorporated by reference), etc.

The term "alkyl" refers to saturated monovalent straight or branched chain hydrocarbyl groups having from 1 to 10 carbon atoms, more particularly from 1 to 5 carbon atoms, and even more particularly 1 to 3 carbon atoms. This term is exemplified by groups such as methyl, ethyl, n-propyl, iso-propyl, n-butyl, t-butyl, n-pentyl, and the like.

The term "substituted alkyl" refers to an alkyl group of from 1 to 10 carbon atoms, more particularly 1 to 5 carbon atoms, having from 1 to 5 substituents, preferably 1 to 3 substituents, independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thiol, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, $SO_3H$, $—S(O)_n$-alkyl, $—S(O)_n$-substituted alkyl, $—S(O)_n$-aryl, $—S(O)_n$-substituted aryl, $—S(O)_n$-heteroaryl, $—S(O)_n$-substituted heteroaryl, $—S(O)_n$-cycloalkyl, $—S(O)_n$-substituted cylcoalkyl, $—S(O)_n$-heterocyclic, $—S(O)_n$-substituted heterocyclic, where n is from zero to two, $—OS(O)_2$-alkyl, $—OS(O)_2$-substituted alkyl, $—OS(O)_2$-aryl, $—OS(O)_2$-substituted aryl, $OS(O)_2$-heteroaryl, $—OS(O)_2$-substituted heteroaryl, $—OS(O)_2$-heterocyclic, $—OS(O)_2$-substituted heterocyclic, and $—OSO_2—NR^{40}R^{40}$, $—NR^{40}S(O)_2—NR^{40}$-alkyl, $—NR^{40}S(O)_2—NR^{40}$-substituted alkyl, $—NR^{40}S(O)_2—NR^{40}$-aryl, $—NR^{40}S(O)_2—NR^{40}$-substituted aryl, $—NR^{40}S(O)_2—NR^{40}$-heteroaryl, $—NR^{40}S(O)_2—NR^{40}$-substituted heteroaryl, $—NR^{40}S(O)_2—NR^{40}$-heterocyclic, and $—NR^{40}S(O)_2—NR^{40}$-substituted heterocyclic, where each $R^{40}$ is independently selected from hydrogen or alkyl. This group is exemplified by groups such as benzyl, benzo[1,3]-dioxol-5-ylmethyl, etc.

The term "alkoxy" refers to the group "alkyl-O—" which includes, by way of example, methoxy, ethoxy, n-propoxy, iso-propoxy, n-butoxy, t-butoxy, sec-butoxy, n-pentoxy, and the like.

The term "substituted alkoxy" refers to the group "substituted alkyl-O—".

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— provided that a nitrogen atom of the heterocyclic or substituted heterocyclic is not bound to the —C(O)— group wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminoacyl" and the prefix "carbamoyl" or "carboxamide" or "substituted carbamoyl" or "substituted carboxamide" refers to the group $—C(O)NR^{42}R^{42}$ where each $R^{42}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic; or where each $R^{42}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "alkenyl" refers to a vinyl unsaturated monovalent hydrocarbyl group having from 2 to 6 carbon atoms, and preferably 2 to 4 carbon atoms, and having at least 1, and preferably from 1 to 2 sites of vinyl (>C=C<) unsaturation. Such groups are exemplified by vinyl (ethen-1-yl), allyl, but-3-enyl and the like.

The term "substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This term includes both E (cis) and Z (trans) isomers as appropriate. It also includes mixtures of both E and Z components. It is understood that any hydroxyl substitution is not pendent to a vinyl carbon atom.

The term "alkynyl" refers to an acetylinic unsaturated monovalent hydrocarbyl groups having from 2 to 6 carbon atoms, and preferably 2 to 3 carbon atoms, and having at least 1, and preferably from 1 to 2 sites of acetylenic (—C≡C—) unsaturation. This group is exemplified by ethyn-1-yl, propyn-1-yl, propyn-2-yl, and the like.

The term "substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. It is understood that any hydroxyl substitution is not pendent to a vinyl carbon atom.

The term "amino" refers to the group —NH$_2$.

The term "substituted amino" refers to the group —NR$^{41}$R$^{41}$, where each R$^{41}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic, provided that both R$^{41}$ groups are not hydrogen; or the R$^{41}$ groups can be joined together with the nitrogen atom to form a heterocyclic or substituted heterocyclic ring. This group is exemplified by phenylamino, methylphenylamino, and the like.

The term "acylamino" refers to the groups —NR$^{45}$C(O)alkyl, —NR$^{45}$C(O)substituted alkyl, —NR$^{45}$C(O)cycloalkyl, —NR$^{45}$C(O)substituted cycloalkyl, —NR$^{45}$C(O)alkenyl, —NR$^{45}$C(O)substituted alkenyl, —NR$^{45}$C(O)alkynyl, —NR$^{45}$C(O)substituted alkynyl, —NR$^{45}$C(O)aryl, —NR$^{45}$C(O)substituted aryl, —NR$^{45}$C(O)heteroaryl, —NR$^{45}$C(O)substituted heteroaryl, —NR$^{45}$C(O)heterocyclic, and —NR$^{45}$C(O)substituted heterocyclic where R$^{45}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are defined herein.

The term "oxycarbonylamino" refers to the groups —NR$^{46}$C(O)O-alkyl, —NR$^{46}$C(O)O-substituted alkyl, —NR$^{46}$C(O)O-alkenyl, —NR$^{46}$C(O)O-substituted alkenyl, —NR$^{46}$C(O)O-alkynyl, —NR$^{46}$C(O)O-substituted alkynyl, —NR$^{46}$C(O)O-cycloalkyl, —NR$^{46}$C(O)O-substituted cycloalkyl, —NR$^{46}$C(O)O-aryl, —NR$^{46}$C(O)O-substituted aryl, —NR$^{46}$C(O)O-heteroaryl, —NR$^{46}$C(O)O-substituted heteroaryl, —N$^{46}$C(O)O-heterocyclic, and —NR$^{46}$C(O)O-substituted heterocyclic where R$^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "oxythiocarbonylamino" refers to the groups —NR$^{46}$C(S)O-alkyl, —NR$^{46}$C(S)O-substituted alkyl, —NR$^{46}$C(S)O-alkenyl, —NR$^{46}$C(S)O-substituted alkenyl, —NR$^{46}$C(S)O-alkynyl, —NR$^{46}$C(S)O-substituted alkynyl, —NR$^{46}$C(S)O-cycloalkyl, —NR$^{46}$C(S)O-substituted cycloalkyl, —NR$^{46}$C(S)O-aryl, —NR$^{46}$C(S)O-substituted aryl, —NR$^{46}$C(S)O-heteroaryl, —NR$^{46}$C(S)O-substituted heteroaryl, —NR$^{46}$C(S)O-heterocyclic, and —NR$^{46}$C(S)O-substituted heterocyclic where R$^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonyloxy" or as a prefix "carbamoyloxy" or "substituted carbamoyloxy" refers to the groups —OC(O)NR$^{47}$R$^{47}$ where each R$^{47}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic; or where each R$^{47}$ is joined to form, together with the nitrogen atom, a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonylamino" refers to the group —NR$^{49}$C(O)NR$^{49}$R$^{49}$ where each R$^{49}$ is independently selected from the group consisting of hydrogen and alkyl.

The term "aminothiocarbonylamino" refers to the group —NR$^{49}$C(S)NR$^{49}$R$^{49}$ where each R$^{49}$ is independently selected from the group consisting of hydrogen and alkyl.

"Amidino" refers to the group —C(=NR$^{52}$)NR$^{50}$R$^{51}$ where R$^{50}$, R$^{51}$, and R$^{52}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7-yl, benzo[1,3]-dioxol-5-yl, 2,3-dihydro-benzo [1,4]dioxin-6-yl, 2,3-dihydro-benzofuran-5-yl, dibenzofuran-4-yl, and the like) provided that the point of attachment is the aryl group. Preferred aryls include phenyl and naphthyl.

The term "substituted aryl" refers to aryl groups, as defined herein, which are substituted with from 1 to 4, particularly 1 to 3, substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amidino, amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters, cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{51}$R$^{51}$, —NR$^{51}$S(O)$_2$—NR$^{51}$-alkyl, —NR$^{51}$S(O)$_2$—NR$^{51}$-substituted alkyl, —NR$^{51}$S(O)$_2$—NR$^{51}$-aryl, —NR$^{51}$S(O)$_2$—NR$^{51}$-substituted aryl, —NR$^{51}$S(O)$_2$—NR$^{51}$-heteroaryl, —NR$^{51}$S(O)$_2$—NR$^{51}$-substituted heteroaryl, —NR$^{51}$S(O)$_2$—NR$^{51}$-heterocyclic, —NR$^{51}$S(O)$_2$—NR$^{51}$-substituted heterocyclic, where each R$^{51}$ is independently selected from hydrogen or alkyl, wherein each of the terms is as defined herein.

The term "aryloxy" refers to the group aryl-O— that includes, by way of example, phenoxy, naphthoxy, and the like.

The term "substituted aryloxy" refers to substituted aryl-O— groups.

The term "aryloxyaryl" refers to the group -aryl-O-aryl.

The term "substituted aryloxyaryl" refers to aryloxyaryl groups substituted with from 1 to 3 substituents on either or both aryl rings as defined above for substituted aryl.

The term "carboxyl" refers to —COOH or salts thereof.

The term "carboxyl esters" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-heteroaryl, —C(O)O-substituted heteroaryl, —C(O)O-heterocyclic, and —C(O)O-substituted heterocyclic.

The term "cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl, and the like.

The term "substituted cycloalkyl" refers to a cycloalkyl group, having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

The term "cycloalkenyl" refers to cyclic alkenyl (but not aromatic) groups of from 5 to 10 carbon atoms having single or multiple cyclic rings and having at least one site of vinyl (>C=C<) unsaturation within the ring cyclo including, by way of example, cyclopentenyl, cyclooctenyl, and the like.

The term "substituted cycloalkenyl" refers to a cycloalkenyl group, having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. It is understood that any hydroxyl substitution is not pendent to a vinyl carbon atom.

The term "cycloalkoxy" refers to —O-cycloalkyl groups.

The term "substituted cycloalkoxy" refers to —O-substituted cycloalkyl groups.

"Guanidino" refers to the group —NHC(=NH)NH$_2$.

The term "halo" or "halogen" refers to fluoro, chloro, bromo, and iodo, and preferably is fluoro, chloro or bromo.

The term "heteroaryl" refers to an aromatic group of from 1 to 15 carbon atoms, preferably from 1 to 10 carbon atoms, and 1 to 4 heteroatoms selected from the group consisting of oxygen, nitrogen, and sulfur within the ring. Such heteroaryl groups can have a single ring (e.g., pyridinyl, furyl, or thienyl) or multiple condensed rings (e.g., indolizinyl or benzothienyl). The nitrogen and/or sulfur ring atoms can optionally be oxidized to provide for the N-oxide or the sulfoxide, and sulfone derivatives. Preferred heteroaryls include pyridinyl, pyrrolyl, indolyl, thiophenyl, thienyl, and furyl.

The term "substituted heteroaryl" refers to heteroaryl groups that are substituted with from 1 to 3 substituents selected from the same group of substituents defined for substituted aryl.

The term "heteroaryloxy" refers to the group —O-heteroaryl, and "substituted heteroaryloxy" refers to the group —O-substituted heteroaryl.

The term "heterocyclyl" or "heterocyclic" refers to a saturated or unsaturated (but not aromatic) group having a single ring or multiple condensed rings, from 1 to 10 carbon atoms, and from 1 to 4 hetero atoms selected from the group consisting of nitrogen, sulfur or oxygen within the ring wherein, in fused ring systems, one or more of the rings can be aryl or heteroaryl provided that the point of attachment is at the heterocycle. The nitrogen and/or sulfur ring atoms can optionally be oxidized to provide for the N-oxide or the sulfoxide, and sulfone derivatives.

The term "substituted heterocyclyl" or "substituted heterocyclic" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic, and "substituted heterocyclyloxy" refers to the group —O-substituted heterocyclic.

"Thiol" or "mercapto" refers to the group —SH. The term "sulfonyl" refers to the group —SO$_2$H.

"Alkylsulfanyl", "alkylthio", and "thioether" refer to the groups —S-alkyl where alkyl is as defined above.

"Thioxo" refers to the atom (=S).

"Substituted alkylthio" and "substituted alkylsulfanyl" refer to the group —S-substituted alkyl where alkyl is as defined above.

"Cycloalkylthio" or "cycloalkylsulfanyl" refers to the groups —S-cycloalkyl where cycloalkyl is as defined above.

"Substituted cycloalkylthio" refers to the group —S-substituted cycloalkyl where substituted cycloalkyl is as defined above.

"Arylthio" or "arylsulfanyl" refers to the group —S-aryl, and "substituted arylthio" refers to the group —S-substituted aryl where aryl and substituted aryl are as defined above.

"Heteroarylthio" or "heteroarylsulfanyl" refers to the group —S-heteroaryl, and "substituted heteroarylthio" refers to the group —S-substituted heteroaryl where heteroaryl and substituted heteroaryl are as defined above.

"Heterocyclicthio" refers to the group —S-heterocyclic, and "substituted heterocyclicthio" refers to the group —S-substituted heterocyclic where heterocyclic, and substituted heterocyclic are as defined above.

"Oxo" refers to the atom (=O) or (—O−).

"Sulfonyl" refers to the divalent group —S(O)$_2$—.

The term "amino acid" refers to any of the naturally occurring amino acids, as well as synthetic analogs (e.g., D-stereoisomers of the naturally occurring amino acids, such as D-threonine), and derivatives thereof. α-Amino acids comprise a carbon atom to which is bonded an amino group, a carboxyl group, a hydrogen atom, and a distinctive group referred to as a "side chain." The side chains of naturally occurring amino acids are well known in the art, and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine, and tryptophan), substituted arylalkyl (e.g., as in tyrosine), and heteroarylalkyl (e.g., as in histidine). Unnatural amino acids are also known in the art, as set forth in, for example, Williams, ed. (1989) Synthesis of Optically Active α-Amino Acids, Pergamon Press; Evans et al. (1990) J. Amer. Chem. Soc. 112:4011-4030; Pu et al. (1991) J. Amer. Chem. Soc. 56:1280-1283; Williams et al. (1991) J. Amer. Chem. Soc. 113:9276-9286; and all references cited therein.

The term "pharmaceutically acceptable salt" refers to pharmaceutically acceptable salts of a compound, which salts are derived from a variety of organic, and inorganic counter ions well known in the art, and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like.

The term "prodrug", as used herein, refers to compounds of formula I that include chemical groups which, in vivo, can be converted into the carboxylate group on the glycine or alanine substituent of the compounds and/or can be split off from the amide N-atom and/or can be split off from the 4-O atom of the pyrrolo[2,3-c]pyridine, or the 7-O atom of the pyrrolo[3,2-c]pyridine, thiazolo[4,5-c]pyridine, or thiazolo[5,4-c]pyridine; and/or can be split off from the N-atom of the pyridyl ring to provide for the active drug, a pharmaceutically acceptable salt thereof, or a biologically active metabolite thereof. Suitable groups are well known in the art and particularly include: for the carboxylic acid moiety on the glycine or alanine substituent, a prodrug selected from, e.g., esters including, but not limited to, those derived from alkyl alcohols, substituted alkyl alcohols, hydroxy substituted aryls and heteroaryls and the like; amides, particularly amides derived from amines of the formula HNR$^{20}$R$^{21}$ where R$^{20}$ and R$^{21}$ are independently hydrogen, alkyl, substituted alkyl, aryl, substituted aryl, and the like; hydroxymethyl, aldehyde and derivatives thereof; and for the pyridyl N atom, a prodrug selected from, e.g., N-oxides and N-alkyl derivatives.

The term "excipient" as used herein means an inert or inactive substance used in the production of pharmaceutical products or other tablets, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group attached to an ethenylic or acetylenic carbon atom). Such impermissible substitution patterns are well known to the skilled artisan.

4. Compound Preparation

The compounds of this invention can be prepared from readily available starting materials using, for example, the following general methods, and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

General Synthetic Scheme to Compounds of Formula I

Scheme 1 illustrates a preferred method for the preparation of the compounds of this invention. The starting materials (compound 101) are either known in the art or commercially available or prepared as illustrated in Scheme 3-6. R as used in the schemes may be, but is not limited to, ethyl. $R^2$, $R^3$, $R^4$, $R^5$, $R^6$, $R^7$, and $R^8$ as used in the synthetic schemes are as defined herein. Functional groups ($R^6$, $R^7$, and/or $R^8$) may or may not undergo conventional chemical transformation under reaction conditions throughout the entire reaction sequence and can be derivatized under conventional conditions to other functional groups.

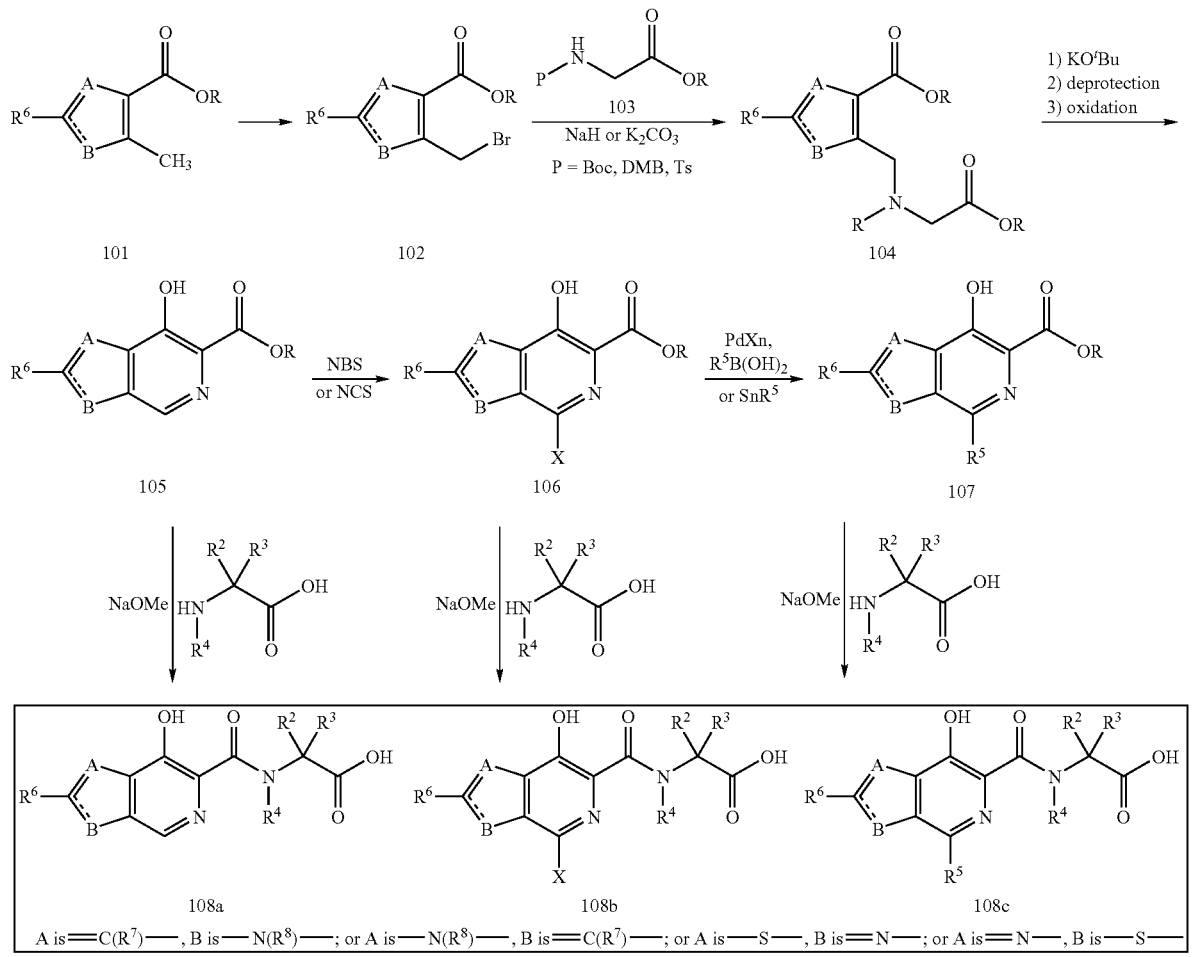

Compound 101 is conventionally brominated with an equivalent of NBS to provide compound 102. Compound 102 is then coupled with protected glycine ester (compound 103) under conventional conditions with, for example, but not limited to, sodium hydride or potassium carbonate, to provide compound 104. Subsequent intramolecular cyclization, removal of the protecting group, and oxidation/aromatization to compound 105 then proceeds under a sequence of conventional conditions; for example, compound 104 is cyclized by treatment with potassium tert-butoxide followed by removal of the protecting group with TFA (P=Boc) or thionyl chloride (P=DMB) and aromatization with or without the presence of an oxidizing agent to provide compound 105.

Amidation of compound 105 with a compound of the formula R$^4$NHCR$^2$R$^3$C(O)OH under conventional conditions with, for example, but not limited to, sodium methoxide, generates compounds of this invention (compound 108a where R$^5$=H). In addition, compound 105 can be halogenated under conventional conditions with, for example, but not limited to, NBS or NCS, to give compound 106 (X=Cl or Br). Compound 106 can then be amidated as above to provide more compounds of this invention (compound 108b where R$^5$=X). Alternatively, palladium-catalyzed alkylation or arylation of compound 106 in the presence of organoboronic acids or organotin reagents gives compound 107 which, when followed by amidation as above, provides for more compounds of this invention (compound 108c where R$^5$ is as described herein).

Alternatively, the compounds of this invention may be prepared by the method illustrated in Scheme 2. Compounds 109 are either known in the art or commercially available or prepared by oxidizing compound 101 under conventional conditions, for example, but not limited to, potassium permanganate, followed by esterification. Mono-deesterification of compound 109 proceeds using a single equivalent of sodium hydroxide to provide a mixture of compounds 110 and 111. The free acid group of compounds 110 and 111 is amidated via conventional methods to provide compounds 112 and 113.

Condensation of compounds 112 and 113 in the presence of a suitable base, such as sodium tert-butoxide, provides compounds 114 and 115. The hydroxyl group alpha to the nitrogen atom of the pyridinyl ring of compounds 114 and 115 is regioselectively substituted with halogen by treatment with excess phosphorous oxyhalide, such as POCl$_3$, to provide compounds 116 and 117. Conventional amidation as described above provides for compounds of this invention (compound 108b and 120b where R$^5$ is a halogen such as Cl or Br). Alternatively, global or partial de-halogenation with hydrogen over a palladium catalyst followed by conventional amidation as above provides for additional compounds of this invention (compound 108a and 120a where R$^5$ is H). In addition, palladium-catalyzed alkylation or arylation of compounds 116 and 117 in the presence of organoboronic acids or organotin reagents gives compounds 118 and 119 which, when followed by amidation as above, provides for more compounds of this invention (compounds 108c and 120c where R$^4$ is as described in the Summary).

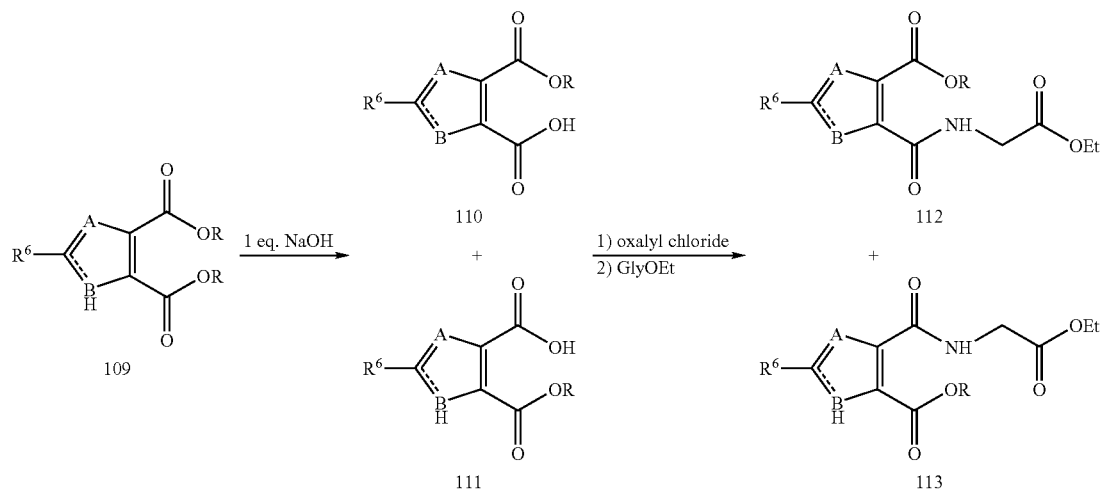

Scheme 2

-continued
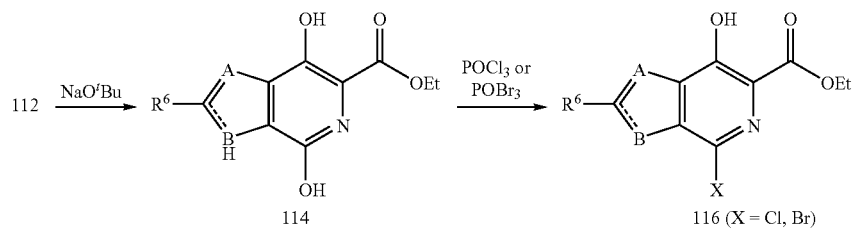
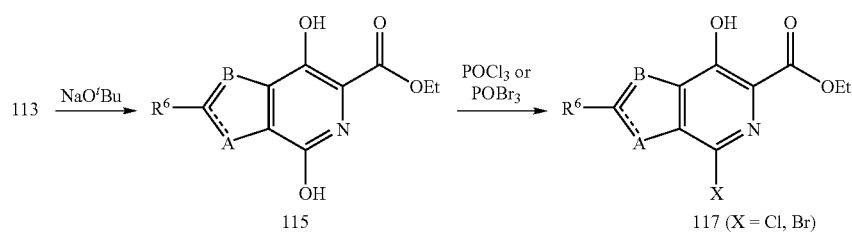
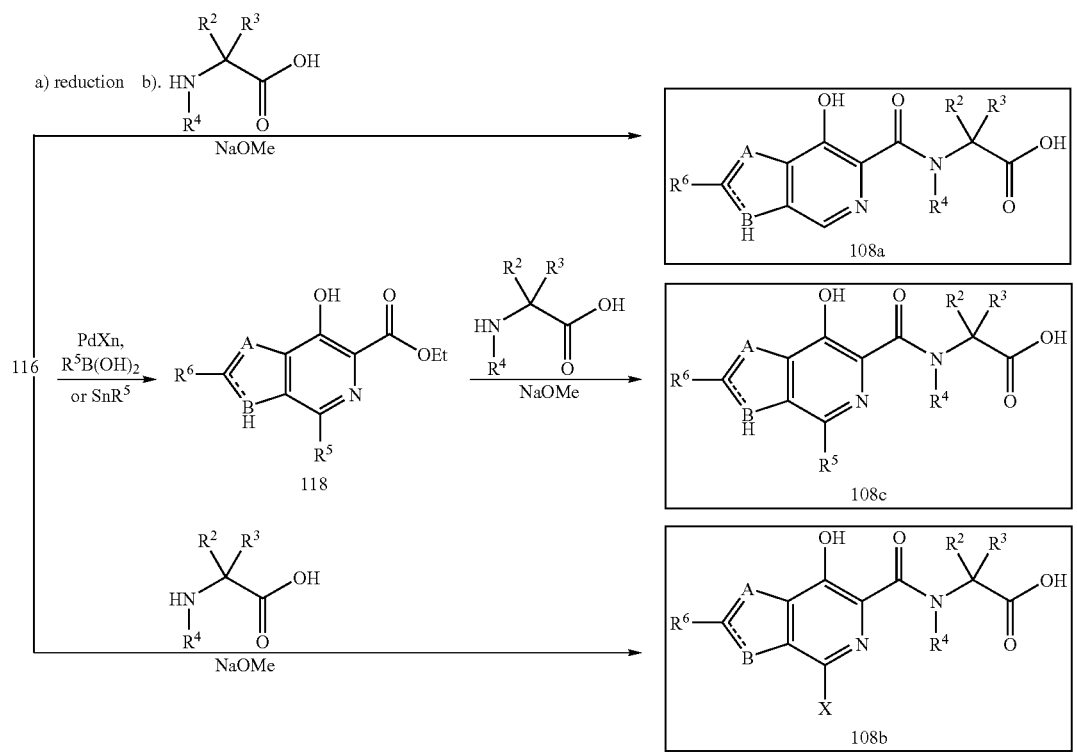

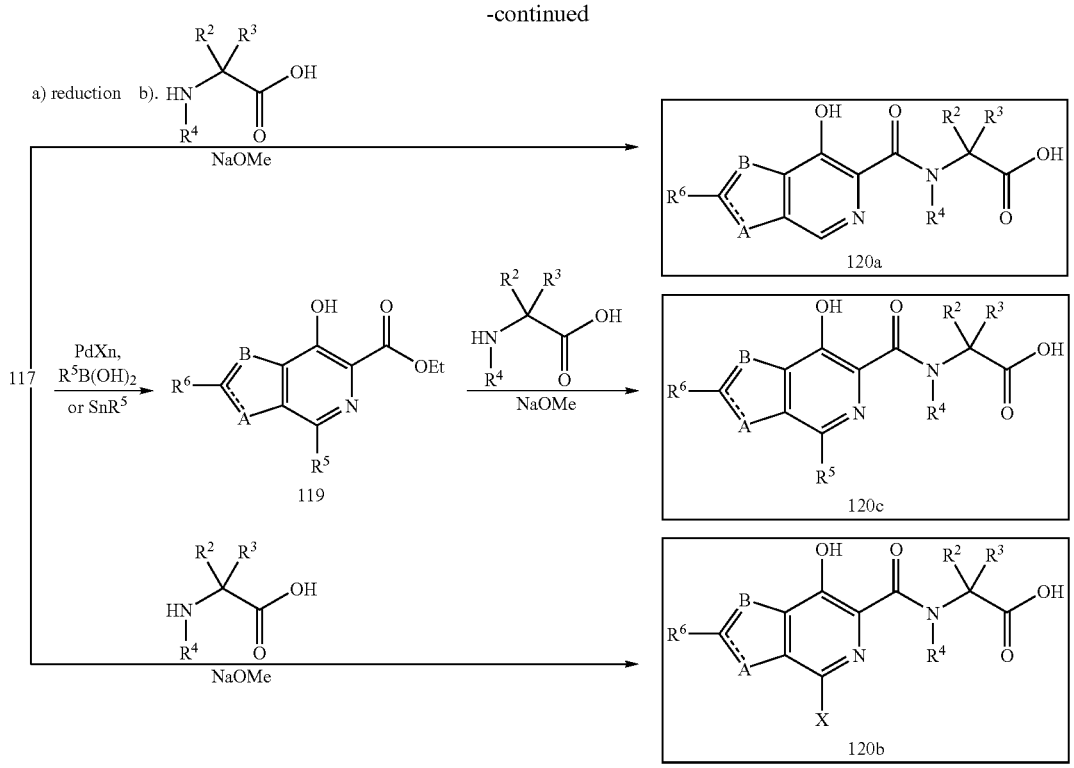

Synthesis of Intermediates for Pyrrolopyridine Series

Scheme 3 illustrates a general protocol for the preparation of the intermediates, namely 1,5-di-substituted-1H-pyrrole-3-carboxylates (compound 204). These intermediates are useful in the synthesis of compounds of this invention as described in Scheme 1 and 2.

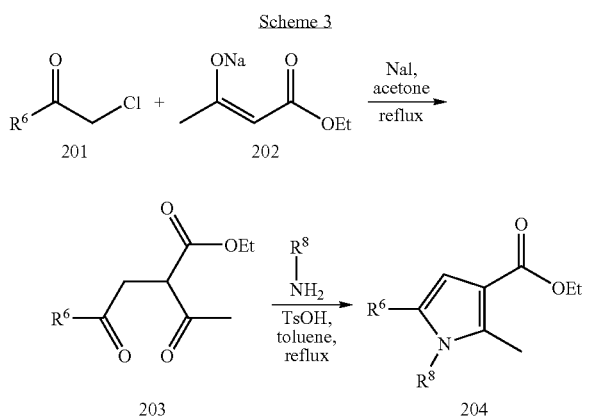

Compound 201 is either known in the art or is commercially available. Compound 201 is coupled with ethyl acetoacetate sodium salt under conventional conditions in the presence of sodium iodide to give compound 203. Condensation of compound 203 with a primary amine ($R^8$—$NH_2$) gives the intermediate compound 204.

Scheme 4 illustrates another general protocol for the preparation of the intermediates, namely 1,4-di-substituted-1H-pyrrole-3-carboxylates (compound 207). These intermediates are useful in the synthesis of the compounds of this invention as described in Scheme 1 and 2.

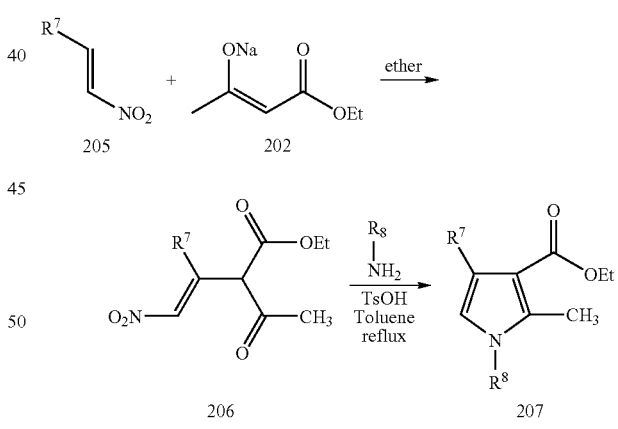

Compound 205 is either known in the art or commercially available. Compound 205 is coupled with ethyl acetoacetate sodium salt under conventional conditions to give compound 206. Condensation of compound 206 with a primary amine ($R^8NH_2$) provides compound 207.

Synthesis of Intermediates for Thiazolopyridine Series

Scheme 5 illustrates a general protocol for the preparation of intermediates, 2-substituted-4-methyl-thiazole-5-carboxylates (compound 209), for the synthesis of the compounds of this invention as described in Scheme 1 and 2.

Scheme 5

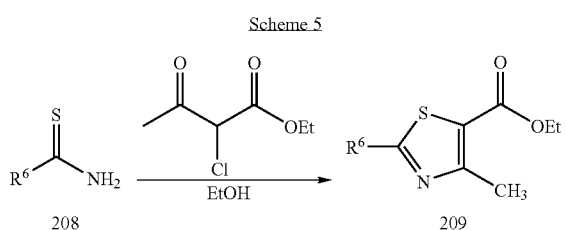

Compound 208 is either known in the art or commercially available. Compound 208 is condensed with ethyl 2-chloroacetoacetate to give compound 209.

Scheme 6 illustrates a general protocol for the preparation of the intermediates, 2-substituted-5-methyl-thiazole-4-carboxylates (compound 212), for the synthesis of the compounds of this invention as described in Scheme 1 and 2.

Scheme 6

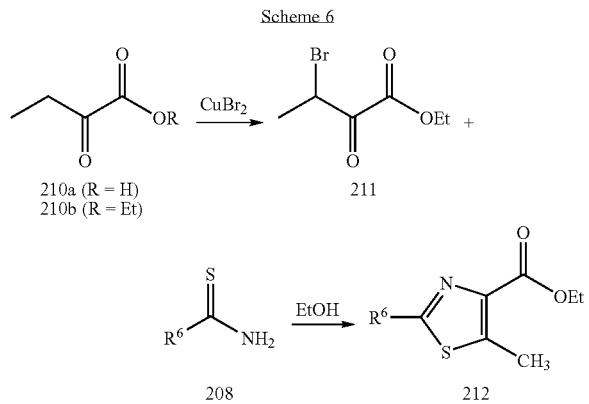

2-Ketobutyric acid (compound 210a) is esterified to give compound 210b which, in turn, when brominated under conventional conditions, for example, but not limited to, copper (II) bromide, gives rise to compound 211. Condensation of compound 211 with compound 208, which is either known in the art or commercially available, provides the intermediate compound 212.

Synthesis of Substituted-1H-indole-3-carboxylic Acid Ethyl Ester for Beta-Carboline Series Scheme 7 illustrates a general protocol for the preparation of the intermediates, substituted-1H-indole-3-carboxylic acid ethyl ester (compound 215), for the synthesis of compounds of this invention as described in Scheme 1 and 2. This synthesis is useful for embodiments of the invention wherein A is =C($R^7$)— and $R^7$ and $R^6$ and the carbon atoms bound thereto join to form an aryl or substituted aryl group. While the illustration below only depicts an unsubstituted phenyl, substitution of the phenyl group is also contemplated.

Scheme 7

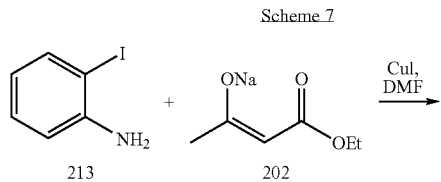

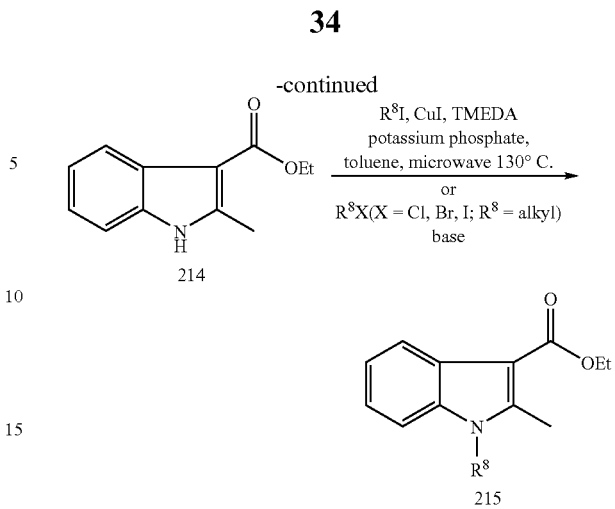

Compound 213 is either known in the art or commercially available. Substituted 2-iodo-phenylamine (compound 213) is coupled with ethyl acetotcetate sodium salt under conventional conditions in the presence of copper(I) iodide to give compound 214, which, in turn, when reacted with $R^8I$ ($R^8$=aryl) under conventional conditions, for example, but not limited to, copper(I) iodide, TMEDA and potassium phosphate in toluene, provides the intermediate compound 215. Compound 214 can also react with $R^8X$ (X=Cl, Br, or I; $R^8$=alkyl) in the presence of a base, for example, but not limited to, sodium hydride (NaH) or potassium carbonate to provide intermediate 215 ($R^8$=alkyl).

Other modifications to arrive at compounds of this invention are well within the skill of the art. For example, modification of the hydroxyl group that is beta to the nitrogen of the 5,6-membered bicyclic ring may be done by conventional means to corresponding ethers, thiols, thioethers, amino, and aminoacyls.

5. Testing and Administration a. Biological Testing

The biological activity of the compounds of the invention may be assessed using any conventionally known methods. Suitable assay methods are well known in the art. The following assays are presented only as examples and are not intended to be limiting. The compounds of the invention are active in at least one of the following assays.

i. Cell-based HIFα Stabilization Assay

Human cells derived from various tissues are separately seeded into 35 mm culture dishes, and grown at 37° C., 20% $O_2$, 5% $CO_2$ in standard culture medium, e.g., DMEM (Dulbecco's modification of Eagle's medium), 10% FBS (fetal bovine serum). When cell layers reach confluence, the media is replaced with OPTI-MEM media (Invitrogen Life Technologies, Carlsbad Calif.), and cell layers are incubated for approximately 24 hours in 20% $O_2$, 5% $CO_2$ at 37° C. Compound or 0.013% DMSO (dimethyl sulfoxide) is then added to existing medium and incubation is continued overnight.

Following incubation, the media is removed, centrifuged, and stored for analysis (see VEGF and EPO assays below). The cells are washed two times in cold phosphate buffered saline (PBS) and then lysed in 1 mL of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates are centrifuged at 3,000×g for 5 minutes at 4° C., and the cytosolic fractions (supernatant) are collected. The nuclei (pellet) are resuspended and lysed in 100 µL of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) are collected.

Nuclear fractions are analyzed for HIF-1α using a QUANTIKINE immunoassay (R&D Systems, Inc., Minneapolis Minn.) according to the manufacturer's instructions.

ii. Cell-based VEGF and EPO ELISA Assays

Conditioned media collected from cell cultures as described above is analyzed for vascular endothelial growth factor (VEGF) and/or erythropoietin (EPO) expression using an appropriate QUANTIKINE immunoassay (R&D Systems) according to the manufacturer's instructions.

iii. HIF-PH Assay

Ketoglutaric acid α-$[1-^{14}C]$-sodium salt, alpha-ketoglutaric acid sodium salt, and HPLC purified peptide may be obtained from commercial sources, e.g., Perkin-Elmer (Wellesley Mass.), Sigma-Aldrich, and SynPep Corp. (Dublin Calif.), respectively. Peptides for use in the assay may be fragments of HIFα as described above or as disclosed in International Publication WO 2005/118836, incorporated by reference herein. HIF-PH, e.g., HIF-PH2 (EGLN1), can be expressed in, e.g., insect Hi5 cells, and partially purified, e.g., through a SP ion exchange chromatography column. Enzyme activity is determined by capturing $^{14}CO_2$ using an assay described by Kivirikko and Myllyla (1982, Methods Enzymol 82:245-304). Assay reactions contain 50 mM HEPES (pH 7.4), 100 µM α-ketoglutaric acid sodium salt, 0.30 µCi/ml ketoglutaric acid α-$[1-^{14}C]$-sodium salt, 40 µM $FeSO_4$, 1 mM ascorbate, 1541.8 units/mL Catalase, with or without 50 µM peptide substrate and various concentrations of compound of the invention. Reactions are initiated by addition of HIF-PH enzyme.

The peptide-dependent percent turnover is calculated by subtracting percent turnover in the absence of peptide from percent turnover in the presence of substrate peptide. Percent inhibition and $IC_{50}$ are calculated using peptide-dependent percent turnover at given inhibitor concentrations. Calculation of $IC_{50}$ values for each inhibitor is conducted using GraFit software (Erithacus Software Ltd., Surrey UK).

All of the compounds of this invention were active in at least one of these assays.

6. Pharmaceutical Formulations and Routes of Administration

The compositions of the present invention can be delivered directly or in pharmaceutical compositions along with suitable carriers or excipients, as is well known in the art. Present methods of treatment can comprise administration of an effective amount of a compound of the invention to a subject in need; e.g., a subject having or at risk for anemia due to, e.g., chronic renal failure, diabetes, cancer, AIDS, radiation therapy, chemotherapy, kidney dialysis, or surgery. In a preferred embodiment, the subject is a mammalian subject, and in a most preferred embodiment, the subject is a human subject.

An effective amount of such agents can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, supra.

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art and include those listed in various pharmacopoeias. (See, e.g., the U.S. Pharmacopeia (USP), Japanese Pharmacopoeia (JP), European Pharmacopoeia (EP), and British pharmacopeia (BP); the U.S. Food and Drug Administration (www.fda.gov) Center for Drug Evaluation and Research (CEDR) publications, e.g., Inactive Ingredient Guide (1996); Ash and Ash, Eds. (2002) Handbook of Pharmaceutical Additives, Synapse Information Resources, Inc., Endicott N.Y.; etc.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms, and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid, or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons dervided from methan and ethan, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages preferably fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Unless otherwise stated all temperatures are in degrees Celsius. Also, in these examples and elsewhere, abbreviations have the following meanings:

| | |
|---|---|
| Atm = | atmosphere |
| aq. = | aqueous |
| 1-BuOH = | 1-butanol |
| Bn = | benzyl |
| Boc = | tert-butoxycarbonyl |
| Br s = | broad singlet |
| BzOOBz = | benzoyl peroxide |
| Ca. = | circa |
| Conc. = | concentrated |
| CuCN = | copper (I) cyanide |
| d = | doublet |
| dd = | double doublet |
| DIEA = | diisopropylethylamine |
| DMA = | dimethylacetamide |
| DMAP = | 4-dimethylaminopyridine |
| DMB = | 2,4-dimethoxy-benzyl |
| DMB = | 2,4-dimethoxybenzyl |
| DMF = | dimethyl formamide |
| DMSO = | dimethyl sulfoxide |
| dppf = | 1,1'-bis(diphenylphophino) ferrocene |
| ESI MS = | Electrospray Ionization Mass Spectrometry |
| EtOAc = | ethyl acetate |
| g = | gram |
| Gly = | glycine |
| GlyOEt = | glycine ethyl ester |
| h = | hour |
| Hz = | hertz |

-continued

| | |
|---|---|
| $K_2CO_3$ = | potassium carbonate |
| KOtBu = | Potassium tert-butoxide |
| L = | liter |
| μL = | microliter |
| M = | molar |
| m = | multiplet |
| m/z = | mass to charge ratio |
| MeCN = | acetonitrile |
| MeOH = | methanol |
| mg = | milligram |
| MHz = | mega Hertz |
| min = | minute |
| mL = | milliliter |
| mmol = | millimole |
| mol = | mole |
| MPLC = | medium pressure liquid chromatography |
| MsCl = | methanesulfonyl chloride |
| MTBE = | methyl tert-butyl ether |
| N = | normal |
| NaOBu = | sodium butoxide |
| NaOMe = | sodium methoxide |
| NBS = | N-bromosuccinimide |
| NCS = | N-chlorosuccinimide |
| NMR = | nuclear magnetic resonance |
| $Pd_2(dba)_3$ = | tris(dibenzylideneacetone)dipalladium(0) |
| $Pd(PPh_3)_2Cl_2$ = | dichlorobis(triphenylphosphine)palladium (II) |
| PSI = | pound per square inch |
| q = | quartet |
| $R_f$ = | retention factor |
| s = | singlet |
| t = | triplet |
| TEA = | triethylamine |
| TFA = | trifluoroacetic acid |
| THF = | tetrahydrofuran |
| TLC = | thin layer chromatography |
| TMEDA = | tetramethylethylenediamine |
| Ts = | p-toluenesulfonyl |
| TSOH = | p-toluenesulfonic acid |
| $Zn(CN)_2$ = | zinc cyanide |

Example 1

[(2-Bromo-4-hydroxy-1-phenyl-1H-pyrrolo[2,3-c] pyridine-5-carbonyl)-amino]-acetic acid a) 2-Methyl-1-phenyl-1H-pyrrole-3-carboxylic acid ethyl ester A solution of 2-methyl-1H-pyrrole-3-carboxylic acid ethyl ester (388 mg, 2.53 mmol), iodobenzene (619 mg, 3.04 mmol), copper(I) iodide (24 mg, 0.127 mmol), N,N'-dimethyl-ethane-1,2-diamine (54 μL, 0.506 mmol), potassium phosphate (1.128 g, 5.31 mmol) in dry toluene (2.5 mL) was irradiated with microwave at 130° C. for 2 h; then the solids were filtered off, the filtrate was concentrated, the resulted residue was purified on column to give the title product (302 mg); The title compound, $^1$H NMR (200 MHz, CDCl$_3$): δ (ppm)=7.5-7.2 (m, 5H), 6.51 (s, 2H), 4.28 (q, 2H, J=7.4 Hz), 2.44 (s, 3H), 1.36 (t, 3H, J=7.4 Hz).

b) 5-Bromo-2-bromomethyl-1-phenyl-1H-pyrrole-3-carboxylic acid ethyl ester

A mixture of 2-methyl-1-phenyl-1H-pyrrole-3-carboxylic acid ethyl ester (216 mg, 0.942 mmol), NBS (343 mg, 1.93 mmol) in tetrachloromethane (5 mL) was refluxed for 40 min, then cooled on ice, the solids were filtered off, the filtrate was concentrated to give the crude title product (407 mg), which was used directly in the next reaction without further purification. The title compound, $^1$H NMR (200 MHz, CDCl$_3$): δ

(ppm)=7.6-7.3 (m, 5H), 6.51 (s, 2H), 4.65 (s, 2H), 4.33 (q, 2H, J=7.4 Hz), 1.38 (t, 3H, J=7.4 Hz).

c) 5-Bromo-2-[(tert-butoxycarbonyl-ethoxycarbonyl-methyl-amino)-methyl]-1phenyl-1H-pyrrole-3-carboxylic acid ethyl ester 5-bromo-2-bromomethyl-1-phenyl-1H-pyrrole-3-carboxylic acid ethyl ester (400 mg, 0.94 mmol) and tert-butoxycarbonylamino-acetic acid ethyl ester (182 mg, 0.897 mmol) were dissolved in dry N,N-dimethylformamide (7 mL) at 0° C. Sodium hydride (44 mg, 1.08 mmol) was then added in one portion; the mixture was stirred for 30 min at 0° C., quenched by addition of saturated ammonium chloride aqueous solution, and then extracted with ethyl acetate. The organic phase was subsequently washed with saturated sodium chloride aqueous solution, dried with anhydrous sodium sulfate, and filtered, concentrated to give an oil, which was purified by column to give the title compound (392 mg); ESI MS (m/z): 531 (M+Na$^+$).

d) 2-Bromo-4-hydroxy-1-phenyl-1H-pyrrolo[2,3-c]pyridine-5-carboxylic acid ethyl ester 5-bromo-2-[(tert-butoxycarbonyl-ethoxycarbonylmethyl-amino)-methyl]-1-phenyl-1H-pyrrole-3-carboxylic acid ethyl ester (390 mg, 0.767 mmol) was dissolved in tetrahydrofuran (5 mL) and then cooled with an acetone-dry ice bath. Potassium tert-butoxide in tetrahydrofuran (0.92 mL, 0.92 mmol, 1 M solution) was added; after addition, the reaction was stirred for 10 min at −78° C. The cold bath was removed and the reaction was stirred for another 30 min at room temperature (RT) before quenching with saturated ammonium chloride aqueous solution and extracting with ethyl acetate. The organic phase was subsequently washed with saturated sodium chloride aqueous solution, dried with anhydrous sodium sulfate, and filtered, concentrated to give an oil containing crude intermediate 2-bromo-4-oxo-1-phenyl-1,4,5,7-tetrahydro-pyrrolo[2,3-c]pyridine-5,6-dicarboxylic acid 6-tert-butyl ester 5-ethyl ester, which was then dissolved in dichloromethane (20 mL) at room temperature. Trifluoroacetic acid (5 mL) was added; the resulting reaction mixture was stirred overnight at room temperature before all solvents were removed. The residue was dissolved in dichloromethane and basified with triethylamine, then air was bubbled through the solution for 5 hours. The solvent was then removed, and the residue was purified with column to give the title compound. $^1$H NMR (200 MHz, CDCl$_3$): δ (ppm)=11.52 (s, 1H), 8.06 (s, 1H), 7.65-7.28 (m, 5H), 7.02 (s, 1H), 4.52 (q, 2H, J=7.4 Hz), 1.48 (t, 3H, J=7.4 Hz).

e) [(2-Bromo-4-hydroxy-1-phenyl-1H-pyrrolo[2,3-c]pyridine-5-carbonyl)-amino]-acetic acid A mixture of 2-bromo-4-hydroxy-1-phenyl-1H-pyrrolo[2,3-c]pyridine-5-carboxylic acid ethyl ester (90 mg, 0.25 mmol), glycine (374 mg, 4.98 mmol) and a solution of sodium methoxide (NaOMe) in methanol (7.5 mL, 3.74 mmol, 0.5 M) was refluxed overnight. The solvent was then removed and the residue was partitioned between EtOAc and water. The aqueous phase was acidified with 2 M HCl to pH 3~4 and extracted with EtOAc. The EtOAc phase was then dried with anhydrous sodium sulfate, filtered, concentrated, and the residue was freeze-dried to give a powder (90 mg), the desired title product. ESI MS (m/z): 390 (M+H$^+$).

Example 2

[(4-Hydroxy-1-phenyl-1H-pyrrolo[2,3-c]pyridine-5-carbonyl)-amino]-acetic acid a) 4-Hydroxy-1-phenyl-1H-pyrrolo[2,3-c]pyridine-5-carboxylic acid ethyl ester A mixture of 2-bromo-4-hydroxy-1-phenyl-1H-pyrrolo[2,3-c]pyridine-5-carboxylic acid ethyl ester (34 mg, 0.094 mmol), 10% palladium on carbon (10 mg), ammonium formate (119 mg, 1.88 mmol) in EtOAc (2 ml) was refluxed overnight; then the mixture was diluted with EtOAc, the solids were filtered off, the filtrate was concentrated and the resulting residue was purified on column to give the title product (22 mg) as a clear oil; ESI MS (m/z): 283 (M+H$^+$).

b) [(4-Hydroxy-1-phenyl-1H-pyrrolo[2,3-c]pyridine-5-carbonyl)-amino]-acetic acid Prepared in analogy to that of Example 1(e) from 4-hydroxy-1-phenyl-1H-pyrrolo[2,3-c]pyridine-5-carboxylic acid ethyl ester. The title compound, ESI MS (m/z): 312 (M+H$^+$).

Example 3

[(2,3-Dibromo-4-hydroxy-1-phenyl-1H-pyrrolo[2,3-c]pyridine-5-carbonyl)-amino]-acetic acid a) 4,5-Dibromo-2-bromomethyl-1-phenyl-1H-pyrrole-3-carboxylic acid ethyl ester A mixture of 2-methyl-1-phenyl-1H-pyrrole-3-carboxylic acid ethyl ester (970 mg, 4.23 mmol), N-bromosuccinimide (NBS)(2.33 g, 13.1 mmol), and benzoyl peroxide (BzOOBz) (103 mg, 0.423 mmol) in benzene (20 mL) was refluxed for 2 h; then the solvent was removed, the residue was redissolved in tetrachloromethane, and cooled, the solids were filtered off, the filtrate was concentrated to give the crude title product (2.13 g); $^1$H NMR (200 MHz, CDCl$_3$): δ (ppm)=7.6-7.3 (m, 5H), 4.60 (s, 2H), 4.39 (q, 2H, J=7.4 Hz), 1.42 (t, 3H, J=7.4 Hz).

b) 4,5-Dibromo-2-[(tert-butoxycarbonyl-ethoxycarbonylmethyl-amino)-methyl]-1-phenyl-1H-pyrrole-3-carboxylic acid ethyl ester Prepared in analogy to that of Example 1(c) from 4,5-dibromo-2-bromomethyl-1-phenyl-1H-pyrrole-3-carboxylic acid ethyl ester and tert-butoxycarbonylamino-acetic acid ethyl ester. The title compound, ESI MS (m/z): 609 (M+Na$^+$).

c) 2,3-Dibromo-4-hydroxy-1-phenyl-1H-pyrrolo[2,3-c]pyridine-5-carboxylic acid ethyl ester Prepared in analogy to that of Example 1(d) from 4,5-dibromo-2-[(tert-butoxycarbonyl-ethoxycarbonylmethyl-amino)-methyl]-1-phenyl-1H-pyrrole-3-carboxylic acid ethyl ester. The title compound, ESI MS (m/z): 439 (M+H$^+$).

d) [(2,3-Dibromo-4-hydroxy-1-phenyl-1H-pyrrolo[2,3-c]pyridine-5-carbonyl)-amino]-acetic acid Prepared in analogy to that of Example 1(e) from 2,3-dibromo-4-hydroxy-1-phenyl-1H-pyrrolo[2,3-c]pyridine-5-carboxylic acid ethyl ester. The title compound, ESI MS (m/z, negative): 466 (M−H$^-$).

Example 4

{[3-Bromo-2-(4-fluoro-phenyl)-4-hydroxy-1-phenyl-1H-pyrrolo[2,3-c]pyridine-5-carbonyl]-amino}-acetic acid a) 2-[2-(4-Fluoro-phenyl)-2-oxo-ethyl]-3-oxo-butyric acid ethyl ester

A mixture of 2-chloro-1-(4-fluoro-phenyl)-ethanone (4.83 g, 28.0 mmol), ethyl acetoacetate sodium salt (4.26 g, 28.0 mmol) and sodium iodide (420 mg, 2.80 mmol) in acetone (50 mL) was refluxed for 1 h; then the solvents were evaporated, the residue was partitioned between EtOAc and 1 M HCl aqueous solution, the organic phase was washed with saturated sodium chloride aqueous solution, dried over anhydrous sodium sulfate, filtered, concentrated, to give a brown liquid, the title product (7.334 g); $^1$H NMR (200 MHz, CDCl$_3$): δ (ppm)=8.1-7.9 (m, 2H), 7.2-7.1 (m, 2H), 4.22 (q, 2H, J=6.8 Hz), 4.2-4.0 (m, 1H), 3.8-3.4 (m, 2H), 2.44 (s, 3H), 1.30 (t, 3H, J=6.8 Hz).

b) 5-(4-Fluoro-phenyl)-2-methyl-1-phenyl-1H-pyrrole-3-carboxylic acid ethyl ester A mixture of 2-[2-(4-fluoro-phenyl)-2-oxo-ethyl]-3-oxo-butyric acid ethyl ester (6.979 g, 26.21 mmol)), aniline (2.9 mL, 31.45 mmol) and p-toluenesulfonic acid (TsOH) monohydrate (249 mg, 1.31 mmol) in toluene (60 mL) was refluxed overnight while the generated water was separated with Dean-Stark distillation head. Then the reaction mixture was diluted with EtOAc, washed with saturated sodium hydrogen carbonate aqueous solution, and saturated sodium chloride aqueous solution, respectively, the organic phase was dried over anhydrous sodium sulfate, filtered, concentrated, the residue was purified with column chromatography to give the title compound (6.768 g); The title compound, ESI MS (m/z): 324 (M+H$^+$).

c) 4-Bromo-2-bromomethyl-5-(4-fluoro-phenyl)-1-phenyl-1H-pyrrole-3-carboxylic acid ethyl ester A mixture of 5-(4-fluoro-phenyl)-2-methyl-1-phenyl-1H-pyrrole-3-carboxylic acid ethyl ester (6.425 g, 19.87 mmol), NBS (7.36 g, 41.33 mmol) and BzOOBz (241 mg, 0.99 mmol) in carbon tetrachloride (100 mL) was refluxed 1.5 h; then the reaction was cooled in ice-water, the solids were filtered off, the filtrate was concentrated to give a solid, the desired title product (10.15 g); ESI MS (m/z): 400 (M–HBr+H$^+$).

d) 4-Bromo-2-[(tert-butoxycarbonyl-ethoxycarbonyl-methyl-amino)-methyl]-5-(4-fluoro-phenyl)-1-phenyl-1H-pyrrole-3-carboxylic acid ethyl ester Prepared in analogy to that of Example 1(c) from 4-bromo-2-bromomethyl-5-(4-fluoro-phenyl)-1-phenyl-1H-pyrrole-3-carboxylic acid ethyl ester and tert-butoxycarbonylamino-acetic acid ethyl ester. The title compound, ESI MS (m/z): 625 (M+Na$^+$).

e) 3-Bromo-2-(4-fluoro-phenyl)-4-hydroxy-1-phenyl-1H-pyrrolo[2,3-c]pyridine-5-carboxylic acid ethyl ester Prepared in analogy to that of Example 1(d) from 4-bromo-2-[(tert-butoxycarbonyl-ethoxycarbonylmethyl-amino)-methyl]-5-(4-fluoro-phenyl)-1-phenyl-1H-pyrrole-3-carboxylic acid ethyl ester. The title compound, ESI MS (m/z): 454 (M+H$^+$).

f) {[3-Bromo-2-(4-fluoro-phenyl)-4-hydroxy-1-phenyl-1H-pyrrolo[2,3-c]pyridine-5-carbonyl]-amino}-acetic acid Prepared in analogy to that of Example 1(e) from 3-bromo-2-(4-fluoro-phenyl)-4-hydroxy-1-phenyl-1H-pyrrolo[2,3-c]pyridine-5-carboxylic acid ethyl ester. The title compound, ESI MS (m/z): 484 (M+H$^+$).

Example 5

[(1-Benzyl-2,3-dibromo-4-hydroxy-1H-pyrrolo[2,3-c]pyridine-5-carbonyl)-amino]-acetic acid a) 1-Benzyl-2-methyl-1H-pyrrole-3-carboxylic acid ethyl ester

A mixture of 2-methyl-1H-pyrrole-3-carboxylic acid ethyl ester (6.05 g, 39.24 mmol), benzyl bromide (5.14 mL, 43.17 mmol) in DMF (50 mL) was cooled with an ice-water bath, then the solids of NaH (1.89 g, 47.09 mmol) were added in one portion, the mixture was stirred at 0° C. for 1.5 h, then quenched with saturated ammonium chloride aqueous solution, diluted with EtOAc, the organic phase was washed with water and saturated sodium chloride aqueous solution, respectively, dried over anhydrous sodium sulfate, filtered, concentrated, and the residue was purified with column chromatography to give the desired title product (5.537 g); $^1$H NMR (200 MHz, CDCl$_3$): δ (ppm)=7.30 (m, 3H), 6.95 (m, 2H), 6.57 (d, 1H, J=3.0 Hz), 6.53 (d, 1H, J=3.0 Hz), 5.03 (s, 2H), 4.25 (q, 2H, J=7.0 Hz), 2.44 (s, 3H), 1.34 (t, 3H, J=7.0 Hz).

b) 1-Benzyl-4,5-dibromo-2-bromomethyl-1H-pyrrole-3-carboxylic acid ethyl ester Prepared in analogy to that of 4,5-dibromo-2-bromomethyl-1-phenyl-1H-pyrrole-3-carboxylic acid ethyl ester (Example 1(a)) from 1-benzyl-2-methyl-1H-pyrrole-3-carboxylic acid ethyl ester; the title product, $^1$H NMR (200 MHz, CDCl$_3$): δ (ppm)=7.30 (m, 3H), 7.00 (m, 2H), 5.40 (s, 2H), 4.77 (s, 2H), 4.35 (q, 2H, J=6.8 Hz), 1.40 (t, 3H, J=6.8 Hz).

c) 1-Benzyl-4,5-dibromo-2-[(tert-butoxycarbonyl-ethoxycarbonylmethyl-amino)-methyl]-1H-pyrrole-3-carboxylic acid ethyl ester Prepared in analogy to that of Example 1(c) from 1-benzyl-4,5-dibromo-2-bromomethyl-1H-pyrrole-3-carboxylic acid ethyl ester and tert-butoxycarbonylamino-acetic acid ethyl ester. The title compound, ESI MS (m/z): 623 (M+Na$^+$).

d) 1-Benzyl-2,3-dibromo-4-hydroxy-1H-pyrrolo[2,3-c]pyridine-5-carboxylic acid ethyl ester Prepared in analogy to that of Example 1(d) from 1-benzyl-4,5-dibromo-2-[(tert-butoxycarbonyl-ethoxycarbonylmethyl-amino)-methyl]-1H-pyrrole-3-carboxylic acid ethyl ester. The title compound, ESI MS (m/z): 453 (M+H$^+$).

e) [(1-Benzyl-2,3-dibromo-4-hydroxy-1H-pyrrolo[2,3-c]pyridine-5-carbonyl)-amino]-acetic acid Prepared in analogy to that of Example 1(e) from 1-benzyl-2,3-dibromo-4-hydroxy-1H-pyrrolo[2,3-c]pyridine-5-carboxylic acid ethyl ester. The title compound, ESI MS (m/z): 482 (M+H$^+$).

Example 6

{[2-(4-Fluoro-phenyl)-4-hydroxy-1-phenyl-1H-pyrrolo[2,3-c]pyridine-5-carbonyl]-amino}-acetic acid a) 2-(4-Fluoro-phenyl)-4-hydroxy-1-phenyl-1H-pyrrolo[2,3-c]pyridine-5-carboxylic acid ethyl ester A mixture of 3-bromo-2-(4-fluoro-phenyl)-4-hydroxy-1-phenyl-1H-pyrrolo[2,3-c]pyridine-5-carboxylic acid ethyl ester (515 mg, 1.13 mmol), 10% Pd/C (116 mg), and ammonium formate (1.43 g, 22.62 mmol) in EtOAc was refluxed overnight; then filtered, the filtrate was washed with saturated sodium chloride aqueous solution, then the organic phase was dried over anhydrous sodium sulfate, filtered, concentrated to give a pure titled product (476 mg); ESI MS (m/z): 377 (M+H$^+$).

b) {[2-(4-Fluoro-phenyl)-4-hydroxy-1-phenyl-1H-pyrrolo[2,3-c]pyridine-5-carbonyl]-amino}-acetic acid Prepared in analogy to that of Example 1(e) from 2-(4-fluoro-phenyl)-4-hydroxy-1-phenyl-1H-pyrrolo[2,3-c]pyridine-5-carboxylic acid ethyl ester. The title compound, ESI MS (m/z): 406 (M+H$^+$).

Example 7

[(1-Benzyl-4-hydroxy-1H-pyrrolo[2,3-c]pyridine-5-carbonyl)-amino]-acetic acid a) 1-Benzyl-4-hydroxy-1H-pyrrolo[2,3-c]pyridine-5-carboxylic acid ethyl ester Prepared in analogy to that of 2-(4-fluoro-phenyl)-4-hydroxy-1-phenyl-1H-pyrrolo[2,3-c]pyridine-5-carboxylic acid ethyl ester from 1-benzyl-2,3-dibromo-4-hydroxy-1H-pyrrolo[2,3-c]pyridine-5-carboxylic acid ethyl ester. The title compound, ESI MS (m/z): 297 (M+H$^+$).

b) [(1-Benzyl-4-hydroxy-1H-pyrrolo[2,3-c]pyridine-5-carbonyl)-amino]-acetic acid Prepared in analogy to that of Example 1(e) from 1-benzyl-4-hydroxy-1H-pyrrolo[2,3-c]pyridine-5-carboxylic acid ethyl ester. The title compound, ESI MS (m/z): 326 (M+H$^+$).

Example 8

{[3-Bromo-1,2-bis-(4-fluoro-phenyl)-4-hydroxy-1H-pyrrolo[2,3-c]pyridine-5-carbonyl]-amino}-acetic acid a) 1,5-Bis-(4-fluoro-phenyl)-2-methyl-1H-pyrrole-3-carboxylic acid ethyl ester Prepared in analogy to that of 5-(4-fluoro-phenyl)-2-methyl-1-phenyl-1H-pyrrole-3-carboxylic acid ethyl ester from 2-[2-(4-fluoro-phenyl)-2-oxo-ethyl]-3-oxo-butyric acid ethyl ester and 4-fluoroaniline. The title compound, ESI MS (m/z): 342 (M+H$^+$).

b) 4-Bromo-2-bromomethyl-1,5-bis-(4-fluoro-phenyl)-1H-pyrrole-3-carboxylic acid ethyl ester Prepared in analogy to that of 4-bromo-2-bromomethyl-5-(4-fluoro-phenyl)-1-phenyl-1H-pyrrole-3-carboxylic acid ethyl ester from 1,5-Bis-(4-fluoro-phenyl)-2-methyl-1H-pyrrole-3-carboxylic acid ethyl ester. The title compound, ESI MS (m/z): 418 (M−HBr+H$^+$).

c) 4-Bromo-2-[(tert-butoxycarbonyl-ethoxycarbonyl-methyl-amino)-methyl]-1,5-bis-(4-fluoro-phenyl)-1H-pyrrole-3-carboxylic acid ethyl ester Prepared in analogy to that of Example 1(c) from 4-bromo-2-bromomethyl-1,5-bis-(4-fluoro-phenyl)-1H-pyrrole-3-carboxylic acid ethyl ester and tert-butoxycarbonylamino-acetic acid ethyl ester. The title compound, ESI MS (m/z): 643 (M+Na$^+$).

d) 3-Bromo-1,2-bis-(4-fluoro-phenyl)-4-hydroxy-1H-pyrrolo[2,3-c]pyridine-5-carboxylic acid ethyl ester Prepared in analogy to that of Example 1(d) from 4-bromo-2-[(tert-butoxycarbonyl-ethoxycarbonylmethyl-amino)-methyl]-1,5-bis-(4-fluoro-phenyl)-1H-pyrrole-3-carboxylic acid ethyl ester. The title compound, ESI MS (m/z): 473 (M+H$^+$).

e) {[3-Bromo-1,2-bis-(4-fluoro-phenyl)-4-hydroxy-1H-pyrrolo[2,3-c]pyridine-5-carbonyl]-amino}-acetic acid Prepared in analogy to that of Example 1(e) from 3-bromo-1,2-bis-(4-fluoro-phenyl)-4-hydroxy-1H-pyrrolo[2,3-c]pyridine-5-carboxylic acid ethyl ester. The title compound, ESI MS (m/z): 502 (M+H$^+$).

Example 9

{[1,2-Bis-(4-fluoro-phenyl)-4-hydroxy-1H-pyrrolo[2,3-c]pyridine-5-carbonyl]-amino}-acetic acid a) 1,2-Bis-(4-fluoro-phenyl)-4-hydroxy-1H-pyrrolo[2,3-c]pyridine-5-carboxylic acid ethyl ester Prepared in analogy to that of 2-(4-fluoro-phenyl)-4-hydroxy-1-phenyl-1H-pyrrolo[2,3-c]pyridine-5-carboxylic acid ethyl ester from 3-bromo-1,2-bis-(4-fluoro-phenyl)-4-hydroxy-1H-pyrrolo[2,3-c]pyridine-5-carboxylic acid ethyl ester. The title compound, ESI MS (m/z): 395 (M+H$^+$).

b) {[1,2-Bis-(4-fluoro-phenyl)-4-hydroxy-1H-pyrrolo[2,3-c]pyridine-5-carbonyl]-amino}-acetic acid Prepared in analogy to that of Example 1(e) from 1,2-bis-(4-fluoro-phenyl)-4-hydroxy-1H-pyrrolo[2,3-c]pyridine-5-carboxylic acid ethyl ester. The title compound, ESI MS (m/z): 424 (M+H$^+$).

Example 10

{[3-Chloro-1,2-bis-(4-fluoro-phenyl)-4-hydroxy-1H-pyrrolo[2,3-c]pyridine-5-carbonyl]-amino}-acetic acid a) 3-Chloro-1,2-bis-(4-fluoro-phenyl)-4-hydroxy-1H-pyrrolo[2,3-c]pyridine-5-carboxylic acid ethyl ester The mixture of 1,2-bis-(4-fluoro-phenyl)-4-hydroxy-1H-pyrrolo[2,3-c]pyridine-5-carboxylic acid ethyl ester (80 mg, 0.203 mmol), N-chlorosuccinimide (NCS)(28 mg, 0.203 mmol) and BzOOBz (2.5 mg) in tetrachloromethane (6 mL) was refluxed overnight, then the solvents were removed, the residue was purified on column to give the desired title compound (65 mg); ESI MS (m/z): 429 (M+H$^+$).

b) {[3-Chloro-1,2-bis-(4-fluoro-phenyl)-4-hydroxy-1H-pyrrolo[2,3-c]pyridine-5-carbonyl]-amino}-acetic acid Prepared in analogy to that of Example 1(e) from 3-chloro-1,2-bis-(4-fluoro-phenyl)-4-hydroxy-1H-pyrrolo[2,3-c]pyridine-5-carboxylic acid ethyl ester. The title compound, ESI MS (m/z): 458 (M+H$^+$).

Example 11

{[3-Bromo-2-(4-fluoro-phenyl)-4-hydroxy-1-(4-methoxy-phenyl)-1H-pyrrolo[2,3-c]pyridine-5-carbonyl]-amino}-acetic acid a) 5-(4-Fluoro-phenyl)-1-(4-methoxy-phenyl)-2-methyl-1H-pyrrole-3-carboxylic acid ethyl ester Prepared in analogy to that of 5-(4-fluoro-phenyl)-2-methyl-1-phenyl-1H-pyrrole-3-carboxylic acid ethyl ester from 2-[2-(4-fluoro-phenyl)-2-oxo-ethyl]-3-oxo-butyric acid ethyl ester and 4-methoxyaniline. The title compound, ESI MS (m/z): 354 (M+H$^+$).

b) 4-Bromo-2-bromomethyl-5-(4-fluoro-phenyl)-1-(4-methoxy-phenyl)-1H-pyrrole-3-carboxylic acid ethyl ester Prepared in analogy to that of 4-bromo-2-bromomethyl-5-(4-fluoro-phenyl)-1-phenyl-1H-pyrrole-3-carboxylic acid ethyl ester from 5-(4-fluoro-phenyl)-1-(4-methoxy-phenyl)-2-methyl-1H-pyrrole-3-carboxylic acid ethyl ester. The title compound, ESI MS (m/z): 430 (M−HBr+H$^+$).

c) 4-Bromo-2-[(tert-butoxycarbonyl-ethoxycarbonyl-methyl-amino)-methyl]-5-(4-fluoro-phenyl)-1-(4-methoxy-phenyl)-1H-pyrrole-3-carboxylic acid ethyl ester Prepared in analogy to that of Example 1(c) from 4-bromo-2-bromomethyl-5-(4-fluoro-phenyl)-1-(4-methoxy-phenyl)-1H-pyrrole-3-carboxylic acid ethyl ester and tert-butoxycarbonylamino-acetic acid ethyl ester. The title compound, ESI MS (m/z): 655 (M+Na$^+$).

d) 3-Bromo-2-(4-fluoro-phenyl)-4-hydroxy-1-(4-methoxy-phenyl)-1H-pyrrolo[2,3-c]pyridine-5-carboxylic acid ethyl ester Prepared in analogy to that of Example 1(d) from 4-bromo-2-[(tert-butoxycarbonyl-ethoxycarbonylmethyl-amino)-methyl]-5-(4-fluoro-phenyl)-1-(4-methoxy-phenyl)-1H-pyrrole-3-carboxylic acid ethyl ester. The title compound, ESI MS (m/z): 485 (M+H$^+$).

e) {[3-Bromo-2-(4-fluoro-phenyl)-4-hydroxy-1-(4-methoxy-phenyl)-1H-pyrrolo[2,3-c]pyridine-5-carbonyl]-amino}-acetic acid Prepared in analogy to that of Example 1(e) from 3-bromo-2-(4-fluoro-phenyl)-4-hydroxy-1-(4-methoxy-phenyl)-1H-pyrrolo[2,3-c]pyridine-5-carboxylic acid ethyl ester. The title compound, ESI MS (m/z): 514 (M+H$^+$).

Example 12

{[2-(4-Fluoro-phenyl)-4-hydroxy-1-(4-methoxy-phenyl)-1H-pyrrolo[2,3-c]pyridine-5-carbonyl]-amino}-acetic acid a) 2-(4-Fluoro-phenyl)-4-hydroxy-1-(4-methoxy-phenyl)-1H-pyrrolo[2,3-c]pyridine-5-carboxylic acid ethyl ester Prepared in analogy to that of 2-(4-fluoro-phenyl)-4-hydroxy-1-phenyl-1H-pyrrolo[2,3-c]pyridine-5-carboxylic acid ethyl ester from 3-bromo-2-(4-fluoro-phenyl)-4-hydroxy-1-(4-methoxy-phenyl)-1H-pyrrolo[2,3-c]pyridine-5-carboxylic acid ethyl ester. The title compound, ESI MS (m/z): 407 (M+H$^+$).

b) {[2-(4-Fluoro-phenyl)-4-hydroxy-1-(4-methoxy-phenyl)-1H-pyrrolo[2,3-c]pyridine-5-carbonyl]-amino}-acetic acid Prepared in analogy to that of Example 1(e) from 2-(4-fluoro-phenyl)-4-hydroxy-1-(4-methoxy-phenyl)-1H-pyrrolo[2,3-c]pyridine-5-carboxylic acid ethyl ester. The title compound, ESI MS (m/z): 436 (M+H$^+$).

Example 13

{[2-Bromo-1-(4-fluoro-phenyl)-4-hydroxy-3-phenyl-1H-pyrrolo[2,3-c]pyridine-5-carbonyl]-amino}-acetic acid a) 2-Acetyl-4-nitro-3-phenyl-butyric acid ethyl ester To a solution of (2-nitro-vinyl)-benzene (2.135 g, 14.3 mmol) in ether (30 mL) at 0° C. was added ethyl acetoacetate sodium salt (2.29 g, 14.3 mmol) portionwise in half minute; after addition, the mixture was stirred at that temperature for 1 hour; then it was diluted with EtOAc, washed with diluted hydrochloride aqueous solution and saturated sodium chloride aqueous solution respectively, the organic phase was dried over anhydrous sodium sulfate, filtered, concentrated, oil-pumped to dryness to give a brown oil, the crude titled product (4.266 g); $^1$H NMR (200 MHz, CDCl$_3$): δ (ppm) =7.4-7.2 (m, 5H), 4.73 (d, 1H, J=5.9 Hz), 4.2-3.9 (m, 4H), 2.30 (s, 3H), 1.01 (m, 3H).

b) 1-(4-Fluoro-phenyl)-2-methyl-4-phenyl-1H-pyrrole-3-carboxylic acid ethyl ester A mixture of 2-acetyl-4-nitro-3-phenyl-butyric acid ethyl ester (4.26 g, 14.3 mmol), 4-fluoroaniline (1.75 g, 15.73 mmol), and TsOH monohydrate (136 mg, 0.72 mmol) in toluene (40 mL) was refluxed overnight, while the generated water was collected with a Dean-Stark distillation head; then the reaction was cooled, diluted with EtOAc, washed with diluted sodium hydrogen carbonate aqueous solution and saturated sodium chloride aqueous solution respective, the organic phase was dried over anhydrous sodium sulfate, filtered, concentrated, the residue was purified on column to give the desired title compound (2.422 g); ESI MS (m/z): 324 (M+H$^+$).

c) 5-Bromo-2-bromomethyl-(4-fluoro-phenyl)-4-phenyl-1H-pyrrole-3-carboxylic acid ethyl ester A mixture of 1-(4-fluoro-phenyl)-2-methyl-4-phenyl-1H-pyrrole-3-carboxylic acid ethyl ester (2.42 g, 7.48 mmol), NBS (2.76 g, 15.34 mmol) and BzOOBz (54 mg, 0.22 mmol) in tetrachloromethane (30 mL) was refluxed for 1 h; then the mixture was cooled in an ice-water bath, the solids were filtered off, the filtrate was concentrated to give a brown oil, the title product; ESI MS (m/z): 400 (M−HBr+H$^+$).

d) 5-Bromo-2-[(tert-butoxycarbonyl-ethoxycarbonyl-methyl-amino)-methyl]-1-(4-fluoro-phenyl)-4-phenyl-1H-pyrrole-3-carboxylic acid ethyl ester Prepared in analogy to that of Example 1(c) from 5-bromo-2-bromomethyl-1-(4-fluoro-phenyl)-4-phenyl-1H-pyrrole-3-carboxylic acid ethyl ester and tert-butoxycarbonylamino-acetic acid ethyl ester. The title compound, ESI MS (m/z): 625 (M+Na$^+$).

e) 2-Bromo-1-(4-fluoro-phenyl)-4-hydroxy-3-phenyl-1H-pyrrolo[2,3-c]pyridine-5-carboxylic acid ethyl ester Prepared in analogy to that of Example 1(d) from 5-bromo-2-[(tert-butoxycarbonyl-ethoxycarbonylmethyl-amino)-methyl]-1-(4-fluoro-phenyl)-4-phenyl-1H-pyrrole-3-carboxylic acid ethyl ester. The title compound, $^1$H NMR (200 MHz, CDCl$_3$): δ (ppm)=11.66 (s, 1H), 8.06 (s, 1H), 7.6-7.2 (m, 9H), 4.50 (q, 2H, J=6.8 Hz), 1.46 (q, 3H, J=6.8 Hz).

f) {[2-Bromo-1-(4-fluoro-phenyl)-4-hydroxy-3-phenyl-1H-pyrrolo[2,3-c]pyridine-5-carbonyl]-amino}-acetic acid Prepared in analogy to that of Example 1(e) from 2-bromo-1-(4-fluoro-phenyl)-4-hydroxy-3-phenyl-1H-pyrrolo[2,3-c]pyridine-5-carboxylic acid ethyl ester. The title compound, ESI MS (m/z): 484 (M+H$^+$).

Example 14

{[1-(4-Fluoro-phenyl)-4-hydroxy-3-phenyl-1H-pyrrolo[2,3-c]pyridine-5-carbonyl]-amino}-acetic acid a) 1-(4-Fluoro-phenyl)-4-hydroxy-3-phenyl-1H-pyrrolo[2,3-c]pyridine-5-carboxylic acid ethyl ester A mixture of 2-bromo-1-(4-fluoro-phenyl)-4-hydroxy-3-phenyl-1H-pyrrolo[2,3-c]pyridine-5-carboxylic acid ethyl ester (514 mg, 1.13 mmol), 10% Pd—C (80 mg), and ammonium formate (1.42 g, 22.6 mmol) in EtOAc (15 mL) was refluxed for two days; then the catalysts were filtered off, the filtrate was concentrated, the left residue was purified on column to give the desired title product, ESI MS (m/z): 377 (M+H$^+$).

b) {[1-(4-Fluoro-phenyl)-4-hydroxy-3-phenyl-1H-pyrrolo[2,3-c]pyridine-5-carbonyl]-amino}-acetic acid Prepared in analogy to that of Example 1(e) from 2-bromo-1-(4-fluoro-phenyl)-4-hydroxy-3-phenyl-1H-pyrrolo[2,3-c]pyridine-5-carboxylic acid ethyl ester. The title compound, ESI MS (m/z): 406 (M+H$^+$).

Example 15

{[7-Chloro-1-(4-fluoro-phenyl)-4-hydroxy-3-phenyl-1H-pyrrolo[2,3-c]pyridine-5-carbonyl]-amino}-acetic acid a) 7-Chloro-1-(4-fluoro-phenyl)-4-hydroxy-3-phenyl-1H-pyrrolo[2,3-c]pyridine-5-carboxylic acid ethyl ester Prepared in analogy to that of 3-chloro-1,2-bis-(4-fluoro-phenyl)-4-hydroxy-1H-pyrrolo[2,3-c]pyridine-5-carboxylic acid ethyl ester from 1-(4-Fluoro-phenyl)-4-hydroxy-3-phenyl-1H-pyrrolo[2,3-c]pyridine-5-carboxylic acid ethyl ester. The title compound, $^1$H NMR (200 MHz, CDCl$_3$): δ (ppm) =11.82 (s, 1H), 7.7-7.1 (m, 10H), 4.51 (q, 2H, J=6.8 Hz), 1.46 (t, 3H, J=6.8 Hz).

b) {[7-Chloro-1-(4-fluoro-phenyl)-4-hydroxy-3-phenyl-1H-pyrrolo[2,3-c]pyridine-5-carbonyl]-amino}-acetic acid Prepared in analogy to that of Example 1(e) from 7-chloro-1-(4-fluoro-phenyl)-4-hydroxy-3-phenyl-1H-pyrrolo[2,3-c]pyridine-5-carboxylic acid ethyl ester. The title compound, ESI MS (m/z): 440 (M+H$^+$).

Example 16

{[1-(4-Fluoro-phenyl)-4-hydroxy-7-methyl-3-phenyl-1H-pyrrolo[2,3-c]pyridine-5-carbonyl]-amino}-acetic acid a) 1-(4-Fluoro-phenyl)-4-hydroxy-7-methyl-3-phenyl-1H-pyrrolo[2,3-c]pyridine-5-carboxylic acid ethyl ester A mixture of 7-chloro-1-(4-fluoro-phenyl)-4-hydroxy-3-phenyl-1H-pyrrolo[2,3-c]pyridine-5-carboxylic acid ethyl ester (60 mg, 0.146 mmol), tetramethyltin (104 mg, 0.584 mmol) and Pd(PPh$_3$)$_2$Cl$_2$ in DMF (1 mL) was stirred at 135° C. for 2 h; then the reaction was cooled, diluted with EtOAc, washed with water and saturated sodium chloride aqueous solution respectively, the organic phase was dried over anhydrous sodium sulfate, filtered, concentrated, the residue was purified on column to give the desired title product (30 mg); ESI MS (m/z): 391 (M+H$^+$).

b) {[1-(4-Fluoro-phenyl)-4-hydroxy-7-methyl-3-phenyl-1H-pyrrolo[2,3-c]pyridine-5-carbonyl]-amino}-acetic acid Prepared in analogy to that of Example 1(e) from 1-(4-fluoro-phenyl)-4-hydroxy-7-methyl-3-phenyl-1H-pyrrolo[2,3-c]pyridine-5-carboxylic acid ethyl ester. The title compound, ESI MS (m/z): 420 (M+H$^+$).

Example 17

{[3-Bromo-2-tert-butyl-1-(4-fluoro-phenyl)-4-hydroxy-1H-pyrrolo[2,3-c]pyridine-5-carbonyl]-amino}-acetic acid a) 2-Acetyl-5,5-dimethyl-4-oxo-hexanoic acid ethyl ester

Prepared in analogy to that of 2-[2-(4-fluoro-phenyl)-2-oxo-ethyl]-3-oxo-butyric acid ethyl ester from 1-chloro-3,3- dimethyl-butan-2-one. The title compound, ¹H NMR (200 MHz, CDCl₃): δ (ppm)=4.19 (q, 2H, J=7.2 Hz), 4.02 (m, 1H), 3.23 (dd, 1H, J=8.2 Hz, 18.4 Hz), 3.00 (dd, J=6.0 Hz, J=18.4 Hz), 2.37 (s, 3H), 1.8 (t, 3H, J=7.2 Hz), 1.17 (s, 9H).

b) 5-tert-Butyl-1-(4-fluoro-phenyl)-2-methyl-1H-pyrrole-3-carboxylic acid ethyl ester Prepared in analogy to that of 5-(4-fluoro-phenyl)-2-methyl-1-phenyl-1H-pyrrole-3-carboxylic acid ethyl ester from 2-Acetyl-5,5-dimethyl-4-oxo-hexanoic acid ethyl ester and 4-fluoroaniline. The title compound, ESI MS (m/z): 304 (M+H⁺).

c) 4-Bromo-2-bromomethyl-5-tert-butyl-1-(4-fluoro-phenyl)-1H-pyrrole-3-carboxylic acid ethyl ester Prepared in analogy to that of 4-bromo-2-bromomethyl-5-(4-fluoro-phenyl)-1-phenyl-1H-pyrrole-3-carboxylic acid ethyl ester from 5-tert-Butyl-1-(4-fluoro-phenyl)-2-methyl-1H-pyrrole-3-carboxylic acid ethyl ester. The title compound, ¹H NMR (200 MHz, CDCl₃): δ (ppm)=7.4-7.0 (m, 4H), 4.40-4.30 (m, 4H), 1.41 (t, 3H, J=7.0 Hz), 1.24 (s, 9H).

d) 4-Bromo-2-[(tert-butoxycarbonyl-ethoxycarbonyl-methyl-amino)-methyl]-5-tert-butyl-1-(4-fluoro-phenyl)-1H-pyrrole-3-carboxylic acid ethyl ester Prepared in analogy to that of Example 1(c) from 4-bromo-2-bromomethyl-5-tert-butyl-1-(4-fluoro-phenyl)-1H-pyrrole-3-carboxylic acid ethyl ester and tert-butoxycarbonylamino-acetic acid ethyl ester. The title compound, ESI MS (m/z): 605 (M+Na⁺).

e) 3-Bromo-2-tert-butyl-1-(4-fluoro-phenyl)-4-hydroxy-1H-pyrrolo[2,3-c]pyridine-5-carboxylic acid ethyl ester Prepared in analogy to that of Example 1(d) from 4-bromo-2-[(tert-butoxycarbonyl-ethoxycarbonylmethyl-amino)-methyl]-5-tert-butyl-1-(4-fluoro-phenyl)-1H-pyrrole-3-carboxylic acid ethyl ester. The title compound, ESI MS (m/z): 435 (M+H⁺).

f) {[3-Bromo-2-tert-butyl-1-(4-fluoro-phenyl)-4-hydroxy-1H-pyrrolo[2,3-c]pyridine-5-carbonyl]-amino}-acetic acid Prepared in analogy to that of Example 1(e) from 3-bromo-2-tert-butyl-1-(4-fluoro-phenyl)-4-hydroxy-1H-pyrrolo[2,3-c]pyridine-5-carboxylic acid ethyl ester. The title compound, ESI MS (m/z): 464 (M+H⁺).

Example 18

{[2-tert-Butyl-1-(4-fluoro-phenyl)-4-hydroxy-1H-pyrrolo[2,3-c]pyridine-5-carbonyl]-amino}-acetic acid a) 2-tert-Butyl-1-(4-fluoro-phenyl)-4-hydroxy-1H-pyrrolo[2,3-c]pyridine-5-carboxylic acid ethyl ester Prepared in analogy to that of 2-(4-fluoro-phenyl)-4-hydroxy-1-phenyl-1H-pyrrolo[2,3-c]pyridine-5-carboxylic acid ethyl ester from 3-bromo-2-tert-butyl-1-(4-fluoro-phenyl)-4-hydroxy-1H-pyrrolo[2,3-c]pyridine-5-carboxylic acid ethyl ester. The title compound, ESI MS (m/z): 357 (M+H⁺).

b) {[2-tert-Butyl-1-(4-fluoro-phenyl)-4-hydroxy-1H-pyrrolo[2,3-c]pyridine-5-carbonyl]-amino}-acetic acid Prepared in analogy to that of Example 1(e) from 2-tert-butyl-1-(4-fluoro-phenyl)-4-hydroxy-1H-pyrrolo[2,3-c]pyridine-5-carboxylic acid ethyl ester. The title compound, ESI MS (m/z): 386 (M+H⁺).

Example 19

[(1-Benzyl-4-hydroxy-2,3-dimethyl-1H-pyrrolo[2,3-c]pyridine-5-carbonyl)-amino]-acetic acid a) 1-Benzyl-2,3-dibromo-4-(2,2-dimethyl-propionyloxy)-1H-pyrrolo[2,3-c]pyridine-5-carboxylic acid ethyl ester To a stirring mixture of 1-benzyl-2,3-dibromo-4-hydroxy-1H-pyrrolo[2,3-c]pyridine-5-carboxylic acid ethyl ester (492 mg, 1.08 mmol), triethylamine (300 μL, 2.16 mmol), and DMAP (13 mg, 0.11 mmol) in anhydrous dichloromethane (5 mL) was added pivaloyl chloride (160 μL, 1.30 mmol); the mixture was stirred for 1 h at room temperature before diluted with EtOAc, then washed with diluted HCl aqueous solution, saturated NaCl aqueous solution respectively; the EtOAc phase was dried over anhydrous sodium sulfate, concentrated, the residue was purified by column to give a foamy brown solid, the desired title compound (495 mg, 85%). The title compound, ESI MS (m/z): 537 (M+H⁺).

b) 1-Benzyl-4-(2,2-dimethyl-propionyloxy)-2,3-dimethyl-1H-pyrrolo[2,3-c]pyridine-5-carboxylic acid ethyl ester A mixture of 1-benzyl-2,3-dibromo-4-(2,2-dimethyl-propionyloxy)-1H-pyrrolo[2,3-c]pyridine-5-carboxylic acid ethyl ester (124 mg, 0.23 mmol), tetramethyltin (255 μL, 1.84 mmol), Pd(PPh₃)₂Cl₂ (49 mg, 0.3 mmol) in DMF (2 mL) was heated to 130° C. for 2 h; then the mixture was diluted with EtOAc, washed with water and saturated NaCl aqueous solution respectively; the EtOAc phase was dried over anhydrous sodium sulfate, concentrated, the residue was purified by column to give a foamy brown solid, the desired title compound (74 mg, 79%). The title compound, ¹H NMR (200 MHz, CDCl₃): δ (ppm)=8.49 (s, 1H), 7.3-7.2 (m, 3H), 7.0-6.9 (m, 2H), 5.35 (s, 2H), 4.39 (q, 2H, J=7.0 Hz), 2.32 (s, 3H), 2.29 (s, 3H), 1.46 (s, 9H), 1.41 (t, 3H, J=7.0 Hz).

c) [(1-Benzyl-4-hydroxy-2,3-dimethyl-1H-pyrrolo[2,3-c]pyridine-5-carbonyl)-amino]-acetic acid A mixture of 1-benzyl-4-(2,2-dimethyl-propionyloxy)-2,3-dimethyl-1H-pyrrolo[2,3-c]pyridine-5-carboxylic acid ethyl ester (70 mg, 0.171 mmol), NaOMe in MeOH (1.02 mL, 0.51 mmol, 0.5 M), and methanol (3 mL) was stirred overnight at 60° C.; then the reaction was cooled to room temperature and acidified to pH=6 with 2 M HCl aqueous solution. The solvents were then removed, and the residue was oil pumped to dryness. The left residue was then refluxed with glycine (257 mg, 3.42 mmol), NaOMe in MeOH (5.13 mL, 2.57 mmol, 0.5 M) overnight; the solvent was removed, the residue was dissolved in water and then extracted once with MTBE, the aqueous layer was acidified with HCl (2 M) aqueous solution to pH=1-2; the precipitated solids were collected by filtration, washed briefly with water and freeze-dried to give powder, the desired title compound (53 mg, 88%); ESI MS (m/z): 354 (M+H⁺).

Example 20

[(2,3-Dibromo-4-hydroxy-1-methyl-1H-pyrrolo[2,3-c]pyridine-5-carbonyl)-amino]-acetic acid a) 1,2-Dimethyl-1H-pyrrole-3-carboxylic acid ethyl ester

To a mixture of 2-methyl-1H-pyrrole-3-carboxylic acid ethyl ester (7.1 g, 46.05 mmol), iodomethane (5.73 mL, 92.1 mmol) in DMF (50 mL) at 0° C. was added sodium hydride (NaH) (2.39 g, 59.9 mmol, 60% in mineral oil) in one portion, the mixture was stirred at 0° C. for 1 h then the mixture was poured into ice-water (300 mL), extracted with EtOAc, the organic phase was washed with diluted HCl aqueous solution, water and saturated NaCl aqueous solution respectively; the EtOAc layer was then dried over anhydrous sodium sulfate, filtered, concentrated, the residue was purified with column to give a colorless oil, the desired title compound (3.25 g); $^1$H NMR (200 MHz, CDCl$_3$): δ (ppm)=6.5-6.4 (m, 2H), 4.24 (q, 2H, J=7.1 Hz), 3.52 (s, 3H), 2.49 (s, 3H), 1.33 (t, 3H, J=7.1 Hz).

b) 4,5-Dibromo-2-bromomethyl-1-methyl-1H-pyrrole-3-carboxylic acid ethyl ester Prepared in analogy to that of 4,5-dibromo-2-bromomethyl-1-phenyl-1H-pyrrole-3-carboxylic acid ethyl ester from 1,2-Dimethyl-1H-pyrrole-3-carboxylic acid ethyl ester; the title product, $^1$H NMR (200 MHz, CDCl$_3$): δ (ppm)=4.93 (s, 2H), 4.34 (q, 2H, J=7.1 Hz), 3.69 (s, 3H), 1.40 (t, 3H, J=7.1 Hz).

c) 4,5-Dibromo-2-[(tert-butoxycarbonyl-ethoxycarbonylmethyl-amino)-methyl]-1-methyl-1H-pyrrole-3-carboxylic acid ethyl ester Prepared in analogy to that of Example 1(c) from 4,5-dibromo-2-bromomethyl-1-methyl-1H-pyrrole-3-carboxylic acid ethyl ester and tert-butoxycarbonylamino-acetic acid ethyl ester. The title compound, ESI MS (m/z): 549 (M+Na$^+$).

d) 2,3-Dibromo-4-hydroxy-1-methyl-1H-pyrrolo[2,3-c]pyridine-5-carboxylic acid ethyl ester Prepared in analogy to that of 2-(4-fluoro-phenyl)-4-hydroxy-1-phenyl-1H-pyrrolo[2,3-c]pyridine-5-carboxylic acid ethyl ester from 4,5-Dibromo-2-[(tert-butoxycarbonyl-ethoxycarbonylmethyl-amino)-methyl]-1-methyl-1H-pyrrole-3-carboxylic acid ethyl ester. The title compound, ESI MS (m/z): 377 (M+H$^+$).

e) [(2,3-Dibromo-4-hydroxy-1-methyl-1H-pyrrolo[2,3-c]pyridine-5-carbonyl)-amino]-acetic acid Prepared in analogy to that of Example 1(e) from 2,3-dibromo-4-hydroxy-1-methyl-1H-pyrrolo[2,3-c]pyridine-5-carboxylic acid ethyl ester. The title compound, ESI MS (m/z): 406 (M+H$^+$).

Example 21

[(4-Hydroxy-1,2,3-trimethyl-1H-pyrrolo[2,3-c]pyridine-5-carbonyl)-amino]-acetic acid a) 2,3-Dibromo-4-(2,2-dimethyl-propionyloxy)-1-methyl-1H-pyrrolo[2,3-c]pyridine-5-carboxylic acid ethyl ester Prepared in analogy to that of 1-benzyl-4-(2,2-dimethyl-propionyloxy)-2,3-dimethyl-1H-pyrrolo[2,3-c]pyridine-5-carboxylic acid ethyl ester from 2,3-Dibromo-4-hydroxy-1-methyl-1H-pyrrolo[2,3-c]pyridine-5-carboxylic acid ethyl ester. The title product, $^1$H NMR (200 MHz, CDCl$_3$): δ (ppm)=8.62 (s, 1H), 4.42 (q, 2H, J=7.0 Hz), 3.94 (s, 3H), 1.49 (s, 9H), 1.42 (t, 3H, J=7.0 Hz).

b) 4-(2,2-Dimethyl-propionyloxy)-1,2,3-trimethyl-1H-pyrrolo[2,3-c]pyridine-5-carboxylic acid ethyl ester Prepared in analogy to that of 1-benzyl-4-(2,2-dimethyl-propionyloxy)-2,3-dimethyl-1H-pyrrolo[2,3-c]pyridine-5-carboxylic acid ethyl ester from 2,3-Dibromo-4-(2,2-dimethyl-propionyloxy)-1-methyl-1H-pyrrolo[2,3-c]pyridine-5-carboxylic acid ethyl ester. The title product, $^1$H NMR (200 MHz, CDCl$_3$): δ (ppm)=8.53 (s, 3H), 4.42 (q, 2H, J=7.0 Hz), 3.76 (s, 3H), 2.34 (s, 3H), 2.29 (s, 3H), 1.46 (s, 9H), 1.41 (t, 3H, J=7.0 Hz).

c) [(4-Hydroxy-1,2,3-trimethyl-1H-pyrrolo[2,3-c]pyridine-5-carbonyl)-amino]-acetic acid Prepared in analogy to that of Example 19(c) from 4-(2,2-dimethyl-propionyloxy)-1,2,3-trimethyl-1H-pyrrolo[2,3-c]pyridine-5-carboxylic acid ethyl ester. The title compound, ESI MS (m/z): 278 (M+H$^+$).

Example 22

{[2-Bromo-3-tert-butyl-1-(4-fluoro-phenyl)-4-hydroxy-1H-pyrrolo[2,3-c]pyridine-5-carbonyl]-amino}-acetic acid a) 3,3-Dimethyl-1-nitro-butan-2-ol

A mixture of nitromethane (5.87 g, 68.1 mmol), 2,2-dimethyl-propionaldehyde (5.4 g, 88.6 mmol), and triethylamine (689 mg, 6.8 mmol) was stirred at room temperature for two days; then the reaction mixture was diluted with EtOAc, washed with diluted HCl aqueous solution, and saturated NaCl aqueous solution respectively, the organic phase was dried over anhydrous sodium sulfate, filtered, concentrated to give a clear oil, the title product (7.35 g); The title product, $^1$H NMR (200 MHz, CDCl$_3$): δ (ppm)=4.52 (dd, 1H, J=2.4 Hz, 12.6 Hz), 4.36 (dd, 1H, J=10.0 Hz, 12.6 Hz), 4.01 (m, 1H), 2.42 (d, 1H, J=4.4 Hz), 0.98 (s, 9H).

b) 3,3-Dimethyl-1-nitro-but-1-ene

To a cold mixture of 3,3-dimethyl-1-nitro-butan-2-ol (7.35 g, 50.0 mmol), and triethylamine (17.4 mL, 125 mmol) in dichloromethane (70 mL) at −78° C. was added MsCl (4.64 mL, 60 mmol) dropwise; the mixture was stirred for 2 hours at −78° C. to room temperature. Then solvents were removed, the residue was partitioned between EtOAc and diluted HCl aqueous solution, the EtOAc phase was washed with saturated NaCl aqueous solution, then dried over anhydrous sodium sulfate, filtered, concentrated, to give an oil, the title compound (6.2 g); The title product, $^1$H NMR (200 MHz, CDCl$_3$): δ (ppm)=7.25 (d, 1H, J=13.4 Hz), 6.88 (d, 1H, J=13.4 Hz), 1.16 (s, 9H).

c) 4-tert-Butyl-1-(4-fluoro-phenyl)-2-methyl-1H-pyrrole-3-carboxylic acid ethyl ester A mixture of 3,3-dimethyl-1-nitro-but-1-ene (6.2 g, 36 mmol) and ethyl acetoacetate, sodium salt (5.76 g, 36 mmol)

in ether (50 mL) was stirred at 0° C. for 30 min; then the reaction was quenched with saturated ammonium chloride aqueous solution, the ether layer was washed with saturated NaCl aqueous solution dried over anhydrous sodium sulfate, filtered, concentrated, to give a mixture, which was used next reaction without further purification and characterization. The above mixture was refluxed with 4-fluoroaniline (4.09 mL, 43.2 mmol), and TsOH monohydrate (343 mg, 1.8 mmol) in toluene (100 mL) was refluxed overnight, the generated water was collected with a Dean-Stark distillation apparatus; then the reaction was cooled to room temperature, diluted with EtOAc, washed with diluted HCl aqueous solution, saturated sodium bicarbonate aqueous solution, and saturated NaCl aqueous solution respectively, then dried over anhydrous sodium sulfate filtered, concentrated, the residue was purified with column to give a slightly brown oil, the title product (1.904 g); The title compound, ESI MS (m/z): 304 (M+H$^+$).

c) 5-Bromo-2-bromomethyl-4-tert-butyl-1-(4-fluoro-phenyl)-1H-pyrrole-3-carboxylic acid ethyl ester A mixture of 4-tert-butyl-1-(4-fluoro-phenyl)-2-methyl-1H-pyrrole-3-carboxylic acid ethyl ester (1.90 g, 6.28 mmol), NBS (2.29 g, 12.87 mmol) and BzOOBz (31 mg, 0.12 mmol) in tetrachloromethane (40 mL) was refluxed for 1 h; then the mixture was cooled in an ice-water bath, the solids were filtered off, the filtrate was concentrated to give a brown oil, the title product; ESI MS (m/z): 380 (M−HBr+H$^+$).

d) 5-Bromo-2-[(tert-butoxycarbonyl-ethoxycarbonyl-methyl-amino)-methyl]-4-tert-butyl-1-(4-fluoro-phenyl)-1H-pyrrole-3-carboxylic acid ethyl ester Prepared in analogy to that of Example 1(c) from 5-bromo-2-bromomethyl-4-tert-butyl-1-(4-fluoro-phenyl)-1H-pyrrole-3-carboxylic acid ethyl ester and tert-butoxycarbonylamino-acetic acid ethyl ester. The title compound, ESI MS (m/z): 605 (M+Na$^+$).

e) 2-Bromo-3-tert-butyl-1-(4-fluoro-phenyl)-4-oxo-1,4,5,7-tetrahydro-pyrrolo[2,3-c]pyridine-5,6-dicarboxylic acid 6-tert-butyl ester 5-ethyl ester To a solution of 5-bromo-2-[(tert-butoxycarbonyl-ethoxycarbonylmethyl-amino)-methyl]-4-tert-butyl-1-(4-fluoro-phenyl)-1H-pyrrole-3-carboxylic acid ethyl ester (4.0 g, ~6.28 mmol) in THF (15 mL) at −78° C. was added a solution of KO$^t$Bu in THF (9.42 mL, 9.42 mmol, 1 M); the reaction was stirred for 30 min at −78° C. and for 30 at room temperature. The reaction was subsequently quenched with saturated ammonium chloride aqueous solution, extracted with EtOAc, washed with water, and saturated NaCl aqueous solution, dried over anhydrous sodium sulfate, filtered, concentrated, to give an oil, the title product (3.24 g, crude), which was not further purified. The title product, $^1$H NMR (200 MHz, CDCl$_3$): δ (ppm)=4.4-7.0 (m, 4H), 4.5-4.1 (m, 5H), 1.6-1.2 (m, 21H).

f) 2-Bromo-3-tert-butyl-1-(4-fluoro-phenyl)-4-hydroxy-1H-pyrrolo[2,3-c]pyridine-5-carboxylic acid ethyl ester and 3-tert-Butyl-1-(4-fluoro-phenyl)-4-hydroxy-1H-pyrrolo[2,3-c]pyridine-5-carboxylic acid ethyl ester A mixture of 2-bromo-3-tert-butyl-1-(4-fluoro-phenyl)-4-oxo-1,4,5,7-tetrahydro-pyrrolo[2,3-c]pyridine-5,6-dicarboxylic acid 6-tert-butyl ester 5-ethyl ester (3.24 g, 6.02 mmol), SOCl$_2$ (0.88 mL, 12.06 mmol) in dichloromethane (15 mL) was stirred for 72 hours at room temperature; then the reaction was diluted with EtOAc, washed with saturated sodium bicarbonate aqueous solution and saturated NaCl aqueous solution, the EtOAc phase was dried over anhydrous sodium sulfate, filtered, concentrated, the residue was purified with column to give two pure fractions, the title products. 2-Bromo-3-tert-butyl-1-(4-fluoro-phenyl)-4-hydroxy-1H-pyrrolo[2,3-c]pyridine-5-carboxylic acid ethyl ester (269 mg), ESI MS (m/z): 435 (M+H)$^+$; 3-tert-Butyl-1-(4-fluoro-phenyl)-4-hydroxy-1H-pyrrolo[2,3-c]pyridine-5-carboxylic acid ethyl ester (238 mg), ESI MS (m/z): 357 (M+H)$^+$.

g) {[2-Bromo-3-tert-butyl-1-(4-fluoro-phenyl)-4-hydroxy-1H-pyrrolo[2,3-c]pyridine-5-carbonyl]-amino}-acetic acid Prepared in analogy to that of Example 1(e) from 2-bromo-3-tert-butyl-1-(4-fluoro-phenyl)-4-hydroxy-1H-pyrrolo[2,3-c]pyridine-5-carboxylic acid ethyl ester. The title compound, ESI MS (m/z): 464 (M+H$^+$).

Example 23

{[3-tert-Butyl-1-(4-fluoro-phenyl)-4-hydroxy-1H-pyrrolo[2,3-c]pyridine-5-carbonyl]-amino}-acetic acid a) {[3-tert-Butyl-1-(4-fluoro-phenyl)-4-hydroxy-1H-pyrrolo[2,3-c]pyridine-5-carbonyl]-amino}-acetic acid Prepared in analogy to that of Example 1(e) from 3-tert-butyl-1-(4-fluoro-phenyl)-4-hydroxy-1H-pyrrolo[2,3-c]pyridine-5-carboxylic acid ethyl ester. The title compound, ESI MS (m/z): 386 (M+H$^+$).

Example 24

[(1-Benzyl-4-hydroxy-2,3-dipropyl-1H-pyrrolo[2,3-c]pyridine-5-carbonyl)-amino]-acetic acid a) [(1-Benzyl-4-hydroxy-2,3-dipropyl-1H-pyrrolo[2,3-c]pyridine-5-carbonyl)-amino]-acetic acid ethyl ester A mixture of 1-benzyl-2,3-dibromo-4-(2,2-dimethyl-propionyloxy)-1H-pyrrolo[2,3-c]pyridine-5-carboxylic acid ethyl ester (990 mg, 1.84 mmol), allyltributyltin (1.71 mL, 5.52 mmol), Pd(PPh$_3$)$_2$Cl$_2$ (258 mg, 0.368 mmol) in DMF (7 mL) was heated to 130° C. for 1 h; then the mixture was diluted with EtOAc, washed with water and saturated NaCl aqueous solution respectively; the EtOAc phase was dried over anhydrous sodium sulfate, concentrated, the residue was purified by column to give a white solid, the desired title compound (716 mg, 85%). The title compound, $^1$H NMR (200 MHz, CDCl$_3$): δ (ppm)=8.49 (s, 1H), 7.3-7.2 (m, 3H), 7.0-6.9 (m, 2H), 6.1-5.7 (m, 2H), 5.38 (s, 2H), 5.1-4.8 (m, 4H), 4.39 (q, 2H, J=6.9 Hz), 3.6-3.4 (m, 4H), 1.45 (s, 9H), 1.40 (t, 3H, J=6.9 Hz).

b) 1-Benzyl-4-(2,2-dimethyl-propionyloxy)-2,3-dipropyl-1H-pyrrolo[2,3-c]pyridine-5-carboxylic acid ethyl ester A mixture of 2,3-diallyl-1-benzyl-4-(2,2-dimethyl-propionyloxy)-1H-pyrrolo[2,3-c]pyridine-5-carboxylic acid ethyl ester (710 mg, 1.54 mmol), 10% Pd—C (100 mg) in EtOAc (20 mL) was stirred at 1 atm hydrogen atmosphere for two days at room temperature. Then the catalysts were filtered off through celite, the filtrate was concentrated to give an oil, the crude product (628 mg), which is pure and used directly in the next step. The title compound: ESI MS (m/z): 465 (M+H$^+$).

c) [(1-Benzyl-4-hydroxy-2,3-dipropyl-1H-pyrrolo[2,3-c]pyridine-5-carbonyl)-amino]-acetic acid The title compound was prepared in analogy to that of Example 19(c). The title compound: ESI MS (m/z): 410 (M+H$^+$).

Example 25

[(1-Benzyl-3,7-dichloro-4-hydroxy-1H-pyrrolo[2,3-c]pyridine-5-carbonyl)-amino]-acetic acid a) 1-Benzyl-3,7-dichloro-4-hydroxy-1H-pyrrolo[2,3-c]pyridine-5-carboxylic acid ethyl ester A mixture of 1-benzyl-4-hydroxy-1H-pyrrolo[2,3-c]pyridine-5-carboxylic acid ethyl ester (60 mg, 0.202 mmol), NCS (57 mg, 0.424 mmol), and BzOOBz (2.4 mg, 0.01 mmol) in carbontetrachloride was refluxed for 1 hour. Then the reaction was cooled, solvent was removed, and the resulting residue was purified on column to give the title compound (48 mg). The title compound: ESI MS (m/z): 410 (M+H$^+$).

b) [(1-Benzyl-3,7-dichloro-4-hydroxy-1H-pyrrolo[2,3-c]pyridine-5-carbonyl)-amino]-acetic acid Prepared in analogy to that of Example 1(e) from 1-benzyl-3,7-dichloro-4-hydroxy-1H-pyrrolo[2,3-c]pyridine-5-carboxylic acid ethyl ester. The title compound, ESI MS (m/z): 394 (M+H$^+$).

Example 26

[(4-Hydroxy-9-phenyl-9H-beta-carboline-3-carbonyl)-amino]-acetic acid a) 2-Methyl-1H-indole-3-carboxylic acid ethyl ester A mixture of 2-iodo-phenylamine (44.30 g, 202 mmol), sodium salt of ethyl acetoacetate (42.1 g, 263 mmol), and Cu(I)I (50.1 g, 263 mmol) in DMF (200 mL) was stirred at 120° C. overnight. Then the reaction mixture was cooled to room temperature, then diluted with methyl tert-butyl ether (MTBE) and water, and concentrated ammonia was added to dissolve the solid, the two layers were separated, the water layer was back extracted with MTBE; all MTBEs were combined and washed with sat. NaCl aqueous solution, dried over anhydrous sodium sulfate, filtered, and concentrated sequentially. The residue was crystallized in hexanes/EtOAc, giving the desired product (10.84 g), the mother liquor was concentrated and purified on column to give an additional batch of product (4.76 g). The title compound, $^1$H NMR (200 MHz, CDCl$_3$): δ (ppm)=8.32 (1H), 8.09 (m, 1H), 7.31-7.13 (m, 3H), 4.39 (q, 2H, J=6.8 Hz), 2.74 (s, 3H), 1.45 (t, 3H, J=6.8 Hz).

b) 2-Methyl-1-phenyl-1H-indole-3-carboxylic acid ethyl ester

Prepared in analogy to that of 2-methyl-1-phenyl-1H-pyrrole-3-carboxylic acid ethyl ester from 2-Methyl-1H-indole-3-carboxylic acid ethyl ester. The title compound, $^1$H NMR (200 MHz, CDCl$_3$): δ (ppm)=8.15 (d, 1H, J=7.4 Hz), 7.6-6.9 (m, 8H), 4.43 (q, 2H, J=7.4 Hz), 2.59 (s, 3H), 1.47 (t, 3H, J=7.4 Hz).

c) 2-Bromomethyl-1-phenyl-1H-indole-3-carboxylic acid ethyl ester

Prepared in analogy to that of 4-bromo-2-bromomethyl-5-(4-fluoro-phenyl)-1-phenyl-1H-pyrrole-3-carboxylic acid ethyl ester from 2-Methyl-1-phenyl-1H-indole-3-carboxylic acid ethyl ester. The title compound, $^1$H NMR (200 MHz, CDCl$_3$): δ (ppm)=8.21 (d, 1H), 7.6-6.9 (m, 8H), 4.89 (s, 2H), 4.47 (q, 2H, J=7.4 Hz), 1.50 (q, 3H, J=7.4 Hz).

d) 2-[(tert-Butoxycarbonyl-ethoxycarbonylmethyl-amino)-methyl]-1-phenyl-1H-indole-3-carboxylic acid ethyl ester Prepared in analogy to that of Example 1(c) from 2-bromomethyl-1-phenyl-1H-indole-3-carboxylic acid ethyl ester and tert-butoxycarbonylamino-acetic acid ethyl ester. The title compound, ESI MS (m/z): 503 (M+Na$^+$).

e) 4-Hydroxy-9-phenyl-9H-b-carboline-3-carboxylic acid ethyl ester

Prepared in analogy to that of Example 1(d) from 2-[(tert-butoxycarbonyl-ethoxycarbonylmethyl-amino)-methyl]-1-phenyl-1H-indole-3-carboxylic acid ethyl ester. The title compound, ESI MS (m/z): 333 (M+Na$^+$).

f) [(4-Hydroxy-9-phenyl-9H-beta-carboline-3-carbonyl)-amino]-acetic acid

Prepared in analogy to that of Example 1(e) from 4-hydroxy-9-phenyl-9H-b-carboline-3-carboxylic acid ethyl ester. The title compound, ESI MS (m/z): 362 (M+H$^+$).

Example 27

[(4-Hydroxy-1-methyl-9-phenyl-9H-beta-carboline-3-carbonyl)-amino]-acetic acid a) 1-Bromo-4-hydroxy-9-phenyl-9H-beta-carboline-3-carboxylic acid ethyl ester A mixture of 4-hydroxy-9-phenyl-9H-b-carboline-3-carboxylic acid ethyl ester (399 mg, 1.20 mmol), NBS (227 mg, 1.26 mmol) and BzOOBz (15 mg, 0.06 mmol) in carbontetrachloride (10 mL) was refluxed for 90 min. Then the reaction was cooled, the mixture was then filtered through a Celite plug, followed by the concentration of filtrate to give the desired product (397 mg). The title compound: ESI MS (m/z): 411 (M+H$^+$).

b) 4-Hydroxy-1-methyl-9-phenyl-9H-beta-carboline-3-carboxylic acid ethyl ester

A mixture of 1-bromo-4-hydroxy-9-phenyl-9H-b-carboline-3-carboxylic acid ethyl ester (78 mg, 0.19 mmol), tetramethyltin (37 mg, 0.21 mmol), and Pd(PPh$_3$)$_2$Cl$_2$ (6.7 mg, 0.0095 mmol) in DMF (1 mL) was stirred at 120° C. for 50 min. The mixture was then diluted with EtOAc, washed with water and saturated NaCl aqueous solution, respectively; the EtOAc phase was dried over anhydrous sodium sulfate, concentrated, and the residue was purified by column to give a white solid, the desired title compound. The title compound, ESI MS (m/z): 347 (M+H$^+$).

c) [(4-Hydroxy-1-methyl-9-phenyl-9H-beta-carboline-3-carbonyl)-amino]-acetic acid Prepared in analogy to that of Example 1(e) from 4-hydroxy-1-methyl-9-phenyl-9H-b-carboline-3-carboxylic acid ethyl ester. The title compound, ESI MS (m/z): 376 (M+H$^+$).

Example 28

[(4-Hydroxy-1,9-diphenyl-9H-beta-carboline-3-carbonyl)-amino]-acetic acid a) 4-Hydroxy-1,9-diphenyl-9H-beta-carboline-3-carboxylic acid ethyl ester A mixture of 1-bromo-4-hydroxy-9-phenyl-9H-beta-carboline-3-carboxylic acid ethyl ester (91 mg, 0.221 mmol), phenyltributyltin (98 mg, 0.265 mmol), and Pd(PPh$_3$)$_2$Cl$_2$ (8 mg, 0.011 mmol) in DMF (1 mL) was stirred at 130° C. for 40 min. The mixture was then diluted with EtOAc, washed with water and saturated NaCl aqueous solution, respectively; the EtOAc phase was dried over anhydrous sodium sulfate, concentrated, and the residue was purified by column to give a white solid, the desired title compound. The title compound, ESI MS (m/z): 409 (M+H$^+$).

b) [(4-Hydroxy-1,9-diphenyl-9H-beta-carboline-3-carbonyl)-amino]-acetic acid

Prepared in analogy to that of Example 1(e) from 4-hydroxy-1,9-diphenyl-9H-beta-carboline-3-carboxylic acid ethyl ester. The title compound, ESI MS (m/z): 438 (M+H$^+$).

Example 29

[(1-Benzyl-3-chloro-4-hydroxy-7-methyl-1H-pyrrolo[2,3-c]pyridine-5-carbonyl)-amino]-acetic acid a) 1-Benzyl-3,7-dichloro-4-hydroxy-1H-pyrrolo[2,3-c]pyridine-5-carboxylic acid ethyl ester A mixture of 1-benzyl-4-hydroxy-1H-pyrrolo[2,3-c]pyridine-5-carboxylic acid ethyl ester (1.814 g, 6.12 mmol), NCS (1.72 g, 12.85 mmol) and BzOOBz (75 mg, 0.31 mmol) in carbontetrachloride (30 mL) was refluxed for 60 min. Then the reaction was cooled and concentrated, the resulting mixture was purified by column to give the title compound (1.469 mg) ESI MS (m/z) 365 (M+H)$^+$; and a by-product, 1-benzyl-2,3,7-trichloro-4-hydroxy-1H-pyrrolo[2,3-c]pyridine-5-carboxylic acid ethyl ester as by product (90 mg) ESI MS (m/z): 399 (M+H)$^+$.

b) 1-Benzyl-3-chloro-4-hydroxy-7-methyl-1H-pyrrolo[2,3-c]pyridine-5-carboxylic acid ethyl ester Prepared in analogy to that of Example 27(b) from 1-benzyl-3,7-dichloro-4-hydroxy-1H-pyrrolo[2,3-c]pyridine-5-carboxylic acid ethyl ester. The title compound, ESI MS (m/z): 345 (M+H$^+$).

e) [(1-Benzyl-3-chloro-4-hydroxy-7-methyl-1H-pyrrolo[2,3-c]pyridine-5-carbonyl)-amino]-acetic acid Prepared in analogy to that of Example 1(e) from 1-benzyl-3-chloro-4-hydroxy-7-methyl-1H-pyrrolo[2,3-c]pyridine-5-carboxylic acid ethyl ester. The title compound, ESI MS (m/z): 374 (M+H$^+$).

Example 30

[(1-Benzyl-3-chloro-4-hydroxy-7-phenyl-1H-pyrrolo[2,3-c]pyridine-5-carbonyl)-amino]-acetic acid a) 1-Benzyl-3-chloro-4-hydroxy-7-phenyl-1H-pyrrolo[2,3-c]pyridine-5-carboxylic acid ethyl ester Prepared in analogy to that of Example 28(a) from 1-benzyl-3,7-dichloro-4-hydroxy-1H-pyrrolo[2,3-c]pyridine-5-carboxylic acid ethyl ester. The title compound, ESI MS (m/z): 407 (M+H$^+$).

b) [(1-Benzyl-3-chloro-4-hydroxy-7-phenyl-1H-pyrrolo[2,3-c]pyridine-5-carbonyl)-amino]-acetic acid Prepared in analogy to that of Example 1(e) from 1-benzyl-3-chloro-4-hydroxy-7-phenyl-1H-pyrrolo[2,3-c]pyridine-5-carboxylic acid ethyl ester. The title compound, ESI MS (m/z): 436 (M+H$^+$).

Example 31

[(1-Benzyl-3-chloro-7-ethyl-4-hydroxy-1H-pyrrolo[2,3-c]pyridine-5-carbonyl)-amino]-acetic acid a) 1-Benzyl-3-chloro-7-ethyl-4-hydroxy-1H-pyrrolo[2,3-c]pyridine-5-carboxylic acid ethyl ester A mixture of 1-benzyl-3,7-dichloro-4-hydroxy-1H-pyrrolo[2,3-c]pyridine-5-carboxylic acid ethyl ester (126.1 mg, 0.19 mmol), tetraethyltin (50 mg, 0.21 mmol), and Pd(PPh$_3$)$_2$Cl$_2$ (6.7 mg, 0.0095 mmol) in DMF (1 mL) was stirred at 120° C. for 2.5 h. The mixture was then diluted with EtOAc, washed with water and saturated NaCl aqueous solution, respectively; the EtOAc phase was dried over anhydrous sodium sulfate, concentrated, and the residue was purified by column to give a white solid, the desired title compound. The title compound, ESI MS (m/z): 359 (M+H$^+$).

b) [(1-Benzyl-3-chloro-7-ethyl-4-hydroxy-1H-pyrrolo[2,3-c]pyridine-5-carbonyl)-amino]-acetic acid Prepared in analogy to that of Example 1(e) from 1-benzyl-3-chloro-7-ethyl-4-hydroxy-1H-pyrrolo[2,3-c]pyridine-5-carboxylic acid ethyl ester. The title compound, ESI MS (m/z): 388 (M+H$^+$).

Example 32

{[2-(4-Fluoro-phenyl)-4-hydroxy-1,3-diphenyl-1H-pyrrolo[2,3-c]pyridine-5-carbonyl]-amino}-acetic acid a) 2-(4-Fluoro-phenyl)-4-hydroxy-1,3-diphenyl-1H-pyrrolo[2,3-c]pyridine-5-carboxylic acid ethyl ester A mixture of 3-bromo-2-(4-fluoro-phenyl)-4-hydroxy-1-phenyl-1H-pyrrolo[2,3-c]pyridine-5-carboxylic acid ethyl ester (180 mg, 0.395 mmol), phenyltributlytin (149 µL, 0.454 mmol), and Pd(PPh$_3$)$_2$Cl$_2$ (14 mg, 0.020 mmol) in DMF (2 mL) was stirred at 130° C. overnight. Then the mixture was diluted with EtOAc, washed with water and saturated NaCl aqueous solution respectively; the EtOAc phase was dried over anhydrous sodium sulfate, concentrated, the residue was purified by column and prep TLC to give a white solid, the desired title compound (59 mg). The title compound, ESI MS (m/z): 453 (M+H$^+$).

b) {[2-(4-Fluoro-phenyl)-4-hydroxy-1,3-diphenyl-1H-pyrrolo[2,3-c]pyridine-5-carbonyl]-amino}-acetic acid Prepared in analogy to that of Example 1(e) from 2-(4-fluoro-phenyl)-4-hydroxy-1,3-diphenyl-1H-pyrrolo[2,3-c]pyridine-5-carboxylic acid ethyl ester. The title compound, $^1$H NMR (200 MHz, DMSO-d6): δ (ppm)=13.3 (s, 1H), 12.7 (s, 1H), 9.09 (t, 1H), 8.02 (s, 1H), 7.4-6.9 (m, 14H), 3.99 (d, 2H, J=6.0 Hz).

Example 33

[(3-Chloro-4-hydroxy-1-phenyl-1H-pyrrolo[2,3-c]pyridine-5-carbonyl)-amino]-acetic acid a) 3-Chloro-4-hydroxy-1-phenyl-1H-pyrrolo[2,3-c]pyridine-5-carboxylic acid ethyl ester A mixture of 4-hydroxy-1-phenyl-1H-pyrrolo[2,3-c]pyridine-5-carboxylic acid ethyl ester (223 mg, 0.789 mmol), NCS (117 mg, 0.869 mmol) and BzOOBz (10 mg, 0.039 mmol) in carbontetrachloride (4 mL) was refluxed for 30 min. Then the reaction was cooled and concentrated, the resulting mixture was purified by column to give the desired product (100 mg). The title compound, $^1$H NMR (200 MHz, CDCl$_3$): δ (ppm)=11.8 (s, 1H), 8.44 (s, 1H), 7.6-7.4 (m, 5H), 7.35 (s, 1H), 4.53 (q, 2H, J=7.4 Hz), 1.49 (t, 3H, J=7.4 Hz).

b) [(3-Chloro-4-hydroxy-1-phenyl-1H-pyrrolo[2,3-c]pyridine-5-carbonyl)-amino]-acetic acid Prepared in analogy to that of Example 1(e) from 3-chloro-4-hydroxy-1-phenyl-1H-pyrrolo[2,3-c]pyridine-5-carboxylic acid ethyl ester. The title compound, $^1$H NMR (200 MHz, DMSO-d6): δ (ppm)=13.3 (s, 1H), 12.7 (s, 1H), 9.09 (t, 1H, J=6.2 Hz), 8.36 (s, 1H), 8.09 (s, 1H), 7.8-7.4 (m, 5H), 3.99 (d, 2H, J=6.2 Hz).

Example 34

[(3-Chloro-4-hydroxy-7-methyl-1-phenyl-1H-pyrrolo[2,3-c]pyridine-5-carbonyl)-amino]-acetic acid a) 3,7-Dichloro-4-hydroxy-1-phenyl-1H-pyrrolo[2,3-c]pyridine-5-carboxylic acid ethyl ester A mixture of 4-hydroxy-1-phenyl-1H-pyrrolo[2,3-c]pyridine-5-carboxylic acid ethyl ester (270 mg, 0.956 mmol), NCS (269 mg, 2.01 mmol) and BzOOBz (12 mg, 0.048 mmol) in carbontetrachloride (4 mL) was refluxed for 30 min. Then the reaction was cooled and concentrated, the resulting mixture was purified by column to give the desired product (173 mg). The title compound, $^1$H NMR (200 MHz, CDCl$_3$): δ (ppm)=11.8 (s, 1H), 7.6-7.3 (m, 6H), 4.52 (q, 2H, J=6.8 Hz), 1.47 (t, 3H, J=6.8 Hz).

b) 3-Chloro-4-hydroxy-7-methyl-1-phenyl-1H-pyrrolo[2,3-c]pyridine-5-carboxylic acid ethyl ester Prepared in analogy to that of Example 27(b) from 3,7-dichloro-4-hydroxy-1-phenyl-1H-pyrrolo[2,3-c]pyridine-5-carboxylic acid ethyl ester. The title compound, $^1$H NMR (200 MHz, DMSO-d6): δ (ppm)=11.67 (s, 1H), 7.6-7.3 (m, 5H), 7.17 (s, 1H), 4.52 (q, 2H, J=6.8 Hz), 2.11 (s, 3H), 1.48 (t, 3H, J=6.8 Hz).

c) [(3-Chloro-4-hydroxy-7-methyl-1-phenyl-1H-pyrrolo[2,3-c]pyridine-5-carbonyl)-amino]-acetic acid Prepared in analogy to that of Example 1(e) from 3-chloro-4-hydroxy-7-methyl-1-phenyl-1H-pyrrolo[2,3-c]pyridine-5-carboxylic acid ethyl ester. The title compound, $^1$H NMR (200 MHz, DMSO-d6): δ (ppm)=13.0 (s, 1H), 12.7 (s, 1H), 8.90 (t, 1H, J=6.4 Hz), 7.83 (1H), 7.56 (s, 5H), 4.99 (d, 2H, J=6.4 Hz), 2.01 (s, 3H).

Example 35

{[1-(Benzo[1,3]dioxol-5-ylmethyl)-3-bromo-2-(4-chloro-phenyl)-4-hydroxy-1H pyrrolo[2,3-c]pyridine-5-carbonyl]-amino}-acetic acid a) 2-[2-(4-Chloro-phenyl)-2-oxo-ethyl]-3-oxo-butyric acid ethyl ester A mixture of 2-chloro-1-(4-chloro-phenyl)-ethanone (10.0 g, 52.9 mmol), ethyl acetotcetate sodium salt (8.85 g, 58.1 mmol) and sodium iodide (794 mg, 5.29 mmol) in acetone (100 mL) was heated to reflux for 3 h. After cooled, reaction mixture was concentrated and partitioned between water and methylene chloride (CH$_2$Cl$_2$). The organic layer was washed with water and brine, dried over sodium sulfate (Na$_2$SO$_4$), filtered and concentrated to give 14.78 g of the product. $^1$H NMR (200 MHz, CDCl$_3$) δ 7.88 (d, J=9.0 Hz, 2H), 7.42 (d, J=8.7 Hz, 2H), 4.27-4.16 (m, 3H), 3.74-3.68 (dd, J=18.4, 8.2 Hz, 1H), 3.51-3.42 (dd, J=14.8, 5.4 Hz, 1H), 2.43 (s, 3H), 1.29 (t, J=7.2 Hz, 3H).

b) 1-Benzo[1,3]dioxol-5-ylmethyl-5-(4-chloro-phenyl)-2-methyl-1H-pyrrole-3-carboxylic acid ethyl ester A mixture of the above ester (2.0 g, 7.07 mmol), piperonylamine (1.18 g, 7.78 mmol) and toluenesulfonic acid monohydrate (67 mg, 0.35 mmol) in toluene (17 mL) was refluxed through a Dean-Stark receiver overnight (18 h). After cooled, reaction mixture was diluted with ethyl acetate and washed with saturated sodium bicarbonate (NaHCO$_3$) solution, 0.5 N hydrochloric acid (HCl) aqueous solution and brine. The organic layer was dried over magnesium sulfate (MgSO$_4$), filtered and concentrated. Residue was purified by silica gel chromatography (eluting with 10%-40% EtOAc in hexanes) to give 2.09 g of the product. MS-(+)-ion: M+1=398.0.

c) 1-Benzo[1,3]dioxol-5-ylmethyl-4-bromo-2-bromomethyl-5-(4-chloro-phenyl)-1H-pyrrole-3-carboxylic acid ethyl ester To a mixture of the above ester (1.7 g, 4.28 mmol) in carbon tetrachloride (CCl$_4$) was added N-bromosuccinimide (NBS) (1.67 g, 9.42 mmol) and benzoyl peroxide (52 mg, 0.21 mmol). Resulting mixture was refluxed for 2.5 h. After cooled, reaction mixture was filtered. Filtrate was concentrated to give 2.60 g of the product. $^1$H NMR (200 MHz, CDCl$_3$) δ 7.34 (d, J=8.6 Hz, 2H), 7.18 (d=8.6 Hz, 2H), 6.70 (d, J=8.2 Hz, 1H), 6.30 (m, 2H), 5.93 (s, 2H), 5.06 (s, 2H), 4.80 (s, 2H), 4.37 (q, J=7.0 Hz, 2H), 1.42 (t, J=7.0 Hz, 3H).

d) 1-Benzo[1,3]dioxol-5-ylmethyl-4-bromo-2-[(tert-butoxycarbonyl-ethoxycarbonylmethyl-amino)-methyl]-5-(4-chloro-phenyl)-1H-pyrrole-3-carboxylic acid ethyl ester To a cold mixture of the above ester (2.60 g, 4.68 mmol) and tert-butoxycarbonylamino-acetic acid ethyl ester (0.95 g, 4.68 mmol) in N,N-dimethylformaide (DMF)(14 mL) at 0° C. was added sodium hydride (NaH)(60%, 281 mg, 7.02 mmol) Resulting mixture was stirred at 0° C. for 1 h. The mixture was quenched with saturated ammonium chloride (NH$_4$Cl) aqueous solution and extracted with ethyl acetate (EtOAc). Organic layer was washed with water and brine, dried over Na$_2$SO$_4$, filtered, and concentrated to give 3.04 g of the product which was used directly for the next reaction. MS-(+)-ion: M+Na=700.90, 698.94.

e) 1-Benzo[1,3]dioxol-5-ylmethyl-3-bromo-2-(4-chloro-phenyl)-4-hydroxy-1H-pyrrolo[2,3-c]pyridine-5-carboxylic acid ethyl ester To a mixture of the above ester (3.04 g, 4.49 mmol) in tetrahydrofuran (THF) at −78° C. was added dropwise a solution of potassium tert-butoxide (KO$^t$Bu) in THF (1M, 6.55 mL, 6.55 mmol) Resulting mixture was stirred at −78° C. for 10 min. and then at room temperature for 1 h. It was quenched with acetic acid (1 mL) and concentrated. Residue was treated with (½) (trifluoroacetic acid/CH$_2$Cl$_2$)(30 mL) and stirred at room temperature for 1 h. Reaction mixture was concentrated and dried in vacuo. Residue was dissolved in CH$_2$Cl$_2$ (150 mL) and neutralized with triethyl amine (NEt$_3$)(3.9 mL). It was bubbled with air for 2 days and concentrated. Residue was partitioned between EtOAc and water. Organic layer was washed with brine, dried over MgSO4, filtered and concentrated. Crude product was purified by silica gel chromatography (eluting with 30%-90% EtOAc/hexanes) to give 810 mg of the product. MS-(+)-ion: M+1=530.92, 528.88.

f) {[1-Benzo[1,3]dioxol-5-ylmethyl-3-bromo-2-(4-chloro-phenyl)-4-hydroxy-1H pyrrolo[2,3-c]pyridine-5-carbonyl]-amino}-acetic acid A mixture of the above ester (72 mg, 0.14 mmol) and glycine (152 mg, 2.04 mmol) in a solution of sodium methoxide (NaOMe)(0.5 M in methanol) was heated in a microwave reactor at 120° C. for 30 min. It was concentrated and dissolved in water (80 mL) Extracted with (2/1) EtOAc/hexanes. Aqueous layer was acidified by 1N HCl to pH=3-4 and extracted with EtOAc. Organic layer was washed with brine, dried over MgSO$_4$, filtered and concentrated to give 71 mg of the product. MS-(+)-ion: M+1=560.97, 559.94, 557.91.

Example 36

{[3-Bromo-2-(4-chloro-phenyl)-4-hydroxy-1-phenyl-1H-pyrrolo[2,3-c]pyridine-5-carbonyl]-amino}-acetic acid a) 5-(4-Chloro-phenyl)-2-methyl-1-phenyl-1H-pyrrole-3-carboxylic acid ethyl ester The title compound was prepared from 2-[2-(4-chloro-phenyl)-2-oxo-ethyl]-3-oxo-butyric acid ethyl ester (from Example 35(a)) and aniline under conditions analogous to Example 35(b). MS-(+)-ion: M+1=340.0.

b) 4-Bromo-2-bromomethyl-5-(4-chloro-phenyl)-1-phenyl-1H-pyrrole-3-carboxylic acid ethyl ester The title compound was prepared under conditions analogous to Example 35(c). $^1$H NMR (200 MHz, CDCl$_3$) δ 7.39-7.05 (m, 9H), 4.67 (s, 2H), 4.42 (q, J=7 Hz, 2H), 1.45 (t, J=7 Hz, 3H).

c) 4-Bromo-2-[(tert-butoxycarbonyl-ethoxycarbonyl-methyl-amino)-methyl]-5-(4-chloro-phenyl)-1-phenyl-1H-pyrrole-3-carboxylic acid ethyl ester The title compound was prepared under conditions analogous to Example 35(d). MS-(+)-ion: M+Na=642.88, 640.90.

d) 3-Bromo-2-(4-chloro-phenyl)-4-hydroxy-1-phenyl-1H-pyrrolo[2,3-c]pyridine-5-carboxylic acid ethyl ester The title compound was prepared under conditions analogous to Example 35(e). MS-(+)-ion: M+1=472.92, 470.93.

e) {[3-Bromo-2-(4-chloro-phenyl)-4-hydroxy-1-phenyl-1H-pyrrolo[2,3-c]pyridine-5-carbonyl]-amino}-acetic acid The title compound was prepared under conditions analogous to Example 35(f). MS-(+)-ion: M+1=501.95, 499.92.

Example 37

[(1-(Benzo[1,3]dioxol-5-ylmethyl)-4-hydroxy-2-phenyl-1H-pyrrolo[2,3-c]pyridine-5-carbonyl)-amino]-acetic acid a) 1-Benzo[1,3]dioxol-5-ylmethyl-4-hydroxy-2-phenyl-1H-pyrrolo[2,3-c]pyridine-5-carboxylic acid ethyl ester To a mixture of 1-benzo[1,3]dioxol-5-ylmethyl-3-bromo-2-(4-chloro-phenyl)-4-hydroxy-1H-pyrrolo[2,3-c]pyridine-5-carboxylic acid ethyl ester (200 mg, 0.38 mmol)(from Example 35(e)) in EtOAc (4 mL) was added palladium/charcoal (Pd/C)(10% wet, containing 50% water) (95 mg) and ammonium formate (HCO$_2$NH$_4$)(495 mg, 7.86 mmol). The mixture was refluxed for 2 h. After cooled, it was diluted with EtOAc and then filtered through a pad of celite. Filtrate was concentrated and the residue was purified by silica gel chromatography (eluting with 30%-60% EtOAc/hexanes) to give the title compound 125 mg. MS-(+)-ion: M+1=417.13.

b) [(1-Benzo[1,3]dioxol-5-ylmethyl-4-hydroxy-2-phenyl-1H-pyrrolo[2,3-c]pyridine-5-carbonyl)-amino]-acetic acid The title compound was prepared under conditions analogous to Example 35(f). MS-(+)-ion: M+1=446.1.

Example 38

{[1-(Benzo[1,3]dioxol-5-ylmethyl)-2-(4-chloro-phenyl)-4-hydroxy-1H-pyrrolo[2,3-c]pyridine-5-carbonyl]-amino}-acetic acid a) 1-Benzo[1,3]dioxol-5-ylmethyl-3-bromo-2-(4-chloro-phenyl)-4-(2,2-dimethyl-propionyloxy)-1H-pyrrolo[2,3-c]pyridine-5-carboxylic acid ethyl ester To a suspension mixture of 1-benzo[1,3]dioxol-5-ylmethyl-3-bromo-2-(4-chloro-phenyl)-4-hydroxy-1H-pyrrolo[2,3-c]pyridine-5-carboxylic acid ethyl ester (320 mg, 0.60 mmol)(from Example 35(e)) in CH$_2$Cl$_2$ (3 mL) at 0° C. was added 2,2-dimethyl-propionyl chloride (87.4 mg, 0.73 mmol) and triethylamine (122 mg, 1.20 mmol). Resulting mixture was stirred at room temperature for 1.5 h. It was diluted with $CH_2Cl_2$ and washed with 0.1 N HCl aqueous solution, water and brine. The organic layer was dried over $MgSO_4$, filtered, and concentrated. The crude residue was purified by silica gel chromatography (eluting with 5%-20% EtOAc in $CH_2Cl_2$) to give the title compound 361 mg. MS-(+)-ion: M+1=614.98, 613.02.

b) 1-Benzo[1,3]dioxol-5-ylmethyl-2-(4-chloro-phenyl)-4-(2,2-dimethyl-propionyloxy)-1H-pyrrolo[2,3-c]pyridine-5-carboxylic acid ethyl ester To a mixture of the above ester (160 mg, 0.26 mmol) in DMF (2.6 mL) was added tetrabutyltin (93%, 388 mg, 1.04 mmol) and $Pd(PPh_3)_2Cl_2$ (27 mg, 0.04 mmol). Resulting mixture was stirred at 130° C. for 2 h. Reaction mixture was diluted with EtOAc and filtered. Filtrate was washed with water and brine, dried over $MgSO_4$, filtered, and concentrated to give the title product 125 mg. MS-(+)-ion: M+1=535.13.

c) 1-Benzo[1,3]dioxol-5-ylmethyl-2-(4-chloro-phenyl)-4-hydroxy-1H-pyrrolo[2,3-c]pyridine-5-carboxylic acid ethyl ester To a mixture of the above ester (120 mg, 0.22 mmol) in MeOH (3 mL) was added a solution of sodium methoxide (NaOMe)(0.5 N in MeOH)(2.64 mL, 1.32 mmol). Resulting mixture was refluxed for 2 h and concentrated. Residue was re-suspended in water and acidified to pH=4-5 using 1N HCl aqueous solution, and then extracted with $CH_2Cl_2$. The organic layer was washed with brine, dried over Mg SO4, filtered, and concentrated to give the title compound 91 mg. MS-(+)-ion: M+1=437.04.

d) {[1-Benzo[1,3]dioxol-5-ylmethyl-2-(4-chloro-phenyl)-4-hydroxy-1H-pyrrolo[2,3-c]pyridine-5-carbonyl]-amino}-acetic acid The title compound was prepared under conditions analogous to Example 35(f). MS-(+)-ion: M+1=479.99.

Example 39

{[1-(Benzo[1,3]dioxol-5-ylmethyl)-2-(4-chloro-phenyl)-4-hydroxy-3-methyl-1H-pyrrolo[2,3-c]pyridine-5-carbonyl]-amino}-acetic acid a) 1-Benzo[1,3]dioxol-5-ylmethyl-2-(4-chloro-phenyl)-4-(2,2-dimethyl-propionyloxy)-3-methyl-1H-pyrrolo[2,3-c]pyridine-5-carboxylic acid ethyl ester To a mixture of 1-benzo[1,3]dioxol-5-ylmethyl-3-bromo-2-(4-chloro-phenyl)-4-(2,2-dimethyl-propionyloxy)-1H-pyrrolo[2,3-c]pyridine-5-carboxylic acid ethyl ester (from Example 38(a))(180 mg, 0.29 mmol) in DMF (2.5 mL) was added tetramethyltin (207 mg, 1.16 mmol) and $Pd(PPh_3)_2Cl_2$ (30 mg, 0.044 mmol). Resulting mixture was stirred at 130° C. for 2 h. Reaction mixture was diluted with EtOAc and filtered. Filtrate was washed with water and brine, dried over $MgSO_4$, filtered, and concentrated to give the title product 161 mg. MS-(+)-ion: M+1=549.14.

b) 1-Benzo[1,3]dioxol-5-ylmethyl-2-(4-chloro-phenyl)-4-hydroxy-3-methyl-1H-pyrrolo[2,3-c]pyridine-5-carboxylic acid ethyl ester The title compound was prepared under conditions analogous to Example 38(c). MS-(+)-ion: M+1=451.10.

c) {[1-Benzo[1,3]dioxol-5-ylmethyl-2-(4-chloro-phenyl)-4-hydroxy-3-methyl-1H-pyrrolo[2,3-c]pyridine-5-carbonyl]-amino}-acetic acid The title compound was prepared under conditions analogous to Example 35(f). MS-(+)-ion: M+1=494.0.

Example 40

[(4-Hydroxy-1,2-diphenyl-1H-pyrrolo[2,3-c]pyridine-5-carbonyl)-amino]-acetic acid a) 4-Hydroxy-1,2-diphenyl-1H-pyrrolo[2,3-c]pyridine-5-carboxylic acid ethyl ester To a mixture of 3-bromo-2-(4-chloro-phenyl)-4-hydroxy-1-phenyl-1H-pyrrolo[2,3-c]pyridine-5-carboxylic acid ethyl ester (200 mg, 0.42 mmol)(from Example 36(d)) in ethanol (12 mL) and DMF (3 mL) was added Pd/C (10% wet, containing 50% water)(120 mg) was stirred under hydrogen atmosphere (balloon pressure) for 30 h. Reaction mixture was filtered through a pad of celite and rinsed with EtOAc. Filtrate was concentrated and purified by silica gel chromatography (eluting with 25%-50% EtOAc/hexanes) to give the title compound 42 mg. MS-(+)-ion: M+1=359.04.

b) [(4-Hydroxy-1,2-diphenyl-1H-pyrrolo[2,3-c]pyridine-5-carbonyl)-amino]-acetic acid The title compound was prepared under conditions analogous to Example 35(f). MS-(+)-ion: M+1=388.11.

Example 41

{[2-(4-Chloro-phenyl)-4-hydroxy-3-methyl-1-phenyl-1H-pyrrolo[2,3-c]pyridine-5-carbonyl]-amino}-acetic acid a) 3-Bromo-2-(4-chloro-phenyl)-4-(2,2-dimethyl-propionyloxy)-1-phenyl-1H-pyrrolo[2,3-c]pyridine-5-carboxylic acid ethyl ester The title compound was prepared from 3-bromo-2-(4-chloro-phenyl)-4-hydroxy-1-phenyl-1H-pyrrolo[2,3-c]pyridine-5-carboxylic acid ethyl ester (from Example 36(d)) under conditions analogous to Example 38(a). MS-(+)-ion: M+1=557.01, 555.02.

b) 2-(4-Chloro-phenyl)-4-(2,2-dimethyl-propionyloxy)-3-methyl-1-phenyl-1H-pyrrolo[2,3-c]pyridine-5-carboxylic acid ethyl ester The title compound was prepared under conditions analogous to Example 39(a). MS-(+)-ion: M+1=491.07.

c) 2-(4-Chloro-phenyl)-4-hydroxy-3-methyl-1-phenyl-1H-pyrrolo[2,3-c]pyridine-5-carboxylic acid ethyl ester The title compound was prepared under conditions analogous to Example 38(c). MS-(+)-ion: M+1=393.3.

d) {[2-(4-Chloro-phenyl)-4-hydroxy-3-methyl-1-phenyl-1H-pyrrolo[2,3-c]pyridine-5-carbonyl]-amino}-acetic acid The title compound was prepared under conditions analogous to Example 35(f). MS-(+)-ion: M+1=463.03.

Example 42

[(7-Hydroxy-2-phenyl-thiazolo[4,5-c]pyridine-6-carbonyl)-amino]-acetic acid a) 4-Bromomethyl-2-phenyl-thiazole-5-carboxylic acid ethyl ester A mixture of 4-methyl-2-phenyl-thiazole-5-carboxylic acid ethyl ester (5.04 g, 0.02 mol), N-bromosuccinimide (3.8 g, 0.02 mol) and benzoyl peroxide (247 mg, 1 mmol) in carbon tetrachloride (60 mL) was refluxed for 17 h before it was cooled to room temperature and filtered. The filtrate was washed with water, saturated aqueous sodium bicarbonate solution, brine, dried over anhydrous sodium sulfate and concentrated in vacuo to give the title compound as a yellow solid (6.55 g): $^1$H NMR (CDCl$_3$, 200 MHz): δ=7.94 (m, 2H), 7.44 (m, 3H), 7.03 (m, 1H), 4.98 (s, 3H), 4.41 (q, J=7.0 Hz, 2H), 1.41 (t, J=7.0 Hz, 3H); MS: (+) m/z 326.0, 328.0 (M+1, $^{79}$Br/$^{81}$Br).

b) 4-{[(2,4-Dimethoxy-benzyl)-ethoxycarbonylmethyl-amino]-methyl}-2-phenyl-thiazole-5-carboxylic acid ethyl ester A mixture of 4-bromomethyl-2-phenyl-thiazole-5-carboxylic acid ethyl ester (5.29 g, 16.3 mmol), (2,4-dimethoxybenzylamino)-acetic acid ethyl ester (4.12 g, 16.3 mmol) and potassium carbonate (3.37 g, 24.4 mmol) in anhydrous dimethylformamide (50 mL) was stirred at room temperature for 16 h before it was quenched with water, extracted with ethyl acetate. The organic layer was washed with water, brine, dried over anhydrous sodium sulfate and concentrated in vacuo. The residue was purified by flash column chromatography on silica gel with a gradient of ethyl acetate and hexanes to give the title compound as a yellow oil (5.72 g): MS: (+) m/z 499.0 (M+H$^+$), 521.2 (M+Na$^+$).

c) 7-Hydroxy-2-phenyl-thiazolo[4,5-c]pyridine-6-carboxylic acid ethyl ester

A yellow solution of 4-{[(2,4-dimethoxy-benzyl)-ethoxycarbonylmethyl-amino]-methyl}-2-phenyl-thiazole-5-carboxylic acid ethyl ester (5.60 g, 0.01 mol) in THF (45 mL) was added 1 M potassium tert-butoxide (KO$^t$Bu) in THF (24.7 mL, 0.02 mmol) at −78° C., a dark red suspension quickly appeared. The mixture was stirred at −78° C. for 20 min, warmed to room temperature and stirred at that temperature for 2 h before it was quenched with aqueous ammonium chloride, extracted with ethyl acetate. The organic layer was washed with water, brine, dried over anhydrous sodium sulfate and concentrated in vacuo to give 5-(2,4-dimethoxybenzyl)-7-oxo-2-phenyl-4,5,6,7-tetrahydro-thiazolo[4,5-c]pyridine-6-carboxylic acid ethyl ester as a yellow oil (4.63 g). It was dissolved in dichloromethane (40 mL) and thionyl chloride (1.12 mL, 0.02 mmol) was added drop wise. The mixture was stirred at room temperature for 3.5 h before it was quenched with saturated sodium bicarbonate, extracted with dichloromethane. The organic layer was washed with water, brine, dried over anhydrous sodium sulfate and concentrated in vacuo. The residue was purified by flash column chromatography on silica gel with a gradient of ethyl acetate and dichloromethane to give the title compound as a yellow solid (2.74 g): $^1$H NMR (CDCl$_3$, 200 MHz): δ=11.52 (s, 1H), 9.00 (s, 1H), 8.13 (m, 2H), 7.55 (m, 3H), 4.58 (q, J=7.0 Hz, 2H), 1.53 (t, J=7.0 Hz, 3H); MS: (+) m/z 301.0 (M+1).

d) [(7-Hydroxy-2-phenyl-thiazolo[4,5-c]pyridine-6-carbonyl)-amino]-acetic acid

A mixture of 7-hydroxy-2-phenyl-thiazolo[4,5-c]pyridine-6-carboxylic acid ethyl ester (63 mg, 0.21 mmol) and glycine (317 mg, 4.22 mmol) in 0.5 M sodium methoxide/methanol (8 mL) was refluxed for 3 days before it was cooled to room temperature and concentrated in vacuo. Water (20 mL) was added and the suspension was adjusted to pH=10 with 1N HCl (3 mL). The mixture was extracted twice with dichloromethane. And the remaining aqueous layer was acidified to pH=3 with 1N HCl (1.5 mL). The white precipitate was filtered, washed with water and dried in vacuo to give the title compound as a white solid (36 mg): $^1$H NMR (DMSO-d$_6$, 200 MHz): δ=9.49 (br s, 1H), 8.91 (s, 1H), 8.18 (m, 2H), 7.63 (m, 2H), 4.03 (d, J=5.8 Hz, 2H); MS: (+) m/z 329.9 (M+1)

Example 43

[(7-Hydroxy-2,4-diphenyl-thiazolo[4,5-c]pyridine-6-carbonyl)-amino]-acetic acid a) 4-Bromo-7-hydroxy-2-phenyl-thiazolo[4,5-c]pyridine-6-carboxylic acid ethyl ester A mixture of 7-hydroxy-2-phenyl-thiazolo[4,5-c]pyridine-6-carboxylic acid ethyl ester (81 mg, 0.27 mmol), N-bromosuccinimide (50 mg, 0.30 mmol) and benzoyl peroxide (3.2 mg, 0.01 mmol) in carbon tetrachloride (2 mL) was refluxed for 4 h before it was cooled to room temperature and partitioned between dichloromethane and water. The organic layer was washed with saturated aqueous sodium bicarbonate solution, brine, dried over anhydrous sodium sulfate and concentrated in vacuo. The residue was purified by flash column chromatography on silica gel with a gradient of ethyl acetate and dichloromethane to give the title compound as a white solid (73 mg): MS: (+) m/z 376.9, 378.9 (M+1, $^{79}$Br/$^{81}$Br), MS: (−) m/z 377.1, 379.1 (M−1, $^{79}$Br/$^{81}$Br)

b) 7-Hydroxy-2,4-diphenyl-thiazolo[4,5-c]pyridine-6-carboxylic acid ethyl ester

A mixture of 4-bromo-7-hydroxy-2-phenyl-thiazolo[4,5-c]pyridine-6-carboxylic acid ethyl ester (81 mg, 0.21 mmol), phenylboronic acid (34 mg, 0.28 mmol), tetrakis(triphenylphosphine)palladium(0)(25 mg, 0.02 mmol) and potassium carbonate (89 mg, 0.64 mmol) in dioxane (3 mL) and water (12 μL) was refluxed for 22 h before it was cooled to room temperature and partitioned between ethyl acetate and water. The organic layer was washed with brine, dried over anhydrous sodium sulfate and concentrated in vacuo. The residue was purified by flash column chromatography on silica gel with a gradient of ethyl acetate and dichloromethane to give the title compound as a white solid (29 mg): $^1$H NMR (CDCl$_3$, 200 MHz): δ=11.46 (s, 1H), 8.49 (m, 2H), 8.14 (m, 2H), 7.53 (m, 6H), 4.56 (q, J=7.0 Hz, 2H), 1.54 (t, J=7.0 Hz, 3H).

c) [(7-Hydroxy-2,4-diphenyl-thiazolo[4,5-c]pyridine-6-carbonyl)-amino]-acetic acid A mixture of 7-hydroxy-2,4-diphenyl-thiazolo[4,5-c]pyridine-6-carboxylic acid ethyl ester (45 mg, 0.12 mmol) and glycine (179 mg, 2.38 mmol) in 0.5 M sodium methoxide/methanol (4.5 mL) was refluxed for four days before it was cooled to room temperature and concentrated in vacuo. The residue was dissolved in water (20 mL) and extracted twice with dichloromethane. The remaining aqueous layer was acidified to pH=3 with 1N HCl (3 mL). The suspension was extracted with ethyl acetate (2×25 mL). The organic layer was dried over sodium sulfate and concentrated in vacuo to give the title compound as a yellow solid (47 mg): $^1$H NMR (DMSO-d$_6$, 200 MHz): δ=9.46 (t, 1H), 8.68 (m, 2H), 8.22 (m, 2H), 7.65 (m, 6H), 4.09 (m, 2H); MS: (+) m/z 406.0 (M+1)

Example 44

[(7-Hydroxy-4-methyl-2-phenyl-thiazolo[4,5-c]pyridine-6-carbonyl)-amino]-acetic acid a) 7-Hydroxy-4-methyl-2-phenyl-thiazolo[4,5-c]pyridine-6-carboxylic acid ethyl ester A mixture of 4-bromo-7-hydroxy-2-phenyl-thiazolo[4,5-c]pyridine-6-carboxylic acid ethyl ester (301 mg, 0.80 mmol), tetramethyltin (442 μL, 3.18 mmol) and bis(triphenylphosphine)palladium(II) dichloride (56 mg, 0.08 mmol) in dimethylformamide (5 mL) was stirred at 130° C. for 30 min before it was cooled to room temperature, quenched with water, filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and hexanes to give the title compound as a white solid (218 mg): $^1$H NMR (CDCl$_3$, 200 MHz): δ=11.39 (s, 1H), 8.09 (m, 2H), 7.50 (m, 3H), 4.57 (q, J=7.0 Hz, 2H), 2.96 (s, 3H), 1.52 (t, J=7.0 Hz, 3H).

b) [(7-Hydroxy-4-methyl-2-phenyl-thiazolo[4,5-c]pyridine-6-carbonyl)-amino]-acetic acid A mixture of 7-hydroxy-4-methyl-2-phenyl-thiazolo[4,5-c]pyridine-6-carboxylic acid ethyl ester (159 mg, 0.51 mmol) and glycine (760 mg, 1.01 mmol) in 0.5 M sodium methoxide/methanol (19.2 mL) was refluxed for three days before it was cooled to room temperature and concentrated in vacuo. The residue was dissolved in water (50 mL) and extracted twice with dichloromethane. The remaining aqueous layer was acidified to pH=3 with 1N HCl (12 mL). The solid precipitate was filtered, washed with water and dried in vacuo to give the title compound as a white solid (127 mg): $^1$H NMR (DMSO-d$_6$, 200 MHz): δ=13.01 (br s, 1H), 9.24 (br s, 1H), 8.14 (m, 2H), 7.62 (m, 3H), 4.03 (d, J=6.2 Hz, 2H), 2.87 (s, 3H); MS: (+) m/z 344.0 (M+1)

Example 45

2-(S)-[(7-Hydroxy-4-methyl-2-phenyl-thiazolo[4,5-c]pyridine-6-carbonyl)-amino]-propionic acid a) 2-[(7-Hydroxy-4-methyl-2-phenyl-thiazolo[4,5-c]pyridine-6-carbonyl)-amino]-propionic acid A mixture of 7-hydroxy-4-methyl-2-phenyl-thiazolo[4,5-c]pyridine-6-carboxylic acid ethyl ester (50 mg, 0.16 mmol) and L-alanine (146 mg, 1.63 mmol) in 0.5 M sodium methoxide/methanol (2.6 mL) was heated at 120° C. in a microwave vessel for 3 h before it was cooled to room temperature and concentrated in vacuo. Water was added to the residue and extracted four times with dichloromethane until no UV spot in the dichloromethane layer. The remaining aqueous layer was acidified to pH=3 with 1N HCl (2 mL). The suspension was extracted with ethyl acetate. The organic layer was dried over sodium sulfate and concentrated in vacuo to give the title compound as a white solid (22 mg): $^1$H NMR (DMSO-d$_6$, 200 MHz): δ=12.98 (br s, 1H), 9.06 (d, J=7.4 Hz, 1H), 8.15 (m, 2H), 7.61 (m, 3H), 4.54 (m, 1H), 2.88 (s, 3H), 1.49 (d, J=7.4 Hz, 3H); MS: (+) m/z 358.04 (M+1).

Example 46

{[7-Hydroxy-2-(4-trifluoromethyl-phenyl)-thiazolo[4,5-c]pyridine-6-carbonyl]-amino}-acetic acid a) 4-Bromomethyl-2-(4-trifluoromethyl-phenyl)-thiazole-5-carboxylic acid ethyl ester A mixture of 4-methyl-2-(4-trifluoromethyl-phenyl)-thiazole-5-carboxylic acid ethyl ester (1.00 g, 3.18 mmol), N-bromosuccinimide (594 mg, 3.34 mol) and benzoyl peroxide (77 mg, 0.32 mmol) in carbon tetrachloride (15 mL) was refluxed for 16 h before it was cooled to room temperature and partitioned between dichloromethane and water. The organic layer was washed with saturated aqueous sodium bicarbonate solution, brine, dried over anhydrous sodium sulfate and concentrated in vacuo to give the title compound as a yellow oil (1.32 g, product is 80% pure by $^1$H NMR, impurities are starting material and dibromonated compound); MS: (+) m/z 393.9, 395.9 (M+1, $^{79}$Br/$^{81}$Br).

b) 4-[(tert-Butoxycarbonyl-ethoxycarbonylmethyl-amino)-methyl]-2-(4-trifluoromethyl-phenyl)-thiazole-5-carboxylic acid ethyl ester A mixture of 4-bromomethyl-2-(4-trifluoromethyl-phenyl)-thiazole-5-carboxylic acid ethyl ester (1.05 g, 2.67 mmol), tert-butoxycarbonylamino-acetic acid ethyl ester (540 mg, 2.66 mmol) and sodium hydride (60% in mineral oil, 128 mg, 3.2 mmol) in anhydrous dimethylformamide (10 mL) was stirred at 0° C. for two hours and room temperature for half an hour before it was quenched with brine. The mixture was filtered and the filtrate was extracted with ethyl acetate. The organic layer was washed with water, brine, dried over anhydrous sodium sulfate and concentrated in vacuo. The residue was purified by flash column chromatography on silica gel with a gradient of ethyl acetate and hexanes to give the title compound as a yellow oil (319 mg): MS: (+) m/z 538.9 (M+Na$^+$).

c) 7-Hydroxy-2-(4-trifluoromethyl-phenyl)-thiazolo[4,5-c]pyridine-6-carboxylic acid ethyl ester A mixture of 4-[(tert-butoxycarbonyl-ethoxycarbonylmethyl-amino)-methyl]-2-(4-trifluoromethyl-phenyl)-thiazole-5-carboxylic acid ethyl ester (302 mg, 0.58 mol) in THF (5 mL) was added drop wise a solution of 1 M KO$^t$Bu in THF (702 μL, 0.70 mmol) at −78° C. The mixture was stirred at −78° C. for 15 min, warmed to room temperature and stirred at that temperature for 1.5 h before it was quenched with brine, extracted with ethyl acetate. The organic layer was washed with brine, dried over anhydrous sodium sulfate and concentrated in vacuo to a yellow foam (469 mg). It was dissolved in dichloromethane (10 mL) and TFA (2.5 mL) was added. The mixture was stirred at room temperature for 1 h before it was concentrated in vacuo. It was redissolved in dichloromethane, triethylamine (923 μL) was added. The mixture was stirred under air overnight before it was partitioned between dichloromethane and water, the organic layer was washed with brine, dried over anhydrous sodium sulfate and concentrated in vacuo. The residue was purified by flash column chromatography on silica gel with a gradient of ethyl acetate and dichloromethane to give the title compound as a white solid (257 mg): MS: (+) m/z 330.0 (M+1).

d) {[7-Hydroxy-2-(4-trifluoromethyl-phenyl)-thiazolo[4,5-c]pyridine-6-carbonyl]-amino}-acetic acid A mixture of 7-hydroxy-2-(4-trifluoromethyl-phenyl)-thiazolo[4,5-c]pyridine-6-carboxylic acid ethyl ester (40 mg, 0.11 mmol) and glycine (162 mg, 2.16 mmol) in 0.5 M sodium methoxide/methanol (4.1 mL) was refluxed for four days before it was cooled to room temperature and concentrated in vacuo. Water (20 mL) and 1N HCl (1.5 mL) was added and the mixture was extracted twice with dichloromethane. The remaining aqueous layer was acidified to pH=3 with 1N HCl (1.5 mL). The suspension was extracted with ethyl acetate. The organic layer was dried over sodium sulfate and concentrated in vacuo to give the title compound as a yellow solid (34 mg): $^1$H NMR (DMSO-$d_6$, 200 MHz): δ=9.48 (br s, 1H), 8.94 (s, 1H), 8.35 (d, 2H), 7.96 (d, 2H), 4.03 (d, J=5.8 Hz, 2H); MS: (+) m/z 329.9 (M+1)

Example 47

{[2-(4-Chloro-phenyl)-7-hydroxy-thiazolo[4,5-c]pyridine-6-carbonyl]-amino}-acetic acid a) 4-Bromomethyl-2-(4-chloro-phenyl)-thiazole-5-carboxylic acid ethyl ester A mixture of 2-(4-chloro-phenyl)-4-methyl-thiazole-5-carboxylic acid ethyl ester (2.50 g, 8.88 mmol), N-bromosuccinimide (2.13 g, 12.0 mmol) and benzoyl peroxide (150 mg, 0.62 mmol) in carbon tetrachloride (50 mL) was refluxed for 24 h before it was cooled to room temperature and partitioned between dichloromethane and water. The organic layer was washed with saturated aqueous sodium bicarbonate solution, brine, dried over anhydrous sodium sulfate and concentrated in vacuo to give the title compound as a yellow solid (3.23 g, product is 69% pure by $^1$H NMR, impurities are starting material and dibromonated compound): $^1$H NMR (CDCl$_3$, 200 MHz): δ=7.90 (d, 2H), 7.44 (d, 2H), 4.96 (s, 3H), 4.38 (q, J=7.0 Hz, 2H), 1.44 (t, J=7.0 Hz, 3H).

b) 4-[(tert-Butoxycarbonyl-ethoxycarbonylmethyl-amino)-methyl]-2-(4-chloro-phenyl)-thiazole-5-carboxylic acid ethyl ester A mixture of 4-bromomethyl-2-(4-chloro-phenyl)-thiazole-5-carboxylic acid ethyl ester (2.22 g, 6.18 mmol), tert-butoxycarbonylamino-acetic acid ethyl ester (1.32 g, 6.48 mmol) and sodium hydride (60% in mineral oil, 296 mg, 7.4 mmol) in anhydrous dimethylformamide (30 mL) was stirred at 0° C. for one hour and room temperature for four hours before it was quenched with brine. The mixture was partitioned between ethyl acetate and water. The organic layer was washed with water, brine, dried over anhydrous sodium sulfate and concentrated in vacuo. The residue was purified by flash column chromatography on silica gel with a gradient of ethyl acetate and hexanes to give the title compound as a yellow oil (964 mg): $^1$H NMR (CDCl$_3$, 200 MHz): δ=7.87 (d, 2H), 7.39 (d, 2H), 4.99 (m, 2H), 4.21 (m, 6H), 1.45 (s, 9H), 1.26 (t, 3H).

c) 2-(4-Chloro-phenyl)-7-hydroxy-thiazolo[4,5-c]pyridine-6-carboxylic acid ethyl ester A mixture of 4-[(tert-butoxycarbonyl-ethoxycarbonylmethyl-amino)-methyl]-2-(4-chloro-phenyl)-thiazole-5-carboxylic acid ethyl ester (964 mg, 2.00 mol) in THF (7.2 mL) was added drop wise a solution of 1 M KO$^t$Bu in THF (2.8 mL, 0.02 mmol) at −78° C. The red solution was stirred at −78° C. for 20 min, warmed to room temperature and stirred at that temperature for two hours before it was quenched with water, extracted with ethyl acetate. The organic layer was washed with brine, dried over anhydrous sodium sulfate and concentrated in vacuo to give a yellow oil. It was dissolved in dichloromethane (4 mL) and TFA (1 mL) was added. The mixture was stirred at room temperature for 1 h before it was concentrated in vacuo. It was redissolved in dichloromethane, triethylamine (1.4 mL) was added. The mixture was stirred under air overnight before it was partitioned between ethyl acetate and water, the organic layer was washed with brine, dried over anhydrous sodium sulfate and concentrated in vacuo. The residue was purified by flash column chromatography on silica gel with a gradient of ethyl acetate and dichloromethane to give the title compound as a white solid (59 mg): MS: (+) m/z 335.0 M+1).

d) {[2-(4-Chloro-phenyl)-7-hydroxy-thiazolo[4,5-c]pyridine-6-carbonyl]-amino}-acetic acid A mixture of 2-(4-chloro-phenyl)-7-hydroxy-thiazolo[4,5-c]pyridine-6-carboxylic acid ethyl ester (58 mg, 0.17 mmol) and glycine (259 mg, 3.45 mmol) in 0.5 M sodium methoxide/methanol (6.6 mL) was refluxed for three days before it was cooled to room temperature and concentrated in vacuo. Water (20 mL) was added and the mixture was extracted with dichloromethane. The remaining aqueous layer was acidified to pH=2 with 1N HCl. The suspension was extracted with ethyl acetate. The organic layer was dried over sodium sulfate and concentrated in vacuo to give the title compound as a yellow solid (11 mg): $^1$H NMR (DMSO-$d_6$, 200 MHz): δ=9.44 (br s, 1H), 8.90 (s, 1H), 8.16 (d, J=8.6 Hz, 2H), 7.66 (d, J=8.6 Hz, 2H), 4.02 (d, 2H); MS: (+) m/z 364.0 (M+1)

Example 48

{[7-Hydroxy-2-(4-methoxy-phenyl)-thiazolo[4,5-c]pyridine-6-carbonyl]-amino}-acetic acid a) 4-Bromomethyl-2-(4-methoxy-phenyl)-thiazole-5-carboxylic acid ethyl ester A mixture of 2-(4-Methoxy-phenyl)-4-methyl-thiazole-5-carboxylic acid ethyl ester (1.41 g, 5.09 mmol), N-bromosuccinimide (951 mg, 5.34 mmol) and benzoyl peroxide (62 mg, 0.25 mmol) in carbon tetrachloride (20 mL) was refluxed for 15 h before it was cooled to room temperature and partitioned between dichloromethane and water, the organic layer was washed with saturated aqueous sodium bicarbonate solution, brine, dried over anhydrous sodium sulfate and concentrated in vacuo to give the title compound as a yellow solid (1.71 g): MS: (+) m/z 355.96, 357.96 (M+1, $^{79}$Br/$^{81}$Br).

b) 4-{[(2,4-Dimethoxy-benzyl)-ethoxycarbonylmethyl-amino]-methyl}-2-(4-methoxy-phenyl)-thiazole-5-carboxylic acid ethyl ester A mixture of 4-bromomethyl-2-(4-methoxy-phenyl)-thiazole-5-carboxylic acid ethyl ester (1.70 g, 4.78 mmol), (2,4- dimethoxy-benzylamino)-acetic acid ethyl ester (1.21 g, 4.78 mmol) and potassium carbonate (992 mg, 7.18 mmol) in anhydrous dimethylformamide (15 mL) was stirred at room temperature for 18 h before it was quenched with water, extracted with ethyl acetate. The organic layer was washed with water, brine, dried over anhydrous sodium sulfate and concentrated in vacuo. The residue was purified by flash column chromatography on silica gel with a gradient of ethyl acetate and hexanes to give the title compound as a yellow oil (5.72 g): MS: (+) m/z 529.10 (M+H$^+$), 551.20 (M+Na$^+$).

c) 7-Hydroxy-2-(4-methoxy-phenyl)-thiazolo[4,5-c]pyridine-6-carboxylic acid ethyl ester A yellow solution of 4-{[(2,4-dimethoxy-benzyl)-ethoxycarbonylmethyl-amino]-methyl}-2-(4-methoxy-phenyl)-thiazole-5-carboxylic acid ethyl ester (1.35 g, 2.56 mmol) in THF (10 mL) was added 1 M KO$^t$Bu in THF (5.6 mL, 5.63 mmol) at −78° C., a dark red suspension quickly appeared. The mixture was stirred at −78° C. for 20 min, warmed to room temperature and stirred at that temperature for 2 h before it was quenched with aqueous ammonium chloride, extracted with ethyl acetate. The organic layer was washed with water, brine, dried over anhydrous sodium sulfate and concentrated in vacuo to give a yellow oil (1.16 g). It was dissolved in dichloromethane (10 mL) and thionyl chloride (348 μL) was added drop wise. The mixture was stirred at room temperature for 3 h before it was quenched with saturated sodium bicarbonate, extracted with dichloromethane. The organic layer was washed with water, brine, dried over anhydrous sodium sulfate and concentrated in vacuo. The residue was purified by flash column chromatography on silica gel with a gradient of ethyl acetate and dichloromethane to give the title compound as a yellow solid (479 mg): $^1$H NMR (CDCl$_3$, 200 MHz): δ=11.50 (s, 1H), 8.95 (s, 1H), 8.06 (m, 2H), 7.02 (m, 2H), 4.58 (q, J=7.0 Hz, 2H), 3.90 (s, 3H), 1.53 (t, J=7.0 Hz, 3H); MS: (+) m/z 331.01 (M+1).

d) {[7-Hydroxy-2-(4-methoxy-phenyl)-thiazolo[4,5-c]pyridine-6-carbonyl]-amino}-acetic acid A mixture of 7-hydroxy-2-(4-methoxy-phenyl)-thiazolo[4,5-c]pyridine-6-carboxylic acid ethyl ester (76 mg, 0.23 mmol) and glycine (345 mg, 4.59 mmol) in 0.5 M sodium methoxide/methanol (8.7 mL) was refluxed for 3 days before it was cooled to room temperature and concentrated in vacuo. Water (20 mL) was added and the suspension was adjusted to pH=10 with 1N HCl (3 mL). The mixture was extracted with dichloromethane. And the remaining aqueous layer was acidified to pH=3 with 1N HCl (5 mL). The suspension was extracted with 2-isopropanol/chloroform (1:3, 50 mL). The organic layer was concentrated and dried in vacuo to give the title compound as a yellow solid (25 mg): $^1$H NMR (DMSO-d$_6$, 200 MHz): δ=12.28 (s, 1H), 9.42 (t, 1H), 8.88 (s, 1H), 8.13 (d, J=8.8 Hz, 2H), 7.16 (d, J=8.8 Hz, 2H), 4.03 (d, J=5.6 Hz, 2H), 3.88 (s, 3H); MS: (+) m/z 359.94 (M+1), (−) m/z 357.92 (M−1).

Example 49

{[2-(4-Fluoro-phenyl)-7-hydroxy-thiazolo[4,5-c]pyridine-6-carbonyl]-amino}-acetic acid a) 2-(4-Fluoro-phenyl)-4-methyl-thiazole-5-carboxylic acid ethyl ester A mixture of 4-fluoro-thiobenzamide (1.25 g, 8.04 mmol) and 2-chloro-3-oxo-butyric acid ethyl ester (1.11 mL, 8.20 mmol) in ethanol (18 mL) was heated at reflux for 16 h before it was cooled to room temperature and concentrated in vacuo. It was partitioned between ethyl acetate and saturated sodium bicarbonate, the organic layer was washed with brine, dried over anhydrous sodium sulfate and concentrated in vacuo to give the title compound as a yellow solid (1.99 g): MS: (+) m/z 266.03 (M+1).

b) 4-Bromomethyl-2-(4-fluoro-phenyl)-thiazole-5-carboxylic acid ethyl ester

A mixture of 2-(4-fluoro-phenyl)-4-methyl-thiazole-5-carboxylic acid ethyl ester (1.95 g, 7.35 mmol), N-bromosuccinimide (1.37 g, 7.71 mol) and benzoyl peroxide (89 mg, 0.37 mmol) in carbon tetrachloride (20 mL) was refluxed for 16 h before it was cooled to room temperature and partitioned between dichloromethane and water. The organic layer was washed with saturated aqueous sodium bicarbonate solution, brine, dried over anhydrous sodium sulfate and concentrated in vacuo to give the title compound as a yellow oil (2.38 g); MS: (+) m/z 343.93, 345.96 (M+1, $^{79}$Br/$^{81}$Br).

c) 4-{[(2,4-Dimethoxy-benzyl)-ethoxycarbonylmethyl-amino]-methyl}-2-(4-fluoro-phenyl)-thiazole-5-carboxylic acid ethyl ester A mixture of 4-bromomethyl-2-(4-fluoro-phenyl)-thiazole-5-carboxylic acid ethyl ester (2.02 g, 5.89 mmol), (2,4-dimethoxy-benzylamino)-acetic acid ethyl ester (1.49 g, 5.89 mmol) and potassium carbonate (1.22 g, 8.83 mmol) in anhydrous dimethylformamide (15 mL) was stirred at room temperature for 18 h before it was quenched with water, extracted with ethyl acetate. The organic layer was washed with water, brine, dried over anhydrous sodium sulfate and concentrated in vacuo. The residue was purified by flash column chromatography on silica gel with a gradient of ethyl acetate and hexanes to give the title compound as a yellow oil (2.39 g): MS: (+) m/z 539.22 (M+Na$^+$).

d) 2-(4-Fluoro-phenyl)-7-hydroxy-thiazolo[4,5-c]pyridine-6-carboxylic acid ethyl ester A solution of 4-{[(2,4-dimethoxy-benzyl)-ethoxycarbonylmethyl-amino]-methyl}-2-(4-fluoro-phenyl)-thiazole-5-carboxylic acid ethyl ester (2.31 g, 4.47 mmol) in THF (16 mL) was added 1 M KO$^t$Bu in THF (9.8 mL, 9.84 mmol) at −78° C. The mixture was stirred at −78° C. for 20 min, warmed to room temperature and stirred at that temperature for 2 h before it was quenched with aqueous ammonium chloride, extracted with ethyl acetate. The organic layer was washed with water, brine, dried over anhydrous sodium sulfate and concentrated in vacuo to give a yellow oil (2.00 g). It was dissolved in dichloromethane (16 mL) and thionyl chloride (617 μL) was added. The mixture was stirred at room temperature for 3 h before it was quenched with saturated sodium bicarbonate, extracted with dichloromethane. The organic layer was washed with water, brine, dried over anhydrous sodium sulfate and concentrated in vacuo. The residue was purified by flash column chromatography on silica gel with a gradient of ethyl acetate and dichloromethane to give the title compound as a yellow solid (947 mg): MS: (+) m/z 318.99 (M+1).

e) {[2-(4-Fluoro-phenyl)-7-hydroxy-thiazolo[4,5-c]pyridine-6-carbonyl]-amino}-acetic acid A mixture of 2-(4-fluoro-phenyl)-7-hydroxy-thiazolo[4,5-c]pyridine-6-carboxylic acid ethyl ester (81 mg, 0.25 mmol) and glycine (190 mg, 5.07 mmol) in 0.5 M sodium methoxide/methanol (4.0 mL) was heated at 120° C. using a CEM microwave reactor for 1H before it was cooled to room temperature and concentrated in vacuo. It was dissolved in water (50 mL) and extracted twice with dichloromethane. The remaining aqueous layer was acidified to pH=3 with 1N HCl (3 mL). The solid precipitate was filtered, washed with water and dried in vacuo to give the title compound as a brown solid (66 mg): $^1$H NMR (DMSO-$d_6$, 200 MHz): δ=13.28 (br s, 1H), 9.44 (br s, 1H), 8.91 (s, 1H), 8.21 (m, 2H), 7.45 (m, 2H), 4.03 (d, J=6.2 Hz, 2H); MS: (+) m/z 348.00 (M+1).

Example 50

[(4-Ethyl-7-hydroxy-2-phenyl-thiazolo[4,5-c]pyridine-6-carbonyl)-amino]-acetic acid a) 4-Ethyl-7-hydroxy-2-phenyl-thiazolo[4,5-c]pyridine-6-carboxylic acid ethyl ester A mixture of 4-bromo-7-hydroxy-2-phenyl-thiazolo[4,5-c]pyridine-6-carboxylic acid ethyl ester (100 mg, 0.26 mmol), tetraethyltin (106 μL, 0.52 mmol) and bis(triphenylphosphine)-palladium(II) dichloride (19 mg, 0.03 mmol) in dimethylformamide (2.5 mL) was stirred at 130° C. for 1H before it was cooled to room temperature, quenched with water, filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and hexanes to give the title compound as a white solid (57 mg): MS: (+) m/z 328.99 (M+1).

b) [(4-Ethyl-7-hydroxy-2-phenyl-thiazolo[4,5-c]pyridine-6-carbonyl)-amino]-acetic acid A mixture of 4-ethyl-7-hydroxy-2-phenyl-thiazolo[4,5-c]pyridine-6-carboxylic acid ethyl ester (57 mg, 0.17 mmol) and glycine (259 mg, 3.45 mmol) in 0.5 M sodium methoxide/methanol (6.5 mL) was refluxed for 21 h before it was cooled to room temperature and concentrated in vacuo. The residue was dissolved in water (10 mL) and extracted twice with dichloromethane. The remaining aqueous layer was acidified to pH=3 with 1N HCl (5 mL). The solid precipitate was filtered, washed with water and dried in vacuo to give the title compound as a white solid (50 mg): $^1$H NMR (DMSO-$d_6$, 200 MHz): δ=13.04 (br s, 1H), 9.22 (br s, 1H), 8.17 (m, 2H), 7.64 (m, 3H), 4.05 (d, J=6.2 Hz, 2H), 3.28 (q, J=7.8 Hz, 2H), 1.42 (t, J=7.8 Hz, 3H); MS: (+) m/z 357.97 (M+1), (−) m/z 355.95 (M−1).

Example 51

[(7-Hydroxy-2-phenoxy-thiazolo[4,5-c]pyridine-6-carbonyl)-amino]-acetic acid a) 4-Methyl-2-phenoxy-thiazole-5-carboxylic acid ethyl ester

A mixture of 2-bromo-4-methyl-thiazole-5-carboxylic acid ethyl ester (1.89 g, 7.57 mmol), phenol (855 mg, 9.09 mmol) and potassium carbonate (1.36 g, 9.84 mmol) in dimethylformamide (18 mL) was heated at 95° C. for 15 h before it was cooled to room temperature and partitioned between ethyl acetate and water, the organic layer was washed with water, aqueous sodium hydroxide (2×), brine, dried over anhydrous sodium sulfate and concentrated in vacuo. The residue was purified by flash column chromatography on silica gel with a gradient of ethyl acetate and hexanes to give the title compound as a yellow oil (1.32 g): MS: (+) m/z 264.0 (M+1).

b) 4-Bromomethyl-2-phenoxy-thiazole-5-carboxylic acid ethyl ester

A mixture of 4-methyl-2-phenoxy-thiazole-5-carboxylic acid ethyl ester (1.31 g, 4.99 mmol), N-bromosuccinimide (905 mg, 5.08 mmol) and benzoyl peroxide (60 mg, 0.25 mmol) in carbon tetrachloride (25 mL) was refluxed for 3 h before it was cooled to room temperature and partitioned between dichloromethane and water, the organic layer was washed with saturated aqueous sodium bicarbonate solution, brine, dried over anhydrous sodium sulfate and concentrated in vacuo to give the title compound as a yellow solid (1.74 g): MS: (+) m/z 342.0, 344.0 (M+1, $^{79}$Br/$^{81}$Br).

c) 4-{[(2,4-Dimethoxy-benzyl)-ethoxycarbonylmethyl-amino]-methyl}-2-phenoxy-thiazole-5-carboxylic acid ethyl ester A mixture of 4-bromomethyl-2-phenoxy-thiazole-5-carboxylic acid ethyl ester (1.71 g, 5.01 mmol), (2,4-dimethoxy-benzylamino)-acetic acid ethyl ester (1.33 g, 5.24 mmol) and potassium carbonate (1.04 g, 7.52 mmol) in anhydrous dimethylformamide (15 mL) was stirred at room temperature for 17 h before it was quenched with water, extracted with ethyl acetate. The organic layer was washed with water, brine, dried over anhydrous sodium sulfate and concentrated in vacuo. The residue was purified by flash column chromatography on silica gel with a gradient of ethyl acetate and hexanes to give the title compound as a yellow oil (1.60 g): MS: (+) m/z 514.93 (M+1).

d) 7-Hydroxy-2-phenoxy-thiazolo[4,5-c]pyridine-6-carboxylic acid ethyl ester A yellow solution of 4-{[(2,4-dimethoxy-benzyl)-ethoxycarbonylmethyl-amino]-methyl}-2-phenoxy-thiazole-5-carboxylic acid ethyl ester (1.58 g, 3.07 mmol) in THF (12 mL) was added 1 M KO$^t$Bu in THF (6.8 mL, 6.76 mmol) at −78° C. The mixture was stirred at −78° C. for 20 min, warmed to room temperature and stirred at that temperature for 2 h before it was quenched with aqueous ammonium chloride, extracted with ethyl acetate. The organic layer was washed with water, brine, dried over anhydrous sodium sulfate and concentrated in vacuo to give a red oil (1.18 g) It was dissolved in dichloromethane (8 mL) and thionyl chloride (272 μL) was added drop wise. The mixture was stirred at room temperature for 3.5 h before it was quenched with saturated sodium bicarbonate, extracted with dichloromethane. The organic layer was washed with water, brine, dried over anhydrous sodium sulfate and concentrated in vacuo. The residue was purified by flash column chromatography on silica gel with a gradient of ethyl acetate and dichloromethane to give the title compound as a yellow solid (313.2 mg): MS: (+) m/z 317.00 (M+1).

e) [(7-Hydroxy-2-phenoxy-thiazolo[4,5-c]pyridine-6-carbonyl)-amino]-acetic acid

A mixture of 7-hydroxy-2-phenoxy-thiazolo[4,5-c]pyridine-6-carboxylic acid ethyl ester (81 mg, 0.26 mmol) and glycine (386 mg, 5.14 mmol) in 0.5 M sodium methoxide/methanol (9.8 mL, 4.88 mmol) was refluxed for 3 days before it was cooled to room temperature and concentrated in vacuo. The residue was dissolved in water and extracted with dichloromethane. The remaining aqueous layer was acidified to pH=3 with 1N HCl (7.3 mL). The suspension was extracted with ethyl acetate. The organic layer was dried over sodium sulfate, concentrated in vacuo and purified on a C18 reverse column with a gradient of 0.1% TFA in water and 0.1% TFA in acetonitrile to give the title compound as a brown solid (49 mg): $^1$H NMR (DMSO-$d_6$, 200 MHz): δ=13.16 (s, 1H), 9.39 (br s, 1H), 8.60 (s, 1H), 7.55 (m, 4H), 7.42 (m, 1H), 4.01 (d, J=6.4 Hz, 2H); MS: (+) m/z 346.00 (M+1).

Example 52

{[7-Hydroxy-2-(methyl-phenyl-amino)-thiazolo[4,5-c]pyridine-6-carbonyl]-amino}-acetic acid a) 4-Methyl-2-(methyl-phenyl-amino)-thiazole-5-carboxylic acid ethyl ester A mixture of 1-methyl-1-phenyl-thiourea (5.03 g, 30.3 mmol) and 2-chloro-3-oxo-butyric acid ethyl ester (4.4 mL, 31.8 mmol) in ethanol (18 mL) was refluxed for 20 h before it was cooled to room temperature and concentrated in vacuo. It was partitioned between ethyl acetate and saturated sodium bicarbonate, the organic layer was washed with brine, dried over anhydrous sodium sulfate and concentrated in vacuo to give the title compound as a brown solid (7.39 g): MS: (+) m/z 277.0 (M+1).

b) 4-Bromomethyl-2-(methyl-phenyl-amino)-thiazole-5-carboxylic acid ethyl ester

A mixture of 4-methyl-2-(methyl-phenyl-amino)-thiazole-5-carboxylic acid ethyl ester (3.32 g, 12.0 mmol), N-bromosuccinimide (2.35 g, 13.2 mol) and benzoyl peroxide (291 mg, 1.2 mmol) in carbon tetrachloride (45 mL) was refluxed for 17 h before it was cooled to room temperature and partitioned between dichloromethane and water. The organic layer was washed with saturated aqueous sodium bicarbonate solution, brine, dried over anhydrous sodium sulfate and concentrated in vacuo. The residue was purified by flash column chromatography on silica gel with a gradient of ethyl acetate and hexanes to give the title compound as a yellow oil: MS: (+) m/z 354.9, 356.9 (M+1, $^{79}$Br/$^{81}$Br).

c) 4-[(tert-Butoxycarbonyl-ethoxycarbonylmethyl-amino)-methyl]-2-(methyl-phenyl-amino)-thiazole-5-carboxylic acid ethyl ester A mixture of 4-bromomethyl-2-(methyl-phenyl-amino)-thiazole-5-carboxylic acid ethyl ester (974 mg, 2.75 mmol), tert-butoxycarbonylamino-acetic acid ethyl ester (559 mg, 2.75 mmol) and sodium hydride (60% in mineral oil, 132 mg, 3.30 mmol) in anhydrous dimethylformamide (10 mL) was stirred at 0° C. for two hours and room temperature for 18 h before it was quenched with brine. It was partitioned between ethyl acetate and water. The organic layer was washed with water, brine, dried over anhydrous sodium sulfate and concentrated in vacuo. The residue was purified by flash column chromatography on silica gel with a gradient of ethyl acetate and hexanes to give the title compound as a yellow oil (652 mg): MS: (+) m/z 500.0 (M+Na$^+$).

d) 7-Hydroxy-2-(methyl-phenyl-amino)-thiazolo[4,5-c]pyridine-6-carboxylic acid ethyl ester A mixture of 4-[(tert-butoxycarbonyl-ethoxycarbonylmethyl-amino)-methyl]-2-(methyl-phenyl-amino)-thiazole-5-carboxylic acid ethyl ester (632 mg, 1.32 mol) in THF (5 mL) was added drop wise a solution of 1 M KO$^t$Bu in THF (1.85 mL, 1.85 mmol) at −78° C. The red solution was stirred at −78° C. for 10 min, warmed to room temperature and stirred at that temperature for 50 min before it was quenched with water, extracted with ethyl acetate. The organic layer was washed with brine, dried over anhydrous sodium sulfate and concentrated in vacuo to give 7-oxo-2-(4-trifluoromethyl-phenyl)-6,7-dihydro-4H-thiazolo[4,5-c]pyridine-5,6-dicarboxylic acid 5-tert-butyl ester 6-ethyl ester as a yellow oil (227 mg). It was dissolved in dichloromethane (40 mL) and TFA (1.5 mL) was added. The mixture was stirred at room temperature for 1 h before it was concentrated in vacuo. It was redissolved in dichloromethane, triethylamine (336 μL) was added. The mixture was stirred under air overnight before it was partitioned between dichloromethane and water, the organic layer was washed with brine, dried over anhydrous sodium sulfate and concentrated in vacuo. The residue was purified by flash column chromatography on silica gel with a gradient of ethyl acetate and dichloromethane to give the title compound as a white solid (31 mg): MS: (+) m/z 369.0 (M+1).

e) {[7-Hydroxy-2-(methyl-phenyl-amino)-thiazolo[4,5-c]pyridine-6-carbonyl]-amino}-acetic acid A mixture of 7-hydroxy-2-(methyl-phenyl-amino)-thiazolo[4,5-c]pyridine-6-carboxylic acid ethyl ester (87 mg, 0.26 mmol) and glycine (399 mg, 5.31 mmol) in 0.5 M sodium methoxide/methanol (10.1 mL) was refluxed for three days before it was cooled to room temperature and concentrated in vacuo. It was dissolved in water (20 mL) and extracted twice with dichloromethane. The remaining aqueous layer was acidified to pH=3 with 1N HCl (6.5 mL). The precipitate was filtered, washed with water and dried under vacuo to give the title compound as a white solid (77 mg): $^1$H NMR (DMSO-$d_6$, 200 MHz): δ=9.18 (br s, 1H), 8.37 (s, 1H), 7.57 (m, 5H), 3.95 (d, J=6.2 Hz, 2H), 3.61 (s, 3H); MS: (+) m/z 359.0 (M+1).

Example 53

[(7-Hydroxy-2-phenylamino-thiazolo[4,5-c]pyridine-6-carbonyl)-amino]-acetic acid a) 4-Methyl-2-phenylamino-thiazole-5-carboxylic acid ethyl ester A mixture of phenylthiourea (5.04 g, 33.1 mmol) and 2-chloro-3-oxo-butyric acid ethyl ester (4.8 mL, 34.8 mmol) in ethanol (50 mL) was refluxed for 19 h before it was cooled to room temperature and concentrated in vacuo. It was partitioned between ethyl acetate and saturated sodium bicarbonate, the organic layer was washed with brine, dried over anhydrous sodium sulfate and concentrated in vacuo to give the title compound as a yellow solid (8.18 g): MS: (+) m/z 263.0 (M+1).

b) 2-(tert-Butoxycarbonyl-phenyl-amino)-4-methyl-thiazole-5-carboxylic acid ethyl ester A mixture of 4-methyl-2-phenylamino-thiazole-5-carboxylic acid ethyl ester (2.00 g, 7.65 mmol), di-tert-butyl dicarbonate (1.84 g, 8.41 mmol), 4-dimethylaminopyridine (47 mg, 0.38 mmol) and triethylamine (1.6 mL, 11.5 mmol) in dichloromethane (30 mL) was stirred at room temperature for 2 h before it was partitioned between dichloromethane and water, the organic layer was washed with brine, dried over anhydrous sodium sulfate and concentrated in vacuo. The residue was purified by flash column chromatography on silica gel with a gradient of ethyl acetate and hexanes to give the title compound as a yellow solid (2.64 g): MS: (+) m/z 263.1 (M+1-Boc).

c) 4-Bromomethyl-2-(tert-butoxycarbonyl-phenyl-amino)-thiazole-5-carboxylic acid ethyl ester A mixture of 2-(tert-butoxycarbonyl-phenyl-amino)-4-methyl-thiazole-5-carboxylic acid ethyl ester (1.61 g, 4.45 mmol), N-bromosuccinimide (833 mg, 4.68 mol) and benzoyl peroxide (54 mg, 0.22 mmol) in carbon tetrachloride (30 mL) was refluxed for 16 h before it was cooled to room temperature and partitioned between dichloromethane and water. The organic layer was washed with saturated aqueous sodium bicarbonate solution, brine, dried over anhydrous sodium sulfate and concentrated in vacuo. The residue was purified by flash column chromatography on silica gel with a gradient of ethyl acetate and hexanes to give the title compound as a yellow oil (1.61 g); MS: (+) m/z 341.0, 343.0 (M+1-Boc, $^{79}$Br/$^{81}$Br).

d) 2-(tert-Butoxycarbonyl-phenyl-amino)-4-{[(2,4-dimethoxy-benzyl)-ethoxycarbonylmethyl-amino]-methyl}-thiazole-5-carboxylic acid ethyl ester A mixture of 4-bromomethyl-2-(tert-butoxycarbonyl-phenyl-amino)-thiazole-5-carboxylic acid ethyl ester (451 mg, 1.02 mmol), (2,4-dimethoxy-benzylamino)-acetic acid ethyl ester (260 mg, 1.02 mmol) and potassium carbonate (213 g, 1.54 mmol) in anhydrous dimethylformamide (4 mL) was stirred at room temperature for 18 h before it was quenched with water, extracted with ethyl acetate. The organic layer was washed with water, brine, dried over anhydrous sodium sulfate and concentrated in vacuo. The residue was purified by flash column chromatography on silica gel with a gradient of ethyl acetate and hexanes to give the title compound as a white solid (562 mg): MS: (+) m/z 614.13 (M+1).

e) 7-Hydroxy-2-phenylamino-thiazolo[4,5-c]pyridine-6-carboxylic acid ethyl ester A solution of 2-(tert-butoxycarbonyl-phenyl-amino)-4-{[(2,4-dimethoxy-benzyl)-ethoxycarbonylmethyl-amino]-methyl}-thiazole-5-carboxylic acid ethyl ester (398 mg, 0.65 mmol) in THF (4 mL) was added 1 M KO$^t$Bu in THF (1.4 mL, 1.43 mmol) at −78° C. The mixture was stirred at −78° C. for 20 min, warmed to room temperature and stirred at that temperature for 2.5 h before it was quenched with water, extracted with ethyl acetate. The organic layer was washed with brine, dried over anhydrous sodium sulfate and concentrated in vacuo to give a yellow oil (203 mg). It was dissolved in dichloromethane (3 mL) and 2M thionyl chloride in dichloromethane (528 μL) was added. The mixture was stirred at room temperature for 2.5 h before it was quenched with saturated sodium bicarbonate, extracted with dichloromethane. The organic layer was washed with water, brine, dried over anhydrous sodium sulfate and concentrated in vacuo. The residue was dissolved in dichloromethane (8 mL) and trifluoroacetic acid (0.5 mL) was added and the mixture was stirred at room temperature for half an hour before it was concentrated in vacuo. The residue was partitioned between dichloromethane and saturated sodium bicarbonate, the organic layer was washed with brine, dried over anhydrous sodium sulfate and concentrated in vacuo. The residue was purified by flash column chromatography on silica gel with a gradient of ethyl acetate and dichloromethane to give the title compound as a yellow solid (48 mg): MS: (+) m/z 316.00 (M+1); MS: (−) m/z 314.00 (M−1).

f) [(7-Hydroxy-2-phenylamino-thiazolo[4,5-c]pyridine-6-carbonyl)-amino]-acetic acid A mixture of 7-hydroxy-2-phenylamino-thiazolo[4,5-c]pyridine-6-carboxylic acid ethyl ester (39 mg, 0.12 mmol) and glycine (186 mg, 2.48 mmol) in 0.5 M sodium methoxide/methanol (4.7 mL) was refluxed for 22 h before it was cooled to room temperature and concentrated in vacuo. It was dissolved in water (20 mL) and extracted twice with dichloromethane. The remaining aqueous layer was acidified to pH=3 with 1N HCl (3.5 mL). The suspension was extracted with ethyl acetate (2×30 mL) and chloroform/isopropanol (3:1, 40 mL). The organic layer was combined and dried in vacuo to give the title compound as a brown solid (35 mg): $^1$H NMR (DMSO-d$_6$, 200 MHz): δ=12.99 (br s, 1H), 11.00 (s, 1H), 9.25 (t, 1H), 8.47 (s, 1H), 7.77 (m, 2H), 7.39 (t, 2H), 7.09 (t, 1H), 4.00 (d, J=6.3 Hz, 2H); MS: (+) m/z 345.07 (M+1).

Example 54

[(7-Hydroxy-2-phenyl-thiazolo[5,4-c]pyridine-6-carbonyl)-amino]-acetic acid a) 5-Methyl-2-phenyl-thiazole-4-carboxylic acid ethyl ester

A solution of 2-ketobutyric acid (25 g, 0.24 mol) in ethanol was added thionyl chloride (89 mL, 1.22 mol). The mixture was refluxed for 7.5 h before it was cooled to room temperature and concentrated in vacuo. The residue was partitioned between dichloromethane and water, the organic layer was washed with saturated sodium bicarbonate, the organic layer was washed with brine, dried over anhydrous sodium sulfate, concentrated in vacuo. The residue was dissolved in ethyl acetate (80 mL) and chloroform (40 mL) and copper (II) bromide (35 g) was added and the mixture was refluxed for 18 h before it was cooled to room temperature, filtered and concentrated in vacuo to give a brown liquid (16.2 g) which was refluxed with thiobenzamide (8.5 g, 0.06 mol) in ethanol (80 mL) for 20 h before it was cooled to room temperature and concentrated in vacuo. It was partitioned between ethyl acetate and saturated sodium bicarbonate, the organic layer was washed with brine, dried over anhydrous sodium sulfate and concentrated in vacuo. The residue was purified by flash column chromatography on silica gel with a gradient of ethyl acetate and hexanes to give the title compound as a yellow solid (7.8 g): MS: (+) m/z 247.9 (M+1)

b) 5-Bromomethyl-2-phenyl-thiazole-4-carboxylic acid ethyl ester

A mixture of 5-methyl-2-phenyl-thiazole-4-carboxylic acid ethyl ester (7.76 g, 0.03 mol), N-bromosuccinimide (5.87 g, 0.03 mol) and benzoyl peroxide (761 mg, 3.30 mmol) in carbon tetrachloride (130 mL) was refluxed for 16 h before it was cooled to room temperature and partitioned between dichloromethane and water. The organic layer was washed with saturated aqueous sodium bicarbonate solution, brine, dried over anhydrous sodium sulfate and concentrated in vacuo to give the title compound as a yellow oil (10.66 g); MS: (+) m/z 325.93, 328.00 (M+1, $^{79}$Br/$^{81}$Br).

c) 5-{[(2,4-Dimethoxy-benzyl)-ethoxycarbonylmethyl-amino]-methyl}-2-phenyl-thiazole-4-carboxylic acid ethyl ester A mixture of 5-bromomethyl-2-phenyl-thiazole-4-carboxylic acid ethyl ester (596 mg, 1.83 mmol), (2,4-dimethoxy-benzylamino)-acetic acid ethyl ester (511 mg, 2.02 mmol) and potassium carbonate (380 mg, 2.75 mmol) in anhydrous dimethylformamide (7 mL) was stirred at room temperature for 20 h before it was quenched with water, extracted with ethyl acetate. The organic layer was washed with water, brine, dried over anhydrous sodium sulfate and concentrated in vacuo. The residue was purified by flash column chromatography on silica gel with a gradient of ethyl acetate and hexanes to give the title compound as a white solid (562 mg): MS: (+) m/z 521.1 (M+Na$^+$).

d) 7-Hydroxy-2-phenyl-thiazolo[5,4-c]pyridine-6-carboxylic acid ethyl ester

A solution of 5-{[(2,4-dimethoxy-benzyl)-ethoxycarbonylmethyl-amino]-methyl}-2-phenyl-thiazole-4-carboxylic acid ethyl ester (200 mg, 0.40 mmol) in THF (3 mL) was added 1 M KO$^t$Bu in THF (882 μL, 0.88 mmol) at −78° C. The mixture was stirred at −78° C. for 20 min, warmed to room temperature and stirred at that temperature for 1.5 h before it was quenched with aqueous ammonium chloride, extracted with ethyl acetate. The organic layer was washed with brine, dried over anhydrous sodium sulfate and concentrated in vacuo to give a yellow oil (117 mg) It was dissolved in dichloromethane (1.5 mL) and thionyl chloride (28 μL) was added. The mixture was stirred at room temperature for 4 h. The solid precipitate was filtered and the remaining solid was partitioned between ethyl acetate and saturated sodium bicarbonate. The organic layer was washed with brine, dried over anhydrous sodium sulfate and concentrated in vacuo. The residue was purified by flash column chromatography on silica gel with a gradient of ethyl acetate and dichloromethane to give the title compound as a white solid (32 mg): MS: (+) m/z 300.96 (M+1).

e) [(7-Hydroxy-2-phenyl-thiazolo[5,4-c]pyridine-6-carbonyl)-amino]-acetic acid

A mixture of 7-hydroxy-2-phenyl-thiazolo[5,4-c]pyridine-6-carboxylic acid ethyl ester (31 mg, 0.10 mmol) and glycine (78 mg, 1.04 mmol) in 0.5 M sodium methoxide/methanol (1.7 mL) was heated at 120° C. using a CEM microwave reactor for 30 min before it was cooled to room temperature and concentrated in vacuo. The residue was dissolved in water (18 mL) and extracted twice with dichloromethane. The remaining aqueous layer was acidified to pH=3 with 1N HCl (1.2 mL). The resulting precipitate was filtered, washed with water and dried in vacuo to give the title compound as a yellow solid (25 mg): $^1$H NMR (DMSO-d$_6$, 200 MHz): δ=13.30 (br s, 1H), 9.42 (t, 1H), 8.96 (s, 1H), 8.14 (m, 2H), 7.67 (m, 3H), 4.02 (d, J=6.2 Hz, 2H); MS: (+) m/z 330.0 (M+1).

Example 55

{[2-(5-Bromo-pyridin-3-yl)-7-hydroxy-thiazolo[4,5-c]pyridine-6-carbonyl]-amino}-acetic acid a) 4-Methyl-2-pyridin-3-yl-thiazole-5-carboxylic acid ethyl ester A mixture of thionicotinamide (10 g, 0.07 mol) and 2-chloro-3-oxo-butyric acid ethyl ester (10 mL, 0.07 mol) in ethanol (100 mL) was heated at reflux for 20 h before it was cooled to room temperature and concentrated in vacuo. It was partitioned between ethyl acetate and saturated sodium bicarbonate, the organic layer was washed with brine, dried over anhydrous sodium sulfate and concentrated in vacuo. The residue was purified by flash column chromatography on silica gel with a gradient of ethyl acetate and hexanes to give the title compound as a yellow oil (12.2 g): MS: (+) m/z 249.0 (M+1).

b) 4-Bromomethyl-2-(5-bromo-pyridin-3-yl)-thiazole-5-carboxylic acid ethyl ester A mixture of 4-methyl-2-pyridin-3-yl-thiazole-5-carboxylic acid ethyl ester (1.5 g, 6.05 mmol), N-bromosuccinimide (2.2 g, 12.40 mol) and benzoyl peroxide (73 mg, 0.30 mmol) in carbon tetrachloride (30 mL) was refluxed for 16 h before it was cooled to room temperature and partitioned between dichloromethane and water. The organic layer was washed with saturated aqueous sodium bicarbonate solution, brine, dried over anhydrous sodium sulfate and concentrated in vacuo. The residue was purified by flash column chromatography on silica gel with a gradient of ethyl acetate and hexanes to give the title compound, which was contaminated with 2-(5-bromo-pyridin-3-yl)-4-methyl-thiazole-5-carboxylic acid ethyl ester, as a white solid (330 mg); MS: (+) m/z 404.87, 406.93, 408.93 (M+1, $^{79}$Br/$^{81}$Br).

c) 2-(5-Bromo-pyridin-3-yl)-4-{[(2,4-dimethoxy-benzyl)-ethoxycarbonylmethyl-amino]-methyl}-thiazole-5-carboxylic acid ethyl ester A mixture of 4-bromomethyl-2-(5-bromo-pyridin-3-yl)-thiazole-5-carboxylic acid ethyl ester (880 mg, 2.18 mmol), (2,4-dimethoxy-benzylamino)-acetic acid ethyl ester (552 mg, 2.18 mmol) and potassium carbonate (452 mg, 3.27 mmol) in anhydrous dimethylformamide (8 mL) was stirred at room temperature for 24 h before it was quenched with water, extracted with ethyl acetate. The organic layer was washed with water, brine, dried over anhydrous sodium sulfate and concentrated in vacuo. The residue was purified by flash column chromatography on silica gel with a gradient of ethyl acetate and hexanes to give the title compound as a yellow oil (495 mg): MS: (+) m/z 600.40, 602.20 (M+Na$^+$, $^{79}$Br/$^{81}$Br).

d) 2-(5-Bromo-pyridin-3-yl)-7-hydroxy-thiazolo[4,5-c]pyridine-6-carboxylic acid ethyl ester A solution of 2-(5-bromo-pyridin-3-yl)-4-{[(2,4-dimethoxy-benzyl)-ethoxycarbonylmethyl-amino]-methyl}-thiazole-5-carboxylic acid ethyl ester (476 mg, 0.82 mmol) in THF (4 mL) was added 1 M KO$^t$Bu in THF (1.8 mL, 1.81 mmol) at −78° C. The mixture was stirred at −78° C. for 20 min, warmed to room temperature and stirred at that temperature for 2.5 h before it was quenched with water, extracted with ethyl acetate. The organic layer was washed with water, brine, dried over anhydrous sodium sulfate and concentrated in vacuo to give an orange oil (335 mg). It was dissolved in dichloromethane (4 mL) and thionyl chloride (918 µL) was added. The mixture was stirred at room temperature for 3 h before it was quenched with saturated sodium bicarbonate, extracted with dichloromethane. The organic layer was washed with water, brine, dried over anhydrous sodium sulfate and concentrated in vacuo. The residue was purified by flash column chromatography on silica gel with a gradient of methanol and dichloromethane to give the title compound as a yellow solid (181 mg): MS: (+) m/z 379.93, 380.93 (M+1, $^{79}$Br/$^{81}$Br); (−) m/z 378.13, 380.13 (M−1, $^{79}$Br/$^{81}$Br).

e) {[2-(5-Bromo-pyridin-3-yl)-7-hydroxy-thiazolo[4,5-c]pyridine-6-carbonyl]-amino}-acetic acid A mixture of 2-(5-bromo-pyridin-3-yl)-7-hydroxy-thiazolo[4,5-c]pyridine-6-carboxylic acid ethyl ester (49 mg, 0.13 mmol) and glycine (193 mg, 2.57 mmol) in 0.5 M sodium methoxide/methanol (4.9 mL) was refluxed for 36 h before it was cooled to room temperature and concentrated in vacuo. It was dissolved in water (15 mL) and extracted twice with dichloromethane. The remaining aqueous layer was acidified to pH=3 with 1N HCl (2 mL). The solid precipitate was filtered, washed with water and dried in vacuo to give the title compound as a yellow solid (13 mg): $^1$H NMR (DMSO-d$_6$, 200 MHz): δ=13.34 (br s, 1H), 12.83 (br s, 1H), 9.46 (t, 1H), 9.30 (d, 1H), 8.91 (m, 2H), 8.73 (m, 1H), 4.02 (d, J=5.8 Hz, 2H); MS: (+) m/z 408.93, 410.87 (M+1, $^{79}$Br/$^{81}$Br).

Example 56

[(7-Hydroxy-2-pyridin-3-yl-thiazolo[4,5-c]pyridine-6-carbonyl)-amino]-acetic acid a) 7-Hydroxy-2-pyridin-3-yl-thiazolo[4,5-c]pyridine-6-carboxylic acid ethyl ester A mixture of 2-(5-bromo-pyridin-3-yl)-7-hydroxy-thiazolo[4,5-c]pyridine-6-carboxylic acid ethyl ester (88 mg, 0.23 mmol), ammonium formate (296 mg, 4.63 mmol) and 10% Pd/C (114 mg) in ethyl acetate (7 mL) was refluxed for 21 h before it was cooled to room temperature and filtered. The filtrate was washed with saturated sodium bicarbonate, water, dried and concentrated in vacuo. The residue was purified by flash column chromatography on silica gel with a gradient of methanol and dichloromethane dried in vacuo to give the title compound as a yellow solid (27 mg): MS: (+) m/z 302.07 (M+1); (−) m/z 300.27 (M−1).

b) [(7-Hydroxy-2-pyridin-3-yl-thiazolo[4,5-c]pyridine-6-carbonyl)-amino]-acetic acid A mixture of 7-hydroxy-2-pyridin-3-yl-thiazolo[4,5-c]pyridine-6-carboxylic acid ethyl ester (27 mg, 0.09 mmol) and glycine (169 mg, 1.80 mmol) in 0.5 M sodium methoxide/methanol (4.5 mL) was refluxed for 3 days before it was cooled to room temperature and concentrated in vacuo. It was dissolved in water (15 mL) and extracted twice with methyl t-butyl ether. The remaining aqueous layer was acidified to pH=3 with 1N HCl (3.3 mL). The solid precipitate was filtered, washed with water and dried in vacuo to give the title compound as a yellow solid (17 mg): $^1$H NMR (DMSO-d$_6$, 200 MHz): δ=9.56 (br s, 1H), 9.34 (s, 1H), 8.94 (s, 1H), 8.80 (d, 1H), 8.53 (m, 1H), 7.66 (m, 1H), 4.03 (d, J=5.8 Hz, 2H); MS: (+) m/z 331.00 (M+1).

Example 57

[(4-Butyl-7-hydroxy-2-phenyl-thiazolo[4,5-c]pyridine-6-carbonyl)-amino]-acetic acid a) 4-Butyl-7-hydroxy-2-phenyl-thiazolo[4,5-c]pyridine-6-carboxylic acid ethyl ester A mixture of 4-bromo-7-hydroxy-2-phenyl-thiazolo[4,5-c]pyridine-6-carboxylic acid ethyl ester (106 mg, 0.28 mmol), tetrabutyltin (198 µL, 0.56 mmol) and bis(triphenylphosphine)-palladium(II) dichloride (20 mg, 0.03 mmol) in dimethylformamide (2 mL) was stirred at 130° C. for 1 h before it was cooled to room temperature, quenched with water, filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and hexanes to give the title compound as a white solid (39 mg): MS: (+) m/z 357.07 (M+1).

b) [(4-Butyl-7-hydroxy-2-phenyl-thiazolo[4,5-c]pyridine-6-carbonyl)-amino]-acetic acid A mixture of 4-butyl-7-hydroxy-2-phenyl-thiazolo[4,5-c]pyridine-6-carboxylic acid ethyl ester (41 mg, 0.12 mmol) and glycine (175 mg, 2.32 mmol) in 0.5 M sodium methoxide/methanol (4.4 mL) was refluxed for 48 h before it was cooled to room temperature and concentrated in vacuo. The residue was dissolved in water (20 mL) and extracted twice with methyl t-butyl ether. The remaining aqueous layer was acidified to pH=3 with 1N HCl (3.5 mL). The solid precipitate was filtered, washed with water and dried in vacuo to give the title compound as a white solid (19 mg): $^1$H NMR (DMSO-d$_6$, 200 MHz): δ=9.19 (br s, 1H), 8.17 (m, 2H), 7.63 (m, 3H), 4.05 (d, J=5.8 Hz, 2H), 3.33 (m, 2H), 1.88 (m, 2H), 1.41 (m, 2H), 0.97 (t, J=7.2 Hz, 3H); MS: (+) m/z 386.13 (M+1), (−) m/z 384.13 (M−1).

Example 58

[(7-Hydroxy-2-pyridin-2-yl-thiazolo[4,5-c]pyridine-6-carbonyl)-amino]-acetic acid a) 2-Bromo-4-bromomethyl-thiazole-5-carboxylic acid ethyl ester A mixture of 2-Bromo-4-methyl-thiazole-5-carboxylic acid ethyl ester (5.67 g, 22.68 mmol), N-bromosuccinimide (4.44 g, 24.95 mmol) and benzoyl peroxide (275 mg, 1.13 mmol) in carbon tetrachloride (25 mL) was refluxed for 16 h before it was cooled to room temperature and partitioned between dichloromethane and water, the organic layer was washed with saturated aqueous sodium bicarbonate solution, brine, dried over anhydrous sodium sulfate and concentrated in vacuo to give the title compound as a white solid (4.46 g): MS: (+) m/z 337.80, 329.93, 331.93 (M+1, $^{79}$Br/$^{81}$Br).

b) 2-Bromo-4-{[(2,4-dimethoxy-benzyl)-ethoxycarbonylmethyl-amino]-methyl}-thiazole-5-carboxylic acid ethyl ester A mixture of 2-bromo-4-bromomethyl-thiazole-5-carboxylic acid ethyl ester (3.57 g, 10.91 mmol), (2,4-dimethoxy-benzylamino)-acetic acid ethyl ester (2.76 g, 10.91 mmol) and potassium carbonate (2.26 g, 16.36 mmol)

in anhydrous dimethylformamide (25 mL) was stirred at room temperature for 17 h before it was quenched with water, extracted with ethyl acetate. The organic layer was washed with water, brine, dried over anhydrous sodium sulfate and concentrated in vacuo. The residue was purified by flash column chromatography on silica gel with a gradient of ethyl acetate and hexanes to give the title compound as a yellow oil (5.27 g): MS: (+) m/z 523.11, 525.04 (M+Na+, $^{79}$Br/$^{81}$Br).

c) 4-{[(2,4-Dimethoxy-benzyl)-ethoxycarbonylmethyl-amino]-methyl}-2-pyridin-2-yl-thiazole-5-carboxylic acid ethyl ester A mixture of 2-bromo-4-{[(2,4-dimethoxy-benzyl)-ethoxycarbonylmethyl-amino]-methyl}-thiazole-5-carboxylic acid ethyl ester (747 mg, 1.49 mmol), tetrabutyltin (717 μL, 2.24 mmol) and bis(triphenylphosphine)palladium(II) dichloride (105 mg, 0.15 mmol) in dimethylformamide (6 mL) was stirred at 130° C. for 5 h before it was cooled to room temperature, quenched with water, filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and hexanes to give the title compound as a white solid (405 mg): MS: (+) m/z 522.27 (M+Na+).

d) 7-Hydroxy-2-pyridin-2-yl-thiazolo[4,5-c]pyridine-6-carboxylic acid ethyl ester A yellow solution of 4-{[(2,4-dimethoxy-benzyl)-ethoxycarbonylmethyl-amino]-methyl}-2-pyridin-2-yl-thiazole-5-carboxylic acid ethyl ester (506 mg, 1.01 mmol) in THF (6 mL) was added 1 M KO$^t$Bu in THF (2.2 mL, 2.22 mmol) at −78° C. The mixture was stirred at −78° C. for 20 min, warmed to room temperature and stirred at that temperature for 2 h before it was quenched with water, extracted with ethyl acetate. The organic layer was washed with water, brine, dried over anhydrous sodium sulfate and concentrated in vacuo to give a yellow oil (306.6 mg). It was dissolved in dichloromethane (4 mL) and 2M thionyl chloride in dichloromethane (4 mL) was added. The mixture was stirred at room temperature for 2 h before it was concentrated in vacuo. The residue was partitioned between ethyl acetate and saturated aqueous sodium bicarbonate. The organic layer was washed with brine, dried over anhydrous sodium sulfate and concentrated in vacuo. The residue was purified by flash column chromatography on silica gel with a gradient of ethyl acetate and dichloromethane to give the title compound as a yellow solid (83 mg): MS: (−) m/z 300.20 (M−1).

e) [(7-Hydroxy-2-pyridin-2-yl-thiazolo[4,5-c]pyridine-6-carbonyl)-amino]-acetic acid A mixture of 7-hydroxy-2-pyridin-2-yl-thiazolo[4,5-c]pyridine-6-carboxylic acid ethyl ester (43 mg, 0.14 mmol) and glycine (214 mg, 2.86 mmol) in 0.5 M sodium methoxide/methanol (5.4 mL, 1.29 mmol) was refluxed for 2 days before it was cooled to room temperature and concentrated in vacuo. The residue was dissolved in water and extracted with methyl tert-butyl ether (2×25 mL). The remaining aqueous layer was acidified to pH=3 with 1N HCl (4 mL). The precipitate was filtered, washed with water and dried in vacuo to give the title compound as a white solid (35 mg): $^1$H NMR (DMSO-d$_6$, 200 MHz): δ=13.16 (br s, 1H), 9.47 (br s, 1H), 8.92 (s, 1H), 8.75 (d, J=4.3 Hz, 1H), 8.32 (d, J=7.8, 1H), 8.05 (m, 1H), 7.65 (m, 1H), 4.03 (d, J=6.3 Hz, 2H); MS: (+) m/z 331.00 (M+1); (−) m/z 329.00 (M−1).

Example 59

{[2-(4-Fluoro-phenyl)-7-hydroxy-4-methyl-thiazolo[4,5-c]pyridine-6-carbonyl]-amino}-acetic acid a) 4-Bromo-2-(4-fluoro-phenyl)-7-hydroxy-thiazolo[4,5-c]pyridine-6-carboxylic acid ethyl ester A mixture of 2-(4-fluoro-phenyl)-7-hydroxy-thiazolo[4,5-c]pyridine-6-carboxylic acid ethyl ester (547 mg, 1.72 mmol), N-bromosuccinimide (321 mg, 1.80 mmol) and benzoyl peroxide (21 mg, 0.08 mmol) in carbon tetrachloride (10 mL) was refluxed for 5 h before it was cooled to room temperature and partitioned between dichloromethane and water. The organic layer was washed with saturated aqueous sodium bicarbonate solution, brine, dried over anhydrous sodium sulfate and concentrated in vacuo. The residue was purified by flash column chromatography on silica gel with a gradient of ethyl acetate and dichloromethane to give the title compound as a white solid (300 mg): MS: (−) m/z 395.07, 396.93 (M−1, $^{79}$Br/$^{81}$Br).

b) 2-(4-Fluoro-phenyl)-7-hydroxy-4-methyl-thiazolo[4,5-c]pyridine-6-carboxylic acid ethyl ester A mixture of 4-bromo-2-(4-fluoro-phenyl)-7-hydroxy-thiazolo[4,5-c]pyridine-6-carboxylic acid ethyl ester (140 mg, 0.35 mmol), tetramethyltin (98 μL, 0.70 mmol) and bis(triphenylphosphine)palladium(II) dichloride (25 mg, 0.03 mmol) in dimethylformamide (2.5 mL) was stirred at 130° C. for 45 min before it was cooled to room temperature, quenched with water, filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and hexanes to give the title compound as a white solid (66 mg): MS: (+) m/z 333.0 (M+1).

c) {[2-(4-Fluoro-phenyl)-7-hydroxy-4-methyl-thiazolo[4,5-c]pyridine-6-carbonyl]-amino}-acetic acid A mixture of 2-(4-fluoro-phenyl)-7-hydroxy-4-methyl-thiazolo[4,5-c]pyridine-6-carboxylic acid ethyl ester (70 mg, 0.21 mmol) and glycine (317 mg, 4.23 mmol) in 0.5 M sodium methoxide/methanol (8 mL) was refluxed for four days before it was cooled to room temperature and concentrated in vacuo. The residue was dissolved in water (25 mL) and extracted twice with dichloromethane. The remaining aqueous layer was acidified to pH=3 with 1N HCl (6 mL). The solid precipitate was filtered, washed with water and dried in vacuo to give the title compound as a white solid (62 mg): $^1$H NMR (DMSO-d$_6$, 200 MHz): δ=13.01 (br s, 1H), 9.22 (br s, 1H), 8.20 (m, 2H), 7.40 (m, 2H), 4.03 (d, J=5.9 Hz, 2H), 2.86 (s, 3H); MS: (+) m/z 361.87 (M+1).

Example 60

[(7-Hydroxy-2-phenyl-4-propyl-thiazolo[4,5-c]pyridine-6-carbonyl)-amino]-acetic acid a) 7-Hydroxy-2-phenyl-4-propyl-thiazolo[4,5-c]pyridine-6-carboxylic acid ethyl ester A mixture of 4-bromo-7-hydroxy-2-phenyl-thiazolo[4,5-c]pyridine-6-carboxylic acid ethyl ester (152 mg, 0.40 mmol), tetra-n-propyltin (211 μL, 0.80 mmol) and bis(triphenylphosphine)-palladium(II) dichloride (28 mg, 0.04 mmol) in dimethylformamide (2.5 mL) was stirred at 130° C. for 1 h before it was cooled to room temperature, quenched with water, filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and hexanes to give the title compound as a white solid (79 mg): MS: (+) m/z 343.00 (M+1), MS: (−) m/z 341.00 (M−1).

b) [(7-Hydroxy-2-phenyl-4-propyl-thiazolo[4,5-c]pyridine-6-carbonyl)-amino]-acetic acid A mixture of 7-hydroxy-2-phenyl-4-propyl-thiazolo[4,5-c]pyridine-6-carboxylic acid ethyl ester (78 mg, 0.23 mmol) and glycine (343 mg, 4.57 mmol) in 0.5 M sodium methoxide/methanol (8.6 mL) was refluxed for three days before it was cooled to room temperature and concentrated in vacuo. The residue was dissolved in water (30 mL) and extracted three times with methyl t-butyl ether. The remaining aqueous layer was acidified to pH=3 with 1N HCl (6 mL). The solid precipitate was filtered, washed with water and dried in vacuo to give the title compound as a white solid (70 mg): $^1$H NMR (DMSO-$d_6$, 200 MHz): δ=13.02 (br s, 1H), 9.21 (br s, 1H), 8.17 (m, 2H), 7.65 (m, 3H), 4.06 (d, J=6.2 Hz, 2H), 3.33 (m, 2H), 1.92 (m, 2H), 1.04 (t, J=7.0 Hz, 3H); MS: (+) m/z 371.93 (M+1).

Example 61

{[7-Hydroxy-2-(4-phenoxy-phenyl)-thiazolo[4,5-c]pyridine-6-carbonyl]-amino}-acetic acid a) 4-Methyl-2-(4-phenoxy-phenyl)-thiazole-5-carboxylic acid ethyl ester

A mixture of 4-phenoxy-thiobenzamide (1.02 g, 4.43 mmole) and 2-chloro-3-oxo-butyric acid ethyl ester (625 μl, 4.52 mmole) in ethanol (15 ml) was refluxed for 18 h before it was cooled to room temperature and concentrated in vacuo. It was partitioned between ethyl acetate and saturated sodium bicarbonate, the organic layer was washed with brine, dried over anhydrous sodium sulfate and concentrated in vacuo to give the title compound as a yellow solid (1.41 g). MS: (+) m/z 340.07 (M+1).

b) 4-Bromomethyl-2-(4-phenoxy-phenyl)-thiazole-5-carboxylic acid ethyl ester A mixture of 4-methyl-2-(4-phenoxy-phenyl)-thiazole-5-carboxylic acid ethyl ester (1.40 g, 4.14 mmole), N-bromosuccinimide (760 mg, 4.27 mole) and benzoyl peroxide (50 mg, 0.21 mmole) in carbon tetrachloride (18 ml) was refluxed for 8 h before it was cooled to room temperature and partitioned between dichloromethane and water. The organic layer was washed with saturated aqueous sodium bicarbonate solution, brine, dried over anhydrous sodium sulfate and concentrated in vacuo to give the title compound as a yellow oil (1.69 g). MS: (+) m/z 417.87, 419.87 (M+1, $^{79}$Br/$^{81}$Br).

c) 4-{[(2,4-Dimethoxy-benzyl)-ethoxycarbonylmethyl-amino]-methyl}-2-(4-phenoxy-phenyl)-thiazole-5-carboxylic acid ethyl ester A mixture of 4-bromomethyl-2-(4-phenoxy-phenyl)-thiazole-5-carboxylic acid ethyl ester (1.12 g, 2.68 mmole), (2,4-dimethoxy-benzylamino)-acetic acid ethyl ester (737 mg, 2.90 mmole) and potassium carbonate (555 mg, 4.03 mmole) in anhydrous dimethylformamide (8 ml) was stirred at room temperature for 20 h before it was quenched with water, extracted with ethyl acetate. The organic layer was washed with water, brine, dried over anhydrous sodium sulfate and concentrated in vacuo. The residue was purified by flash column chromatography on silica gel with a gradient of ethyl acetate and hexanes to give the title compound as a yellow oil (1.20 g). MS: (+) m/z 613.07 (M+Na$^+$).

d) 7-Hydroxy-2-(4-phenoxy-phenyl)-thiazolo[4,5-c]pyridine-6-carboxylic acid ethyl ester A solution of 4-{[(2,4-dimethoxy-benzyl)-ethoxycarbonylmethyl-amino]-methyl}-2-(4-phenoxy-phenyl)-thiazole-5-carboxylic acid ethyl ester (1.17 g, 1.99 mmole) in THF (8 ml) was added 1 M KO$^t$Bu in THF (4.4 ml, 4.38 mmole) at −78° C. The mixture was stirred at −78° C. for 20 min, warmed to room temperature and stirred at that temperature for 2 h before it was quenched with aqueous ammonium chloride, extracted with ethyl acetate. The organic layer was washed with water, brine, dried over anhydrous sodium sulfate and concentrated in vacuo to give a yellow oil (953 mg). It was dissolved in dichloromethane (5 ml) and thionyl chloride (255 μl) was added. The mixture was stirred at room temperature for 4 h before it was quenched with saturated sodium bicarbonate, extracted with dichloromethane. The organic layer was washed with water, brine, dried over anhydrous sodium sulfate and concentrated in vacuo. The residue was purified by flash column chromatography on silica gel with a gradient of ethyl acetate and dichloromethane to give the title compound as a yellow solid (207 mg). MS: (+) m/z 392.87 (M+1).

e) {[7-Hydroxy-2-(4-phenoxy-phenyl)-thiazolo[4,5-c]pyridine-6-carbonyl]-amino}-acetic acid A mixture of 7-hydroxy-2-(4-phenoxy-phenyl)-thiazolo[4,5-c]pyridine-6-carboxylic acid ethyl ester (75 mg, 0.19 mmole) and glycine (286 mg, 3.81 mmole) in 0.5 M sodium methoxide/methanol (7.2 ml) was refluxed for three days before it was cooled to room temperature and concentrated in vacuo. Water (75 ml) was added and pH was adjusted to 10 with 1N HCl (2 ml). The mixture was extracted with methyl tert-butyl ether (2×30 ml) and dichloromethane (30 ml). The remaining aqueous layer was acidified to pH=3 with 1N HCl (3 ml). The solid precipitate was filtered, washed with water and dried in vacuo to give the title compound as a white solid (55 mg). $^1$H NMR (DMSO-$d_6$, 200 MHz): δ=9.45 (br s, 1H), 8.87 (s, 1H), 8.17 (m, 2H), 7.47 (m, 2H), 7.17 (m, 5H), 4.03 (d, J=6.3 Hz, 2H); MS: (+) m/z 421.07 (M+1). (−) m/z 419.87 (M−1).

Example 62

[(4-Cyano-7-hydroxy-2-phenyl-thiazolo[4,5-c]pyridine-6-carbonyl)-amino]-acetic acid a) 4-Cyano-7-hydroxy-2-phenyl-thiazolo[4,5-c]pyridine-6-carboxylic acid ethyl ester A mixture of 4-bromo-7-hydroxy-2-phenyl-thiazolo[4,5-c]pyridine-6-carboxylic acid ethyl ester (124 mg, 0.33 mmole), tris(dibenzylideneacetone)dipalladium(0)(15 mg, 0.02 mmole), 1,1'-bis(diphenylphosphino)ferrocene (18 mg, 0.03 mmole), zinc cyanide (23 mg, 0.20 mmole) and zinc (3 mg, 0.04 mmole) in dimethylacetamide (0.65 ml) was stirred at 120° C. for 4 h and twenty minutes before it was cooled to room temperature, quenched with water, filtered. The filtrate was partitioned between chloroform/isopropanol (3:1) and water. The organic layer was washed with brine, dried over anhydrous sodium sulfate and concentrated in vacuo. The residue was purified by flash column chromatography on silica gel with a gradient of methanol and dichloromethane to give the title compound as a white solid (41 mg). MS: (+) m/z 325.87 (M+1), MS: (−) m/z 324.00 (M−1), b) [(4-Cyano-7-hydroxy-2-phenyl-thiazolo[4,5-c]pyridine-6-carbonyl)-amino]-acetic acid A mixture of 4-cyano-7-hydroxy-2-phenyl-thiazolo[4,5-c]pyridine-6-carboxylic acid ethyl ester (39 mg, 0.12 mmole) and glycine (182 mg, 2.41 mmole) in 0.5 M sodium methoxide/methanol (4.6 ml) was refluxed for 28 hours before it was cooled to room temperature and concentrated in vacuo. The residue was dissolved in water (15 ml) and extracted twice with methyl tert-butyl ether. The remaining aqueous layer was acidified to pH=3 with 1N HCl (3.5 ml). The solid precipitate was filtered, washed with water and dried in vacuo to give the title compound as a yellow solid (34 mg). $^1$H NMR (DMSO-$d_6$, 200 MHz): δ=9.73 (br s, 1H), 8.20 (m, 2H), 7.66 (m, 3H), 4.02 (d, J=6.2 Hz, 2H); MS: (−) m/z 352.82 (M−1).

Example 63

[(7-Hydroxy-4-isobutyl-2-phenyl-thiazolo[4,5-c]pyridine-6-carbonyl)-amino]-acetic acid a) 7-Hydroxy-4-(2-methyl-allyl)-2-phenyl-thiazolo[4,5-c]pyridine-6-carboxylic acid ethyl ester A mixture of 4-bromo-7-hydroxy-2-phenyl-thiazolo[4,5-c]pyridine-6-carboxylic acid ethyl ester (301.5 mg, 0.80 mmole), methallyltri-n-butyltin (529 μl, 1.60 mmole) and bis(triphenylphosphine)palladium(II) dichloride (56 mg, 0.08 mmole) in dimethylformamide (4 ml) was stirred at 130° C. for 45 min before it was cooled to room temperature, quenched with water, filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and hexanes to give the title compound as a white solid (128 mg). MS: (+) m/z 355.02 (M+1).

b) 7-Hydroxy-4-isobutyl-2-phenyl-thiazolo[4,5-c]pyridine-6-carboxylic acid ethyl ester A mixture of 7-hydroxy-4-(2-methyl-allyl)-2-phenyl-thiazolo[4,5-c]pyridine-6-carboxylic acid ethyl ester (128 mg, 0.36 mmole) and 10% Pd/C (100 mg) in ethyl acetate (12 ml), ethanol (3 ml) and formic acid (15 μl) was hydrogenated at 20 psi for a week before it was filtered, concentrated and partitioned between ethyl acetate and saturated aqueous sodium bicarbonate. The sodium bicarbonate layer was washed with dichloromethane. The organic layer was combined and washed with brine, dried over anhydrous sodium sulfate and concentrated in vacuo. The residue was purified by flash column chromatography on silica gel with a gradient of ethyl acetate and hexanes to give the title compound as a white solid (35 mg). MS: (+) m/z 356.96 (M+1).

c) [(7-Hydroxy-4-isobutyl-2-phenyl-thiazolo[4,5-c]pyridine-6-carbonyl)-amino]-acetic acid A mixture of 7-hydroxy-4-isobutyl-2-phenyl-thiazolo[4,5-c]pyridine-6-carboxylic acid ethyl ester (35 mg, 0.10 mmole) and glycine (146 mg, 1.95 mmole) in 0.5 M sodium methoxide/methanol (3.7 ml) was refluxed for 4 days before it was cooled to room temperature and concentrated in vacuo. The residue was dissolved in water (12 ml) and extracted three times with methyl t-butyl ether. The remaining aqueous layer was acidified to pH=3 with 1N HCl (2.5 ml). The solid precipitate was filtered, washed with water and dried in vacuo to give the title compound as a white solid (30 mg). $^1$H NMR (DMSO-$d_6$, 200 MHz): δ=9.18 (br s, 1H), 8.15 (m, 2H), 7.62 (m, 3H), 4.02 (d, J=5.9 Hz, 2H), 3.12 (d, 2H, J=7.4 Hz), 2.41 (m, 1H), 0.93 (d, 2H, J=6.6 Hz); MS: (+) m/z 385.98 (M+1); (−) m/z 383.99 (M−1)

Example 64

{[7-Hydroxy-2-(3-methoxy-phenyl)-thiazolo[4,5-c]pyridine-6-carbonyl]-amino}-acetic acid a) 2-(3-Methoxy-phenyl)-4-methyl-thiazole-5-carboxylic acid ethyl ester A mixture of 3-methoxy-thiobenzamide (1.99 g, 11.88 mmole) and 2-chloro-3-oxo-butyric acid ethyl ester (1.7 ml, 12.11 mmole) in ethanol (20 ml) was refluxed for 18 h before it was cooled to room temperature and concentrated in vacuo. It was partitioned between ethyl acetate and saturated sodium bicarbonate, the organic layer was washed with brine, dried over anhydrous sodium sulfate and concentrated in vacuo to give the title compound as a yellow solid (3.02 g). MS: (+) m/z 277.93 (M+1).

b) 4-Bromomethyl-2-(3-methoxy-phenyl)-thiazole-5-carboxylic acid ethyl ester

A mixture of 2-(3-methoxy-phenyl)-4-methyl-thiazole-5-carboxylic acid ethyl ester (3.01 g, 10.88 mmole), N-bromosuccinimide (2.03 g, 11.42 mole) and benzoyl peroxide (132 mg, 0.54 mmole) in carbon tetrachloride (40 ml) was refluxed for 16 h before it was cooled to room temperature and partitioned between dichloromethane and water. The organic layer was washed with saturated aqueous sodium bicarbonate solution, brine, dried over anhydrous sodium sulfate and concentrated in vacuo to give the title compound as a yellow solid (3.66 g). MS: (+) m/z 355.92, 357.92 (M+1, $^{79}$Br/$^{81}$Br).

c) 4-{[(2,4-Dimethoxy-benzyl)-ethoxycarbonylmethyl-amino]-methyl}-2-(3-methoxy-phenyl)-thiazole-5-carboxylic acid ethyl ester A mixture of 4-bromomethyl-2-(3-methoxy-phenyl)-thiazole-5-carboxylic acid ethyl ester (2.03 g, 5.71 mmole), (2,4-dimethoxy-benzylamino)-acetic acid ethyl ester (1.45 g, 5.71 mmole) and potassium carbonate (1.18 g, 8.56 mmole) in anhydrous dimethylformamide (18 ml) was stirred at room temperature for 16 h before it was quenched with water, extracted with ethyl acetate. The organic layer was washed with water, brine, dried over anhydrous sodium sulfate and concentrated in vacuo. The residue was purified by flash column chromatography on silica gel with a gradient of ethyl acetate and hexanes to give the title compound as a yellow oil (2.31 g). MS: (+) m/z 551.13 (M+Na$^+$).

d) 7-Hydroxy-2-(3-methoxy-phenyl)-thiazolo[4,5-c] pyridine-6-carboxylic acid ethyl ester A solution of 4-{[(2,4-dimethoxy-benzyl)-ethoxycarbonylmethyl-amino]-methyl}-2-(3-methoxy-phenyl)-thiazole-5-carboxylic acid ethyl ester (2.23 g, 4.22 mmole) in THF (12.6 ml) was added 1 M KO$^t$Bu in THF (8.4 ml, 8.43 mmole) at −78° C. The mixture was stirred at −78° C. for 20 min, warmed to room temperature and stirred at that temperature for 2 h before it was quenched with aqueous ammonium chloride, extracted with ethyl acetate. The organic layer was washed with water, brine, dried over anhydrous sodium sulfate and concentrated in vacuo to give a yellow oil (1.85 g). It was dissolved in dichloromethane (8 ml) and thionyl chloride (421 µl) was added. The mixture was stirred at room temperature for 3 h before the precipitate was filtered, washed with cold dichloromethane (2 ml) and cold ethyl acetate/hexanes (1:1, 20 ml) and dried to give the title compound as a yellow solid (1.16 mg). MS: (+) m/z 331.48 (M+1).

e) {[7-Hydroxy-2-(3-methoxy-phenyl)-thiazolo[4,5-c]pyridine-6-carbonyl]-amino}-acetic acid A mixture of 7-hydroxy-2-(3-methoxy-phenyl)-thiazolo[4,5-c]pyridine-6-carboxylic acid ethyl ester (129 mg, 0.39 mmole) and glycine (588 mg, 7.83 mmole) in 0.5 M sodium methoxide/methanol (14.8 ml) was refluxed for 3 days before it was cooled to room temperature and concentrated in vacuo. It was dissolved in water (50 ml) and extracted twice with methyl t-butyl ether. The remaining aqueous layer was acidified to pH=3 with 1N HCl (9 ml). The solid precipitate was filtered, washed with water and dried in vacuo to give the title compound as a white solid (122 mg). $^1$H NMR (DMSO-d$_6$, 200 MHz): δ=9.48 (br s, 1H), 8.89 (s, 1H), 7.69 (m, 2H), 7.51 (m, 1H), 7.22 (m, 1H). 4.02 (d, J=6.2 Hz, 2H), 3.86 (s, 3H); MS: (+) m/z 359.90 (M+1); (−) m/z 357.92 (M−1).

Example 65

[(4-Furan-2-yl-7-hydroxy-2-phenyl-thiazolo[4,5-c]pyridine-6-carbonyl)-amino]-acetic acid a) 4-Furan-2-yl-7-hydroxy-2-phenyl-thiazolo[4,5-c]pyridine-6-carboxylic acid ethyl ester A mixture of 4-bromo-7-hydroxy-2-phenyl-thiazolo[4,5-c]pyridine-6-carboxylic acid ethyl ester (248 mg, 0.66 mmole), 2-(tributylstannyl)furan (414 µl, 1.31 mmole) and bis(triphenylphosphine)-palladium(II) dichloride (46 mg, 0.06 mmole) in dimethylformamide (2.5 ml) was stirred at 130° C. for 25 min before it was cooled to room temperature, quenched with water, filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and hexanes to give the title compound as a white solid (140 mg). MS: (+) m/z 367.00 (M+1).

b) [(4-Furan-2-yl-7-hydroxy-2-phenyl-thiazolo[4,5-c]pyridine-6-carbonyl)-amino]-acetic acid A mixture of 4-furan-2-yl-7-hydroxy-2-phenyl-thiazolo[4,5-c]pyridine-6-carboxylic acid ethyl ester (78 mg, 0.21 mmole) and glycine (320 mg, 4.26 mmoles) in 0.5 M sodium methoxide/methanol (8.1 ml) was refluxed for 4 days before it was cooled to room temperature and concentrated in vacuo. Water (100 ml) and 0.1 N HCl (2.5 ml) were added to the residue and the suspension was extracted with dichloromethane (3×50 ml) and methyl tert-butyl ether (1×50 ml). The resulting yellow-green aqueous solution was acidified to pH=2 with 0.1 N HCl (3.5 ml). The resulting suspension was extracted with dichloromethane, washed with brine, dried over sodium sulfate and concentrated in vacuo to give the title compound as a yellow solid (44 mg). $^1$H NMR (DMSO-d$_6$, 200 MHz): δ=9.17 (t, 1H), 8.25 (m, 2H), 7.94 (m, 1H), 7.82 (m, 1H), 7.64 (m, 3H), 6.76 (m, 1H), 4.08 (d, J=6.2 Hz, 2H); MS: (+) m/z 395.94 (M+1), (−) m/z 393.94 (M−1).

Example 66

[(7-Hydroxy-2-phenyl-4-thiazol-2-yl-thiazolo[4,5-c]pyridine-6-carbonyl)-amino]-acetic acid a) 7-Hydroxy-2-phenyl-4-thiazol-2-yl-thiazolo[4,5-c]pyridine-6-carboxylic acid ethyl ester A mixture of 4-bromo-7-hydroxy-2-phenyl-thiazolo[4,5-c]pyridine-6-carboxylic acid ethyl ester (246 mg, 0.65 mmole), 2-(tributylstannyl)thiazole (410 µl, 1.30 mmole) and bis(triphenylphosphine)-palladium(II) dichloride (46 mg, 0.06 mmole) in dimethylformamide (3 ml) was stirred at 130° C. for one hour before it was cooled to room temperature, quenched with water, filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and hexanes. Fractions containing the title compound was concentrated and repurified by preparative TLC with a gradient of methanol, dichloromethane and acetic acid to give the title compound as a yellow solid (29 mg). MS: (+) m/z 383.87 (M+1), m/z 406.00 (M+Na$^+$).

b) [(7-Hydroxy-2-phenyl-4-thiazol-2-yl-thiazolo[4,5-c]pyridine-6-carbonyl)-amino]-acetic acid A mixture of 7-hydroxy-2-phenyl-4-thiazol-2-yl-thiazolo[4,5-c]pyridine-6-carboxylic acid ethyl ester (25 mg, 0.06 mmole) and glycine (96 mg, 1.28 mmole) in 0.5 M sodium methoxide/methanol (2.4 ml) was refluxed for 3 days before it was cooled to room temperature and concentrated in vacuo. It was dissolved in water (25 ml) and extracted with dichloromethane (2×50 ml). The remaining aqueous solution was acidified to pH=2 with 0.1 N HCl (1.8 ml). The resulting suspension was extracted with isopropanol/chloroform (50 ml, 1:3) dichloromethane, washed with brine, dried over sodium sulfate and concentrated in vacuo to give a yellow solid which was further purified by MPLC on a C18 column with a gradient of formic acid, acetonitrile and water to give the title compound as a yellow solid (8 mg). $^1$H NMR (DMSO-d$_6$, 200 MHz): δ=8.21 (m, 2H), 8.01 (m, 1H), 7.89 (m, 1H), 7.63 (m, 3H), 6.51 (m, 1H), 4.10 (d, J=5.4 Hz, 2H); MS: (+) m/z 413.22 (M+1).

Example 67

{[7-Hydroxy-2-(2-methoxy-phenyl)-thiazolo[4,5-c]pyridine-6-carbonyl]-amino}-acetic acid a) 2-Bromo-4-bromomethyl-thiazole-5-carboxylic acid ethyl ester

A mixture of 2-Bromo-4-methyl-thiazole-5-carboxylic acid ethyl ester (5.67 g, 22.68 mmole), N-bromosuccinimide (4.44 g, 24.95 mmole) and benzoyl peroxide (275 mg, 1.13 mmole) in carbon tetrachloride (25 ml) was refluxed for 16 h before it was cooled to room temperature and partitioned between dichloromethane and water, the organic layer was washed with saturated aqueous sodium bicarbonate solution, brine, dried over anhydrous sodium sulfate and concentrated in vacuo to give the title compound as a white solid (4.46 g): MS: (+) m/z 337.80, 329.93, 331.93 (M+1, $^{79}$Br/$^{81}$Br).

b) 2-Bromo-4-{[(2,4-dimethoxy-benzyl)-ethoxycarbonylmethyl-amino]-methyl}-thiazole-5-carboxylic acid ethyl ester A mixture of 2-bromo-4-bromomethyl-thiazole-5-carboxylic acid ethyl ester (3.57 g, 10.91 mmole), (2,4-dimethoxy-benzylamino)-acetic acid ethyl ester (2.76 g, 10.91 mmole) and potassium carbonate (2.26 g, 16.36 mmole) in anhydrous dimethylformamide (25 ml) was stirred at room temperature for 17 h before it was quenched with water, extracted with ethyl acetate. The organic layer was washed with water, brine, dried over anhydrous sodium sulfate and concentrated in vacuo. The residue was purified by flash column chromatography on silica gel with a gradient of ethyl acetate and hexanes to give the title compound as a yellow oil (5.27 g): MS: (+) m/z 523.11, 525.04 (M+Na$^+$, $^{79}$Br/$^{81}$Br)

c) 4-{[(2,4-Dimethoxy-benzyl)-ethoxycarbonylmethyl-amino]-methyl}-2-(2-methoxy-phenyl)-thiazole-5-carboxylic acid ethyl ester A mixture of 2-bromo-4-{[(2,4-dimethoxy-benzyl)-ethoxycarbonylmethyl-amino]-methyl}-thiazole-5-carboxylic acid ethyl ester (747 mg, 1.49 mmole), 2-methoxyphenylboronic acid (663.3 mg, 4.36 mmole), cesium carbonate (2.13 g, 4.76 mmole) and tetrakis(triphenylphosphine)palladium (252 mg, 0.16 mmole) in dioxane (7 ml) was refluxed for 5 h before it was cooled to room temperature, quenched with water and filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and hexanes to give the title compound as a yellow oil (1.07 g). MS: (+) m/z 551.20 (M+Na$^+$)

d) 7-Hydroxy-2-(2-methoxy-phenyl)-thiazolo[4,5-c]pyridine-6-carboxylic acid ethyl ester A yellow solution of 4-{[(2,4-dimethoxy-benzyl)-ethoxycarbonylmethyl-amino]-methyl}-2-(2-methoxy-phenyl)-thiazole-5-carboxylic acid ethyl ester (1.07 g, 2.02 mmole) in THF (6 ml) was added 1 M KO$^t$Bu in THF (4 ml, 4.05 mmole) at −78° C. The mixture was stirred at −78° C. for 20 min, warmed to room temperature and stirred at that temperature for 2 h before it was quenched with water, extracted with ethyl acetate. The organic layer was washed with water, brine, dried over anhydrous sodium sulfate and concentrated in vacuo to give a yellow foam (790 mg). It was dissolved in dichloromethane (4 ml) and thionyl chloride (179 µl) was added. The mixture was stirred at room temperature for 3 h before it was filtered, washed with dichloromethane (1 ml), cold ethyl acetate/hexanes (1:1, 20 ml) and dried to give the title compound as a yellow solid (83 mg). MS: (+) m/z 331.26 (M+1).

e) {[7-Hydroxy-2-(2-methoxy-phenyl)-thiazolo[4,5-c]pyridine-6-carbonyl]-amino}-acetic acid A mixture of 7-hydroxy-2-(2-methoxy-phenyl)-thiazolo[4,5-c]pyridine-6-carboxylic acid ethyl ester (120 mg, 0.36 mmole) and glycine (546 mg, 7.27 mmole) in 0.5 M sodium methoxide/methanol (13.8 ml, 6.91 mmole) was refluxed for 3 days before it was cooled to room temperature and concentrated in vacuo. The residue was dissolved in water (25 ml) and extracted with methyl tert-butyl ether (2×25 ml). The remaining aqueous layer was acidified to pH=3 with 1N HCl (9 ml). The resulting jelly was extracted with dichloromethane and ethyl acetate. The organic layer was combined, washed with brine and dried in vacuo to give the title compound as a yellow solid (94 mg): $^1$H NMR (DMSO-d$_6$, 200 MHz): δ=9.39 (br s, 1H), 8.88 (s, 1H), 8.45 (d, 1H), 7.62 (m, 1H), 7.33 (d, 1H), 7.18 (t, 1H), 4.01 (s, 3H), 4.03 (d, 2H); MS: (+) m/z 360.25 (M+1).

Example 68

[(7-Hydroxy-4-methyl-2-phenyl-thiazolo[5,4-c]pyridine-6-carbonyl)-amino]-acetic acid a) 4-Bromo-7-hydroxy-2-phenyl-thiazolo[5,4-c]pyridine-6-carboxylic acid ethyl ester A mixture of 7-hydroxy-2-phenyl-thiazolo[5,4-c]pyridine-6-carboxylic acid ethyl ester (2.10 g, 7.01 mmole), N-bromosuccinimide (1.31 g, 7.36 mmole) and benzoyl peroxide (84.9 mg, 0.35 mmole) in carbon tetrachloride (40 ml) was refluxed for 2 h before it was cooled to room temperature and partitioned between dichloromethane and water. The organic layer was washed with saturated aqueous sodium bicarbonate solution, brine, dried over anhydrous sodium sulfate and concentrated in vacuo. The residue was purified by flash column chromatography on silica gel with a gradient of ethyl acetate and dichloromethane to give the title compound as a white solid (1.89 g). MS: (+) m/z 379.18, 381.18 (M+1, $^{79}$Br/$^{81}$Br).

b) 7-Hydroxy-4-methyl-2-phenyl-thiazolo[5,4-c]pyridine-6-carboxylic acid ethyl ester A mixture of 4-bromo-7-hydroxy-2-phenyl-thiazolo[5,4-c]pyridine-6-carboxylic acid ethyl ester (217 mg, 0.80 mmole), tetramethyltin (318 µl, 2.30 mmole) and bis(triphenylphosphine)palladium(II) dichloride (52 mg, 0.07 mmole) in dimethylformamide (3 ml) was stirred at 130° C. for 100 min before it was cooled to room temperature, quenched with water, filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and hexanes to give the title compound as a yellow solid (105 mg). MS: (+) m/z 315.29 (M+1)

c) [(7-Hydroxy-4-methyl-2-phenyl-thiazolo[5,4-c]pyridine-6-carbonyl)-amino]-acetic acid A mixture of 7-hydroxy-4-methyl-2-phenyl-thiazolo[5,4-c]pyridine-6-carboxylic acid ethyl ester (105 mg, 0.33 mmole) and glycine (500 mg, 6.65 mmole) in 0.5 M sodium methoxide/methanol (12.6 ml) was refluxed for 3 days before it was cooled to room temperature and concentrated in vacuo. The residue was dissolved in water (30 ml) and extracted twice with methyl t-butyl ether. The remaining aqueous layer was acidified to pH=3 with 1N HCl (9 ml). The resulting precipitate was filtered, washed with water and dried in vacuo to give the title compound as a yellow solid (25 mg): $^1$H NMR (DMSO-d$_6$, 200 MHz): δ=13.08 (br s, 1H), 9.22 (t, 1H), 8.13 (m, 2H), 7.61 (m, 3H), 4.02 (d, J=6.2 Hz, 2H), 2.72 (s, 3H); MS: (+) m/z 344.26 (M+1).

Example 69

{[2-(4-Cyano-phenyl)-7-hydroxy-thiazolo[4,5-c]pyridine-6-carbonyl]-amino}-acetic acid a) 2-(4-Cyano-phenyl)-4-{[(2,4-dimethoxy-benzyl)-ethoxycarbonylmethyl-amino]-methyl}-thiazole-5-carboxylic acid ethyl ester A mixture of 2-bromo-4-{[(2,4-dimethoxy-benzyl)-ethoxycarbonylmethyl-amino]-methyl}-thiazole-5-carboxylic acid ethyl ester (1.19 g, 2.39 mmole), 4-cyanophenylboronic acid (702 mg, 4.77 mmole), cesium carbonate (2.33 g, 7.16 mmole) and tetrakis(triphenylphosphine)palladium (221 mg, 0.19 mmole) in dioxane (8 ml) was refluxed for 18 h before it was cooled to room temperature, quenched with water and filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and hexanes to give the title compound as a yellow oil (448 mg). MS: (+) m/z 524.30 (M+H$^+$)

b) 2-(4-Cyano-phenyl)-7-hydroxy-thiazolo[4,5-c]pyridine-6-carboxylic acid ethyl ester A yellow solution of 2-(4-cyano-phenyl)-4-{[(2,4-dimethoxy-benzyl)-ethoxycarbonylmethyl-amino]-methyl}-thiazole-5-carboxylic acid ethyl ester (448 mg, 0.86 mmole) in THF (2.6 ml) was added 1 M KO$^t$Bu in THF (1.7 ml, 1.71 mmole) at −78° C. The mixture was stirred at −78° C. for 20 min, warmed to room temperature and stirred at that temperature for 80 min before it was quenched with water, extracted with ethyl acetate. The organic layer was washed with water, brine, dried over anhydrous sodium sulfate and concentrated in vacuo to give a yellow foam (326 mg). It was dissolved in dichloromethane (2 ml) and thionyl chloride (85 μl) was added. The mixture was stirred at room temperature for 3 h before it was filtered, washed with ethyl acetate/hexanes (1:1, 15 ml) and dried to give the title compound as a yellow solid (200 mg). MS: (+) m/z 326.28 (M+1), MS: (−) m/z 324.24 (M−1), c) {[2-(4-Cyano-phenyl)-7-hydroxy-thiazolo[4,5-c]pyridine-6-carbonyl]-amino}-acetic acid A mixture of 2-(4-cyano-phenyl)-7-hydroxy-thiazolo[4,5-c]pyridine-6-carboxylic acid ethyl ester (111 mg, 0.34 mmole) and glycine (512 mg, 6.82 mmole) in 0.5 M sodium methoxide/methanol (13 ml, 6.48 mmole) was refluxed for 45 h before it was cooled to room temperature and concentrated in vacuo. The residue was dissolved in water (35 ml) and extracted with methyl tert-butyl ether (2×25 ml). The remaining aqueous layer was acidified to pH=3 with 1N HCl (9 ml). The suspension was extracted with chloroform/isopropanol (3:1, 35 ml). The organic suspension was concentrated, washed with water and dried in vacuo to give the title compound as a brown solid (52 mg). $^1$H NMR (DMSO-d$_6$, 200 MHz): δ=9.52 (t, 1H), 8.90 (s, 1H), 8.30 (d, 1H, J=8.2 Hz), 8.04 (d, 1H, J=8.2 Hz), 4.00 (d, 2H, J=5.8 Hz); MS: (+) m/z 355.22 (M+1).

Example 70

[(7-Hydroxy-2,4-diphenyl-thiazolo[5,4-c]pyridine-6-carbonyl)-amino]-acetic acid a) 7-Hydroxy-2,4-diphenyl-thiazolo[5,4-c]pyridine-6-carboxylic acid ethyl ester A mixture of 4-bromo-7-hydroxy-2-phenyl-thiazolo[5,4-c]pyridine-6-carboxylic acid ethyl ester (202 mg, 0.53 mmole), phenylboronic acid (130 mg, 1.07 mmole), cesium carbonate (522 mg, 1.60 mmole) and tetrakis(triphenylphosphine)palladium (62 mg, 0.05 mmole) in dioxane (2.8 ml) was refluxed for 16 h before it was cooled to room temperature, quenched with water and filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and dichloromethane to give the title compound as a yellow oil (93 mg). MS: (+) m/z 377.27 (M+H$^+$)

b) [(7-Hydroxy-2,4-diphenyl-thiazolo[5,4-c]pyridine-6-carbonyl)-amino]-acetic acid A mixture of 7-hydroxy-2,4-diphenyl-thiazolo[5,4-c]pyridine-6-carboxylic acid ethyl ester (93 mg, 0.25 mmole) and glycine (372 mg, 4.95 mmole) in 0.5 M sodium methoxide/methanol (9.4 ml) was refluxed for 4 days before it was cooled to room temperature and concentrated in vacuo. The residue was dissolved in water (50 ml) and extracted twice with methyl t-butyl ether. The remaining aqueous layer was acidified to pH=3 with 1N HCl (7 ml). The resulting precipitate was filtered, washed with water and dried in vacuo to give the title compound as a yellow solid (79 mg). $^1$H NMR (DMSO-d$_6$, 200 MHz): δ=13.28 (br s, 1H), 9.42 (t, 1H, J=6.2 Hz), 8.16 (m, 4H), 7.62 (m, 6H), 4.07 (d, 2H, J=5.8 Hz); MS: (+) m/z 406.27 (M+1).

Example 71

{[2-(3-Chloro-4-fluoro-phenyl)-7-hydroxy-thiazolo[4,5-c]pyridine-6-carbonyl]-amino}-acetic acid a) 2-(3-Chloro-4-fluoro-phenyl)-4-{[(2,4-dimethoxy-benzyl)-ethoxycarbonylmethyl-amino]-methyl}-thiazole-5-carboxylic acid ethyl ester A mixture of 2-bromo-4-{[(2,4-dimethoxy-benzyl)-ethoxycarbonylmethyl-amino]-methyl}-thiazole-5-carboxylic acid ethyl ester (1.04 g, 2.08 mmole), 3-chloro-4-fluorophenylboronic acid (726 mg, 4.16 mmole), cesium carbonate (2.04 g, 6.25 mmole) and tetrakis(triphenylphosphine)palladium (241 mg, 0.21 mmole) in dioxane (7 ml) was refluxed for 16 h before it was cooled to room temperature, quenched with water and filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and hexanes to give the title compound as a yellow oil (649 mg). MS: (+) m/z 551.26 (M+H$^+$)

b) 2-(3-Chloro-4-fluoro-phenyl)-7-hydroxy-thiazolo [4,5-c]pyridine-6-carboxylic acid ethyl ester A yellow solution of 2-(3-chloro-4-fluoro-phenyl)-4-{[(2, 4-dimethoxy-benzyl)-ethoxycarbonylmethyl-amino]-methyl}-thiazole-5-carboxylic acid ethyl ester (615 mg, 1.12 mmole) in THF (3.4 ml) was added 1 M KO$^t$Bu in THF (2.2 ml, 2.24 mmole) at −78° C. The mixture was stirred at −78° C. for 20 min, warmed to room temperature and stirred at that temperature for 2 h before it was quenched with water, extracted with ethyl acetate. The organic layer was washed with water, brine, dried over anhydrous sodium sulfate and concentrated in vacuo to give a yellow oil (523 mg). It was dissolved in dichloromethane (3 ml) and thionyl chloride (114 µl) was added. The mixture was stirred at room temperature for 3 h before it was filtered, washed with dichloromethane (1 ml), cold ethyl acetate/hexanes (1:1, 20 ml) and dried to give the title compound as a yellow solid (140 mg). MS: (+) m/z 353.24 (M+1).

c) {[2-(3-Chloro-4-fluoro-phenyl)-7-hydroxy-thiazolo[4,5-c]pyridine-6-carbonyl]-amino}-acetic acid A mixture of 2-(3-chloro-4-fluoro-phenyl)-7-hydroxy-thiazolo[4,5-c]pyridine-6-carboxylic acid ethyl ester (101 mg, 0.29 mmole) and glycine (429 mg, 5.72 mmole) in 0.5 M sodium methoxide/methanol (10.9 ml, 5.43 mmole) was refluxed for 4 days before it was cooled to room temperature and concentrated in vacuo. The residue was dissolved in water (100 ml) and extracted with dichloromethane (3×50 ml). The remaining aqueous layer was acidified to pH=3 with 1N HCl (6.5 ml). The resulting precipitate was filtered, washed with water and dried in vacuo to give the title compound as a brown solid (58 mg). $^1$H NMR (DMSO-d$_6$, 200 MHz): δ=9.50 (br s, 1H), 8.89 (s, 1H), 8.36 (m, 1H), 8.16 (m, 1H), 7.65 (t, 1H), 4.03 (d, 2H, J=5.8 Hz); MS: (+) m/z 382.19 (M+1).

Example 72

[(4-Benzyl-7-hydroxy-2-phenyl-thiazolo[5,4-c]pyridine-6-carbonyl)-amino]-acetic acid a) 4-Benzyl-7-hydroxy-2-phenyl-thiazolo[5,4-c]pyridine-6-carboxylic acid ethyl ester A mixture of 4-bromo-7-hydroxy-2-phenyl-thiazolo[5,4-c]pyridine-6-carboxylic acid ethyl ester (351 mg, 0.93 mmole), B-benzyl-9-BBN (4.6 ml, 2.3 mmole, 0.5 M in THF), potassium phosphate (592 mg, 2.79 mmole), (2-(dicyclohexylphosphino)-2',6'-dimethoxybiphenyl)(76 mg, 0.18 mmole) and palladium acetate (21 mg, 0.09 mmole) in dimethylformamide (1 ml) was refluxed for 20 h before it was cooled to room temperature and partitioned between ethyl acetate and water. The mixture was filtered and the organic layer was washed with brine, dried over anhydrous sodium sulfate and concentrated in vacuo. The residue was purified by flash column chromatography on silica gel with a gradient of ethyl acetate and dichloromethane to give the title compound as a yellow oil (65 mg). MS: (+) m/z 391.29 (M+H$^+$)

b) [(4-Benzyl-7-hydroxy-2-phenyl-thiazolo[5,4-c]pyridine-6-carbonyl)-amino]-acetic acid A mixture of 4-benzyl-7-hydroxy-2-phenyl-thiazolo[5,4-c]pyridine-6-carboxylic acid ethyl ester (48 mg, 0.12 mmole) and glycine (185 mg, 2.46 mmole) in 0.5 M sodium methoxide/methanol (4.7 ml) was refluxed for 45 h before it was cooled to room temperature and concentrated in vacuo. The residue was dissolved in water (15 ml) and extracted twice with dichloromethane. The remaining aqueous layer was acidified to pH=3 with 1N HCl (3.5 ml). The resulting precipitate was filtered, washed with water and dried in vacuo to give the title compound as a yellow solid (38 mg). $^1$H NMR (DMSO-d$_6$, 200 MHz): δ=13.13 (br s, 1H), 9.34 (t, 1H, J=6.0 Hz), 8.08 (m, 2H), 7.58 (m, 3H), 7.33 (m, 5H), 4.36 (s, 2H), 4.06 (d, 2H, J=5.8 Hz); MS: (+) m/z 420.29 (M+1), MS: (−) m/z 418.29 (M−1).

Example 73

{[7-Hydroxy-4-(4-morpholin-4-yl-phenyl)-2-phenyl-thiazolo[5,4-c]pyridine-6-carbonyl]-amino}-acetic acid a) 7-Hydroxy-4-(4-morpholin-4-yl-phenyl)-2-phenyl-thiazolo[5,4-c]pyridine-6-carboxylic acid ethyl ester A mixture of 4-bromo-7-hydroxy-2-phenyl-thiazolo[5,4-c]pyridine-6-carboxylic acid ethyl ester (230 mg, 0.61 mmole), 4-morpholinophenylboronic acid (252 mg, 1.22 mmole), cesium carbonate (596 mg, 1.83 mmole) and tetrakis(triphenylphosphine)-palladium (70 mg, 0.06 mmole) in dioxane (3 ml) was refluxed for 18 h before it was cooled to room temperature, quenched with water and filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and dichloromethane to give the title compound as a white solid (57 mg). MS: (+) m/z 462.35 (M+H$^+$)

b) {[7-Hydroxy-4-(4-morpholin-4-yl-phenyl)-2-phenyl-thiazolo[5,4-c]pyridine-6-carbonyl]-amino}-acetic acid A mixture of 7-Hydroxy-4-(4-morpholin-4-yl-phenyl)-2-phenyl-thiazolo[5,4-c]pyridine-6-carboxylic acid ethyl ester (56 mg, 0.12 mmole) and glycine (182 mg, 2.43 mmole) in 0.5 M sodium methoxide/methanol (4.4 ml) was refluxed for 5 days before it was cooled to room temperature and concentrated in vacuo. The residue was dissolved in water (120 ml) and extracted with dichloromethane. The remaining aqueous layer was acidified to pH=3 with 1N HCl (5 ml). The resulting suspension was extracted with ethyl acetate, washed with brine and dried in vacuo to give the title compound as a yellow solid (44 mg). $^1$H NMR (DMSO-d$_6$, 200 MHz): δ=13.1 (br s, 1H), 9.37 (t, 1H), 8.15 (m, 2H), 8.04 (m, 2H), 7.62 (m, 3H), 7.10 (m, 2H), 4.06 (d, 2H, J=5.8 Hz), 3.77 (m, 4H); MS: (+) m/z 491.22 (M+1).

Example 74

{[4-(4-Cyano-phenyl)-7-hydroxy-2-phenyl-thiazolo[4,5-c]pyridine-6-carbonyl]-amino}-acetic acid a) 4-(4-Cyano-phenyl)-7-hydroxy-2-phenyl-thiazolo[4,5-c]pyridine-6-carboxylic acid ethyl ester A mixture of 4-bromo-7-hydroxy-2-phenyl-thiazolo[4,5-c]pyridine-6-carboxylic acid ethyl ester (300 mg, 0.79 mmole), para-cyanophenylboronic acid (233 mg, 1.59 mmole), cesium carbonate (776 mg, 2.38 mmole) and tetrakis (triphenylphosphine)palladium (92 mg, 0.08 mmole) in dioxane (4 ml) was refluxed for 16 h before it was cooled to room temperature, quenched with water and filtered. The filtrate was partitioned between dichloromethane and water. The organic layer was washed with brine, dried over anhydrous sodium sulfate and concentrated in vacuo. The residue was purified by flash column chromatography on silica gel with a gradient of dichloromethane and hexanes to give the title compound as a white solid (136 mg). MS: (+) m/z 402.32 (M+H$^+$)

b) {[4-(4-Cyano-phenyl)-7-hydroxy-2-phenyl-thiazolo[4,5-c]pyridine-6-carbonyl]-amino}-acetic acid A mixture of 4-(4-cyano-phenyl)-7-hydroxy-2-phenyl-thiazolo[4,5-c]pyridine-6-carboxylic acid ethyl ester (132 mg, 0.33 mmole) and glycine (2.46 g, 32.8 mmole) in 0.5 M sodium methoxide/methanol (49 ml) was refluxed for 16 h before it was cooled to room temperature and concentrated in vacuo. It was dissolved in water (100 ml) and extracted with dichloromethane (2×50 ml). The remaining aqueous solution was acidified to pH=2 with 0.1 N HCl (28 ml). The resulting precipitate was filtered, washed with water and dried to give the title compound as a white solid (76 mg). $^1$H NMR (DMSO-d$_6$, 200 MHz): δ=9.56 (t, 1H), 8.91 (d, J=8.2 Hz, 2H), 8.19 (m, 2H), 8.00 (d, J=8.2 Hz, 2H), 7.64 (m, 3H), 4.07 (d, J=6.2 Hz, 2H); MS: (+) m/z 429.23 (M−1).

Example 75

{[4-Cyano-2-(4-fluoro-phenyl)-7-hydroxy-thiazolo[4,5-c]pyridine-6-carbonyl]-amino}-acetic acid a) 4-Cyano-2-(4-fluoro-phenyl)-7-hydroxy-thiazolo[4,5-c]pyridine-6-carboxylic acid ethyl ester A mixture of 4-bromo-2-(4-fluoro-phenyl)-7-hydroxy-thiazolo[4,5-c]pyridine-6-carboxylic acid ethyl ester (157 mg, 0.40 mmole), tris(dibenzylideneacetone)-dipalladium(0) (18 mg, 0.02 mmole), 1,1'-bis(diphenylphosphino)ferrocene (22 mg, 0.04 mmole), zinc cyanide (28 mg, 0.24 mmole) and zinc (3 mg, 0.05 mmole) in dimethylacetamide (0.8 ml) was stirred at 120° C. for 4.5 h before it was cooled to room temperature, partitioned between ethyl acetate and water, filtered. The filtrate washed with brine, dried over anhydrous sodium sulfate and concentrated in vacuo. The residue was purified by flash column chromatography on silica gel with a gradient of methanol and dichloromethane to give the title compound as a yellow solid (64 mg). MS: (+) m/z 344.26 (M+1), MS: (−) m/z 342.27 (M−1).

b) {[4-Cyano-2-(4-fluoro-phenyl)-7-hydroxy-thiazolo[4,5-c]pyridine-6-carbonyl]-amino}-acetic acid A mixture of 4-cyano-2-(4-fluoro-phenyl)-7-hydroxy-thiazolo[4,5-c]pyridine-6-carboxylic acid ethyl ester (67 mg, 0.19 mmole) and glycine (875 mg, 11.66 mmole) in 0.5 M sodium methoxide/methanol (9.7 ml) was refluxed for 22 h before it was cooled to room temperature and concentrated in vacuo. The residue was dissolved in water (50 ml) and extracted twice with dichloromethane. The remaining aqueous layer was acidified to pH=3 with 1N HCl (12 ml). The suspension was extracted with ethyl acetate. The organic layer was washed with water and dried in vacuo to give the title compound as a yellow solid (59 mg). MS: (+) m/z 373.24 (M+1).

Example 76

{[4-Cyano-7-hydroxy-2-(3-methoxy-phenyl)-thiazolo[4,5-c]pyridine-6-carbonyl]-amino}-acetic acid a) 4-Bromo-7-hydroxy-2-(3-methoxy-phenyl)-thiazolo[4,5-c]pyridine-6-carboxylic acid ethyl ester A mixture of 7-hydroxy-2-(3-methoxy-phenyl)-thiazolo[4,5-c]pyridine-6-carboxylic acid ethyl ester (643 mg, 1.95 mmole), N-bromosuccinimide (364 mg, 2.04 mmole) and benzoyl peroxide (23 mg, 9.74 mmole) in carbon tetrachloride (9.5 ml) was refluxed for 5 h before it was cooled to room temperature and partitioned between dichloromethane and water. The organic layer was washed with saturated aqueous sodium bicarbonate solution, brine, dried over anhydrous sodium sulfate and concentrated in vacuo. The residue was purified by flash column chromatography on silica gel with a gradient of ethyl acetate and dichloromethane to give the title compound as a white solid (338 mg). MS: (+) m/z 409.11, 411.11 (M+1, $^{79}$Br/$^{81}$Br).

b) 4-Cyano-7-hydroxy-2-(3-methoxy-phenyl)-thiazolo[4,5-c]pyridine-6-carboxylic acid ethyl ester A mixture of 4-bromo-7-hydroxy-2-(3-methoxy-phenyl)-thiazolo[4,5-c]pyridine-6-carboxylic acid ethyl ester (197 mg, 0.48 mmole), tris(dibenzylideneacetone)-dipalladium(0) (22 mg, 0.02 mmole), 1,1'-bis(diphenylphosphino)ferrocene (27 mg, 0.04 mmole), zinc cyanide (27 mg, 0.29 mmole) and zinc (4 mg, 0.06 mmole) in dimethylacetamide (968 µl) was stirred at 120° C. for 4.5 h before it was cooled to room temperature, partitioned between ethyl acetate and water, filtered. The filtrate washed with brine, dried over anhydrous sodium sulfate and concentrated in vacuo. The residue was purified by flash column chromatography on silica gel with a gradient of methanol and dichloromethane to give the title compound as a yellow solid (32 mg). MS: (+) m/z 356.24 (M+1), MS: (−) m/z 354.24 (M−1).

c) {[4-Cyano-7-hydroxy-2-(3-methoxy-phenyl)-thiazolo[4,5-c]pyridine-6-carbonyl]-amino}-acetic acid A mixture of 4-cyano-7-hydroxy-2-(3-methoxy-phenyl)-thiazolo[4,5-c]pyridine-6-carboxylic acid ethyl ester (34 mg, 0.10 mmole) and glycine (538 mg, 7.16 mmole) in 0.5 M sodium methoxide/methanol (9.5 ml) was refluxed for 21 h before it was cooled to room temperature and concentrated in vacuo. The residue was dissolved in water (25 ml) and extracted twice with dichloromethane. The remaining aqueous layer was acidified to pH=3 with 1N HCl (7 ml). The suspension was extracted with ethyl acetate and dichloromethane. The organic layers were combined and washed with water, dried over anhydrous sodium sulfate and concentrated in vacuo to give the title compound as a yellow solid (34 mg). MS: (+) m/z 385.17 (M+1), MS: (−) m/z 383.13 (M−1).

Example 77

[(4-Cyano-7-hydroxy-2-phenyl-thiazolo[5,4-c]pyridine-6-carbonyl)-amino]-acetic acid a) [(4-Bromo-7-hydroxy-2-phenyl-thiazolo[5,4-c]pyridine-6-carbonyl)-amino]-acetic acid A mixture of 4-bromo-7-hydroxy-2-phenyl-thiazolo[5,4-c]pyridine-6-carboxylic acid ethyl ester (191 mg, 0.50 mmole) and glycine (1.33 g, 17.69 mmole) in 0.5 M sodium methoxide/methanol (25.3 ml) was refluxed for 28 h before it was cooled to room temperature and concentrated in vacuo. The residue was dissolved in water (120 ml) and extracted with dichloromethane (3×100 ml). The remaining aqueous layer was acidified to pH=2 with 1N HCl. The resulting precipitate was filtered, washed with water and dried in vacuo to give the title compound as a yellow solid (137 mg). MS: (+) m/z 408.12, 410.09 (M+1, $^{79}$Br/$^{81}$Br), (−) m/z 406.08, 408.05 (M−1, $^{79}$Br/$^{81}$Br).

b) [(4-Cyano-7-hydroxy-2-phenyl-thiazolo[5,4-c] pyridine-6-carbonyl)-amino]-acetic acid A mixture of [(4-bromo-7-hydroxy-2-phenyl-thiazolo[5,4-c]pyridine-6-carbonyl)-amino]-acetic acid (130 mg, 0.32 mmole), tris(dibenzylideneacetone)dipalladium(0)(15 mg, 0.02 mmole), 1,1'-bis(diphenylphosphino)ferrocene (18 mg, 0.04 mmole), zinc cyanide (23 mg, 0.19 mmole) and zinc (3 mg, 0.04 mmole) in dimethylacetamide (640 µl) was stirred at 120° C. for 3 h before it was cooled to room temperature, partitioned between ethyl acetate and 1N NaOH (50 ml). The aqueous layer was acidified with 5 N HCl (10 ml) to pH=2, extracted with ethyl acetate, washed with brine, dried over anhydrous sodium sulfate and concentrated in vacuo. The residue was purified by column chromatography on a C18 column with a gradient of water and acetonitrile in formic acid to give the title compound as a yellow solid (46 mg). MS: (+) m/z 355.22 (M+1), MS: (−) m/z 353.18 (M−1).

Example 78

[(4-Ethynyl-7-hydroxy-2-phenyl-thiazolo[4,5-c]pyridine-6-carbonyl)-amino]-acetic acid a) 7-Hydroxy-2-phenyl-4-trimethylsilanylethynyl-thiazolo[4,5-c]pyridine-6 carboxylic acid ethyl ester A mixture of 4-bromo-7-hydroxy-2-phenyl-thiazolo[4,5-c]pyridine-6-carboxylic acid ethyl ester (636 mg, 1.68 mmole), trimethylsilylacetylene (309 µl, 2.19 mmole), bis(triphenylphosphine)palladium chloride (35 mg, 0.05 mmole), copper(I) iodide (19 mg, 0.10 mmole) and triethylamine (352 µl, 2.52 mmole) in tetrahydrofuran (3.4 ml) was stirred at room temperature for 3.5 h before it was partitioned between ethyl acetate and water, washed with brine, dried over anhydrous sodium sulfate and concentrated in vacuo. The residue was purified by column chromatography on silica gel with a gradient of dichloromethane and hexanes to give the title compound as a yellow solid (448 mg). MS: (+) m/z 397.28 (M+1), MS: (−) m/z 395.18 (M−1).

b) [(4-Ethynyl-7-hydroxy-2-phenyl-thiazolo[4,5-c] pyridine-6-carbonyl)-amino]-acetic acid A mixture of 7-hydroxy-2-phenyl-4-trimethylsilanylethynyl-thiazolo[4,5-c]pyridine-6 carboxylic acid ethyl ester (113 mg, 0.28 mmole) and glycine (750 mg, 9.99 mmole) in 0.5 M sodium methoxide/methanol (20 ml) was refluxed for 3 days before it was cooled to room temperature and concentrated in vacuo. The residue was dissolved in water (30 ml) and extracted with dichloromethane (2×40 ml). The remaining aqueous layer was acidified to pH=2 with 1N HCl. The suspension was extracted with ethyl acetate (2×40 ml), washed with brine, dried over anhydrous sodium sulfate and concentrated in vacuo to give the title compound as a yellow solid (96 mg). MS: (+) m/z 354.20 (M+1), (−) m/z 352.16 (M−1).

Example 79

[(4-Acetyl-7-hydroxy-2-phenyl-thiazolo[4,5-c]pyridine-6-carbonyl)-amino]-acetic acid a) [(4-Acetyl-7-hydroxy-2-phenyl-thiazolo[4,5-c] pyridine-6-carbonyl)-amino]-acetic acid A mixture of [(4-ethynyl-7-hydroxy-2-phenyl-thiazolo[4,5-c]pyridine-6-carbonyl)-amino]-acetic acid (52 mg, 0.15 mmole), mercury sulfate (44 mg, 0.15 mmole), concentrated sulfuric acid (19 mg, 0.19 mmole) in 80% aqueous acetone (1.6 ml) was refluxed for 2 h before it was cooled to room temperature and concentrated. The residue was washed with water and filtered. The remaining solid was dissolved in 0.5 N NaOH (15 ml) and extracted with dichloromethane (2×20 ml). The remaining aqueous layer was acidified with 1N HCl (8 ml) to pH=2. The suspension was extracted with ethyl acetate (20 ml) and dichloromethane (20 ml). The organic layer was combined, concentrated and purified by column chromatography on a C18 column with a gradient of water and acetonitrile in formic acid to give the title compound as a yellow solid (24 mg): MS: (+) m/z 372.24 (M+1), MS: (−) m/z 370.27 (M−1).

Example 80

[(7-Hydroxy-2-phenyl-4-piperidin-1-yl-thiazolo[4,5-c]pyridine-6-carbonyl)-amino]-acetic acid a) 7-Hydroxy-4-iodo-2-phenyl-thiazolo[4,5-c]pyridine-6-carboxylic acid ethyl ester A mixture of 7-hydroxy-2-phenyl-thiazolo[4,5-c]pyridine-6-carboxylic acid ethyl ester (1.02 g, 3.39 mmole) and bis(2,4,6-trimethylpyridine)iodine(I) hexafluorophosphate (2.61 g, 5.08 mmole) in dichloromethane (30 ml) was stirred at room temperature for 16 h before it was concentrated and purified by flash column chromatography on silica gel with a gradient of dichloromethane and hexanes to give the title compound as a yellow solid (1.00 g). MS: (+) m/z 427.05 (M+1), MS: (−) m/z 425.01 (M−1).

b) 7-Benzyloxy-4-iodo-2-phenyl-thiazolo[4,5-c]pyridine-6-carboxylic acid ethyl ester A mixture of 7-hydroxy-4-iodo-2-phenyl-thiazolo[4,5-c]pyridine-6-carboxylic acid ethyl ester (405 mg, 0.95 mmole), benzyl bromide (170 µl, 1.43 mmole), potassium carbonate (329 mg, 2.38 mmole) in dimethylformamide (5 ml) was stirred at room temperature for four hours before it was partitioned between ethyl acetate and water, washed with brine, dried over anhydrous sodium sulfate and concentrated in vacuo. The residue was purified by flash column chromatography on silica gel with a gradient of ethyl acetate and hexanes to give the title compound as a white solid (451 mg). MS: (+) m/z 517.04 (M+1).

c) 7-Benzyloxy-2-phenyl-4-piperidin-1-yl-thiazolo[4,5-c]pyridine-6-carboxylic acid ethyl ester A mixture of 7-benzyloxy-4-iodo-2-phenyl-thiazolo[4,5-c]pyridine-6-carboxylic acid ethyl ester (165 mg, 0.32 mmole), piperidine (95 µl, 0.96 mmole) and triethylamine (89 µl, 0.64 mmole) in ethanol (1.6 ml) was heated at 130° C. in a CEM microwave synthesizer for 30 min before it was cooled to room temperature, concentrated and purified by flash column chromatography on silica gel with a gradient of ethyl acetate and hexanes to give the title compound as a green oil (24 mg). MS: (+) m/z 474.55 (M+1).

d) 7-Hydroxy-2-phenyl-4-piperidin-1-yl-thiazolo[4,5-c]pyridine-6-carboxylic acid ethyl ester A mixture of 7-benzyloxy-2-phenyl-4-piperidin-1-yl-thiazolo[4,5-c]pyridine-6-carboxylic acid ethyl ester (47 mg, 0.10 mmole) and 10% Pd/C (20 mg) in a mixture of ethanol and ethyl acetate (3 ml, 1:5) was hydrogenated at room temperature for 7 h before it was filtered, washed with ethyl acetate and concentrated in vacuo to give the title compound as a yellow oil (39 mg). MS: (+) m/z 384.34 (M+1), MS: (−) m/z 382.37 (M−1).

e) [(7-Hydroxy-2-phenyl-4-piperidin-1-yl-thiazolo[4,5-c]pyridine-6-carbonyl)-amino]-acetic acid A mixture of 7-hydroxy-2-phenyl-4-piperidin-1-yl-thiazolo[4,5-c]pyridine-6-carboxylic acid ethyl ester (39 mg, 0.10 mmole) and glycine (573 mg, 7.63 mmole) in 0.5 M sodium methoxide/methanol (10.2 ml) was refluxed for 25 h before it was cooled to room temperature and concentrated in vacuo. The residue was dissolved in water (40 ml) and extracted three times with dichloromethane. The remaining aqueous layer was acidified to pH=3 with 1N HCl (6 ml). The suspension was extracted with ethyl acetate (2×40 ml). The organic layers were combined, washed with brine, dried over anhydrous sodium sulfate and concentrated in vacuo to give the title compound as a yellow solid (40 mg). MS: (+) m/z 413.30 (M+1), MS: (−) m/z 411.33 (M−1).

Example 81

{[2-(4-tert-Butyl-phenyl)-7-hydroxy-thiazolo[4,5-c]pyridine-6-carbony]-amino}-acetic acid a) 2-Bromo-4-bromomethyl-thiazole-5-carboxylic acid ethyl ester

2-Bromo-4-methyl-thiazole-5-carboxylic acid ethyl ester (17 g, 68.0 mmol, purchased from Ryan Scientific), N-bromosuccinimide (12.7 g, 71.4 mmol), and benzoyl peroxide (1.65 g, 6.8 mmol) were suspended in 222 mL of benzene and heated at reflux temperature for 16 h. The reaction mixture was cooled and diluted with ethyl acetate. The reaction mixture was washed successively with saturated bicarbonate solution, brine, saturated ammonium chloride solution, and brine. The organic solvent was dried, filtered, and concentrated. The crude product was purified by flash chromatography eluting from silica gel with a gradient of 0-20% ethyl acetate in hexanes to produce 22.1 g of a light yellow solid. $^1$H NMR (CDCl$_3$, 200 MHz): δ=4.88 (s, 2H), 4.37 (q, 2H, J=7.0 Hz), and 1.39 (t, 3H, J=7.0 Hz).

b) 2-Bromo-4-{[(2,4-dimethoxy-benzyl)-ethoxycarbonylmethyl-amino]-methyl}-thiazole-5-carboxylic acid ethyl ester 2-Bromo-4-bromomethyl-thiazole-5-carboxylic acid ethyl ester (22.1 g, 67.3 mmol) was dissolved in 169 mL of dry N,N-dimethylformamide. N-(2,4-dimethoxy-benzyl) glycine ethyl ester (17.1 g, 67.3 mmol) and potassium carbonate (10.2 g, 74.0 mmol) were added and the reaction was stirred at room temperature for 18 h. The reaction mixture was diluted with ethyl acetate and washed with water and brine. The organic fraction was dried over anhydrous sodium sulfate, and concentrated. The crude product was purified by flash chromatography eluting from silica gel with a gradient of 0-70% ethyl acetate in hexanes to produce 19.5 g of a light yellow solid. MS: (+) m/z 501.1 (M+1).

c) 2-(4-tert-Butyl-phenyl)-4-{[(2,4-dimethoxy-benzyl)-ethoxycarbonylmethyl-amino]-methyl}-thiazole-5-carboxylic acid ethyl ester Under a nitrogen atmosphere, 2-bromo-4-{[(2,4-dimethoxy-benzyl)-ethoxycarbonylmethyl-amino]-methyl}-thiazole-5-carboxylic acid ethy ester (1.0 g, 2.0 mmol), 4-tert-butylphenyl boronic acid (0.71 mg, 4.0 mmol), cesium carbonate (1.43 g, 4.4 mmol), and tetrakis(triphenylphosphine)palladium(0)(347 mg, 0.3 mmol) were suspended in 10 mL of 1,4-dioxane. The reaction was heated at reflux temperature overnight, cooled to room temperature and diluted with ethyl acetate. The organic mixture was successively washed with saturated sodium bicarbonate and brine solutions. The organic fractions were dried over anhydrous sodium sulfate and concentrated to an oil residue, which was then purified by column chromatography, eluting the title compound from silica gel with a gradient of (0-70%) ethyl acetate in hexanes to yield 1.11 g of a yellow oil. MS: (+) m/z 577.2 (M+Na$^+$).

d) 2-(4-tert-Butyl-phenyl)-5-(2,4-dimethoxy-benzyl)-7-oxo-4,5,6,7-tetrahydro-thiazolo[4,5-c]pyridine-6-carboxylic acid ethyl ester 2-(4-tert-Butyl-phenyl)-4-{[(2,4-dimethoxy-benzyl)-ethoxycarbonylmethyl-amino]-methyl}-thiazole-5-carboxylic acid ethy este (1.11 g, 2.0 mmol) was dissolved in 21 mL of anhydrous THF and cooled to −15° C. in a brine dry ice bath. A solution of 4.4 mL of 1.0 M potassium tert-butoxide in THF was added slowly to cold solution, and the reaction was stirred at −15° C. for 30 min. and then at room temperature for 2 h. The reaction was quenched with 4.4 mL of 1N HCl and 150 mL of saturated ammonium chloride aqueous solution, and extracted twice with 150 mL of chloroform. The organic fractions were washed with brine, dried over anhydrous sodium sulfate and concentrated. The crude product was purified by flash chromatography eluting from silica gel with a gradient of 0-70% ethyl acetate in hexanes to produce 0.5 g of a yellow froth. MS: (+) m/z 508.9 (M+1).

e) 2-(4-tert-Butyl-phenyl)-7-hydroxy-thiazolo[4,5-c]pyridine-6-carboxylic acid ethyl ester 2-(4-tert-Butyl-phenyl)-5-(2,4-dimethoxy-benzyl)-7-oxo-4,5,6,7-tetrahydro-thiazolo[4,5-c]pyridine-6-carboxylic acid ethyl ester (0.5 g, 0.98 mmol) was dissolved in 6.7 mL of anhydrous dichloromethane. To the solution was added 108 μL of thionyl chloride, and the reaction was stirred for 5 h. The solution was filtered on a fine glass frit filter to collect a white solid precipitate. The solid was washed twice with cold dichloromethane and then partitioned between saturated sodium bicarbonate solution and ethyl acetate. The organic fraction was washed with brine, dried over anhydrous sodium sulfate, and concentrated to produce 0.21 g of a yellow solid. MS: (+) m/z 357.0 (M+1).

f) {[2-(4-tert-Butyl-phenyl)-7-hydroxy-thiazolo[4,5-c]pyridine-6-carbonyl]-amino}-acetic acid 2-(4-tert-Butyl-phenyl)-7-hydroxy-thiazolo[4,5-c]pyridine-6-carboxylic acid ethyl ester (100 mg, 0.28 mmol) and glycine (442 mg, 5.89 mmol) were suspended in 11.2 mL of 0.5 N sodium methoxide in methanol. The reaction was heated at reflux temperature overnight, cooled, and concentrated. The residue was dissolved in water (30 mL), and the solution was acidified to pH 1~2 with 2 N HCl, extracted with ethyl acetate. The combined organic layers were dried, filtered and concentrated to produce 63 mg of a yellow solid. MS: (+) m/z 386.0 (M+1).

Example 82

{[2-(2,3-Dihydro-benzo[1,4]dioxin-6-yl)-7-hydroxy-thiazolo[4,5-c]pyridine-6-carbonyl]-amino}-acetic acid a) 2-(2,3-Dihydro-benzo[1,4]dioxin-6-yl)-4-{[(2,4-dimethoxy-benzyl)-ethoxycarbonyl-methyl-amino]-methyl}-thiazole-5-carboxylic acid ethyl ester Prepared from 2-bromo-4-{[(2,4-dimethoxy-benzyl)-ethoxycarbonylmethyl-amino]-methyl}-thiazole-5-carboxylic acid ethy ester, example 81(b), and 2-(2,3-dihydro-1,4-benzodioxin-6-yl)boronic acid under conditions analogous to experimental example 81(c). MS: (+) m/z 557.49 (M+1).

b) 2-(2,3-Dihydro-benzo[1,4]dioxin-6-yl)-5-(2,4-dimethoxy-benzyl)-7-oxo-4,5,6,7-tetrahydro-thiazolo[4,5-c]pyridine-6-carboxylic acid ethyl ester Prepared from 2-(2,3-dihydro-benzo[1,4]dioxin-6-yl)-4-{[(2,4-dimethoxy-benzyl)-ethoxycarbonylmethyl-amino}-thiazole-5-carboxylic acid ethyl ester under conditions analogous to experimental example 81(d). MS: (+) m/z 533.1 (M+Na$^+$).

c) 2-(2,3-Dihydro-benzo[1,4]dioxin-6-yl)-7-hydroxy-thiazolo[4,5-c]pyridine-6-carboxylic acid ethyl ester Prepared from 2-(2,3-dihydro-benzo[1,4]dioxin-6-yl)-5-(2,4-dimethoxy-benzyl)-7-oxo-4,5,6,7-tetrahydro-thiazolo[4,5-c]pyridine-6-carboxylic acid ethyl ester under conditions analogous to experimental example 81(e). MS: (+) m/z 359.2 (M+1).

d) {[2-(2,3-Dihydro-benzo[1,4]dioxin-6-yl)-7-hydroxy-thiazolo[4,5-c]pyridine-6-carbonyl]-amino}-acetic acid Prepared from 2-(2,3-dihydro-benzo[1,4]dioxin-6-yl)-7-hydroxy-thiazolo[4,5-c]pyridine-6-carboxylic acid ethyl ester under conditions analogous to experimental example 81(f). MS: (+) m/z 388.2 (M+1).

Example 83

[(2-Benzo[b]thiophen-3-yl-7-hydroxy-thiazolo[4,5-c]pyridine-6-carbonyl)-amino]-acetic acid a) 2-Benzo[b]thiophen-3-yl-4-{[(2,4-dimethoxy-benzyl)-ethoxycarbonylmethyl-amino]-methyl}-thiazole-5-carboxylic acid ethyl ester Prepared from 2-bromo-4-{[(2,4-dimethoxy-benzyl)-ethoxycarbonylmethyl-amino]-methyl}-thiazole-5-carboxylic acid ethy ester, example 81(b), and 1-benzothiophen-3-yl-boronic acid under conditions analogous to experimental example 81(c). MS: (+) m/z 555.5 (M+1).

b) 2-Benzo[b]thiophen-3-yl-5-(2,4-dimethoxy-benzyl)-7-oxo-4,5,6,7-tetrahydro-thiazolo[4,5-c]pyridine-6-carboxylic acid ethyl ester Prepared from 2-benzo[b]thiophen-3-yl-4-{[(2,4-dimethoxy-benzyl)-ethoxycarbonylmethyl-amino]-methyl}-thiazole-5-carboxylic acid ethyl ester under conditions analogous to experimental example 81(d). MS: (+) m/z 508.7 (M+1).

c) 2-Benzo[b]thiophen-3-yl-7-hydroxy-thiazolo[4,5-c]pyridine-6-carboxylic acid ethyl ester Prepared from 2-benzo[b]thiophen-3-yl-5-(2,4-dimethoxy-benzyl)-7-oxo-4,5,6,7-tetrahydro-thiazolo[4,5-c]pyridine-6-carboxylic acid ethyl ester under conditions analogous to experimental example 81(e). MS: (+) m/z 357.2 (M+1).

d) [(2-Benzo[b]thiophen-3-yl-7-hydroxy-thiazolo[4,5-c]pyridine-6-carbonyl)-amino]-acetic acid Prepared from 2-benzo[b]thiophen-3-yl-7-hydroxy-thiazolo[4,5-c]pyridine-6-carboxylic acid ethyl ester under conditions analogous to experimental example 81(f). MS: (+) m/z 385.9 (M+1).

Example 84

[(2-Biphenyl-4-yl-7-hydroxy-thiazolo[4,5-c]pyridine-6-carbonyl)-amino]-acetic acid a) 2-Biphenyl-4-yl-4-{[(2,4-dimethoxy-benzyl)-ethoxycarbonylmethyl-amino]-methyl}-thiazole-5-carboxylic acid ethyl ester Prepared from 2-bromo-4-{[(2,4-dimethoxy-benzyl)-ethoxycarbonylmethyl-amino]-methyl}-thiazole-5-carboxylic acid ethy ester, example 81(b), and 1,1'-biphenyl-4-yl-boronic acid under conditions analogous to experimental example 81(c). MS: (+) m/z 575.0 (M+1).

b) 2-Biphenyl-4-yl-5-(2,4-dimethoxy-benzyl)-7-oxo-4,5,6,7-tetrahydro-thiazolo[4,5-c]pyridine-6-carboxylic acid ethyl ester Prepared from 2-biphenyl-4-yl-4-{[(2,4-dimethoxy-benzyl)-ethoxycarbonylmethyl-amino]-methyl}-thiazole-5-carboxylic acid ethyl ester under conditions analogous to experimental example 81(d). MS: (+) m/z 551.1 (M+Na$^+$).

c) 2-Biphenyl-4-yl-7-hydroxy-thiazolo[4,5-c]pyridine-6-carboxylic acid ethyl ester Prepared from 2-biphenyl-4-yl-5-(2,4-dimethoxy-benzyl)-7-oxo-4,5,6,7-tetrahydro-thiazolo[4,5-c]pyridine-6-carboxylic acid ethyl ester under conditions analogous to experimental example 81(e). MS: (+) m/z 377.0 (M+1).

d) [(2-Biphenyl-4-yl-7-hydroxy-thiazolo[4,5-c]pyridine-6-carbonyl)-amino]-acetic acid Prepared from 2-biphenyl-4-yl-7-hydroxy-thiazolo[4,5-c]pyridine-6-carboxylic acid ethyl ester under conditions analogous to experimental example 81(f). MS: (+) m/z 406.3 (M+1).

Example 85

[(2-Benzo[b]thiophen-2-yl-7-hydroxy-thiazolo[4,5-c]pyridine-6-carbonyl)-amino]-acetic acid a) 2-Benzo[b]thiophen-2-yl-4-{[(2,4-dimethoxy-benzyl)-ethoxycarbonylmethyl-amino]-methyl}-thiazole-5-carboxylic acid ethyl ester Prepared from 2-bromo-4-{[(2,4-dimethoxy-benzyl)-ethoxycarbonylmethyl-amino]-methyl}-thiazole-5-carboxylic acid ethy ester, example 81(b), and 1-benzothiophen-2-yl-boronic acid under conditions analogous to experimental example 81(c). MS: (+) m/z 555.4 (M+1).

b) 2-Benzo[b]thiophen-2-yl-5-(2,4-dimethoxy-benzyl)-7-oxo-4,5,6,7-tetrahydro-thiazolo[4,5-c]pyridine-6-carboxylic acid ethyl ester Prepared from 2-benzo[b]thiophen-2-yl-4-{[(2,4-dimethoxy-benzyl)-ethoxycarbonylmethyl-amino]-methyl}-thiazole-5-carboxylic acid ethyl ester under conditions analogous to experimental example 81(d). MS: (+) m/z 508.7 (M+1).

c) 2-Benzo[b]thiophen-2-yl-7-hydroxy-thiazolo[4,5-c]pyridine-6-carboxylic acid ethyl ester Prepared from 2-benzo[b]thiophen-2-yl-5-(2,4-dimethoxy-benzyl)-7-oxo-4,5,6,7-tetrahydro-thiazolo[4,5-c]pyridine-6-carboxylic acid ethyl ester under conditions analogous to experimental example 81(e). MS: (+) m/z 357.3 (M+1).

d) [(2-Benzo[b]thiophen-2-yl-7-hydroxy-thiazolo[4,5-c]pyridine-6-carbonyl)-amino]-acetic acid Prepared from 2-benzo[b]thiophen-2-yl-7-hydroxy-thiazolo[4,5-c]pyridine-6-carboxylic acid ethyl ester under conditions analogous to experimental example 81(f). MS: (−) m/z 384.2 (M−1).

Example 86

[(7-Hydroxy-2-quinolin-3-yl-thiazolo[4,5-c]pyridine-6-carbonyl)-amino]-acetic acid a) 4-[(2,4-Dimethoxy-benzyl)-ethoxycarbonylmethyl-amino]-methyl-2-quinolin-3-yl-thiazole-5-carboxylic acid ethyl ester Prepared from 2-bromo-4-{[(2,4-dimethoxy-benzyl)-ethoxycarbonylmethyl-amino]-methyl}-thiazole-5-carboxylic acid ethy ester, example 81(b), and 3-quinolinylboronic acid under conditions analogous to experimental example 81(c). MS: (+) m/z 550.4 (M+1).

b) 5-(2,4-Dimethoxy-benzyl)-7-oxo-2-quinolin-3-yl-4,5,6,7-tetrahydro-thiazolo[4,5-c]pyridine-6-carboxylic acid ethyl ester Prepared from 4-{[(2,4-dimethoxy-benzyl)-ethoxycarbonylmethyl-amino]-methyl}-2-quinolin-3-yl-thiazole-5-carboxylic acid ethyl ester under conditions analogous to experimental example 81(d). MS: (+) m/z 504.3 (M+1).

c) 7-Hydroxy-2-quinolin-3-yl-thiazolo[4,5-c]pyridine-6-carboxylic acid ethyl ester Prepared from 5-(2,4-dimethoxy-benzyl)-7-oxo-2-quinolin-3-yl-4,5,6,7-tetrahydro-thiazolo[4,5-c]pyridine-6-carboxylic acid ethyl ester under conditions analogous to experimental example 81(e). MS: (+) m/z 352.3 (M+1).

d) [(7-Hydroxy-2-quinolin-3-yl-thiazolo[4,5-c]pyridine-6-carbonyl)-amino]-acetic acid Prepared from 7-hydroxy-2-quinolin-3-yl-thiazolo[4,5-c]pyridine-6-carboxylic acid ethyl ester under conditions analogous to experimental example 81(f). MS: (−) m/z 379.3 (M−1).

Example 87

[(2-Benzofuran-2-yl-7-hydroxy-thiazolo[4,5-c]pyridine-6-carbonyl)-amino]-acetic acid a) 2-Benzofuran-2-yl-4-{[(2,4-dimethoxy-benzyl)-ethoxycarbonylmethyl-amino]-methyl}-thiazole-5-carboxylic acid ethyl ester Prepared from 2-bromo-4-{[(2,4-dimethoxy-benzyl)-ethoxycarbonylmethyl-amino]-methyl}-thiazole-5-carboxylic acid ethy ester, example 81(b), and 1-benzofuran-2-yl-boronic acid under conditions analogous to experimental example 81(c). MS: (+) m/z 539.4 (M+1).

b) 2-Benzofuran-2-yl-5-(2,4-dimethoxy-benzyl)-7-oxo-4,5,6,7-tetrahydro-thiazolo[4,5-c]pyridine-6-carboxylic acid ethyl ester Prepared from 2-benzofuran-2-yl-4-{[(2,4-dimethoxy-benzyl)-ethoxycarbonylmethyl-amino]-methyl}-thiazole-5-carboxylic acid ethyl ester under conditions analogous to experimental example 81(d). MS: (+) m/z 493.3 (M+1).

c) 2-Benzofuran-2-yl-7-hydroxy-thiazolo[4,5-c]pyridine-6-carboxylic acid ethyl ester Prepared from 2-benzofuran-2-yl-5-(2,4-dimethoxy-benzyl)-7-oxo-4,5,6,7-tetrahydro-thiazolo[4,5-c]pyridine-6-carboxylic acid ethyl ester under conditions analogous to experimental example 81(e). MS: (+) m/z 341.3 (M+1).

d) [(2-Benzofuran-2-yl-7-hydroxy-thiazolo[4,5-c]pyridine-6-carbonyl)-amino]-acetic acid Prepared from 2-benzofuran-2-yl-7-hydroxy-thiazolo[4,5-c]pyridine-6-carboxylic acid ethyl ester under conditions analogous to experimental example 81(f). MS: (−) m/z 368.2 (M−1).

Example 88

[(2-Dibenzofuran-4-yl-7-hydroxy-thiazolo[4,5-c]pyridine-6-carbonyl)-amino]-acetic acid a) 2-Dibenzofuran-4-yl-4-{[(2,4-dimethoxy-benzyl)-ethoxycarbonylmethyl-amino]-methyl}-thiazole-5-carboxylic acid ethyl ester Prepared from 2-bromo-4-{[(2,4-dimethoxy-benzyl)-ethoxycarbonylmethyl-amino]-methyl}-thiazole-5-carboxylic acid ethy ester, example 81(b), and dibenzo[b,d]furan-4- yl-boronic acid under conditions analogous to experimental example 81(c). MS: (+) m/z 589.4 (M+1).

b) 2-Dibenzofuran-4-yl-5-(2,4-dimethoxy-benzyl)-7-oxo-4,5,6,7-tetrahydro-thiazolo[4,5-c]pyridine-6-carboxylic acid ethyl ester Prepared from 2-dibenzofuran-4-yl-4-{[(2,4-dimethoxy-benzyl)-ethoxycarbonylmethyl-amino]-methyl}-thiazole-5-carboxylic acid ethyl ester under conditions analogous to experimental example 81(d). MS: (+) m/z 543.3 (M+1).

c) 2-Dibenzofuran-4-yl-7-hydroxy-thiazolo[4,5-c]pyridine-6-carboxylic acid ethyl ester Prepared from 2-dibenzofuran-4-yl-5-(2,4-dimethoxy-benzyl)-7-oxo-4,5,6,7-tetrahydro-thiazolo[4,5-c]pyridine-6-carboxylic acid ethyl ester under conditions analogous to experimental example 81(e). MS: (+) m/z 391.3 (M+1).

d) [(2-Dibenzofuran-4-yl-7-hydroxy-thiazolo[4,5-c]pyridine-6-carbonyl)-amino]-acetic acid Prepared from 2-dibenzofuran-4-yl-7-hydroxy-thiazolo[4,5-c]pyridine-6-carboxylic acid ethyl ester under conditions analogous to experimental example 81(f). MS: (−) m/z 323.4 (M−1).

Example 89

{[2-(2,3-Dihydro-benzofuran-5-yl)-7-hydroxy-thiazolo[4,5-c]pyridine-6-carbonyl]-amino}-acetic acid a) 2-(2,3-Dihydro-benzofuran-5-yl)-4-{[(2,4-dimethoxy-benzyl)-ethoxycarbonylmethyl-amino]-methyl}-thiazole-5-carboxylic acid ethyl ester Prepared from 2-bromo-4-{[(2,4-dimethoxy-benzyl)-ethoxycarbonylmethyl-amino]-methyl}-thiazole-5-carboxylic acid ethy ester, example 81(b), and 2,3-dihydro-1-benzofuran-5-yl-boronic acid under conditions analogous to experimental example 81(c). MS: (+) m/z 541.4 (M+1).

b) 2-(2,3-Dihydro-benzofuran-5-yl)-5-(2,4-dimethoxy-benzyl)-7-oxo-4,5,6,7-tetrahydro-thiazolo[4,5-c]pyridine-6-carboxylic acid ethyl ester Prepared from 2-(2,3-dihydro-benzofuran-5-yl)-4-{[(2,4-dimethoxy-benzyl)-ethoxycarbonylmethyl-amino]-methyl}-thiazole-5-carboxylic acid ethyl ester under conditions analogous to experimental example 81(d). MS: (+) m/z 495.3 (M+1).

c) 2-(2,3-Dihydro-benzofuran-5-yl)-7-hydroxy-thiazolo[4,5-c]pyridine-6-carboxylic acid ethyl ester Prepared from 2-(2,3-dihydro-benzofuran-5-yl)-5-(2,4-dimethoxy-benzyl)-7-oxo-4,5,6,7-tetrahydro-thiazolo[4,5-c]pyridine-6-carboxylic acid ethyl ester under conditions analogous to experimental example 81(e). MS: (+) m/z 343.3 (M+1).

d) {[2-(2,3-Dihydro-benzofuran-5-yl)-7-hydroxy-thiazolo[4,5-c]pyridine-6-carbonyl]-amino}-acetic acid Prepared from 2-(2,3-dihydro-benzofuran-5-yl)-7-hydroxy-thiazolo[4,5-c]pyridine-6-carboxylic acid ethyl ester under conditions analogous to experimental example 81(f). MS: (−) m/z 370.3 (M−1).

Example 90

[(7-Hydroxy-2-pyrimidin-5-yl-thiazolo[4,5-c]pyridine-6-carbonyl)-amino]-acetic acid a) 4-[(2,4-Dimethoxy-benzyl)-ethoxycarbonylmethyl-amino]-methyl-2-pyrimidin-5-yl-thiazole-5-carboxylic acid ethyl ester Prepared from 2-bromo-4-{[(2,4-dimethoxy-benzyl)-ethoxycarbonylmethyl-amino]-methyl}-thiazole-5-carboxylic acid ethy ester, example 81(b), and pyrimidine-5-boronic acid under conditions analogous to experimental example 81(c). MS: (+) m/z 501.4 (M+1).

b) 5-(2,4-Dimethoxy-benzyl)-7-oxo-2-pyrimidin-5-yl-4,5,6,7-tetrahydro-thiazolo[4,5-c]pyridine-6-carboxylic acid ethyl ester Prepared from 4-{[(2,4-dimethoxy-benzyl)-ethoxycarbonylmethyl-amino]-methyl}-2-pyrimidin-5-yl-thiazole-5-carboxylic acid ethyl ester under conditions analogous to experimental example 81(d). MS: (+) m/z 455.3 (M+1).

c) 7-Hydroxy-2-pyrimidin-5-yl-thiazolo[4,5-c]pyridine-6-carboxylic acid ethyl ester Prepared from 5-(2,4-dimethoxy-benzyl)-7-oxo-2-pyrimidin-5-yl-4,5,6,7-tetrahydro-thiazolo[4,5-c]pyridine-6-carboxylic acid ethyl ester under conditions analogous to experimental example 81(e). MS: (+) m/z 303.3 (M+1).

d) [(7-Hydroxy-2-pyrimidin-5-yl-thiazolo[4,5-c]pyridine-6-carbonyl)-amino]-acetic acid Prepared from 7-hydroxy-2-pyrimidin-5-yl-thiazolo[4,5-c]pyridine-6-carboxylic acid ethyl ester under conditions analogous to experimental example 81(f). MS: (−) m/z 330.2 (M−1).

Example 91

{[2-(1-Benzyl-1H-pyrazol-4-yl)-7-hydroxy-thiazolo[4,5-c]pyridine-6-carbonyl]-amino}-acetic acid a) 2-(1-Benzyl-1H-pyrazol-4-yl)-4-{[(2,4-dimethoxy-benzyl)-ethoxycarbonylmethyl-amino]-methyl}-thiazole-5-carboxylic acid ethyl ester Prepared from 2-bromo-4-{[(2,4-dimethoxy-benzyl)-ethoxycarbonylmethyl-amino]-methyl}-thiazole-5-carboxylic acid ethy ester, example 81(b), and 1-benzyl-1H-pyrazole-4-boronic acid under conditions analogous to experimental example 81(c). MS: (+) m/z 579.4 (M+1).

b) 2-(1-Benzyl-1H-pyrazol-4-yl)-5-(2,4-dimethoxy-benzyl)-7-oxo-4,5,6,7-tetrahydro-thiazolo[4,5-c]pyridine-6-carboxylic acid ethyl ester Prepared from 2-(1-benzyl-1H-pyrazol-4-yl)-4-{[(2,4-dimethoxy-benzyl)-ethoxycarbonylmethyl-amino]-methyl}-thiazole-5-carboxylic acid ethyl ester under conditions analogous to experimental example 81(d). MS: (+) m/z 533.4 (M+1).

c) 2-(1-Benzyl-1H-pyrazol-4-yl)-7-hydroxy-thiazolo[4,5-c]pyridine-6-carboxylic acid ethyl ester Prepared from 2-(1-benzyl-1H-pyrazol-4-yl)-5-(2,4-dimethoxy-benzyl)-7-oxo-4,5,6,7-tetrahydro-thiazolo[4,5-c]pyridine-6-carboxylic acid ethyl ester under conditions analogous to experimental example 81(e). MS: (+) m/z 381.3 (M+1).

d) {[2-(1-Benzyl-1H-pyrazol-4-yl)-7-hydroxy-thiazolo[4,5-c]pyridine-6-carbonyl]-amino}-acetic acid Prepared from 2-(1-benzyl-1H-pyrazol-4-yl)-7-hydroxy-thiazolo[4,5-c]pyridine-6-carboxylic acid ethyl ester under conditions analogous to experimental example 81(f). MS: (−) m/z 408.3 (M−1).

Example 92

{[2-(6-Chloro-pyridin-3-yl)-7-hydroxy-thiazolo[4,5-c]pyridine-6-carbonyl]-amino}-acetic acid a) 2-(6-Chloro-pyridin-3-yl)-4-{[(2,4-dimethoxy-benzyl)-ethoxycarbonylmethyl-amino]-methyl}-thiazole-5-carboxylic acid ethyl ester Prepared from 2-bromo-4-{[(2,4-dimethoxy-benzyl)-ethoxycarbonylmethyl-amino]-methyl}-thiazole-5-carboxylic acid ethy ester, example 81(b), and 2-chloropyridine-5-boronic acid under conditions analogous to experimental example 81(c). MS: (+) m/z 534.3 (M+1).

b) 2-(6-Chloro-pyridin-3-yl)-5-(2,4-dimethoxy-benzyl)-7-oxo-4,5,6,7-tetrahydro-thiazolo[4,5-c]pyridine-6-carboxylic acid ethyl ester Prepared from 2-(6-chloro-pyridin-3-yl)-4-{[(2,4-dimethoxy-benzyl)-ethoxycarbonylmethyl-amino]-methyl}-thiazole-5-carboxylic acid ethyl ester under conditions analogous to experimental example 81(d). MS: (+) m/z 488.2 (M+1).

c) 2-(6-Chloro-pyridin-3-yl)-7-hydroxy-thiazolo[4,5-c]pyridine-6-carboxylic acid ethyl ester Prepared from 2-(6-chloro-pyridin-3-yl)-5-(2,4-dimethoxy-benzyl)-7-oxo-4,5,6,7-tetrahydro-thiazolo[4,5-c]pyridine-6-carboxylic acid ethyl ester under conditions analogous to experimental example 81(e). MS: (+) m/z 336.3 (M+1).

d) {[2-(6-Chloro-pyridin-3-yl)-7-hydroxy-thiazolo[4,5-c]pyridine-6-carbonyl]-amino}-acetic acid Prepared from 2-(6-chloro-pyridin-3-yl)-7-hydroxy-thiazolo[4,5-c]pyridine-6-carboxylic acid ethyl ester under conditions analogous to experimental example 81(f). MS: (−) m/z 363.2 (M−1).

Example 93

{[2-(6-Butoxy-pyridin-3-yl)-7-hydroxy-thiazolo[4,5-c]pyridine-6-carbonyl]-amino}-acetic acid a) {[2-(6-Butoxy-pyridin-3-yl)-7-hydroxy-thiazolo[4,5-c]pyridine-6-carbonyl]-amino}-acetic acid methyl ester 2-(6-Chloro-pyridin-3-yl)-7-hydroxy-thiazolo[4,5-c]pyridine-6-carboxylic acid ethyl ester, example 92(c)(0.15 g, 0.45 mmol) was added to a solution of sodium 1-butoxide in 1-butanol (prepared by dissolving sodium (45.2 mg, 1.96 mmol) in 10 mL of anhydrous 1-butanol) at ambient temperature. After the reaction mixture was refluxed overnight, the solvent was evaporated off. The resulting residue was added to a suspension of N-(3-dimethylaminopropyl)-N'-ethylcarbodiimide hydrochloride (94.3 mg, 0.49 mmol), glycine methyl ester hydrochloride (61.8 mg, 0.49 mmol), hydrochloric acid (10 N, 98.3 µL, 0.983 mmol), and 4-dimethylaminopyridine (5.46 mg, 0.045 mmol) in N,N-dimethylformamide at ambient temperature. The reaction mixture was stirred at ambient temperature overnight before 60 mL of chloroform was added. The organic solution was washed with saturated ammonium chloride solution, brine, saturated sodium bicarbonate solution, and brine, dried, filtered, and concentrated. The crude product was purified by flash chromatography eluting from silica gel with a gradient of 0-100% ethyl acetate in hexanes to produce 10.6 mg of a white solid. MS: (+) m/z 417.3 (M+1).

b) {[2-(6-Butoxy-pyridin-3-yl)-7-hydroxy-thiazolo[4,5-c]pyridine-6-carbonyl]-amino}-acetic acid To a solution of {[2-(6-butoxy-pyridin-3-yl)-7-hydroxy-thiazolo[4,5-c]pyridine-6-carbonyl]-amino}-acetic acid methyl ester (10.6 mg, 0.026 mmol) in methanol (1 mL) was added lithium hydroxide aqueous solution (1N, 0.51 mL) at ambient temperature. The reaction mixture was stirred at 50° C. for 1.5 h. After the solvent was evaporated off, 10 mL of water was added. The aqueous solution was adjusted to pH 2-3 by addition of 1N hydrochloric acid, and extracted twice with ethyl acetate. The combined organic layers were dried, filtered, and concentrated to afford 6.5 mg of a white solid. MS: (+) m/z 403.3 (M+1).

Example 94

{[7-Hydroxy-2-(6-phenylsulfanyl-pyridin-3-yl)-thiazolo[4,5-c]pyridine-6-carbonyl]-amino}-acetic acid a) 7-Hydroxy-2-(6-phenylsulfanyl-pyridin-3-yl)-thiazolo[4,5-c]pyridine-6-carboxylic acid ethyl ester A suspension of 2-(6-chloro-pyridin-3-yl)-7-hydroxy-thiazolo[4,5-c]pyridine-6-carboxylic acid ethyl ester, example 92(c)(0.25 g, 0.75 mmol) and triethylamine (0.21 mL, 1.49 mmol) in thiophenol was heated at 100° C. overnight. 100 mL of chloroform was added. The organic solution was washed with saturated sodium bicarbonate solution and brine, dried, filtered, and concentrated. The crude product was purified by flash chromatography eluting from silica gel with a gradient of 0-100% ethyl acetate in hexanes to produce 49.0 mg of a light yellow solid. MS: (+) m/z 410.3 (M+1).

b) {[7-Hydroxy-2-(6-phenylsulfanyl-pyridin-3-yl)-thiazolo[4,5-c]pyridine-6-carbonyl]-amino}-acetic acid Prepared from 7-hydroxy-2-(6-phenylsulfanyl-pyridin-3-yl)-thiazolo[4,5-c]pyridine-6-carboxylic acid ethyl ester under conditions analogous to experimental example 81(f). MS: (−) m/z 437.2 (M−1).

Example 95

{[2-(1-Benzyl-1H-pyrazol-4-yl)4-cyano-7-hydroxy-thiazolo[4,5-c]pyridine-6-carbonyl]-amino}-acetic acid a) 2-(1-Benzyl-1H-pyrazol-4-yl)-4-bromo-7-hydroxy-thiazolo[4,5-c]pyridine-6-carboxylic acid ethyl ester A suspension of 2-(1-benzyl-1H-pyrazol-4-yl)-7-hydroxy-thiazolo[4,5-c]pyridine-6-carboxylic acid ethyl ester, example 91(c)(0.48 g, 1.26 mmol), N-bromosuccinimide (0.24 g, 1.32 mmol), and benzoyl peroxide (30.5 mg, 0.126 mmol) in 4.2 mL of benzene was heated at reflux temperature for 5 h. The reaction mixture was washed successively with saturated sodium bicarbonate, brine, saturated ammonium chloride solution, and brine. The organic solution was dried, filtered, and concentrated. The crude product was purified by flash chromatography eluting from silica gel with a gradient of 0-100% ethyl acetate in hexanes to produce 0.44 g of a white solid. MS: (+) m/z 459.2 (M+1).

b) 2-(1-Benzyl-1H-pyrazol-4-yl)-4-cyano-7-hydroxy-thiazolo[4,5-c]pyridine-6-carboxylic acid ethyl ester To a mixture of 2-(1-benzyl-1H-pyrazol-4-yl)-4-bromo-7-hydroxy-thiazolo[4,5-c]pyridine-6-carboxylic acid ethyl ester (0.25 mg, 0.54 mmol), 1,1'-bis(diphenylphosphino)ferrocene (30.7 mg, 0.055 mmol), zinc dust (4.2 mg, 0.065 mmol), and zinc cyanide (38.3 mg, 0.33 mmol) in N,N-dimethylacetamide (1.11 mL) was added tris(dibenzylideneacetone)dipalladium(0)(24.9 mg, 0.027 mmol). The reaction mixture was heated at 120° C. for 5 h before ethyl acetate (70 mL) was added. The organic solution was washed with saturated ammonium chloride aqueous solution and saturated sodium chloride aqueous solution, dried over anhydrous sodium sulfate, and concentrated. The crude product was purified by flash chromatography eluting from silica gel with a gradient of 0-100% ethyl acetate in hexanes to produce 0.19 g of the title compound as a light yellow solid. MS: (+) m/z 406.3 (M+1).

c) {[2-(1-Benzyl-1H-pyrazol-4-yl)4-cyano-7-hydroxy-thiazolo[4,5-c]pyridine-6-carbonyl]-amino}-acetic acid Prepared from 2-(1-benzyl-1H-pyrazol-4-yl)-4-cyano-7-hydroxy-thiazolo[4,5-c]pyridine-6-carboxylic acid ethyl ester under conditions analogous to experimental example 81(f). MS: (−) m/z 433.2 (M−1).

Example 96

{[2,3-Dichloro-7-cyano-4-hydroxy-1-(3-methyl-butyl)-1H-pyrrolo[2,3-c]pyridine-5-carbonyl]-amino}-acetic acid a) 2-Methyl-1H-pyrrole-3-carboxylic acid ethyl ester

Ammonium hydroxide (28 to 30% (HCl titration (as $NH_3$)), 290 mL, 4.3 mol) was added dropwise to a mixture of chloroacetaldehyde (50% wt aqueous solution, 182 mL, 1.43 mol) and ethyl acetoacetate (183 mL, 1.43 mol) at 0° C. The ice bath was removed, and the reaction mixture was stirred at ambient temperature overnight. The reaction mixture was extracted twice with ethyl acetate. The combined organic layers were washed with 2N hydrochloric acid and saturated sodium chloride aqueous solution, dried over anhydrous sodium sulfate, and concentrated. The crude product was purified by flash chromatography eluting from silica gel with a gradient of 0-50% ethyl acetate in hexanes to afford 73.1 g of the title compound as a yellow solid. $^1$H NMR (200 MHz, CDCl$_3$) δ 6.55 (2H, d, J=2.4 Hz), 4.26 (2H, q, J=7.4 Hz), 2.52 (3H, s), and 1.34 (3H, t, J=7.4 Hz).

b) 2-Methyl-1-(3-methyl-butyl)-1H-pyrrole-3-carboxylic acid ethyl ester

To a solution of 2-methyl-1H-pyrrole-3-carboxylic acid ethyl ester (15 g, 97.3 mmol) in 124 mL of N,N'-dimethylformamide at 0° C. was added sodium hydride (60% dispersion in mineral oil, 4.66 g, 2.80 mmol). The ice bath was then removed, and the reaction mixture was stirred at ambient temperature for 10 min. After the reaction mixture was cooled at 0° C., 1-bromo-3-methylbutane was added. The ice bath was removed, and the reaction mixture was stirred at ambient temperature for 2 hours. Saturated ammonium chloride aqueous solution (200 mL) and ethyl acetate (600 mL) were added to quench the reaction. The organic layer was washed with water and saturated sodium chloride aqueous solution, dried, filtered, and concentrated. The crude product was purified by flash chromatography eluting from silica gel with a gradient of 0-30% ethyl acetate in hexanes to afford 18.3 g of the title compound as a colorless oil. MS: (+) m/z 224.4 (M+1).

c) 4,5-Dichloro-2-methyl-1-(3-methyl-butyl)-1H-pyrrole-3-carboxylic acid ethyl ester A solution of 2-methyl-1-(3-methyl-butyl)-1H-pyrrole-3-carboxylic acid ethyl ester (16.5 g, 73.7 mmol) and N-chlorosuccinimide (20.7 g, 154.7 mmol) in 247 mL of N,N'-dimethylformamide was heated at 100° C. for 4 hours. Ethyl acetate (800 mL) was added. The organic solution was washed with water, dried over anhydrous sodium sulfate, and concentrated. The crude produce was purified by flash chromatography from silica gel with a gradient of 0-20% ethyl acetate in hexanes to afford 12.9 g of the title compound as a colorless oil. $^1$H NMR (200 MHz, CDCl$_3$) δ 4.28 (2H, q, J=7.0 Hz), 3.86 (2H, t, J=7.8 Hz), 2.51 (s, 3H), 1.74-1.42 (m, 3H), 1.35 (3H, t, J=7.0 Hz), and 0.95 (6H, d, J=6.6 Hz).

d) 2,3-Dichloro-4-hydroxy-1-(3-methyl-butyl)-1H-pyrrolo[2,3-c]pyridine-5-carboxylic acid ethyl ester 4,5-Dichloro-2-methyl-1-(3-methyl-butyl)-1H-pyrrole-3-carboxylic acid ethyl ester (14.3 g, 48.9 mmol), N-bromosuccinimide (8.93 g, 50.2 mmol), and benzoyl peroxide (1.18 g, 4.89 mmol) were suspended in 123 mL of benzene and heated at reflux temperature for 16 hours. The reaction mixture was cooled and diluted with ethyl acetate. The reaction mixture was washed successively with saturated bicarbonate solution, brine, saturated ammonium chloride solution, and brine. The organic solvent was dried, filtered, and concentrated to afford 18.1 g of the crude 4,5-dichloro-2-bromomethyl-1-(3-methyl-butyl)-1H-pyrrole-3-carboxylic acid ethyl ester as a brown oil.

To a solution of tert-butoxycarbonylamino-acetic acid ethyl ester (10.4 g, 51.3 mmol) in 90 mL of N,N'-dimethylformamide at 0° C. was added sodium hydride (60% dispersion in mineral oil, 2.35 g, 58.7 mmol). The ice bath was then removed, and the reaction mixture was stirred at ambient temperature for 10 min. After the reaction mixture was cooled at 0° C., the crude 4,5-dichloro-2-bromomethyl-1-(3-methyl-butyl)-1H-pyrrole-3-carboxylic acid ethyl ester (18.1 g, 48.9 mmol) in 20 mL of N,N'-dimethylformamide was added. The ice bath was removed, and the reaction mixture was stirred at ambient temperature for 1 hour. Saturated ammonium chloride aqueous solution (200 mL) and ethyl acetate (350 mL) were added to quench the reaction. The organic layer was washed with water and saturated sodium chloride aqueous solution, dried, filtered, and concentrated to afford 24.1 g of the crude 2-[(tert-butoxycarbonyl-ethoxycarbonylmethyl-amino)-methyl]-4,5-dichloro-1-(3-methyl-butyl)-1H-pyrrole-3-carboxylic acid ethyl ester as a black oil.

The crude 2-[(tert-butoxycarbonyl-ethoxycarbonylmethyl-amino)-methyl]-4,5-dichloro-1-(3-methyl-butyl)-1H-pyrrole-3-carboxylic acid ethyl ester (24.1 g, 48.9 mmol) was dissolved in 110 mL of anhydrous THF and cooled to −78° C. in a acetone dry ice bath. A solution of 77.0 mL of 1.0 M potassium tert-butoxide in THF was added slowly to cold solution, and the reaction was stirred at −78° C. for 30 min. and then at room temperature for 10 min. The reaction was quenched with 9.2 mL of acetic acid. The solvent was evaporated off, and the residue was dissolved in methylene chloride (184 mL). Trifluoroacetic acid (184 mL) was added, and the reaction mixture was stirred at ambient temperature for 1 h. The solvent was evaporated off, and the residue was dissolved in 100 mL of methylene chloride. Triethylamine was added until the solution was basic. After air passed the reaction mixture overnight, the solvent was evaporated off. The residue was dissolved in 350 mL of ethyl acetate, and the organic solution was washed with water and saturated sodium chloride solution, dried, filtered, and concentrated. The crude product was purified by flash chromatography eluting from silica gel with a gradient of 0-100% ethyl acetate in hexanes to produce 2.23 g of a brown froth. MS: (+) m/z 345.2 (M+1).

e) 7-Bromo-2,3-dichloro-4-hydroxy-1-(3-methyl-butyl)-1H-pyrrolo[2,3-c]pyridine-5-carboxylic acid ethyl ester A suspension of 2,3-dichloro-4-hydroxy-1-(3-methyl-butyl)-1H-pyrrolo[2,3-c]pyridine-5-carboxylic acid ethyl ester (2.23 g, 6.46 mmol), N-bromosuccinimide (1.38 g, 7.75 mmol), and benzoyl peroxide (156 mg, 0.646 mmol) in 50 mL of benzene was heated at reflux temperature for 5 hours. The reaction mixture was washed successively with saturated sodium bicarbonate, brine, saturated ammonium chloride solution, and brine. The organic solution was dried, filtered, and concentrated. The crude product was purified by flash chromatography eluting from silica gel with a gradient of 0-2% ethyl acetate in hexanes to produce 1.36 g of a white solid. MS: (+) m/z 423.1 (M+1).

f) 7-Cyano-2,3-dichloro-4-hydroxy-1-(3-methyl-butyl)-1H-pyrrolo[2,3-c]pyridine-5-carboxylic acid ethyl ester To a mixture of 7-bromo-2,3-dichloro-4-hydroxy-1-(3-methyl-butyl)-1H-pyrrolo[2,3-c]pyridine-5-carboxylic acid ethyl ester (1.16 g, 2.74 mmol), 1,1'-bis(diphenylphosphino)ferrocene (228 mg, 0.411 mmol), zinc dust (32.1 mg, 0.493 mmol), and zinc cyanide (290 mg, 2.47 mmol) in N,N-dimethylacetamide (8.7 mL) was added tris(dibenzylideneacetone)dipalladium(0)(188 mg, 0.21 mmol). The reaction mixture was heated at 120° C. for 1.5 hours before ethyl acetate (100 mL) was added. The organic solution was washed with saturated ammonium chloride aqueous solution and saturated sodium chloride aqueous solution, dried over anhydrous sodium sulfate, and concentrated. The crude product was purified by flash chromatography eluting from silica gel with a gradient of 0-30% ethyl acetate in hexanes to produce 0.65 g of the title compound as a light yellow solid. MS: (+) m/z 370.2 (M+1).

g) {[2,3-Dichloro-7-cyano-4-hydroxy-1-(3-methyl-butyl)-1H-pyrrolo[2,3-c]pyridine-5-carbonyl]-amino}-acetic acid 7-Cyano-2,3-dichloro-4-hydroxy-1-(3-methyl-butyl)-1H-pyrrolo[2,3-c]pyridine-5-carboxylic acid ethyl ester (80 mg, 0.22 mmol) and glycine (324 mg, 4.32 mmol) were suspended in 8.64 mL of 0.5 N sodium methoxide in methanol. The reaction was heated at reflux temperature overnight, cooled, and concentrated. The residue was dissolved in water (15 mL), and the solution was acidified to pH 1-2 with 1 N hydrochloric acid. The title compound (60 mg) was collected by filtration as a light yellow solid. MS: (+) m/z 399.2 (M+1).

Example 97

{[7-Cyano-4-hydroxy-1-(3-methyl-butyl)-1H-pyrrolo[2,3-c]pyridine-5-carbonyl]-amino}-acetic acid a) 7-Cyano-4-hydroxy-1-(3-methyl-butyl)-1H-pyrrolo[2,3-c]pyridine-5-carboxylic acid ethyl ester To a suspension of 7-cyano-2,3-dichloro-4-hydroxy-1-(3-methyl-butyl)-1H-pyrrolo[2,3-c]pyridine-5-carboxylic acid ethyl ester (0.66 g, 1.78 mmol), example 96(f), and ammonium formate (2.25 g, 35.7 mmol) in 62 mL of ethyl acetate was added 10 wt. % palladium on carbon (312 mg). The reaction mixture was refluxed for 1 h. The catalyst was filtered off, and the filtrate was concentrated to afford 0.48 g of a white solid. MS: (+) m/z 302.3 (M+1).

b) {[7-Cyano-4-hydroxy-1-(3-methyl-butyl)-1H-pyrrolo[2,3-c]pyridine-5-carbonyl]-amino}-acetic acid Prepared from 7-cyano-4-hydroxy-1-(3-methyl-butyl)-1H-pyrrolo[2,3-c]pyridine-5-carboxylic acid ethyl ester, under conditions analogous to experimental example 96(g). MS: (+) m/z 331.3 (M+1).

Example 98

{[3-Chloro-7-cyano-4-hydroxy-1-(3-methyl-butyl)-1H-pyrrolo[2,3-c]pyridine-5-carbonyl]-amino}-acetic acid a) 4-Acetoxy-7-cyano-1-(3-methyl-butyl)-1H-pyrrolo[2,3-c]pyridine-5-carboxylic acid ethyl ester To a solution of 7-cyano-4-hydroxy-1-(3-methyl-butyl)-1H-pyrrolo[2,3-c]pyridine-5-carboxylic acid ethyl ester (0.4 g, 1.33 mmol), example 97(a), and acetic anhydride (0.25 mL, 2.65 mmol) in methylene chloride (8 mL) at ambient temperature was added triethylamine (0.37 mL, 2.65 mmol). The reaction mixture was stirred at ambient temperature for 2.5 h before 100 mL of methylene chloride was added. The organic solution was washed with 80 mL of water, dried, filtered, and concentrated. The crude product was purified by flash chromatography eluting from silica gel with a gradient of 0-50% ethyl acetate in hexanes to produce 0.44 g of a colorless oil. MS: (+) m/z 344.3 (M+1).

b) 4-Acetoxy-3-chloro-7-cyano-1-(3-methyl-butyl)-1H-pyrrolo[2,3-c]pyridine-5-carboxylic acid ethyl ester A solution of 4-acetoxy-7-cyano-1-(3-methyl-butyl)-1H-pyrrolo[2,3-c]pyridine-5-carboxylic acid ethyl ester (0.44 g, 1.28 mmol) and N-chlorosuccinimide (0.188 g, 1.41 mmol) in 8 mL of N,N'-dimethylformamide was heated at 100° C. for 1 h. Ethyl acetate (100 mL) was added. The organic solution was washed with water, dried over anhydrous sodium sulfate, and concentrated. The crude produce was purified by flash chromatography from silica gel with a gradient of 0-40% ethyl acetate in hexanes to afford 0.27 g of the title compound as a white solid. MS: (+) m/z 378.3 (M+1).

c) {[3-Chloro-7-cyano-4-hydroxy-1-(3-methyl-butyl)-1H-pyrrolo[2,3-c]pyridine-5-carbonyl]-amino}-acetic acid Prepared from 4-acetoxy-3-chloro-7-cyano-1-(3-methyl-butyl)-1H-pyrrolo[2,3-c]pyridine-5-carboxylic acid ethyl ester, under conditions analogous to experimental example 96(g). MS: (−) m/z 363.3 (M−1).

Example 99

{[2,3-Dichloro-7-cyano-1-cyclohexylmethyl-4-hydroxy-1H-pyrrolo[2,3-c]pyridine-5-carbonyl]-amino}-acetic acid a) 2-Methyl-1-cyclohexylmethyl-1H-pyrrole-3-carboxylic acid ethyl ester Prepared from 2-methyl-1H-pyrrole-3-carboxylic acid ethyl ester, example 96(a), and (bromomethyl)cyclohexane under conditions analogous to experimental example 96(b). $^1$H NMR (200 MHz, CDCl$_3$) δ 6.50 (1H, d, J=3.2 Hz), 6.43 (1H, d, J=3.2 Hz), 4.23 (2H, q, J=7.0 Hz), 3.62 (2H, d, J=6.6 Hz), 2.50 (3H, s), 1.78-0.88 (11H, m), and 1.33 (3H, t, J=7.0 Hz).

b) 4,5-Dichloro-2-methyl-1-cyclohexylmethyl-1H-pyrrole-3-carboxylic acid ethyl ester Prepared from 2-methyl-1-cyclohexylmethyl-1H-pyrrole-3-carboxylic acid ethyl ester under conditions analogous to experimental example 96(c). MS: (+) m/z 318.3 (M+1).

c) 2,3-Dichloro-4-hydroxy-1-cyclohexylmethyl-1H-pyrrolo[2,3-c]pyridine-5-carboxylic acid ethyl ester Prepared from 4,5-dichloro-2-methyl-1-cyclohexylmethyl-1H-pyrrole-3-carboxylic acid ethyl ester, under conditions analogous to experimental example 96(d). MS: (+) m/z 371.3 (M+1).

d) 7-Bromo-2,3-dichloro-4-hydroxy-1-cyclohexylmethyl-1H-pyrrolo[2,3-c]pyridine-5-carboxylic acid ethyl ester Prepared from 2,3-dichloro-4-hydroxy-1-cyclohexylmethyl-1H-pyrrolo[2,3-c]pyridine-5-carboxylic acid ethyl ester, under conditions analogous to experimental example 96(e). MS: (+) m/z 449.0 (M+1).

e) 7-Cyano-2,3-dichloro-4-hydroxy-1-cyclohexylmethyl-1H-pyrrolo[2,3-c]pyridine-5-carboxylic acid ethyl ester Prepared from 7-bromo-2,3-dichloro-4-hydroxy-1-cyclohexylmethyl-1H-pyrrolo[2,3-c]pyridine-5-carboxylic acid ethyl ester, under conditions analogous to experimental example 96(f). MS: (+) m/z 396.1 (M+1).

f) {[2,3-Dichloro-7-cyano-4-hydroxy-1-cyclohexylmethyl-1H-pyrrolo[2,3-c]pyridine-5-carbonyl]-amino}-acetic acid Prepared from 7-cyano-2,3-dichloro-4-hydroxy-1-cyclohexylmethyl-1H-pyrrolo[2,3-c]pyridine-5-carboxylic acid ethyl ester under conditions analogous to experimental example 96(g). MS: (+) m/z 425.1 (M+1).

Example 100

{[7-Cyano-4-hydroxy-1-cyclohexylmethyl-1H-pyrrolo[2,3-c]pyridine-5-carbonyl]-amino}-acetic acid a) 7-Cyano-4-hydroxy-1-cyclohexylmethyl-1H-pyrrolo[2,3-c]pyridine-5-carboxylic acid ethyl ester Prepared from 7-cyano-2,3-dichloro-4-hydroxy-1-cyclohexylmethyl-1H-pyrrolo[2,3-c]pyridine-5-carboxylic acid ethyl ester, example 99(e), under conditions analogous to experimental example 97(a). MS: (+) m/z 328.2 (M+1).

b) {[7-Cyano-4-hydroxy-1-cyclohexylmethyl-1H-pyrrolo[2,3-c]pyridine-5-carbonyl]-amino}-acetic acid Prepared from 7-cyano-4-hydroxy-1-cyclohexylmethyl-1H-pyrrolo[2,3-c]pyridine-5-carboxylic acid ethyl ester under conditions analogous to experimental example 96(g). MS: (+) m/z 357.2 (M+1).

Example 101

[(1-Benzyl-3-chloro-4-hydroxy-1H-pyrrolo[2,3-c]pyridine-5-carbonyl)-amino]-acetic acid a) 1-Benzyl-4-(2,2-dimethyl-propionyloxy)-1H-pyrrolo[2,3-c]pyridine-5-carboxylic acid ethyl ester A mixture of 1-benzyl-4-hydroxy-1H-pyrrolo[2,3-c]pyridine-5-carboxylic acid ethyl ester (500 mg, 1.68 mmol), pivaloyl chloride (0.250 mL, 2.02 mmol), 4-dimethylaminopyridine (21 mg, 0.168 mmol) and triethyl amine (0.468 mL, 3.36 mmol) in dichloromethane (5 mL) was stirred at room temperature for 1 h; then the reaction mixture was diluted with EtOAc, washed with saturated NaCl solution and subsequently the organic phase was dried over anhydrous sodium sulfate, filtered, concentrated and the residue was purified with column to give the desired product as a clear oil (599 mg, 93%). $^1$H NMR (200 MHz, CDCl$_3$): δ (ppm)=8.62 (s, 1H), 7.31-7.20 (m, 6H), 6.53-6.51 (m, 1H), 5.40 (s, 2H), 4.41 (q, 2H, J=7.3 Hz), 1.47 (s, 9H), 1.41 (t, 3H, J=7.3 Hz).

b) 1-Benzyl-3-chloro-4-(2,2-dimethyl-propionyloxy)-1H-pyrrolo[2,3-c]pyridine-5-carboxylic acid ethyl ester A mixture of 1-benzyl-4-(2,2-dimethyl-propionyloxy)-1H-pyrrolo[2,3-c]pyridine-5-carboxylic acid ethyl ester (67 mg, 0.176 mmol), NCS (28 mg), BzOOBz (2.3 mg) in carbon tetrachloride (2 mL) was refluxed for 1 h; then cooled, solvent was removed and the residue was purified with column to give the desired product (67 mg). $^1$H NMR (200 MHz, CDCl$_3$): δ

(ppm)=8.63 (s, 1H), 7.4-7.2 (m, 6H), 5.35 (s, 2H), 4.41 (q, J=7.1 Hz), 1.46 (s, 9H), 1.41 (t, 3H, J=7.1 Hz).

c) [(1-Benzyl-3-chloro-4-hydroxy-1H-pyrrolo[2,3-c]pyridine-5-carbonyl)-amino]-acetic acid A mixture of 1-benzyl-3-chloro-4-(2,2-dimethyl-propionyloxy)-1H-pyrrolo[2,3-c]pyridine-5-carboxylic acid ethyl ester (65 mg) and NaOMe/HOMe (0.94 mL, 0.5 M) was refluxed for 1 h; then cooled, partitioned between EtOAc and diluted HCl solution, organic phase was washed with sat. NaCl solution, dried over sodium sulfate and then filtered, concentrated to give a residue, which was refluxed with glycine (236 mg) and NaOMe/HOMe (4.71 mL) overnight; the solvent was subsequently removed, the residue was partitioned between MTBE (methyl tert-butyl ether) and water, the aqueous phase was then acidified with 2 M HCl to pH=1-2, the solids were collected with filtration after cooled in an ice/water bath, the solids were then freeze dried to give the title compound (27 mg). ESI (m/z): 360 (M+H)$^+$.

Example 102

[(4-Hydroxy-9-methyl-9H-beta-carboline-3-carbonyl)-amino]-acetic acid a) 1,2-Dimethyl-1H-indole-3-carboxylic acid ethyl ester To an ice-water bath cooled solution of 2-methyl-1H-indole-3-carboxylic acid ethyl ester (5.197 g, prepared according to Suzuki et al. (1984) Synthesis (Stuttgart) 7:616-617), MeI (2.07 mL) in DMF (25 mL) was added NaH (1.33 g, 60% purity in mineral oil) under nitrogen gas stream. The reaction was stirred for 10 min at 0° C. and 20 min at room temperature and then quenched with diluted HCl solution, diluted with ice/water to a volume of ~200 mL; the mixture was cooled with ice/water bath and the solids were collected with filtration, washed with water, and dried under high vacuum to give the desired crude product (5.87 g) as loose brown to yellow solid. $^1$H NMR (200 MHz, CDCl$_3$): δ (ppm)=8.14-8.0 (m, 1H), 7.3-7.1 (m, 3H), 4.38 (q, 2H, J=7.1 Hz), 3.69 (s, 3H), 2.77 (s, 3H), 1.45 (t, 3H, J=7.1 Hz).

b) 5,7-Dibromo-2-bromomethyl-1-methyl-1H-indole-3-carboxylic acid ethyl ester

Prepared in analogy to that of Example 3 (a) from 1,2-dimethyl-1H-indole-3-carboxylic acid ethyl ester, NBS and BzOOBz. The title compound: $^1$H NMR (200 MHz, CDCl$_3$): δ (ppm)=8.35 (s, 1H), 7.58 (s, 1H), 5.08 (s, 2H), 4.41 (q, 2H, J=7.0 Hz), 3.75 (s, 3H), 1.46 (t, 3H, J=7.0 Hz).

c) 5,7-Dibromo-2-[(tert-butoxycarbonyl-ethoxycarbonylmethyl-amino)-methyl]-1-methyl-1H-indole-3-carboxylic acid ethyl ester Prepared in analogy to that of Example 1(c) from 5,7-dibromo-2-bromomethyl-1-methyl-1H-indole-3-carboxylic acid ethyl ester and tert-butoxycarbonylamino-acetic acid ethyl ester. The title compound, $^1$H NMR (200 MHz, CDCl$_3$): δ (ppm)=8.36 (s, 1H), 7.62 (s, 1H), 5.18 (s, 2H), 4.4-3.79 (m, 8H), 1.6-1.0 (m, 15H).

d) 6,8-Dibromo-4-hydroxy-9-methyl-9H-beta-carboline-3-carboxylic acid ethyl ester Prepared in analogy to that of Example 1(d) from 5,7-dibromo-2-[(tert-butoxycarbonyl-ethoxycarbonylmethylamino)-methyl]-1-methyl-1H-indole-3-carboxylic acid ethyl ester. The title compound: $^1$H NMR (200 MHz, DMSO-d6): δ (ppm)=11.6 (br, s, 1H), 8.69 (s, 1H), 8.43 (s, 1H), 8.30 (s, 1H), 4.43 (q, 2H, J=7.1 Hz), 4.01 (s, 3H), 1.39 (t, 3H, J=7.1 Hz).

e) 4-Hydroxy-9-methyl-9H-beta-carboline-3-carboxylic acid ethyl ester

Prepared in analogy to that of Example 6(a) from 6,8-dibromo-4-hydroxy-9-methyl-9H-beta-carboline-3-carboxylic acid ethyl ester, ammonium formate and Pd/C. The title compound: $^1$H NMR (200 MHz, CDCl$_3$): δ (ppm)=11.71 (s, 1H), 8.51 (s, 1H), 8.41 (d, 1H, J=7.8 Hz), 7.64-7.24 (m, 3H), 4.56 (q, 2H, J=7.1 Hz), 3.97 (s, 3H), 1.52 (t, 3H, J=7.1 Hz).

f) [(4-Hydroxy-9-methyl-9H-beta-carboline-3-carbonyl)-amino]-acetic acid

Prepared in analogy to that of Example 1(e) from 4-hydroxy-9-methyl-9H-beta-carboline-3-carboxylic acid ethyl ester. The title compound, ESI MS (m/z): 300 (M+H)$^+$.

Example 103

[(4-Hydroxy-1,9-dimethyl-9H-beta-carboline-3-carbonyl)-amino]-acetic acid a) 1-Bromo-4-hydroxy-9-methyl-9H-beta-carboline-3-carboxylic acid ethyl ester A mixture of 4-hydroxy-9-methyl-9H-beta-carboline-3-carboxylic acid ethyl ester (511 mg), NBS (354 mg), and BzOOBz (12.7 mg) in carbon tetrachloride (20 mL) was refluxed for 25 min; then cooled, solvents were removed, the residue was purified with column to give the title compound (773 mg). ESI MS (m/z): 349 (M+H)$^+$.

b) 4-Hydroxy-1,9-dimethyl-9H-beta-carboline-3-carboxylic acid ethyl ester

A mixture of 1-bromo-4-hydroxy-9-methyl-9H-beta-carboline-3-carboxylic acid ethyl ester (197 mg), tetramethyl tin (0.094 mL), and Pd(PPh$_3$)$_2$Cl$_2$ (20 mg) in DMF (2 mL) was heated at 120° C. for 45 min. The reaction was then partitioned between EtOAc and water, the organic phase was subsequently washed with sat. NaCl solution, dried over anhydrous sodium sulfate and then filtered, concentrated; the residue was purified with column to give the title compound (118 mg). ESI MS (m/z): 285 (M+H)$^+$.

c) [(4-Hydroxy-1,9-dimethyl-9H-beta-carboline-3-carbonyl)-amino]-acetic acid

Prepared in analogy to that of Example 1(e) from 4-hydroxy-1,9-dimethyl-9H-beta-carboline-3-carboxylic acid ethyl ester. The title compound, ESI MS (m/z): 314 (M+H)

Example 104

[(4-Hydroxy-9-methyl-1-phenyl-9H-beta-carboline-3-carbonyl)-amino]-acetic acid a) 4-Hydroxy-9-methyl-1-phenyl-9H-b-carboline-3-carboxylic acid ethyl ester A mixture of 1-bromo-4-hydroxy-9-methyl-9H-beta-carboline-3-carboxylic acid ethyl ester (150 mg), tributyl phenyl tin (0.169 mL), and Pd(PPh$_3$)$_2$Cl$_2$ (15 mg) in DMF (1.5 mL)

was heated at 120° C. for 41 min. The reaction was then partitioned between EtOAc and water, the organic phase was subsequently washed with sat. NaCl solution, dried over anhydrous sodium sulfate and then filtered, concentrated; the residue was purified with column to give the title compound (94 mg). ESI MS (m/z): 347 (M+H)$^+$.

b) [(4-Hydroxy-9-methyl-1-phenyl-9H-beta-carboline-3-carbonyl)-amino]-acetic acid Prepared in analogy to that of Example 1(e) from 4-hydroxy-9-methyl-1-phenyl-9H-b-carboline-3-carboxylic acid ethyl ester. The title compound, ESI MS (m/z): 376 (M+H)

Example 105

[(1-Cyano-4-hydroxy-9-methyl-9H-beta-carboline-3-carbonyl)-amino]-acetic acid a) 1-Cyano-4-hydroxy-9-methyl-9H-beta-carboline-3-carboxylic acid ethyl ester A mixture of 1-bromo-4-hydroxy-9-methyl-9H-beta-carboline-3-carboxylic acid ethyl ester (256 mg), CuCN (132 mg) in NMP (N-methyl 2-pyrrolidinone, 2 mL) was heated at 120° C. for 67 min. The mixture was poured into a stirring mixture of EtOAc and diluted ammonium hydroxide solution, then acidified with conc. HCl; then the organic phase was separated from aqueous and washed with sat. NaCl solution, dried over anhydrous sodium sulfate, filtered, concentrated; the residue was purified with column to give the desired product (84 mg). The title compound, ESI MS (m/z): 296 (M+H)$^+$.

b) [(1-Cyano-4-hydroxy-9-methyl-9H-beta-carboline-3-carbonyl)-amino]-acetic acid Prepared in analogy to that of Example 1(e) from 1-cyano-4-hydroxy-9-methyl-9H-beta-carboline-3-carboxylic acid ethyl ester. The title compound, ESI MS (m/z): 325 (M+H)

Example 106

{[3-Bromo-7-cyano-2-(4-fluoro-phenyl)-4-hydroxy-1-phenyl-1H-pyrrolo[2,3-c]pyridine-5-carbonyl]-amino}-acetic acid a) 3,7-Dibromo-2-(4-fluoro-phenyl)-4-hydroxy-1-phenyl-1H-pyrrolo[2,3-c]pyridine-5-carboxylic acid ethyl ester Prepared in analogy to that of Example 103(a) from 3-bromo-2-(4-fluoro-phenyl)-4-hydroxy-1-phenyl-1H-pyrrolo[2,3-c]pyridine-5-carboxylic acid ethyl ester. The title compound, ESI MS (m/z): 533 (M+H)$^+$.

b) 3-Bromo-7-cyano-2-(4-fluoro-phenyl)-4-hydroxy-1-phenyl-1H-pyrrolo[2,3-c]pyridine-5-carboxylic acid ethyl ester Prepared in analogy to that of Example 105(a) from 3,7-dibromo-2-(4-fluoro-phenyl)-4-hydroxy-1-phenyl-1H-pyrrolo[2,3-c]pyridine-5-carboxylic acid ethyl ester. The title compound, ESI MS (m/z): 480 (M+H)$^+$.

c) {[3-Bromo-7-cyano-2-(4-fluoro-phenyl)-4-hydroxy-1-phenyl-1H-pyrrolo[2,3-c]pyridine-5-carbonyl]-amino}-acetic acid Prepared in analogy to that of Example 1(e) from 3-bromo-7-cyano-2-(4-fluoro-phenyl)-4-hydroxy-1-phenyl-1H-pyrrolo[2,3-c]pyridine-5-carboxylic acid ethyl ester. The title compound, ESI MS (m/z): 509 (M+H)$^+$.

Example 107

{[7-Cyano-2-(4-fluoro-phenyl)-4-hydroxy-1-phenyl-1H-pyrrolo[2,3-c]pyridine-5-carbonyl]-amino}-acetic acid a) 7-Cyano-2-(4-fluoro-phenyl)-4-hydroxy-1-phenyl-1H-pyrrolo[2,3-c]pyridine-5-carboxylic acid ethyl ester Prepared in analogy to that of Example 6(a) from 3-bromo-7-cyano-2-(4-fluoro-phenyl)-4-hydroxy-1-phenyl-1H-pyrrolo[2,3-c]pyridine-5-carboxylic acid ethyl ester, ammonium formate and Pd/C. The title compound, ESI MS (m/z): 402 (M+H)$^+$.

b) {[7-Cyano-2-(4-fluoro-phenyl)-4-hydroxy-1-phenyl-1H-pyrrolo[2,3-c]pyridine-5-carbonyl]-amino}-acetic acid Prepared in analogy to that of Example 1(e) from 7-cyano-2-(4-fluoro-phenyl)-4-hydroxy-1-phenyl-1H-pyrrolo[2,3-c]pyridine-5-carboxylic acid ethyl ester. The title compound, ESI MS (m/z): 431 (M+H)$^+$.

Example 108

[(4-Hydroxy-5-phenyl-5H-pyrido[4,3-b]indole-3-carbonyl)-amino]-acetic acid a) 3-Methyl-1H-indole-2-carboxylic acid ethyl ester)

A mixture of phenyl hydrazine (8.92 g), 2-oxo-butyric acid (10.11 g), TsOH mono hydrate (47.1 g) in EtOH (200 mL) was refluxed overnight, then cooled, the solids were filtered off and briefly washed with EtOH, all liquids were combined and concentrated to give a residue, which was subsequently partitioned between EtOAc and water, the organic phase was washed with sat. NaHCO$_3$ solution, and sat. NaCl solution respectively, then dried over anhydrous sodium sulfate, filtered, concentrated and crystallized to give product (15.6 g). $^1$H NMR (200 MHz, CDCl$_3$): δ (ppm)=8.65 (br, s, 1H), 7.63 (d, 1H), 7.40-7.10 (m, 3H), 4.40 (q, 2H, J=7.1 Hz), 2.61 (s, 3H), 1.43 (t, 3H, J=7.1 Hz).

b) 3-Methyl-1-phenyl-1H-indole-2-carboxylic acid ethyl ester

Prepared in analogy to that of Example 1(a) from 3-methyl-1H-indole-2-carboxylic acid ethyl ester, iodobenzene, CuI, N,N'-dimethylethylenediamine, and potassium phosphate. $^1$H NMR (200 MHz, CDCl$_3$): δ (ppm)=7.7-7.0 (m, 9H), 4.15 (q, 2H, J=7.1 Hz), 2.67 (s, 3H), 1.10 (t, 3H, J=7.1 Hz).

c) 4-Hydroxy-5-phenyl-5H-pyrido[4,3-b]indole-3-carboxylic acid ethyl ester

A mixture of 3-methyl-1-phenyl-1H-indole-2-carboxylic acid ethyl ester (1.708 g), NBS (2.17 g), and BzOOBz (60 mg) in carbon tetrachloride (20 mL) was refluxed for 2 h; then the mixture was cooled, the solids were filtered off, the filtrate was concentrated to give intermediate bromide (1.263 g).

The above intermediate bromide (1.263 g) was allowed to react with tert-butoxycarbonylamino-acetic acid ethyl ester (586 mg) and NaH (150 mg, 60% purity in mineral oil) in analogy to the reaction in Example 1(c) to give the intermediate (1.291 g).

This intermediate was then subjected to cyclization (KO$^t$Bu), Boc-removal (TFA) and air mediated aromatization conditions similar to those in Example 1(d) to give the title product. $^1$H NMR (200 MHz, CDCl$_3$): δ (ppm)=11.37 (s, 1H), 9.04 (s, 1H), 8.20 (d, 1H), 7.60-7.20 (m, 8H), 4.54 (q, 2H, J=7.0 Hz), 1.50 (t, 3H, J=7.0 Hz).

d) [(4-Hydroxy-5-phenyl-5H-pyrido[4,3-b]indole-3-carbonyl)-amino]-acetic acid Prepared in analogy to that of Example 1(e) from 4-hydroxy-5-phenyl-5H-pyrido[4,3-b]indole-3-carboxylic acid ethyl ester. The title compound, ESI MS (m/z): 362 (M+H)$^+$.

Example 109

[(1-Cyano-4-hydroxy-5-phenyl-5H-pyrido[4,3-b]indole-3-carbonyl)-amino]-acetic acid a) 1-Bromo-4-hydroxy-5-phenyl-5H-pyrido[4,3-b]indole-3-carboxylic acid ethyl ester Prepared in analogy to that of Example 103(a) from 4-hydroxy-5-phenyl-5H-pyrido[4,3-b]indole-3-carboxylic acid ethyl ester, NBS and BzOOBz. The title compound, ESI MS (m/z): 411 (M+H)$^+$.

b) 1-Cyano-4-hydroxy-5-phenyl-5H-pyrido[4,3-b]indole-3-carboxylic acid ethyl ester Prepared in analogy to that of Example 105(a) from 1-bromo-4-hydroxy-5-phenyl-5H-pyrido[4,3-b]indole-3-carboxylic acid ethyl ester and CuCN. The title compound, ESI MS (m/z): 358 (M+H)$^+$.

c) [(1-Cyano-4-hydroxy-5-phenyl-5H-pyrido[4,3-b]indole-3-carbonyl)-amino]-acetic acid Prepared in analogy to that of Example 1(e) from 1-cyano-4-hydroxy-5-phenyl-5H-pyrido[4,3-b]indole-3-carboxylic acid ethyl ester, glycine and NaOMe/HOMe. The title compound, ESI MS (m/z): 385 (M−1)$^−$.

Example 110

[(4-Hydroxy-1-methyl-5-phenyl-5H-pyrido[4,3-b]indole-3-carbonyl)-amino]-acetic acid a) 4-Hydroxy-1-methyl-5-phenyl-5H-pyrido[4,3-b]indole-3-carboxylic acid ethyl ester Prepared in analogy to that of Example 103(b) from 1-bromo-4-hydroxy-5-phenyl-5H-pyrido[4,3-b]indole-3-carboxylic acid ethyl ester, tetramethyl tin, and bis(triphenylphosphine)-palladium(II) dichloride (Pd(PPh$_3$)$_2$Cl$_2$). The title compound, ESI MS (m/z): 347 (M+H)$^+$.

b) [(4-Hydroxy-1-methyl-5-phenyl-5H-pyrido[4,3-b]indole-3-carbonyl)-amino]-acetic acid Prepared in analogy to that of Example 1(e) from 4-hydroxy-1-methyl-5-phenyl-5H-pyrido[4,3-b]indole-3-carboxylic acid ethyl ester, glycine and NaOMe/HOMe. The title compound, ESI MS (m/z): 376 (M+H)$^+$.

Example 111

[(1-Benzyl-3-chloro-7-cyano-4-hydroxy-1H-pyrrolo[2,3-c]pyridine-5-carbonyl)-amino]-acetic acid a) 1-Benzyl-3-chloro-7-cyano-4-hydroxy-1H-pyrrolo[2,3-c]pyridine-5-carboxylic acid ethyl ester A mixture of 1-benzyl-3,7-dichloro-4-hydroxy-1H-pyrrolo[2,3-c]pyridine-5-carboxylic acid ethyl ester (155 mg), Zn(CN)$_2$ (30 mg), Zn dust (3.3 mg), Pd$_2$(dba)$_3$ (19.4 mg), dppf (23.5 mg) in DMA (1.5 mL) was heated to 120° C. for 90 min; then the mixture was partitioned between EtOAc and water, the organic phase was then washed with sat. NaCl solution, dried over anhydrous sodium sulfate, filtered and concentrated sequentially to give a residue, which was purified with column to give desired title compound (100 mg). $^1$H NMR (200 MHz, CDCl$_3$): δ(ppm)=12.16 (s, 1H), 7.4-7.1 (m, 6H), 5.71 (s, 2H), 4.53 (q, 2H, J=7.1 Hz), 1.49 (t, 3H, J=7.1 Hz).

b) [(1-Benzyl-3-chloro-7-cyano-4-hydroxy-1H-pyrrolo[2,3-c]pyridine-5-carbonyl)-amino]-acetic acid Prepared in analogy to that of Example 1(e) from 1-benzyl-3-chloro-7-cyano-4-hydroxy-1H-pyrrolo[2,3-c]pyridine-5-carboxylic acid ethyl ester, glycine and NaOMe/HOMe. The title compound, ESI MS (m/z): 385 (M+H)$^+$.

Example 112

{[3-Cyano-2-(4-fluoro-phenyl)-4-hydroxy-1-phenyl-1H-pyrrolo[2,3-c]pyridine-5-carbonyl]-amino}-acetic acid a) 3-Cyano-2-(4-fluoro-phenyl)-4-hydroxy-1-phenyl-1H-pyrrolo[2,3-c]pyridine-5-carboxylic acid ethyl ester A mixture of 3-bromo-2-(4-fluoro-phenyl)-4-hydroxy-1-phenyl-1H-pyrrolo[2,3-c]pyridine-5-carboxylic acid ethyl ester (200 mg), Zn(CN)$_2$ (31 mg), Zn dust (3.5 mg), Pd$_2$(dba)$_3$ (20 mg), dppf (24.4 mg) in DMA (1 mL) was heated to 120° C. for 145 min; then the mixture was partitioned between EtOAc and water, the organic phase was then washed with sat. NaCl solution, dried over anhydrous sodium sulfate, filtered and concentrated sequentially to give a residue, which was purified with column to give desired title compound (83 mg). The title compound, ESI MS (m/z): 402 (M+H)$^+$.

b) {[3-Cyano-2-(4-fluoro-phenyl)-4-hydroxy-1-phenyl-1H-pyrrolo[2,3-c]pyridine-5-carbonyl]-amino}-acetic acid Prepared in analogy to that of Example 1(e) from 3-cyano-2-(4-fluoro-phenyl)-4-hydroxy-1-phenyl-1H-pyrrolo[2,3-c]pyridine-5-carboxylic acid ethyl ester, glycine and NaOMe/HOMe. The title compound, ESI MS (m/z): 431 (M+H)$^+$.

Example 113

{[3-Cyano-2-(4-fluoro-phenyl)-4-hydroxy-7-methyl-1-phenyl-1H-pyrrolo[2,3-c]pyridine-5-carbonyl]-amino}-acetic acid a) 7-Bromo-3-cyano-2-(4-fluoro-phenyl)-4-hydroxy-1-phenyl-1H-pyrrolo[2,3-c]pyridine-5-carboxylic acid ethyl ester Prepared in analogy to that of Example 103(a) from 3-cyano-2-(4-fluoro-phenyl)-4-hydroxy-1-phenyl-1H-pyrrolo[2,3-c]pyridine-5-carboxylic acid ethyl ester, NBS and BzOOBz. The title compound, ESI MS (m/z): 480 (M+H)$^+$.

b) 3-Cyano-2-(4-fluoro-phenyl)-4-hydroxy-7-methyl-1-phenyl-1H-pyrrolo[2,3-c]pyridine-5-carboxylic acid ethyl ester Prepared in analogy to that of Example 103(b) from 7-bromo-3-cyano-2-(4-fluoro-phenyl)-4-hydroxy-1-phenyl-1H-pyrrolo[2,3-c]pyridine-5-carboxylic acid ethyl ester, tetramethyl tin, and Pd(PPh$_3$)$_2$Cl$_2$. The title compound, ESI MS (m/z): 416 (M+H)$^+$.

c) {[3-Cyano-2-(4-fluoro-phenyl)-4-hydroxy-7-methyl-1-phenyl-1H-pyrrolo[2,3-c]pyridine-5-carbonyl]-amino}-acetic acid Prepared in analogy to that of Example 1(e) from 3-cyano-2-(4-fluoro-phenyl)-4-hydroxy-7-methyl-1-phenyl-1H-pyrrolo[2,3-c]pyridine-5-carboxylic acid ethyl ester, glycine and NaOMe/HOMe. The title compound, ESI MS (m/z): 445 (M+H)$^+$.

Example 114

{[3,7-Dicyano-2-(4-fluoro-phenyl)-4-hydroxy-1-phenyl-1H-pyrrolo[2,3-c]pyridine-5-carbonyl]-amino}-acetic acid a) 3,7-Dicyano-2-(4-fluoro-phenyl)-4-hydroxy-1-phenyl-1H-pyrrolo[2,3-c]pyridine-5-carboxylic acid ethyl ester Prepared in analogy to that of Example 105(a) from 7-bromo-3-cyano-2-(4-fluoro-phenyl)-4-hydroxy-1-phenyl-1H-pyrrolo[2,3-c]pyridine-5-carboxylic acid ethyl ester and CuCN. The title compound, ESI MS (m/z): 427 (M+H)$^+$.

b) {[3,7-Dicyano-2-(4-fluoro-phenyl)-4-hydroxy-1-phenyl-1H-pyrrolo[2,3-c]pyridine-5-carbonyl]-amino}-acetic acid Prepared in analogy to that of Example 1(e) from 3,7-dicyano-2-(4-fluoro-phenyl)-4-hydroxy-1-phenyl-1H-pyrrolo[2,3-c]pyridine-5-carboxylic acid ethyl ester, glycine and NaOMe/HOMe. The title compound, ESI MS (m/z): 454 (M−1)$^−$.

Example 115

[(7-Cyano-4-hydroxy-1-phenyl-1H-pyrrolo[2,3-c]pyridine-5-carbonyl)-amino]-acetic acid a) 2,3,7-Tribromo-4-hydroxy-1-phenyl-1H-pyrrolo[2,3-c]pyridine-5-carboxylic acid ethyl ester Prepared in analogy to that of Example 103(a) from 2,3-dibromo-4-hydroxy-1-phenyl-1H-pyrrolo[2,3-c]pyridine-5-carboxylic acid ethyl ester, NBS and BzOOBz. The title compound, ESI MS (m/z): 517 (M+H)$^+$.

b) 2,3-Dibromo-7-cyano-4-hydroxy-1-phenyl-1H-pyrrolo[2,3-c]pyridine-5-carboxylic acid ethyl ester Prepared in analogy to that of Example 105(a) from 2,3,7-tribromo-4-hydroxy-1-phenyl-1H-pyrrolo[2,3-c]pyridine-5-carboxylic acid ethyl ester and CuCN. The title compound, ESI MS (m/z): 464 (M+H)$^+$.

c) 7-Cyano-4-hydroxy-1-phenyl-1H-pyrrolo[2,3-c]pyridine-5-carboxylic acid ethyl ester Prepared in analogy to that of Example 6(a) from 2,3-dibromo-7-cyano-4-hydroxy-1-phenyl-1H-pyrrolo[2,3-c]pyridine-5-carboxylic acid ethyl ester, ammonium formate and Pd/C. The title compound, ESI MS (m/z): 308 (M+H)$^+$.

d) [(7-Cyano-4-hydroxy-1-phenyl-1H-pyrrolo[2,3-c]pyridine-5-carbonyl)-amino]-acetic acid Prepared in analogy to that of Example 1(e) from 7-cyano-4-hydroxy-1-phenyl-1H-pyrrolo[2,3-c]pyridine-5-carboxylic acid ethyl ester, glycine and NaOMe/HOMe. The title compound, ESI MS (m/z): 337 (M+H)$^+$.

Example 116

[(3-Chloro-7-cyano-4-hydroxy-1-phenyl-1H-pyrrolo[2,3-c]pyridine-5-carbonyl)-amino]-acetic acid a) 3,7-Dichloro-4-hydroxy-1-phenyl-1H-pyrrolo[2,3-c]pyridine-5-carboxylic acid ethyl ester Prepared in analogy to that of Example 25(a) from 4-hydroxy-1-phenyl-1H-pyrrolo[2,3-c]pyridine-5-carboxylic acid ethyl ester, NCS and BzOOBz. The title compound, $^1$H NMR (200 MHz, CDCl$_3$): δ (ppm)=11.76 (s, 1H), 7.6-7.2 (m, 6HH0, 4.51 (q, 2H, J=7.0 Hz), 1.47 (t, 3H, J=7.0 Hz).

b) 3-Chloro-7-cyano-4-hydroxy-1-phenyl-1H-pyrrolo[2,3-c]pyridine-5-carboxylic acid ethyl ester Prepared in analogy to that of Example 111(a) from 3,7-dichloro-4-hydroxy-1-phenyl-1H-pyrrolo[2,3-c]pyridine-5-carboxylic acid ethyl ester, Zn(CN)$_2$, Zn dust, Pd$_2$(dba)$_3$, and dppf. The title compound, $^1$H NMR (200 MHz, CDCl$_3$): δ (ppm)=12.22 (s, 1H), 7.59-7.40 (m, 5H), 7.33 (s, 1H), 4.54 (q, 2H, J=7.1 Hz), 1.49 (t, 3H, J=7.1 Hz).

c) [(3-Chloro-7-cyano-4-hydroxy-1-phenyl-1H-pyrrolo[2,3-c]pyridine-5-carbonyl)-amino]-acetic acid Prepared in analogy to that of Example 1(e) from 3-chloro-7-cyano-4-hydroxy-1-phenyl-1H-pyrrolo[2,3-c]pyridine-5-carboxylic acid ethyl ester, glycine and NaOMe/HOMe. The title compound, ESI MS (m/z): 369 (M−1)$^−$.

Example 117

{[2,3-Dibromo-1-(4-fluoro-benzyl)-4-hydroxy-1H-pyrrolo[2,3-c]pyridine-5-carbonyl]-amino}-acetic acid a) 1-(4-Fluoro-benzyl)-2-methyl-1H-pyrrole-3-carboxylic acid ethyl ester Prepared in analogy to that of Example 5(a) from 2-methyl-1H-pyrrole-3-carboxylic acid ethyl ester. The title compound, ESI MS (m/z): 262 (M+H)$^+$.

b) 4,5-Dibromo-2-bromomethyl-1-(4-fluoro-benzyl)-1H-pyrrole-3-carboxylic acid ethyl ester Prepared in analogy to that of Example 5(b) from 1-(4-fluoro-benzyl)-2-methyl-1H-pyrrole-3-carboxylic acid ethyl ester, NBS and BzOOBz in CCl$_4$. The title compound, ESI MS (m/z): 416 (M−HBr+H)$^+$.

c) 4,5-Dibromo-2-[(tert-butoxycarbonyl-ethoxycarbonylmethyl-amino)-methyl]-1-(4-fluoro-benzyl)-1H-pyrrole-3-carboxylic acid ethyl ester Prepared in analogy to that of Example 1(c) from 1-4,5-dibromo-2-bromomethyl-1-(4-fluoro-benzyl)-1H-pyrrole-3-carboxylic acid ethyl ester and tert-butoxycarbonylamino-acetic acid ethyl ester. The title compound, ESI MS (m/z): 641 (M+Na$^+$).

d) 2,3-Dibromo-1-(4-fluoro-benzyl)-4-hydroxy-1H-pyrrolo[2,3-c]pyridine-5-carboxylic acid ethyl ester Prepared in analogy to that of Example 1(d) from 4,5-dibromo-2-[(tert-butoxycarbonyl-ethoxycarbonylmethyl-amino)-methyl]-1-(4-fluoro-benzyl)-1H-pyrrole-3-carboxylic acid ethyl ester. The title compound, ESI MS (m/z): 573 (M+H$^+$).

e) {[2,3-Dibromo-1-(4-fluoro-benzyl)-4-hydroxy-1H-pyrrolo[2,3-c]pyridine-5-carbonyl]-amino}-acetic acid Prepared in analogy to that of Example 1(e) from 2,3-dibromo-1-(4-fluoro-benzyl)-4-hydroxy-1H-pyrrolo[2,3-c]pyridine-5-carboxylic acid ethyl ester, glycine and NaOMe/HOMe. The title compound, ESI MS (m/z): 500 (M+H)$^+$.

Example 118

[(4-Hydroxy-1-phenethyl-1H-pyrrolo[2,3-c]pyridine-5-carbonyl)-amino]-acetic acid a) 2-Methyl-1-phenethyl-1H-pyrrole-3-carboxylic acid ethyl ester To an ice/water bath cooled solution of 2-methyl-1H-pyrrole-3-carboxylic acid ethyl ester (11.43 g) and (2-bromo-ethyl)-benzene (20.20 mL) in DMF (100 mL) was carefully added NaH (3.88 g, 60% suspension in mineral oil). The mixture was subsequently stirred at room temperature overnight, and cooled with ice/water bath again, another 20.20 mL of (2-brom-ethyl)-benzene and 3.88 of NaH were added to the reaction, which was allowed to stir for another 5 h; then the mixture was quenched by pouring into a mixture of ammonium chloride and ice/water, extracted with EtOAc; EtOAc phase was washed with water twice, saturated NaCl solution (once) and then dried over anhydrous sodium sulfate, filtered, concentrated; the residue was purified with silica column to give the desired title product (3.30 g) with recovered starting pyrrole (6.31 g). The title compound, ESI MS (m/z): 258 (M+H)$^+$.

b) 4-Hydroxy-1-phenethyl-1H-pyrrolo[2,3-c]pyridine-5-carboxylic acid ethyl ester A mixture of 2-methyl-1-phenethyl-1H-pyrrole-3-carboxylic acid ethyl ester (3.30 g), NBS (6.99 g), and BzOOBz (157 mg) in carbon tetrachloride (50 mL) was refluxed for 4 h; then the mixture was cooled, the solids were filtered off, the filtrate was concentrated and purified with column to give intermediate bromide (6.44 g).

The above intermediate bromide (1.263 g) was allowed to react with tert-butoxycarbonylamino-acetic acid ethyl ester (2.605 g) and NaH (667 mg, 60% purity in mineral oil) in analogy to the reaction in Example 1(c) to give the intermediate (7.51 g).

This intermediate was then subjected to cyclization (KO$^t$Bu), Boc-removal (TFA) and air mediated aromatization conditions similar to that in Example 1(d) to give the intermediate (2.93 g).

The above intermediate (2.93 g) was then refluxed with ammonium formate (7.89 g), and Pd on C (666 mg, 10% Pd—C, 50% water) in EtOAc (50 mL) overnight; then cooled, filtered through a short plug of Celite, filtrate was then washed once with water and dried over anhydrous sodium sulfate, filtered, concentrated, the resulting residue was purified with column to give the title compound (1.625 g). The title compound, ESI MS (m/z): 311 (M+H)$^+$.

c) [(4-Hydroxy-1-phenethyl-1H-pyrrolo[2,3-c]pyridine-5-carbonyl)-amino]-acetic acid Prepared in analogy to that of Example 1(e) from 4-hydroxy-1-phenethyl-1H-pyrrolo[2,3-c]pyridine-5-carboxylic acid ethyl ester, glycine and NaOMe/HOMe. The title compound, ESI MS (m/z): 340 (M+H)$^+$.

Example 119

{[2,3-Dibromo-7-cyano-1-(4-fluoro-benzyl)-4-hydroxy-1H-pyrrolo[2,3-c]pyridine-5-carbonyl]-amino}-acetic acid a) 2,3,7-Tribromo-1-(4-fluoro-benzyl)-4-hydroxy-1H-pyrrolo[2,3-c]pyridine-5-carboxylic acid ethyl ester Prepared in analogy to that of Example 103(a) from 2,3-dibromo-1-(4-fluoro-benzyl)-4-hydroxy-1H-pyrrolo[2,3-c]pyridine-5-carboxylic acid ethyl ester, NBS and BzOOBz. The title compound, ESI MS (m/z): 549 (M+H)$^+$.

b) 2,3-Dibromo-7-cyano-1-(4-fluoro-benzyl)-4-hydroxy-1H-pyrrolo[2,3-c]pyridine-5-carboxylic acid ethyl ester Prepared in analogy to that of Example 105(a) from 2,3,7-tribromo-1-(4-fluoro-benzyl)-4-hydroxy-1H-pyrrolo[2,3-c]pyridine-5-carboxylic acid ethyl ester and CuCN. The title compound, ESI MS (m/z): 496 (M+H)$^+$.

c) {[2,3-Dibromo-7-cyano-1-(4-fluoro-benzyl)-4-hydroxy-1H-pyrrolo[2,3-c]pyridine-5-carbonyl]-amino}-acetic acid Prepared in analogy to that of Example 1(e) from 2,3-dibromo-7-cyano-1-(4-fluoro-benzyl)-4-hydroxy-1H-pyrrolo[2,3-c]pyridine-5-carboxylic acid ethyl ester, glycine and NaOMe/HOMe. The title compound, ESI MS (m/z): 525 (M+H)$^+$.

Example 120

[(3-Bromo-7-cyano-4-hydroxy-1-phenyl-1H-pyrrolo[2,3-c]pyridine-5-carbonyl)-amino]-acetic acid a) 4-Acetoxy-7-cyano-1-phenyl-1H-pyrrolo[2,3-c]pyridine-5-carboxylic acid ethyl ester A mixture of 7-cyano-4-hydroxy-1-phenyl-1H-pyrrolo[2,3-c]pyridine-5-carboxylic acid ethyl ester (206 mg), acetic anhydride (0.127 mL), and triethyl amine (0.187 mL) in dichloromethane (2 mL) was stirred at room temperature for 1 h; then the mixture was concentrated, the residue was purified with column to give the title compound (201 mg). The title compound, ESI MS (m/z): 350 (M+H)⁺.

b) 4-Acetoxy-3-bromo-7-cyano-1-phenyl-1H-pyrrolo [2,3-c]pyridine-5-carboxylic acid ethyl ester (1317-67-A)

Prepared in analogy to a bromination procedure in that of Example 103(a) from 4-Acetoxy-7-cyano-1-phenyl-1H-pyrrolo[2,3-c]pyridine-5-carboxylic acid ethyl ester, NBS and BzOOBz. The title compound, ESI MS (m/z): 428 (M+H)⁺.

c) [(3-Bromo-7-cyano-4-hydroxy-1-phenyl-1H-pyrrolo[2,3-c]pyridine-5-carbonyl)-amino]-acetic acid Prepared in analogy to that of Example 1(e) from 4-acetoxy-3-bromo-7-cyano-1-phenyl-1H-pyrrolo[2,3-c]pyridine-5-carboxylic acid ethyl ester, glycine and NaOMe/HOMe. The title compound, ESI MS (m/z): 428 (M+H)⁺.

Example 121

{[7-Cyano-1-(4-fluoro-benzyl)-4-hydroxy-1H-pyrrolo[2,3-c]pyridine-5-carbonyl]-amino}-acetic acid a) 7-Cyano-1-(4-fluoro-benzyl)-4-hydroxy-1H-pyrrolo[2,3-c]pyridine-5-carboxylic acid ethyl ester Prepared in analogy to that of Example 6(a) from 2,3-dibromo-7-cyano-1-(4-fluoro-benzyl)-4-hydroxy-1H-pyrrolo[2,3-c]pyridine-5-carboxylic acid ethyl ester, ammonium formate and Pd/C. The title compound, ESI MS (m/z): 340 (M+H)⁺.

b) {[7-Cyano-1-(4-fluoro-benzyl)-4-hydroxy-1H-pyrrolo[2,3-c]pyridine-5-carbonyl]-amino}-acetic acid Prepared in analogy to that of Example 1(e) from 7-cyano-1-(4-fluoro-benzyl)-4-hydroxy-1H-pyrrolo[2,3-c]pyridine-5-carboxylic acid ethyl ester, glycine and NaOMe/HOMe. The title compound, ESI MS (m/z): 369 (M+H)⁺.

Example 122

[(3-Chloro-7-cyano-4-hydroxy-1-phenethyl-1H-pyrrolo[2,3-c]pyridine-5-carbonyl)-amino]-acetic acid a) 3,7-Dichloro-4-hydroxy-1-phenethyl-1H-pyrrolo [2,3-c]pyridine-5-carboxylic acid ethyl ester Prepared in analogy to that of Example 25(a) from 4-hydroxy-1-phenethyl-1H-pyrrolo[2,3-c]pyridine-5-carboxylic acid ethyl ester, NCS and BzOOBz. The title compound, ESI MS (m/z): 379 (M+H)⁺.

b) 3-Chloro-7-cyano-4-hydroxy-1-phenethyl-1H-pyrrolo[2,3-c]pyridine-5-carboxylic acid ethyl ester Prepared in analogy to that of Example 111(a) from 3,7-dichloro-4-hydroxy-1-phenethyl-1H-pyrrolo[2,3-c]pyridine-5-carboxylic acid ethyl ester, Zn(CN)₂, Zn dust, Pd₂(dba)₃, and dppf. The title compound, ESI MS (m/z): 370 (M+H)⁺.

c) [(3-Chloro-7-cyano-4-hydroxy-1-phenethyl-1H-pyrrolo[2,3-c]pyridine-5-carbonyl)-amino]-acetic acid Prepared in analogy to that of Example 1(e) from 3-chloro-7-cyano-4-hydroxy-1-phenethyl-1H-pyrrolo[2,3-c]pyridine-5-carboxylic acid ethyl ester, glycine and NaOMe/HOMe. The title compound, ESI MS (m/z): 399 (M+H)⁺.

Example 123

{[2,3-Dibromo-4-hydroxy-1-(1(S)-phenyl-ethyl)-1H-pyrrolo[2,3-c]pyridine-5-carbonyl]-amino}-acetic acid a) 2-Methyl-1-(1S-phenyl-ethyl)-1H-pyrrole-3-carboxylic acid ethyl ester A neat mixture of 1S-phenyl-ethylamine (28.05 g) and ethyl acetoacetate (31 mL) was stirred at room temperature for 2 h; then triethyl amine (64.4 mL) was added to the above mixture, followed by cooling with an ice/water bath, chloroacetaldehyde (88.2 mL, 50 wt % solution in water) was slowly added to keep the inner temperature below 20° C.; the mixture was then stirred at room temperature overnight. Water (50 mL) was added to allow easier stirring; the mixture was heated at 100° C. overnight again. The dark mixture was cooled, partitioned between EtOAc and diluted HCl solution, the EtOAc phase was washed with saturated NaCl solution, dried over anhydrous sodium sulfate and equal volume of hexanes was added, the mixture was then passed through a plug of silica to partially remove dark stuff; then concentrated, the residue was purified with column to give desired product (7.725 g). The title compound, ESI MS (m/z): 258 (M+H)⁺.

b) 2,3-Dibromo-4-hydroxy-1-(1S-phenyl-ethyl)-1H-pyrrolo[2,3-c]pyridine-5-carboxylic acid ethyl ester A mixture of 2-methyl-1-(1S-phenyl-ethyl)-1H-pyrrole-3-carboxylic acid ethyl ester (7.72 g), NBS (16.02 g), and BzOOBz (363 mg) in carbon tetrachloride (80 mL) was refluxed for 1 h; then the mixture was cooled, the solids were filtered off, the filtrate was concentrated and purified with column to give intermediate bromide (17.07 g) with ESI MS (m/z): 493 (M+H)⁺.

The above intermediate bromide (17.07 g) was allowed to react with tert-butoxycarbonylamino-acetic acid ethyl ester (6.10 g) and NaH (1.56 g, 60% purity in mineral oil) in analogy to the reaction in Example 1(c) to give the intermediate (17.36 g) with ESI MS (m/z): 637 (M+Na)⁺.

This intermediate (17.36 g) was then subjected to cyclization (KOᵗBu), Boc-removal (TFA) and air mediated aromatization conditions similar to those in Example 1(d) to give the intermediate (7.375 g). The title compound, ESI MS (m/z): 467 (M+H)⁺.

c) {[2,3-Dibromo-4-hydroxy-1-(1(S)-phenyl-ethyl)-1H-pyrrolo[2,3-c]pyridine-5-carbonyl]-amino}-acetic acid Prepared in analogy to that of Example 1(e) from 2,3-dibromo-4-hydroxy-1-(1S-phenyl-ethyl)-1H-pyrrolo[2,3-c]

pyridine-5-carboxylic acid ethyl ester, glycine and NaOMe/HOMe. The title compound, ESI MS (m/z): 496 (M+H)+.

Example 124

{[3-Chloro-7-cyano-1-(4-fluoro-benzyl)-4-hydroxy-1H-pyrrolo[2,3-c]pyridine-5-carbonyl]-amino}-acetic acid a) 4-Acetoxy-7-cyano-1-(4-fluoro-benzyl)-1H-pyrrolo[2,3-c]pyridine-5-carboxylic acid ethyl ester Prepared in analogy to that of Example 120(a) from 7-cyano-1-(4-fluoro-benzyl)-4-hydroxy-1H-pyrrolo[2,3-c]pyridine-5-carboxylic acid ethyl ester, acetic anhydride, and triethyl amine. The title compound, ESI MS (m/z): 382 (M+H)+.

b) 4-Acetoxy-3-chloro-7-cyano-1-(4-fluoro-benzyl)-1H-pyrrolo[2,3-c]pyridine-5-carboxylic acid ethyl ester A mixture of 4-acetoxy-7-cyano-1-(4-fluoro-benzyl)-1H-pyrrolo[2,3-c]pyridine-5-carboxylic acid ethyl ester (103 mg), NCS (38 mg) in MeCN (2 mL) in a closed vial was heated at 90° C. for 1 h. Then the solvent was removed, the residue was purified with column to give the desired product (67 mg). The title compound, ESI MS (m/z): 416 (M+H)+.

c) {[3-Chloro-7-cyano-1-(4-fluoro-benzyl)-4-hydroxy-1H-pyrrolo[2,3-c]pyridine-5-carbonyl]-amino}-acetic acid Prepared in analogy to that of Example 1(e) from 4-acetoxy-3-chloro-7-cyano-1-(4-fluoro-benzyl)-1H-pyrrolo[2,3-c]pyridine-5-carboxylic acid ethyl ester, glycine and NaOMe/HOMe. The title compound, ESI MS (m/z): 403 (M+H)+.

Example 125

[(1-Benzyl-2,3-dichloro-7-cyano-4-hydroxy-1H-pyrrolo[2,3-c]pyridine-5-carbonyl)-amino]-acetic acid a) 1-Benzyl-2,3-dichloro-7-cyano-4-hydroxy-1H-pyrrolo[2,3-c]pyridine-5-carboxylic acid ethyl ester Prepared in analogy to that of Example 111(a) from 1-benzyl-2,3,7-trichloro-4-hydroxy-1H-pyrrolo[2,3-c]pyridine-5-carboxylic acid ethyl ester, Zn(CN)$_2$, Zn dust, Pd$_2$(dba)$_3$, and dppf. The title compound, ESI MS (m/z): 390 (M+H)+.

b) [(1-Benzyl-2,3-dichloro-7-cyano-4-hydroxy-1H-pyrrolo[2,3-c]pyridine-5-carbonyl)-amino]-acetic acid Prepared in analogy to that of Example 1(e) from 1-benzyl-2,3-dichloro-7-cyano-4-hydroxy-1H-pyrrolo[2,3-c]pyridine-5-carboxylic acid ethyl ester, glycine and NaOMe/HOMe. The title compound, ESI MS (m/z): 419 (M+H)+.

Example 126

{[4-Hydroxy-1-(1S-phenyl-ethyl)-1H-pyrrolo[2,3-c]pyridine-5-carbonyl]-amino}-acetic acid a) 4-Hydroxy-1-(1S-phenyl-ethyl)-1H-pyrrolo[2,3-c]pyridine-5-carboxylic acid ethyl ester Prepared in analogy to that of Example 6(a) from 2,3-dibromo-4-hydroxy-1-(1S-phenyl-ethyl)-1H-pyrrolo[2,3-c]pyridine-5-carboxylic acid ethyl ester, ammonium formate and Pd/C. The title compound, ESI MS (m/z): 311 (M+H)+.

b) {[4-Hydroxy-1-(1S-phenyl-ethyl)-1H-pyrrolo[2,3-c]pyridine-5-carbonyl]-amino}-acetic acid Prepared in analogy to that of Example 1(e) from 4-hydroxy-1-(1S-phenyl-ethyl)-1H-pyrrolo[2,3-c]pyridine-5-carboxylic acid ethyl ester, glycine and NaOMe/HOMe. The title compound, ESI MS (m/z): 340 (M+H)+.

Example 127

[(2,3-Dichloro-7-cyano-4-hydroxy-1-phenyl-1H-pyrrolo[2,3-c]pyridine-5-carbonyl)-amino]-acetic acid a) 2,3,7-Trichloro-4-hydroxy-1-phenyl-1H-pyrrolo[2,3-c]pyridine-5-carboxylic acid ethyl ester A mixture of 4-hydroxy-1-phenyl-1H-pyrrolo[2,3-c]pyridine-5-carboxylic acid ethyl ester (112 mg), NCS (163 mg) in MeCN (2 mL) in a closed vial was heated at ~95° C. overnight. Then the solvent was removed, the residue was purified with column to give the desired product (101 mg). The title compound, ESI MS (m/z): 385 (M+H)+.

b) 2,3-Dichloro-7-cyano-4-hydroxy-1-phenyl-1H-pyrrolo[2,3-c]pyridine-5-carboxylic acid ethyl ester Prepared in analogy to that of Example 111(a) from 2,3,7-trichloro-4-hydroxy-1-phenyl-1H-pyrrolo[2,3-c]pyridine-5-carboxylic acid ethyl ester, Zn(CN)$_2$, Zn dust, Pd$_2$(dba)$_3$, and dppf in DMA (N,N-dimethylacetamide). The title compound, ESI MS (m/z): 376 (M+H)+.

c) [(2,3-Dichloro-7-cyano-4-hydroxy-1-phenyl-1H-pyrrolo[2,3-c]pyridine-5-carbonyl)-amino]-acetic acid Prepared in analogy to that of Example 1(e) from 2,3-dichloro-7-cyano-4-hydroxy-1-phenyl-1H-pyrrolo[2,3-c]pyridine-5-carboxylic acid ethyl ester, glycine and NaOMe/HOMe. The title compound, ESI MS (m/z): 405 (M+H)+.

Example 128

[(2,3-Dichloro-7-cyano-4-hydroxy-1-phenethyl-1H-pyrrolo[2,3-c]pyridine-5-carbonyl)-amino]-acetic acid a) 2,3,7-Trichloro-4-hydroxy-1-phenethyl-1H-pyrrolo[2,3-c]pyridine-5-carboxylic acid ethyl ester Prepared in analogy to that of Example 127(a) from 4-hydroxy-1-phenethyl-1H-pyrrolo[2,3-c]pyridine-5-carboxylic acid ethyl ester, and NCS in MeCN. The title compound, ESI MS (m/z): 413 (M+H)+.

b) 2,3-Dichloro-7-cyano-4-hydroxy-1-phenethyl-1H-pyrrolo[2,3-c]pyridine-5-carboxylic acid ethyl ester Prepared in analogy to that of Example 111(a) from 2,3,7-trichloro-4-hydroxy-1-phenethyl-1H-pyrrolo[2,3-c]pyridine-5-carboxylic acid ethyl ester, Zn(CN)$_2$, Zn dust, Pd$_2$(dba)$_3$, and dppf in DMA. The title compound, ESI MS (m/z): 404 (M+H)+.

c) [(2,3-Dichloro-7-cyano-4-hydroxy-1-phenethyl-1H-pyrrolo[2,3-c]pyridine-5-carbonyl)-amino]-acetic acid Prepared in analogy to that of Example 1(e) from 2,3-dichloro-7-cyano-4-hydroxy-1-phenethyl-1H-pyrrolo[2,3-c]pyridine-5-carboxylic acid ethyl ester, glycine and NaOMe/HOMe. The title compound, ESI MS (m/z): 433 (M+H)$^+$.

Example 129

{[2,3-Dichloro-7-cyano-4-hydroxy-1-(1S-phenyl-ethyl)-1H-pyrrolo[2,3-c]pyridine-5-carbonyl]-amino}-acetic acid a) 2,3,7-Trichloro-4-hydroxy-1-(1S-phenyl-ethyl)-1H-pyrrolo[2,3-c]pyridine-5-carboxylic acid ethyl ester Prepared in analogy to that of Example 127(a) from 4-hydroxy-1-(1S-phenyl-ethyl)-1H-pyrrolo[2,3-c]pyridine-5-carboxylic acid ethyl ester, and NCS in MeCN. The title compound, ESI MS (m/z): 413 (M+H)$^+$.

b) 2,3-Dichloro-7-cyano-4-hydroxy-1-(1S-phenyl-ethyl)-1H-pyrrolo[2,3-c]pyridine-5-carboxylic acid ethyl ester Prepared in analogy to that of Example 111(a) from 2,3,7-trichloro-4-hydroxy-1-(1S-phenyl-ethyl)-1H-pyrrolo[2,3-c]pyridine-5-carboxylic acid ethyl ester, Zn(CN)$_2$, Zn dust, Pd$_2$(dba)$_3$, and dppf in DMA. The title compound, ESI MS (m/z): 404 (M+H)$^+$.

c) {[2,3-Dichloro-7-cyano-4-hydroxy-1-(1S-phenyl-ethyl)-1H-pyrrolo[2,3-c]pyridine-5-carbonyl]-amino}-acetic acid Prepared in analogy to that of Example 1(e) from 2,3-dichloro-7-cyano-4-hydroxy-1-(1S-phenyl-ethyl)-1H-pyrrolo[2,3-c]pyridine-5-carboxylic acid ethyl ester, glycine and NaOMe/HOMe. The title compound, ESI MS (m/z): 433 (M+H)$^+$.

Example 130

[(1-Benzyl-3-bromo-7-cyano-4-hydroxy-1H-pyrrolo[2,3-c]pyridine-5-carbonyl)-amino]-acetic acid a) 1-Benzyl-2,3,7-tribromo-4-hydroxy-1H-pyrrolo[2,3-c]pyridine-5-carboxylic acid ethyl ester Prepared in analogy to that of Example 103(a) from 1-benzyl-2,3-dibromo-4-hydroxy-1H-pyrrolo[2,3-c]pyridine-5-carboxylic acid ethyl ester, NBS and BzOOBz. The title compound, ESI MS (m/z): 531 (M+H)$^+$.

b) 1-Benzyl-2,3-dibromo-7-cyano-4-hydroxy-1H-pyrrolo[2,3-c]pyridine-5-carboxylic acid ethyl ester Prepared in analogy to that of Example 105(a) from 1-benzyl-2,3,7-tribromo-4-hydroxy-1H-pyrrolo[2,3-c]pyridine-5-carboxylic acid ethyl ester and CuCN. The title compound, ESI MS (m/z): 478 (M+H)$^+$.

c) 1-Benzyl-7-cyano-4-hydroxy-1H-pyrrolo[2,3-c]pyridine-5-carboxylic acid ethyl ester Prepared in analogy to that of Example 6(a) from 1-benzyl-2,3-dibromo-7-cyano-4-hydroxy-1H-pyrrolo[2,3-c]pyridine-5-carboxylic acid ethyl ester, ammonium formate and Pd/C. The title compound, ESI MS (m/z): 322 (M+H)$^+$.

d) 4-Acetoxy-1-benzyl-7-cyano-1H-pyrrolo[2,3-c]pyridine-5-carboxylic acid ethyl ester Prepared in analogy to that of Example 120(a) from 1-benzyl-7-cyano-4-hydroxy-1H-pyrrolo[2,3-c]pyridine-5-carboxylic acid ethyl ester, acetic anhydride, and triethylamine. The title compound, ESI MS (m/z): 364 (M+H)$^+$.

e) 4-Acetoxy-1-benzyl-3-bromo-7-cyano-1H-pyrrolo[2,3-c]pyridine-5-carboxylic acid ethyl ester A mixture of 4-acetoxy-1-benzyl-7-cyano-1H-pyrrolo[2,3-c]pyridine-5-carboxylic acid ethyl ester (225 mg), NBS (116 mg) in MeCN (3 mL) in a closed vial was heated at 90° C. overnight. Then the solvent was removed, the residue was purified with column to give the desired product (232 mg). The title compound, ESI MS (m/z): 442 (M+H)$^+$.

f) [(1-Benzyl-3-bromo-7-cyano-4-hydroxy-1H-pyrrolo[2,3-c]pyridine-5-carbonyl)-amino]-acetic acid Prepared in analogy to that of Example 1(e) from 4-acetoxy-1-benzyl-3-bromo-7-cyano-1H-pyrrolo[2,3-c]pyridine-5-carboxylic acid ethyl ester, glycine and NaOMe/HOMe. The title compound, ESI MS (m/z): 429 (M+H)$^+$.

Example 131

{[4-Hydroxy-1-(1R-phenyl-ethyl)-1H-pyrrolo[2,3-c]pyridine-5-carbonyl]-amino}-acetic acid a) 2,3-Dibromo-4-hydroxy-1-(1R-phenyl-ethyl)-1H-pyrrolo[2,3-c]pyridine-5-carboxylic acid ethyl ester Prepared according to a reaction sequence in Example 123 steps (a) and (b) for the synthesis of 2,3-dibromo-4-hydroxy-1-(1S-phenyl-ethyl)-1H-pyrrolo[2,3-c]pyridine-5-carboxylic acid ethyl ester starting from 1R-phenyl-ethylamine, ethyl acetoacetate, chloroacetaldehyde, and triethyl amine. The title compound, ESI MS (m/z): 467 (M+H)$^+$.

b) 4-Hydroxy-1-(1R-phenyl-ethyl)-1H-pyrrolo[2,3-c]pyridine-5-carboxylic acid ethyl ester Prepared in analogy to that of Example 6(a) from 2,3-dibromo-4-hydroxy-1-(1R-phenyl-ethyl)-1H-pyrrolo[2,3-c]pyridine-5-carboxylic acid ethyl ester, ammonium formate and Pd/C. The title compound, ESI MS (m/z): 311 (M+H)$^+$.

c) {[4-Hydroxy-1-(1R-phenyl-ethyl)-1H-pyrrolo[2,3-c]pyridine-5-carbonyl]-amino}-acetic acid Prepared in analogy to that of Example 1(e) from 4-hydroxy-1-(1R-phenyl-ethyl)-1H-pyrrolo[2,3-c]pyridine-5-carboxylic acid ethyl ester, glycine and NaOMe/HOMe. The title compound, ESI MS (m/z): 340 (M+H)$^+$.

Example 132

{[4-Hydroxy-1-(4-methoxy-benzyl)-1H-pyrrolo[2,3-c]pyridine-5-carbonyl]-amino}-acetic acid a) 2,3-Dibromo-4-hydroxy-1-(4-methoxy-benzyl)-1H-pyrrolo[2,3-c]pyridine-5-carboxylic acid ethyl ester Prepared similarly according to a reaction sequence in Example 117 steps (a), (b), (c) and (d) for the synthesis of 2,3-dibromo-1-(4-fluoro-benzyl)-4-hydroxy-1H-pyrrolo[2,3-c]pyridine-5-carboxylic acid ethyl ester starting from 2-methyl-1H-pyrrole-3-carboxylic acid ethyl ester, 4-methoxybenzyl bromide. The title compound, ESI MS (m/z): 483 (M+H)$^+$.

b) {[2,3-Dibromo-4-hydroxy-1-(4-methoxy-benzyl)-1H-pyrrolo[2,3-c]pyridine-5-carbonyl]-amino}-acetic acid Prepared in analogy to that of Example 1(e) from 2,3-dibromo-4-hydroxy-1-(4-methoxy-benzyl)-1H-pyrrolo[2,3-c]pyridine-5-carboxylic acid ethyl ester, glycine and NaOMe/HOMe. The title compound, ESI MS (m/z): 512 (M+H)$^+$.

c) {[4-Hydroxy-1-(4-methoxy-benzyl)-1H-pyrrolo[2,3-c]pyridine-5-carbonyl]-amino}-acetic acid Prepared in analogy to that of Example 6(a) from {[2,3-dibromo-4-hydroxy-1-(4-methoxy-benzyl)-1H-pyrrolo[2,3-c]pyridine-5-carbonyl]-amino}-acetic acid, ammonium formate and Pd/C. The title compound, ESI MS (m/z): 356 (M+H)$^+$.

Example 133

{[7-Cyano-4-hydroxy-(4-methoxy-benzyl)-1H-pyrrolo[2,3-c]pyridine-5-carbonyl]-amino}-acetic acid a) 2,3,7-Tribromo-4-hydroxy-1-(4-methoxy-benzyl)-1H-pyrrolo[2,3-c]pyridine-5-carboxylic acid ethyl ester A mixture of 2,3-dibromo-4-hydroxy-1-(4-methoxy-benzyl)-1H-pyrrolo[2,3-c]pyridine-5-carboxylic acid ethyl ester (4.05 g), and NBS (1.61 g) in MeCN (30 mL) was refluxed for 10 min, then the reaction mixture was cooled with ice/water bath, the precipitates were collected as the desired product (1.418 g). The title compound, ESI MS (m/z): 583 (M+H)$^+$.

b) 2,3-Dibromo-7-cyano-4-hydroxy-1-(4-methoxy-benzyl)-1H-pyrrolo[2,3-c]pyridine-5-carboxylic acid ethyl ester Prepared in analogy to that of Example 105(a) from 2,3,7-tribromo-4-hydroxy-1-(4-methoxy-benzyl)-1H-pyrrolo[2,3-c]pyridine-5-carboxylic acid ethyl ester and CuCN. The title compound, ESI MS (m/z): 530 (M+H)$^+$.

c) 7-Cyano-4-hydroxy-1-(4-methoxy-benzyl)-1H-pyrrolo[2,3-c]pyridine-5-carboxylic acid ethyl ester Prepared in analogy to that of Example 6(a) from 2,3-dibromo-7-cyano-4-hydroxy-1-(4-methoxy-benzyl)-1H-pyrrolo[2,3-c]pyridine-5-carboxylic acid ethyl ester, ammonium formate and Pd/C. The title compound, ESI MS (m/z): 352 (M+H)$^+$.

d) {[7-Cyano-4-hydroxy-1-(4-methoxy-benzyl)-1H-pyrrolo[2,3-c]pyridine-5-carbonyl]-amino}-acetic acid Prepared in analogy to that of Example 1(e) from 7-cyano-4-hydroxy-1-(4-methoxy-benzyl)-1H-pyrrolo[2,3-c]pyridine-5-carboxylic acid ethyl ester, glycine and NaOMe/HOMe. The title compound, ESI MS (m/z): 381 (M+H)$^+$.

Example 134

[(1-Benzyl-7-cyano-4-hydroxy-3-methyl-1H-pyrrolo[2,3-c]pyridine-5-carbonyl)-amino]-acetic acid a) 4-Acetoxy-1-benzyl-7-cyano-3-methyl-1H-pyrrolo[2,3-c]pyridine-5-carboxylic acid ethyl ester Prepared in analogy to a Stille methylation step in the Example 103(b) from 4-acetoxy-1-benzyl-3-bromo-7-cyano-1H-pyrrolo[2,3-c]pyridine-5-carboxylic acid ethyl ester, tetramethyl tin, and Pd(PPh$_3$)$_2$Cl$_2$. The title compound, ESI MS (m/z): 378 (M+H)$^+$.

b) [(1-Benzyl-7-cyano-4-hydroxy-3-methyl-1H-pyrrolo[2,3-c]pyridine-5-carbonyl)-amino]-acetic acid Prepared in analogy to that of Example 1(e) from 4-acetoxy-1-benzyl-7-cyano-3-methyl-1H-pyrrolo[2,3-c]pyridine-5-carboxylic acid ethyl ester, glycine and NaOMe/HOMe. The title compound, ESI MS (m/z): 365 (M+H)$^+$.

Example 135

{[2,3-Dichloro-7-cyano-4-hydroxy-1-(4-methoxy-benzyl)-1H-pyrrolo[2,3-c]pyridine-5-carbonyl]-amino}-acetic acid a) 2,3-Dichloro-7-cyano-4-hydroxy-1-(4-methoxy-benzyl)-1H-pyrrolo[2,3-c]pyridine-5-carboxylic acid ethyl ester A mixture of 7-cyano-4-hydroxy-1-(4-methoxy-benzyl)-1H-pyrrolo[2,3-c]pyridine-5-carboxylic acid ethyl ester (123 mg), and NCS (98 mg) in MeCN (3 mL) was refluxed for 1 h. The reaction mixture was cooled and solvent was removed, the residue was purified with column to give the desired product (105 mg). The title compound, ESI MS (m/z): 420 (M+H)$^+$.

b) {[2,3-Dichloro-7-cyano-4-hydroxy-1-(4-methoxy-benzyl)-1H-pyrrolo[2,3-c]pyridine-5-carbonyl]-amino}-acetic acid Prepared in analogy to that of Example 1(e) from 2,3-dichloro-7-cyano-4-hydroxy-1-(4-methoxy-benzyl)-1H-pyrrolo[2,3-c]pyridine-5-carboxylic acid ethyl ester, glycine and NaOMe/HOMe. The title compound, ESI MS (m/z): 449 (M+H)$^+$.

Example 136

{[2,3-Dichloro-7-cyano-4-hydroxy-1-(1R-phenyl-ethyl)-1H-pyrrolo[2,3-c]pyridine-5-carbonyl]-amino}-acetic acid Prepared similarly according to a reaction sequence in Example 129 steps (a), (b), and (c) for the synthesis of the enantiomer: {[2,3-dichloro-7-cyano-4-hydroxy-1-(1S-phenyl-ethyl)-1H-pyrrolo[2,3-c]pyridine-5-carbonyl]-amino}-acetic acid starting from 4-hydroxy-1-(1R-phenyl-ethyl)-1H-pyrrolo[2,3-c]pyridine-5-carboxylic acid ethyl ester. The title compound, ESI MS (m/z): 433 (M+H)$^+$.

Example 137

{[3-Chloro-7-cyano-4-hydroxy-1-(4-methoxy-benzyl)-1H-pyrrolo[2,3-c]pyridine-5-carbonyl]-amino}-acetic acid a) 4-Acetoxy-7-cyano-1-(4-methoxy-benzyl)-1H-pyrrolo[2,3-c]pyridine-5-carboxylic acid ethyl ester Prepared in analogy to that of Example 120(a) from 7-cyano-4-hydroxy-1-(4-methoxy-benzyl)-1H-pyrrolo[2,3-c]pyridine-5-carboxylic acid ethyl ester, acetic anhydride, and triethylamine. The title compound, ESI MS (m/z): 394 (M+H)$^+$.

b) 4-Acetoxy-3-chloro-7-cyano-1-(4-methoxy-benzyl)-1H-pyrrolo[2,3-c]pyridine-5-carboxylic acid ethyl ester Prepared in analogy to that of Example 124(b) from 4-acetoxy-7-cyano-1-(4-methoxy-benzyl)-1H-pyrrolo[2,3-c]pyridine-5-carboxylic acid ethyl ester and NCS in MeCN. The title compound, ESI MS (m/z): 428 (M+H)$^+$.

c) {[3-Chloro-7-cyano-4-hydroxy-1-(4-methoxy-benzyl)-1H-pyrrolo[2,3-c]pyridine-5-carbonyl]-amino}-acetic acid Prepared in analogy to that of Example 1(e) from 4-acetoxy-3-chloro-7-cyano-1-(4-methoxy-benzyl)-1H-pyrrolo[2,3-c]pyridine-5-carboxylic acid ethyl ester, glycine and NaOMe/HOMe. The title compound, ESI MS (m/z): 415 (M+H)$^+$.

Example 138

{[7-Cyano-4-hydroxy-1-(4-methoxy-phenyl)-1H-pyrrolo[2,3-c]pyridine-5-carbonyl]-amino}-acetic acid a) 1-(4-Methoxy-phenyl)-2-methyl-1H-pyrrole-3-carboxylic acid ethyl ester 2-Bromoacetaldehyde (prepared from the distillates from heating 18.212 g of 2-bromoacetaldehyde diethyl acetal and 25.63 g of oxalic acid dihydrate, see U.S. Pat. No. 4,087,539 for detail) was added to an ice/water bath cooled mixture of ethyl acetoacetate sodium salt (9.84 g) in ethanol (100 mL) carefully; after addition, the mixture was stirred at rt for 1 h and para-anisidine (9.56 g) was added, the resulting mixture was subsequently refluxed in an oil bath for 1 h. Then, reaction was cooled, solvents were removed, the residue was partitioned between EtOAc and 1 M HCl aqueous solution; the organic phase was sequentially washed with water, sat. NaCl solution and dried over anhydrous sodium sulfate, filtered, concentrated; the resulting residue was column-purified to give the desired product (8.08 g). The title compound, ESI MS (m/z): 260 (M+H)$^+$.

b) 2,3-Dibromo-4-hydroxy-1-(4-methoxy-phenyl)-1H-pyrrolo[2,3-c]pyridine-5-carboxylic acid ethyl ester Prepared similarly according to a reaction sequence in Example 3 steps (a), (b), and (c) for the synthesis of 2,3-dibromo-4-hydroxy-1-phenyl-1H-pyrrolo[2,3-c]pyridine-5-carboxylic acid ethyl ester starting from 1-(4-Methoxy-phenyl)-2-methyl-1H-pyrrole-3-carboxylic acid ethyl ester. The title compound, ESI MS (m/z): 469 (M+H)$^+$.

c) 2,3,7-Tribromo-4-hydroxy-1-(4-methoxy-phenyl)-1H-pyrrolo[2,3-c]pyridine-5-carboxylic acid ethyl ester Prepared in analogy to that of Example 133(a) from 2,3-Dibromo-4-hydroxy-1-(4-methoxy-phenyl)-1H-pyrrolo[2,3-c]pyridine-5-carboxylic acid ethyl ester and NBS in MeCN. The title compound, ESI MS (m/z): 547 (M+H)$^+$.

d) 2,3-Dibromo-7-cyano-4-hydroxy-1-(4-methoxy-phenyl)-1H-pyrrolo[2,3-c]pyridine-5-carboxylic acid ethyl ester Prepared in analogy to that of Example 105(a) from 2,3,7-tribromo-4-hydroxy-1-(4-methoxy-phenyl)-1H-pyrrolo[2,3-c]pyridine-5-carboxylic acid ethyl ester and CuCN. The title compound, ESI MS (m/z): 494 (M+H)$^+$.

e) 7-Cyano-4-hydroxy-1-(4-methoxy-benzyl)-1H-pyrrolo[2,3-c]pyridine-5-carboxylic acid ethyl ester Prepared in analogy to that of Example 6(a) from 2,3-Dibromo-7-cyano-4-hydroxy-1-(4-methoxy-phenyl)-1H-pyrrolo[2,3-c]pyridine-5-carboxylic acid ethyl ester, ammonium formate and Pd/C. The title compound, ESI MS (m/z): 338 (M+H)$^+$.

f) {[7-Cyano-4-hydroxy-1-(4-methoxy-phenyl)-1H-pyrrolo[2,3-c]pyridine-5-carbonyl]-amino}-acetic acid Prepared in analogy to that of Example 1(e) from 7-cyano-4-hydroxy-1-(4-methoxy-benzyl)-1H-pyrrolo[2,3-c]pyridine-5-carboxylic acid ethyl ester, glycine and NaOMe/HOMe. The title compound, ESI MS (m/z): 367 (M+H)$^+$.

Example 139

{[2,3-Dichloro-7-cyano-4-hydroxy-1-(4-methoxy-phenyl)-1H-pyrrolo[2,3-c]pyridine-5-carbonyl]-amino}-acetic acid a) 2,3-Dichloro-7-cyano-4-hydroxy-1-(4-methoxy-phenyl)-1H-pyrrolo[2,3-c]pyridine-5-carboxylic acid ethyl ester Prepared in analogy to that of Example 135(a) from 7-cyano-4-hydroxy-1-(4-methoxy-benzyl)-1H-pyrrolo[2,3-c]pyridine-5-carboxylic acid ethyl ester and NCS in MeCN. The title compound, ESI MS (m/z): 406 (M+H)$^+$.

b) {[2,3-Dichloro-7-cyano-4-hydroxy-1-(4-methoxy-phenyl)-1H-pyrrolo[2,3-c]pyridine-5-carbonyl]-amino}-acetic acid Prepared in analogy to that of Example 1(e) from 2,3-dichloro-7-cyano-4-hydroxy-1-(4-methoxy-phenyl)-1H-pyrrolo[2,3-c]pyridine-5-carboxylic acid ethyl ester, glycine and NaOMe/HOMe. The title compound, ESI MS (m/z): 435 (M+H)$^+$.

Example 140

{[3-Chloro-7-cyano-4-hydroxy-1-(4-methoxy-phenyl)-1H-pyrrolo[2,3-c]pyridine-5-carbonyl]-amino}-acetic acid a) 4-Acetoxy-7-cyano-1-(4-methoxy-phenyl)-1H-pyrrolo[2,3-c]pyridine-5-carboxylic acid ethyl ester Prepared in analogy to that of Example 120(a) from 7-cyano-4-hydroxy-1-(4-methoxy-benzyl)-1H-pyrrolo[2,3-c]pyridine-5-carboxylic acid ethyl ester, acetic anhydride, and triethyl amine. The title compound, ESI MS (m/z): 380 (M+H)$^+$.

b) 4-Acetoxy-3-chloro-7-cyano-1-(4-methoxy-phenyl)-1H-pyrrolo[2,3-c]pyridine-5-carboxylic acid ethyl ester Prepared in analogy to that of Example 124(b) from 4-acetoxy-7-cyano-1-(4-methoxy-phenyl)-1H-pyrrolo[2,3-c]pyridine-5-carboxylic acid ethyl ester and NCS in MeCN. The title compound, ESI MS (m/z): 414 (M+H)$^+$.

c) {[3-Chloro-7-cyano-4-hydroxy-1-(4-methoxy-phenyl)-1H-pyrrolo[2,3-c]pyridine-5-carbonyl]-amino}-acetic acid Prepared in analogy to that of Example 1(e) from 4-acetoxy-3-chloro-7-cyano-1-(4-methoxy-phenyl)-1H-pyrrolo[2,3-c]pyridine-5-carboxylic acid ethyl ester, glycine and NaOMe/HOMe. The title compound, ESI MS (m/z): 401 (M+H)$^+$.

Example 141

{[1-(4-Fluoro-benzyl)-4-hydroxy-2,3-dimethyl-1H-pyrrolo[2,3-c]pyridine-5-carbonyl]-amino}-acetic acid a) 4-Acetoxy-2,3-dibromo-1-(4-fluoro-benzyl)-1H-pyrrolo[2,3-c]pyridine-5-carboxylic acid ethyl ester Prepared in analogy to that of Example 120(a) from 2,3-dibromo-1-(4-fluoro-benzyl)-4-hydroxy-1H-pyrrolo[2,3-c]pyridine-5-carboxylic acid ethyl ester, acetic anhydride, and triethyl amine. The title compound, ESI MS (m/z): 513 (M+H)$^+$.

b) 4-Acetoxy-1-(4-fluoro-benzyl)-2,3-dimethyl-1H-pyrrolo[2,3-c]pyridine-5-carboxylic acid ethyl ester Prepared in analogy to that of Example 19(b) from 4-acetoxy-2,3-dibromo-1-(4-fluoro-benzyl)-1H-pyrrolo[2,3-c]pyridine-5-carboxylic acid ethyl ester, tetramethyltin and Pd(PPh$_3$)$_2$Cl$_2$. The title compound, ESI MS (m/z): 385 (M+H)$^+$.

c) {[1-(4-Fluoro-benzyl)-4-hydroxy-2,3-dimethyl-1H-pyrrolo[2,3-c]pyridine-5-carbonyl]-amino}-acetic acid Prepared in analogy to that of Example 1(e) from 4-acetoxy-1-(4-fluoro-benzyl)-2,3-dimethyl-1H-pyrrolo[2,3-c]pyridine-5-carboxylic acid ethyl ester, glycine and NaOMe/HOMe. The title compound, ESI MS (m/z): 372 (M+H)$^+$.

Example 142

{[7-Cyano-1-(4-fluoro-phenyl)-4-hydroxy-1H-pyrrolo[2,3-c]pyridine-5-carbonyl]-amino}-acetic acid a) 2,3-Dibromo-1-(4-fluoro-phenyl)-4-hydroxy-1H-pyrrolo[2,3-c]pyridine-5-carboxylic acid ethyl ester Prepared similarly according to a reaction sequence in Example 138 steps (a) and (b) for the synthesis of 2,3-dibromo-4-hydroxy-1-(4-methoxy-phenyl)-1H-pyrrolo[2,3-c]pyridine-5-carboxylic acid ethyl ester starting from 4-fluoroaniline. The title compound, ESI MS (m/z): 457 (M+H)$^+$.

b) 2,3,7-Tribromo-4-hydroxy-1-(4-fluoro-phenyl)-1H-pyrrolo[2,3-c]pyridine-5-carboxylic acid ethyl ester Prepared in analogy to that of Example 133(a) from 2,3-dibromo-1-(4-fluoro-phenyl)-4-hydroxy-1H-pyrrolo[2,3-c]pyridine-5-carboxylic acid ethyl ester and NBS in MeCN. The title compound, ESI MS (m/z): 535 (M+H)$^+$.

c) 2,3-Dibromo-7-cyano-4-hydroxy-1-(4-fluoro-phenyl)-1H-pyrrolo[2,3-c]pyridine-5-carboxylic acid ethyl ester Prepared in analogy to that of Example 105(a) from 2,3,7-tribromo-4-hydroxy-1-(4-fluoro-phenyl)-1H-pyrrolo[2,3-c]pyridine-5-carboxylic acid ethyl ester and CuCN. The title compound, ESI MS (m/z): 482 (M+H)$^+$.

d) 7-Cyano-1-(4-fluoro-phenyl)-4-hydroxy-1H-pyrrolo[2,3-c]pyridine-5-carboxylic acid ethyl ester Prepared in analogy to that of Example 6(a) from 2,3-dibromo-7-cyano-4-hydroxy-1-(4-fluoro-phenyl)-1H-pyrrolo[2,3-c]pyridine-5-carboxylic acid ethyl ester, ammonium formate and Pd/C. The title compound, ESI MS (m/z): 326 (M+H)$^+$.

e) {[7-Cyano-1-(4-fluoro-phenyl)-4-hydroxy-1H-pyrrolo[2,3-c]pyridine-5-carbonyl]-amino}-acetic acid Prepared in analogy to that of Example 1(e) from 7-cyano-1-(4-fluoro-phenyl)-4-hydroxy-1H-pyrrolo[2,3-c]pyridine-5-carboxylic acid ethyl ester, glycine and NaOMe/HOMe. The title compound, ESI MS (m/z): 355 (M+H)$^+$.

Example 143

{[2,3-Dichloro-7-cyano-4-hydroxy-1-(4-fluoro-phenyl)-1H-pyrrolo[2,3-c]pyridine-5-carbonyl]-amino}-acetic acid a) 2,3-Dichloro-7-cyano-4-hydroxy-1-(4-methoxy-phenyl)-1H-pyrrolo[2,3-c]pyridine-5-carboxylic acid ethyl ester Prepared in analogy to that of Example 135(a) from 7-cyano-4-hydroxy-1-(4-fluoro-benzyl)-1H-pyrrolo[2,3-c]pyridine-5-carboxylic acid ethyl ester and NCS in MeCN. The title compound, ESI MS (m/z): 394 (M+H)$^+$.

b) {[2,3-Dichloro-7-cyano-4-hydroxy-1-(4-fluoro-phenyl)-1H-pyrrolo[2,3-c]pyridine-5-carbonyl]-amino}-acetic acid Prepared in analogy to that of Example 1(e) from 2,3-dichloro-7-cyano-4-hydroxy-1-(4-fluoro-phenyl)-1H-pyrrolo[2,3-c]pyridine-5-carboxylic acid ethyl ester, glycine and NaOMe/HOMe. The title compound, ESI MS (m/z): 423 (M+H)$^+$.

Example 144

{[3-Chloro-7-cyano-4-hydroxy-1-(4-fluoro-phenyl)-1H-pyrrolo[2,3-c]pyridine-5-carbonyl]-amino}-acetic acid a) 4-Acetoxy-7-cyano-1-(4-fluoro-phenyl)-1H-pyrrolo[2,3-c]pyridine-5-carboxylic acid ethyl ester Prepared in analogy to that of Example 120(a) from 7-cyano-4-hydroxy-1-(4-fluoro-benzyl)-1H-pyrrolo[2,3-c]pyridine-5-carboxylic acid ethyl ester, acetic anhydride, and triethyl amine. The title compound, ESI MS (m/z): 368 (M+H)$^+$.

b) 4-Acetoxy-3-chloro-7-cyano-1-(4-fluoro-phenyl)-1H-pyrrolo[2,3-c]pyridine-5-carboxylic acid ethyl ester Prepared in analogy to that of Example 124(b) from 4-acetoxy-7-cyano-1-(4-fluoro-phenyl)-1H-pyrrolo[2,3-c]pyridine-5-carboxylic acid ethyl ester and NCS in MeCN. The title compound, ESI MS (m/z): 402 (M+H)$^+$.

c) {[3-Chloro-7-cyano-4-hydroxy-1-(4-fluoro-phenyl)-1H-pyrrolo[2,3-c]pyridine-5-carbonyl]-amino}-acetic acid Prepared in analogy to that of Example 1(e) from 4-acetoxy-3-chloro-7-cyano-1-(4-fluoro-phenyl)-1H-pyrrolo[2,3-c]pyridine-5-carboxylic acid ethyl ester, glycine and NaOMe/HOMe. The title compound, ESI MS (m/z): 389 (M+H)$^+$.

Example 145

{[1-(4-Fluoro-benzyl)-4-hydroxy-1H-pyrrolo[2,3-c]pyridine-5-carbonyl]-amino}-acetic acid a) 1-(4-Fluoro-benzyl)-4-hydroxy-1H-pyrrolo[2,3-c]pyridine-5-carboxylic acid ethyl ester Prepared in analogy to that of Example 6(a) from 2,3-dibromo-1-(4-fluoro-benzyl)-4-hydroxy-1H-pyrrolo[2,3-c]pyridine-5-carboxylic acid ethyl ester, ammonium formate and Pd/C. The title compound, ESI MS (m/z): 315 (M+H)$^+$.

b) {[1-(4-Fluoro-benzyl)-4-hydroxy-1H-pyrrolo[2,3-c]pyridine-5-carbonyl]-amino}-acetic acid Prepared in analogy to that of Example 1(e) from 1-(4-fluoro-benzyl)-4-hydroxy-1H-pyrrolo[2,3-c]pyridine-5-carboxylic acid ethyl ester, glycine and NaOMe/HOMe. The title compound, ESI MS (m/z): 344 (M+H)$^+$.

Example 146

[(2-Cyano-4-hydroxy-1-phenyl-1H-pyrrolo[2,3-c]pyridine-5-carbonyl)-amino]-acetic acid a) [(2-Cyano-4-hydroxy-1-phenyl-1H-pyrrolo[2,3-c]pyridine-5-carbonyl)-amino]-acetic acid A mixture of [(2-bromo-4-hydroxy-1-phenyl-1H-pyrrolo[2,3-c]pyridine-5-carbonyl)-amino]-acetic acid (50 mg), Zn(CN)$_2$ (9.0 mg), Zn dust (1.0 mg), Pd$_2$(dba)$_3$ (5.9 mg), dppf (7.1 mg) in DMA (1 mL) was heated to 120° C. for 60 min; then the mixture was cooled, diluted with DMSO and purified by C18 reverse phase chromatography to give the desired title compound (33 mg). The title compound, ESI MS (m/z): 337 (M+H)$^+$.

Example 147

{[1-(2-Fluoro-benzyl)-4-hydroxy-1H-pyrrolo[2,3-c]pyridine-5-carbonyl]-amino}-acetic acid a) 2,3-Dibromo-1-(2-fluoro-benzyl)-4-hydroxy-1H-pyrrolo[2,3-c]pyridine-5-carboxylic acid ethyl ester Prepared similarly according to a reaction sequence in Example 117 steps (a), (b), (c) and (d) for the synthesis of 2,3-dibromo-1-(4-fluoro-benzyl)-4-hydroxy-1H-pyrrolo[2,3-c]pyridine-5-carboxylic acid ethyl ester starting from 2-methyl-1H-pyrrole-3-carboxylic acid ethyl ester, 2-fluorobenzyl bromide. The title compound, ESI MS (m/z): 471 (M+H)$^+$.

b) 1-(2-Fluoro-benzyl)-4-hydroxy-1H-pyrrolo[2,3-c]pyridine-5-carboxylic acid ethyl ester Prepared in analogy to that of Example 6(a) from 2,3-dibromo-1-(2-fluoro-benzyl)-4-hydroxy-1H-pyrrolo[2,3-c]pyridine-5-carboxylic acid ethyl ester, ammonium formate and Pd/C. The title compound, ESI MS (m/z): 315 (M+H)$^+$.

c) {[1-(2-Fluoro-benzyl)-4-hydroxy-1H-pyrrolo[2,3-c]pyridine-5-carbonyl]-amino}-acetic acid Prepared in analogy to that of Example 1(e) from 1-(2-fluoro-benzyl)-4-hydroxy-1H-pyrrolo[2,3-c]pyridine-5-carboxylic acid ethyl ester, glycine and NaOMe/HOMe. The title compound, ESI MS (m/z): 344 (M+H)$^+$.

Example 148

{[4-Hydroxy-1-(2-methoxy-benzyl)-1H-pyrrolo[2,3-c]pyridine-5-carbonyl]-amino}-acetic acid a) 2,3-Dibromo-1-(2-methoxy-benzyl)-4-hydroxy-1H-pyrrolo[2,3-c]pyridine-5-carboxylic acid ethyl ester Prepared similarly according to a reaction sequence in Example 117 steps (a), (b), (c) and (d) for the synthesis of 2,3-dibromo-1-(4-fluoro-benzyl)-4-hydroxy-1H-pyrrolo[2,3-c]pyridine-5-carboxylic acid ethyl ester starting from 2-methyl-1H-pyrrole-3-carboxylic acid ethyl ester, 2-methoxybenzyl chloride. The title compound, ESI MS (m/z): 483 (M+H)$^+$.

b) 1-(2-Methoxy-benzyl)-4-hydroxy-1H-pyrrolo[2,3-c]pyridine-5-carboxylic acid ethyl ester Prepared in analogy to that of Example 6(a) from 2,3-dibromo-1-(2-methoxy-benzyl)-4-hydroxy-1H-pyrrolo[2,3-c]pyridine-5-carboxylic acid ethyl ester, ammonium formate and Pd/C. The title compound, ESI MS (m/z): 327 (M+H)$^+$.

c) {[4-Hydroxy-1-(2-methoxy-benzyl)-1H-pyrrolo[2,3-c]pyridine-5-carbonyl]-amino}-acetic acid Prepared in analogy to that of Example 1(e) from 1-(2-methoxy-benzyl)-4-hydroxy-1H-pyrrolo[2,3-c]pyridine-5- carboxylic acid ethyl ester, glycine and NaOMe/HOMe. The title compound, ESI MS (m/z): 356 (M+H)$^+$.

Example 149

{[4-Hydroxy-1-(3-methoxy-benzyl)-1H-pyrrolo[2,3-c]pyridine-5-carbonyl]-amino}-acetic acid a) 2,3-Dibromo-1-(3-methoxy-benzyl)-4-hydroxy-1H-pyrrolo[2,3-c]pyridine-5-carboxylic acid ethyl ester Prepared similarly according to a reaction sequence in Example 117 steps (a), (b), (c) and (d) for the synthesis of 2,3-dibromo-1-(4-fluoro-benzyl)-4-hydroxy-1H-pyrrolo[2,3-c]pyridine-5-carboxylic acid ethyl ester starting from 2-methyl-1H-pyrrole-3-carboxylic acid ethyl ester, 3-methoxybenzyl chloride. The title compound, ESI MS (m/z): 483 (M+H)$^+$.

b) 1-(3-Methoxy-benzyl)-4-hydroxy-1H-pyrrolo[2,3-c]pyridine-5-carboxylic acid ethyl ester Prepared in analogy to that of Example 6(a) from 2,3-dibromo-1-(3-methoxy-benzyl)-4-hydroxy-1H-pyrrolo[2,3-c]pyridine-5-carboxylic acid ethyl ester, ammonium formate and Pd/C. The title compound, ESI MS (m/z): 327 (M+H)$^+$.

c) {[4-Hydroxy-1-(3-methoxy-benzyl)-1H-pyrrolo[2,3-c]pyridine-5-carbonyl]-amino}-acetic acid Prepared in analogy to that of Example 1(e) from 1-(3-methoxy-benzyl)-4-hydroxy-1H-pyrrolo[2,3-c]pyridine-5-carboxylic acid ethyl ester, glycine and NaOMe/HOMe. The title compound, ESI MS (m/z): 356 (M+H)$^+$.

Example 150

{[7-Cyano-1-(4-fluoro-phenyl)-4-hydroxy-3-phenyl-1H-pyrrolo[2,3-c]pyridine-5-carbonyl]-amino}-acetic acid a) {[7-Cyano-1-(4-fluoro-phenyl)-4-hydroxy-3-phenyl-1H-pyrrolo[2,3-c]pyridine-5-carbonyl]-amino}-acetic acid A mixture of {[7-chloro-1-(4-fluoro-phenyl)-4-hydroxy-3-phenyl-1H-pyrrolo[2,3-c]pyridine-5-carbonyl]-amino}-acetic acid (30 mg), Zn(CN)$_2$ (4.0 mg), Zn dust (0.5 mg), Pd$_2$(dba)$_3$ (3.2 mg), dppf (3.8 mg) in DMA (1 mL) was heated to 120° C. for 90 min; then the mixture was cooled, diluted with DMSO and purified by C18 reverse phase chromatography to give the desired title compound (11 mg). The title compound, ESI MS (m/z): 431 (M+H)$^+$.

Example 151

{[7-Cyano-1-(2-fluoro-benzyl)-4-hydroxy-1H-pyrrolo[2,3-c]pyridine-5-carbonyl]-amino}-acetic acid a) 2,3,7-Tribromo-1-(2-fluoro-benzyl)-4-hydroxy-1H-pyrrolo[2,3-c]pyridine-5-carboxylic acid ethyl ester Prepared in analogy to that of Example 103(a) from 2,3-dibromo-1-(2-fluoro-benzyl)-4-hydroxy-1H-pyrrolo[2,3-c]pyridine-5-carboxylic acid ethyl ester, NBS and BzOOBz in carbontetrachloride. The title compound, ESI MS (m/z): 549 (M+H)$^+$.

b) 2,3-Dibromo-7-cyano-1-(2-fluoro-benzyl)-4-hydroxy-1H-pyrrolo[2,3-c]pyridine-5-carboxylic acid ethyl ester Prepared in analogy to that of Example 105(a) from 2,3,7-tribromo-1-(2-fluoro-benzyl)-4-hydroxy-1H-pyrrolo[2,3-c]pyridine-5-carboxylic acid ethyl ester and CuCN. The title compound, ESI MS (m/z): 496 (M+H)$^+$.

c) 7-Cyano-1-(2-fluoro-benzyl)-4-hydroxy-1H-pyrrolo[2,3-c]pyridine-5-carboxylic acid ethyl ester Prepared in analogy to that of Example 6(a) from 2,3-dibromo-7-cyano-1-(2-fluoro-benzyl)-4-hydroxy-1H-pyrrolo[2,3-c]pyridine-5-carboxylic acid ethyl ester, ammonium formate and Pd/C. The title compound, ESI MS (m/z): 340 (M+H)$^+$.

d) {[7-Cyano-1-(2-fluoro-benzyl)-4-hydroxy-1H-pyrrolo[2,3-c]pyridine-5-carbonyl]-amino}-acetic acid Prepared in analogy to that of Example 1(e) from 7-cyano-1-(2-fluoro-benzyl)-4-hydroxy-1H-pyrrolo[2,3-c]pyridine-5-carboxylic acid ethyl ester, glycine and NaOMe/HOMe. The title compound, ESI MS (m/z): 369 (M+H)$^+$.

Example 152

{[7-Cyano-1-(2-methoxy-benzyl)-4-hydroxy-1H-pyrrolo[2,3-c]pyridine-5-carbonyl]-amino}-acetic acid a) 2,3,7-Tribromo-1-(2-methoxy-benzyl)-4-hydroxy-1H-pyrrolo[2,3-c]pyridine-5-carboxylic acid ethyl ester Prepared in analogy to that of Example 103(a) from 2,3-dibromo-1-(2-methoxy-benzyl)-4-hydroxy-1H-pyrrolo[2,3-c]pyridine-5-carboxylic acid ethyl ester, NBS and BzOOBz in carbontetrachloride. The title compound, ESI MS (m/z): 561 (M+H)$^+$.

b) 2,3-Dibromo-7-cyano-1-(2-methoxy-benzyl)-4-hydroxy-1H-pyrrolo[2,3-c]pyridine-5-carboxylic acid ethyl ester Prepared in analogy to that of Example 105(a) from 2,3,7-tribromo-1-(2-methoxy-benzyl)-4-hydroxy-1H-pyrrolo[2,3-c]pyridine-5-carboxylic acid ethyl ester and CuCN. The title compound, ESI MS (m/z): 508 (M+H)$^+$.

c) 7-Cyano-1-(2-methoxy-benzyl)-4-hydroxy-1H-pyrrolo[2,3-c]pyridine-5-carboxylic acid ethyl ester Prepared in analogy to that of Example 6(a) from 2,3-dibromo-7-cyano-1-(2-methoxy-benzyl)-4-hydroxy-1H-pyrrolo[2,3-c]pyridine-5-carboxylic acid ethyl ester, ammonium formate and Pd/C. The title compound, ESI MS (m/z): 352 (M+H)$^+$.

d) {[7-Cyano-1-(2-methoxy-benzyl)-4-hydroxy-1H-pyrrolo[2,3-c]pyridine-5-carbonyl]-amino}-acetic acid Prepared in analogy to that of Example 1(e) from 7-cyano-1-(2-methoxy-benzyl)-4-hydroxy-1H-pyrrolo[2,3-c]pyridine-5-carboxylic acid ethyl ester, glycine and NaOMe/HOMe. The title compound, ESI MS (m/z): 381 (M+H)$^+$.

Example 153

{[7-Cyano-1-(3-methoxy-benzyl)-4-hydroxy-1H-pyrrolo[2,3-c]pyridine-5-carbonyl]-amino}-acetic acid a) 2,3,7-Tribromo-1-(3-methoxy-benzyl)-4-hydroxy-1H-pyrrolo[2,3-c]pyridine-5-carboxylic acid ethyl ester Prepared in analogy to that of Example 103(a) from 2,3-dibromo-1-(3-methoxy-benzyl)-4-hydroxy-1H-pyrrolo[2,3-c]pyridine-5-carboxylic acid ethyl ester, NBS and BzOOBz in carbontetrachloride. The title compound, ESI MS (m/z): 561 (M+H)$^+$.

b) 2,3-Dibromo-7-cyano-1-(3-methoxy-benzyl)-4-hydroxy-1H-pyrrolo[2,3-c]pyridine-5-carboxylic acid ethyl ester Prepared in analogy to that of Example 105(a) from 2,3,7-tribromo-1-(3-methoxy-benzyl)-4-hydroxy-1H-pyrrolo[2,3-c]pyridine-5-carboxylic acid ethyl ester and CuCN. The title compound, ESI MS (m/z): 508 (M+H)$^+$.

c) 7-Cyano-1-(3-methoxy-benzyl)-4-hydroxy-1H-pyrrolo[2,3-c]pyridine-5-carboxylic acid ethyl ester Prepared in analogy to that of Example 6(a) from 2,3-dibromo-7-cyano-1-(3-methoxy-benzyl)-4-hydroxy-1H-pyrrolo[2,3-c]pyridine-5-carboxylic acid ethyl ester, ammonium formate and Pd/C. The title compound, ESI MS (m/z): 352 (M+H)$^+$.

d) {[7-Cyano-1-(3-methoxy-benzyl)-4-hydroxy-1H-pyrrolo[2,3-c]pyridine-5-carbonyl]-amino}-acetic acid Prepared in analogy to that of Example 1(e) from 7-cyano-1-(3-methoxy-benzyl)-4-hydroxy-1H-pyrrolo[2,3-c]pyridine-5-carboxylic acid ethyl ester, glycine and NaOMe/HOMe. The title compound, ESI MS (m/z): 381 (M+H)$^+$.

Example 154

{[2-Cyano-1-(3-fluoro-benzyl)-4-hydroxy-1H-pyrrolo[2,3-c]pyridine-5-carbonyl]-amino}-acetic acid a) 1-(3-Fluoro-benzyl)-2-methyl-1H-pyrrole-3-carboxylic acid ethyl ester Prepared in analogy to that of Example 5(a) from 2-methyl-1H-pyrrole-3-carboxylic acid ethyl ester and 3-fluorobenzyl bromide. The title compound, ESI MS (m/z): 262 (M+H)$^+$.

b) 2,3-Dibromo-1-(3-fluoro-benzyl)-4-hydroxy-1H-pyrrolo[2,3-c]pyridine-5-carboxylic acid ethyl ester and 2-bromo-1-(3-fluoro-benzyl)-4-hydroxy-1H-pyrrolo[2,3-c]pyridine-5-carboxylic acid ethyl ester A mixture of 1-(3-fluoro-benzyl)-2-methyl-1H-pyrrole-3-carboxylic acid ethyl ester (9.75 g), NBS (20.33 g), and BzOOBz (452 mg) in carbon tetrachloride (150 mL) was refluxed for 2 h; it gave a mixture of di- and tri-brominated products. The mixture was cooled, the solids were filtered off; the filtrate was concentrated to give intermediate bromides (17.18 g).

The above intermediate bromides (17.18 g) was mixed with tert-butoxycarbonylamino-acetic acid ethyl ester (7.59 g) in THF (100 mL), and then cooled with an ice/water bath, followed by slow addition of KOBu-t (94 mL, 1.0 M solution in THF). The reaction had been stirred in the cold bath before it was quenched with saturated ammonium chloride solution; the mixture was then extracted with ethyl acetate and the organic phase was washed with water, sat. NaCl solution respectively and dried over anhydrous sodium sulfate, filtered, concentrated to give the cyclized intermediate (19.77 g).

This intermediate was then subjected to Boc-removal (TFA) and air mediated aromatization conditions similar to those in Example 1(d) to give the title products after column purification. 2,3-Dibromo-1-(3-fluoro-benzyl)-4-hydroxy-1H-pyrrolo[2,3-c]pyridine-5-carboxylic acid ethyl ester (3.019 g) with ESI MS (m/z): 471 (M+H)$^+$ and 2-bromo-1-(3-fluoro-benzyl)-4-hydroxy-1H-pyrrolo[2,3-c]pyridine-5-carboxylic acid ethyl ester (5.263 g) with ESI MS (m/z): 393 (M+H)$^+$.

c) 2-Cyano-1-(3-fluoro-benzyl)-4-hydroxy-1H-pyrrolo[2,3-c]pyridine-5-carboxylic acid ethyl ester A mixture of 2-bromo-1-(3-fluoro-benzyl)-4-hydroxy-1H-pyrrolo[2,3-c]pyridine-5-carboxylic acid ethyl ester (1000 mg), Zn(CN)$_2$ (150 mg), Zn dust (17 mg), Pd$_2$(dba)$_3$ (59 mg), dppf (71 mg) in DMA (8 mL) was heated to 120° C. for 90 min; then the mixture was partitioned between EtOAc and water, the organic phase was then washed with sat. NaCl solution, dried over anhydrous sodium sulfate, filtered and concentrated sequentially to give a residue, which was purified with column to give desired title compound (270 mg). The title compound, ESI MS (m/z): 340 (M+H)$^+$.

d) {[2-Cyano-1-(3-fluoro-benzyl)-4-hydroxy-1H-pyrrolo[2,3-c]pyridine-5-carbonyl]-amino}-acetic acid Prepared in analogy to that of Example 1(e) from 2-cyano-1-(3-fluoro-benzyl)-4-hydroxy-1H-pyrrolo[2,3-c]pyridine-5-carboxylic acid ethyl ester, glycine and NaOMe/HOMe. The title compound, ESI MS (m/z): 369 (M+H)$^+$.

Example 155

{[2,3-Dichloro-7-cyano-1-(2-fluoro-benzyl)-4-hydroxy-1H-pyrrolo[2,3-c]pyridine-5-carbonyl]-amino}-acetic acid a) 2,3-Dichloro-7-cyano-1-(2-fluoro-benzyl)-4-hydroxy-1H-pyrrolo[2,3-c]pyridine-5-carboxylic acid ethyl ester Prepared in analogy to that of Example 135(a) from 7-cyano-1-(2-fluoro-benzyl)-4-hydroxy-1H-pyrrolo[2,3-c]pyridine-5-carboxylic acid ethyl ester and NCS in MeCN. The title compound, ESI MS (m/z): 408 (M+H)$^+$.

b) {[2,3-Dichloro-7-cyano-1-(2-fluoro-benzyl)-4-hydroxy-1H-pyrrolo[2,3-c]pyridine-5-carbonyl]-amino}-acetic acid Prepared in analogy to that of Example 1(e) from 2,3-dichloro-7-cyano-1-(2-fluoro-benzyl)-4-hydroxy-1H-pyrrolo[2,3-c]pyridine-5-carboxylic acid ethyl ester, glycine and NaOMe/HOMe. The title compound, ESI MS (m/z): 437 (M+H)$^+$.

Example 156

{[1-(3-Fluoro-benzyl)-4-hydroxy-1H-pyrrolo[2,3-c]pyridine-5-carbonyl]-amino}-acetic acid a) 1-(3-Fluoro-benzyl)-4-hydroxy-1H-pyrrolo[2,3-c]pyridine-5-carboxylic acid ethyl ester Prepared in analogy to that of Example 6(a) from 2,3-dibromo-1-(3-fluoro-benzyl)-4-hydroxy-1H-pyrrolo[2,3-c]pyridine-5-carboxylic acid ethyl ester, ammonium formate and Pd/C. The title compound, ESI MS (m/z): 315 (M+H)$^+$.

b) {[1-(3-Fluoro-benzyl)-4-hydroxy-1H-pyrrolo[2,3-c]pyridine-5-carbonyl]-amino}-acetic acid Prepared in analogy to that of Example 1(e) from 1-(3-fluoro-benzyl)-4-hydroxy-1H-pyrrolo[2,3-c]pyridine-5-carboxylic acid ethyl ester, glycine and NaOMe/HOMe. The title compound, ESI MS (m/z): 344 (M+H)$^+$.

Example 157

{[3-Chloro-7-cyano-1-(2-fluoro-benzyl)-4-hydroxy-1H-pyrrolo[2,3-c]pyridine-5-carbonyl]-amino}-acetic acid a) 4-Acetoxy-7-cyano-1-(2-fluoro-benzyl)-1H-pyrrolo[2,3-c]pyridine-5-carboxylic acid ethyl ester Prepared in analogy to that of Example 120(a) from 7-cyano-1-(2-fluoro-benzyl)-4-hydroxy-1H-pyrrolo[2,3-c]pyridine-5-carboxylic acid ethyl ester, acetic anhydride, and triethyl amine. The title compound, ESI MS (m/z): 382 (M+H)$^+$.

b) 4-Acetoxy-3-chloro-7-cyano-1-(2-fluoro-benzyl)-1H-pyrrolo[2,3-c]pyridine-5-carboxylic acid ethyl ester Prepared in analogy to that of Example 124(b) from 4-acetoxy-7-cyano-1-(2-fluoro-benzyl)-1H-pyrrolo[2,3-c]pyridine-5-carboxylic acid ethyl ester and NCS in MeCN. The title compound, ESI MS (m/z): 416 (M+H)$^+$.

c) {[3-Chloro-7-cyano-1-(2-fluoro-benzyl)-4-hydroxy-1H-pyrrolo[2,3-c]pyridine-5-carbonyl]-amino}-acetic acid Prepared in analogy to that of Example 1(e) from 4-acetoxy-3-chloro-7-cyano-1-(2-fluoro-benzyl)-1H-pyrrolo[2,3-c]pyridine-5-carboxylic acid ethyl ester, glycine and NaOMe/HOMe. The title compound, ESI MS (m/z): 403 (M+H)$^+$.

Example 158

{[3-Chloro-7-cyano-4-hydroxy-1-(3-methoxy-benzyl)-1H-pyrrolo[2,3-c]pyridine-5-carbonyl]-amino}-acetic acid a) 4-Acetoxy-7-cyano-1-(3-methoxy-benzyl)-1H-pyrrolo[2,3-c]pyridine-5-carboxylic acid ethyl ester Prepared in analogy to that of Example 120(a) from 7-cyano-1-(3-methoxy-benzyl)-4-hydroxy-1H-pyrrolo[2,3-c]pyridine-5-carboxylic acid ethyl ester, acetic anhydride, and triethyl amine. The title compound, ESI MS (m/z): 394 (M+H)$^+$.

b) 4-Acetoxy-3-chloro-7-cyano-1-(3-methoxy-benzyl)-1H-pyrrolo[2,3-c]pyridine-5-carboxylic acid ethyl ester Prepared in analogy to that of Example 124(b) from 4-acetoxy-7-cyano-1-(3-methoxy-benzyl)-1H-pyrrolo[2,3-c]pyridine-5-carboxylic acid ethyl ester and NCS in MeCN. The title compound, ESI MS (m/z): 428 (M+H)$^+$.

c) {[3-Chloro-7-cyano-4-hydroxy-1-(3-methoxy-benzyl)-1H-pyrrolo[2,3-c]pyridine-5-carbonyl]-amino}-acetic acid Prepared in analogy to that of Example 1(e) from 4-acetoxy-3-chloro-7-cyano-1-(3-methoxy-benzyl)-1H-pyrrolo[2,3-c]pyridine-5-carboxylic acid ethyl ester, glycine and NaOMe/HOMe. The title compound, ESI MS (m/z): 415 (M+H)$^+$.

Example 159

{[7-Cyano-1-(3-fluoro-benzyl)-4-hydroxy-1H-pyrrolo[2,3-c]pyridine-5-carbonyl]-amino}-acetic acid a) 7-Cyano-1-(3-fluoro-benzyl)-4-hydroxy-1H-pyrrolo[2,3-c]pyridine-5-carboxylic acid ethyl ester Prepared in analogy to that of Example 133(a) from 2,3-dibromo-1-(3-fluoro-benzyl)-4-hydroxy-1H-pyrrolo[2,3-c]pyridine-5-carboxylic acid ethyl ester and NBS in MeCN to give tribromo intermediate; which was subjected to a cyanation condition CuCN/NMP similar to that of Example 105(a) to give the C-7 CN intermediate; which was further subjected to a reductive debromination condition (ammonium formate, Pd/C in refluxing EtOAc) similar to that of Example 6(a) to give the desired title compound. The title compound, ESI MS (m/z): 340 (M+H)$^+$.

b) {[7-Cyano-1-(3-fluoro-benzyl)-4-hydroxy-1H-pyrrolo[2,3-c]pyridine-5-carbonyl]-amino}-acetic acid Prepared in analogy to that of Example 1(e) from 7-cyano-1-(3-fluoro-benzyl)-4-hydroxy-1H-pyrrolo[2,3-c]pyridine-5-carboxylic acid ethyl ester, glycine and NaOMe/HOMe. The title compound, ESI MS (m/z): 369 (M+H)$^+$.

Example 160

{[7-Cyano-1-(3,4-difluoro-benzyl)-4-hydroxy-1H-pyrrolo[2,3-c]pyridine-5-carbonyl]-amino}-acetic acid a) 1-(3,4-Difluoro-benzyl)-2-methyl-1H-pyrrole-3-carboxylic acid ethyl ester Prepared in analogy to that of Example 5(a) from 2-methyl-1H-pyrrole-3-carboxylic acid ethyl ester and 3,4-difluorobenzyl bromide. The title compound, ESI MS (m/z): 280 (M+H)$^+$.

b) 4,5-Dibromo-2-[(tert-butoxycarbonyl-ethoxycarbonylmethyl-amino)-methyl]-1-(4-fluoro-benzyl)-1H-pyrrole-3-carboxylic acid ethyl ester 1-(3,4-Difluoro-benzyl)-2-methyl-1H-pyrrole-3-carboxylic acid ethyl ester (12.48 g) was subjected to a tribromination condition (NBS and BzOOBz in CCl$_4$) similar to that of Example 5(b) to give the crude tribromo intermediate (24.57 g); which was subjected to a condensation condition similar to that of Example 1(c) to give the title crude product (29.59 g). The title compound, ESI MS (m/z): 637 (M+H)⁺.

c) 2,3-Dibromo-1-(3,4-difluoro-benzyl)-4-hydroxy-1H-pyrrolo[2,3-c]pyridine-5-carboxylic acid ethyl ester To an ice/water bath cooled crude 4,5-dibromo-2-[(tert-butoxycarbonyl-ethoxycarbonylmethyl-amino)-methyl]-1-(4-fluoro-benzyl)-1H-pyrrole-3-carboxylic acid ethyl ester (29.49 g) in toluene (100 mL) was added a 25% (weight) concentration of potassium tert-pentoxide in toluene (67.04 mL) during a course of ~5 min; after that, the reaction was stirred for 1 h in the cold bath and then poured to a stirring mixture of ice/water and ammonium chloride, organic phase was separated and washed with water and saturated sodium chloride solution, dried over anhydrous sodium sulfate, filtered, concentrated to give the cyclized intermediate. The intermediate was then dissolved in 50 mL toluene and 50 mL TFA and stirred at room temperature for 1 h, then concentrated, the residue was partitioned between toluene and water; the organic phase was washed once with saturated sodium hydrogen carbonate, saturated sodium chloride solution respectively, then dried over anhydrous sodium sulfate, filtered, and air bubbled through the filtrate for a period of overnight. The precipitates were collected as the first crop of the title product (8.161 g). The filtrate was concentrated and purified with column directly to give the second crop of the title product (4.98 g). The title compound, ESI MS (m/z): 489 (M+H)⁺.

d) 2,3-Dibromo-7-cyano-1-(3,4-difluoro-benzyl)-4-hydroxy-1H-pyrrolo[2,3-c]pyridine-5-carboxylic acid ethyl ester 2,3-Dibromo-1-(3,4-difluoro-benzyl)-4-hydroxy-1H-pyrrolo[2,3-c]pyridine-5-carboxylic acid ethyl ester (4.98 g) was brominated similar to the synthesis of Example 103(a) to give the crude tribromo product, which was subjected to a cyanation condition CuCN/NMP similar to that of Example 105(a) to give the C-7 CN title product. The title compound, ESI MS (m/z): 514 (M+H)⁺.

e) 7-Cyano-1-(3,4-difluoro-benzyl)-4-hydroxy-1H-pyrrolo[2,3-c]pyridine-5-carboxylic acid ethyl ester Prepared in analogy to that of Example 6(a) from 2,3-dibromo-7-cyano-1-(3,4-difluoro-benzyl)-4-hydroxy-1H-pyrrolo[2,3-c]pyridine-5-carboxylic acid ethyl ester, ammonium formate and Pd/C. The title compound, ESI MS (m/z): 358 (M+H)⁺.

f) {[7-Cyano-1-(3,4-difluoro-benzyl)-4-hydroxy-1H-pyrrolo[2,3-c]pyridine-5-carbonyl]-amino}-acetic acid Prepared in analogy to that of Example 1(e) from 7-cyano-1-(3,4-difluoro-benzyl)-4-hydroxy-1H-pyrrolo[2,3-c]pyridine-5-carboxylic acid ethyl ester, glycine and NaOMe/HOMe. The title compound, ESI MS (m/z): 387 (M+H)⁺.

Example 161

{[3-Chloro-7-cyano-1-(3,4-difluoro-benzyl)-4-hydroxy-1H-pyrrolo[2,3-c]pyridine-5-carbonyl]-amino}-acetic acid a) 4-Acetoxy-7-cyano-1-(3,4-difluoro-benzyl)-1H-pyrrolo[2,3-c]pyridine-5-carboxylic acid ethyl ester Prepared in analogy to that of Example 120(a) from 7-cyano-1-(3,4-difluoro-benzyl)-4-hydroxy-1H-pyrrolo[2,3-c]pyridine-5-carboxylic acid ethyl ester, acetic anhydride, and triethyl amine. The title compound, ESI MS (m/z): 400 (M+H)⁺.

b) 4-Acetoxy-3-chloro-7-cyano-1-(3,4-difluoro-benzyl)-1H-pyrrolo[2,3-c]pyridine-5-carboxylic acid ethyl ester Prepared in analogy to that of Example 124(b) from 4-acetoxy-7-cyano-1-(3,4-difluoro-benzyl)-1H-pyrrolo[2,3-c]pyridine-5-carboxylic acid ethyl ester and NCS in MeCN. The title compound, ESI MS (m/z): 434 (M+H)⁺.

c) {[3-Chloro-7-cyano-1-(3,4-difluoro-benzyl)-4-hydroxy-1H-pyrrolo[2,3-c]pyridine-5-carbonyl]-amino}-acetic acid Prepared in analogy to that of Example 1(e) from 4-acetoxy-3-chloro-7-cyano-1-(3,4-difluoro-benzyl)-1H-pyrrolo[2,3-c]pyridine-5-carboxylic acid ethyl ester, glycine and NaOMe/HOMe. The title compound, ESI MS (m/z): 421 (M+H)⁺.

Example 162

{[2,3-Dichloro-7-cyano-1-(3-fluoro-benzyl)-4-hydroxy-1H-pyrrolo[2,3-c]pyridine-5-carbonyl]-amino}-acetic acid a) 2,3-Dichloro-7-cyano-1-(3-fluoro-benzyl)-4-hydroxy-1H-pyrrolo[2,3-c]pyridine-5-carboxylic acid ethyl ester Prepared in analogy to that of Example 135(a) from 7-cyano-1-(3-fluoro-benzyl)-4-hydroxy-1H-pyrrolo[2,3-c]pyridine-5-carboxylic acid ethyl ester and NCS in MeCN. The title compound, ESI MS (m/z): 408 (M+H)⁺.

b) {[2,3-Dichloro-7-cyano-1-(3-fluoro-benzyl)-4-hydroxy-1H-pyrrolo[2,3-c]pyridine-5-carbonyl]-amino}-acetic acid Prepared in analogy to that of Example 1(e) from 2,3-dichloro-7-cyano-1-(3-fluoro-benzyl)-4-hydroxy-1H-pyrrolo[2,3-c]pyridine-5-carboxylic acid ethyl ester, glycine and NaOMe/HOMe. The title compound, ESI MS (m/z): 437 (M+H)⁺.

Example 163

{[3-Chloro-7-cyano-1-(3-fluoro-benzyl)-4-hydroxy-1H-pyrrolo[2,3-c]pyridine-5-carbonyl]-amino}-acetic acid a) 4-Acetoxy-7-cyano-1-(3-fluoro-benzyl)-1H-pyrrolo[2,3-c]pyridine-5-carboxylic acid ethyl ester (1354-189-A)

Prepared in analogy to that of Example 120(a) from 7-cyano-1-(3,4-difluoro-benzyl)-4-hydroxy-1H-pyrrolo[2,3-c]pyridine-5-carboxylic acid ethyl ester, acetic anhydride, and triethylamine. The title compound, ESI MS (m/z): 382 (M+H)⁺.

b) 4-Acetoxy-3-chloro-7-cyano-1-(3-fluoro-benzyl)-1H-pyrrolo[2,3-c]pyridine-5-carboxylic acid ethyl ester Prepared in analogy to that of Example 124(a) from 4-acetoxy-7-cyano-1-(3-fluoro-benzyl)-1H-pyrrolo[2,3-c]pyridine-5-carboxylic acid ethyl ester and NCS in MeCN. The title compound, ESI MS (m/z): 416 (M+H)$^+$.

c) {[3-Chloro-7-cyano-1-(3-fluoro-benzyl)-4-hydroxy-1H-pyrrolo[2,3-c]pyridine-5-carbonyl]-amino}-acetic acid Prepared in analogy to that of Example 1(e) from 4-acetoxy-3-chloro-7-cyano-1-(3-fluoro-benzyl)-1H-pyrrolo[2,3-c]pyridine-5-carboxylic acid ethyl ester, glycine and NaOMe/HOMe. The title compound, ESI MS (m/z): 403 (M+H)$^+$.

Example 164

{[2,3-Dichloro-7-cyano-1-(3,4-difluoro-benzyl)-4-hydroxy-1H-pyrrolo[2,3-c]pyridine-5-carbonyl]-amino}-acetic acid a) 2,3-Dichloro-7-cyano-1-(3,4-difluoro-benzyl)-4-hydroxy-1H-pyrrolo[2,3-c]pyridine-5-carboxylic acid ethyl ester Prepared in analogy to that of Example 135(a) from 7-cyano-1-(3,4-difluoro-benzyl)-4-hydroxy-1H-pyrrolo[2,3-c]pyridine-5-carboxylic acid ethyl ester and NCS in MeCN. The title compound, ESI MS (m/z): 426 (M+H)$^+$.

b) {[2,3-Dichloro-7-cyano-1-(3,4-difluoro-benzyl)-4-hydroxy-1H-pyrrolo[2,3-c]pyridine-5-carbonyl]-amino}-acetic acid Prepared in analogy to that of Example 1(e) from 2,3-dichloro-7-cyano-1-(3,4-difluoro-benzyl)-4-hydroxy-1H-pyrrolo[2,3-c]pyridine-5-carboxylic acid ethyl ester, glycine and NaOMe/HOMe. The title compound, ESI MS (m/z): 455 (M+H)$^+$.

Example 165

[(1-Benzyl-2,3-dichloro-7-hydroxy-1H-pyrrolo[3,2-c]pyridine-6-carbonyl)-amino]-acetic acid a) 1-Benzyl-3-methyl-1H-pyrrole-2-carboxylic acid methyl ester

To an ice/water-bath cooled solution of 3-methyl-1H-pyrrole-2-carboxylic acid methyl ester (1.196 g, prepared according to the literature: W. G. Terry, G. W. Kenner, and G. Kornis *J. Chem. Soc.* 1965, 4389-4393) and benzyl bromide (1.15 mL) in N,N-dimethylformamide (17 mL) was carefully added NaH (413 mg, 60% purity in mineral oil) under nitrogen. The mixture was stirred in the ice bath for 25 min and then quenched saturated ammonium chloride solution (5 mL). It was extracted with EtOAc, and the organic phase was washed with water and saturated NaCl solution, dried over anhydrous sodium sulfate, filtered and concentrated. The crude residue was column-purified to give the title compound (1.536 g) as white solid. $^1$H NMR (200 MHz, CDCl$_3$) δ=7.32-6.98 (m, 5H), 6.75 (d, 1H, J=2.5 Hz), 6.02 (d, 1H, J=2.5 Hz), 5.48 (s, 2H), 3.75 (s, 3H), 2.33 (s, 3H).

b) 1-Benzyl-4,5-dichloro-3-chloromethyl-1H-pyrrole-2-carboxylic acid methyl ester To a mixture of the above ester (200 mg, 0.87 mmol) in DMF (2.8 mL) in an ice bath was added trichloroisocyanuric acid (TCIA)(135 mg, 0.67 mmol) in portions over 5 min. Resulting mixture was stirred at room temperature for 1 h at which time additional TCIA (45 mg, 0.29 mmol) was added and the reaction was continued for extra 2 h. The reaction mixture was poured into ice/water and extracted with ethyl acetate. Organic phase was washed with water, saturated sodium chloride solution, dried over magnesium sulfate, filtered and concentrated. The residue was purified by silica gel chromatography (eluting with 5%-30% ethyl acetate/hexanes) to provide the title compound 125 mg. $^1$H NMR (200 MHz, CDCl$_3$) δ=7.26 (m, 3H), 7.05 (m, 2H), 5.67 (s, 2H), 4.81 (s, 2H), 3.84 (s, 3H).

c) 1-Benzyl-4,5-dichloro-3-{[(2,4-dimethoxy-benzyl)-ethoxycarbonylmethyl-amino]-methyl}-1H-pyrrole-2-carboxylic acid methyl ester To a mixture of the above ester (120 mg, 0.36 mmol) and (2,4-dimethoxy-benzylamino)-acetic acid ethyl ester (109 mg, 0.43 mmol) in acetonitrile (4 mL) was added potassium iodide (89.6 mg, 0.54 mmol) and potassium carbonate (149 mg, 1.08 mmol). Resulting mixture was stirred at room temperature overnight, and then diluted with ethyl acetate. Insoluble solid was filtered off, and the filtrate was washed with water and saturated sodium chloride solution, dried over magnesium sulfate, filtered and concentrated. The residue was purified by silica gel chromatography (eluting with 15%-70% ethyl acetate/hexanes) to provide the title compound 179 mg. MS: (+) m/z 551.13; 549.09 (M+1).

d) 1-Benzyl-2,3-dichloro-7-hydroxy-1H-pyrrolo[3,2-c]pyridine-6-carboxylic acid ethyl ester A solution of the above ester (175 mg, 0.32 mmol) in THF (2.5 ml) was added 1 M KO$^t$Bu in THF (0.64 ml, 0.64 mmol) at −78° C. The mixture was stirred at −78° C. for 30 min, warmed to room temperature and stirred at that temperature for 1.5 h. Reaction mixture was quenched with aqueous ammonium chloride and extracted with ethyl acetate. The organic layer was washed with water, brine, dried over anhydrous magnesium sulfate and concentrated in vacuo to give a yellow oil (149 mg). It was dissolved in dichloromethane (1 ml) and thionyl chloride (32 μl) was added. The reaction mixture was stirred at room temperature for 3 h and then concentrated. The residue was partitioned between saturated sodium bicarbonate solution and ethyl acetate. Organic phase was washed saturated sodium chloride solution, dried over magnesium sulfate, filtered and concentrated. The residue was purified by silica gel chromatography (eluting with 10%-60% ethyl acetate/hexanes) to provide the title compound 51.3 mg. MS: (+) m/z 367.07; 365.10 (M+1).

e) [(1-Benzyl-2,3-dichloro-7-hydroxy-1H-pyrrolo[3,2-c]pyridine-6-carbonyl)-amino]-acetic acid To a solid mixture of the above ester (50 mg, 0.14 mmol) and glycine (210 mg, 2.80 mmol) was added a solution of sodium methoxide in methanol (0.5 M, 4.2 mL). Resulting mixture was refluxed for 20 h, and after cooled was concentrated. The residue was dissolved in water (100 mL) and extracted with ethyl acetate (not vigorously shaking). Aqueous layer was acidified by 1 N HCl solution to pH=3-4.

Precipitate was collected, rinsed with water, and dried in vacuo to provide the title compound (30 mg) as an off-white solid. MS: (+) m/z 394.10; 396.07 (M+1).

Example 166

[(2-tert-Butyl-7-hydroxy-thiazolo[4,5-c]pyridine-6-carbonyl)-amino]-acetic acid a) 2-tert-Butyl-4-methyl-thiazole-5-carboxylic acid ethyl ester A solution of 2,2-dimethyl-thiopropionamide (7.7 g, 65.8 mmol) and ethyl 2-chloroacetate (9.26 mL, 67 mmol) in 150 mL of ethanol was heated at reflux temperature for 24 h. The reaction mixture was concentrated under reduced pressure, suspended in ethyl acetate, and washed with saturated aqueous sodium bicarbonate and brine solutions. The organic fraction was dried over anhydrous magnesium sulfate and concentrated to 14.1 g of an orange viscous material. MS (ESI+): 229.4 (M+1).

b) 2-tert-Butyl-4-{[(2,4-dimethoxy-benzyl)-ethoxycarbonylmethyl-amino]-methyl}-thiazole-5-carboxylic acid ethyl ester A solution of 2-tert-butyl-4-methyl-thiazole-5-carboxylic acid ethyl ester (14.1 g, 62.1 mmol), N-bromosuccinamide (11.6 g, 65.2 mmol), and benzoyl peroxide (1.4 g, 6.2 mmol) in 160 mL of carbon tetrachloride was heated at reflux temperature for 16 h, then cooled and filtered through a silica gel plug which was washed with dichloromethane. The solution was concentrated to 19.6 g of yellow liquid and used directly in the next step.

A portion of the crude 4-bromomethyl-2-tert-butyl-thiazole-5-carboxylic acid ethyl ester (12.6 g, 41.0 mmol), N-(2,4-dimethoxy-benzyl)glycine ethyl ester (11.6 g, 41.0 mmol), and potassium carbonate (6.2 g, 45 mmol) in 100 ml of anhydrous DMF was stirred for 18 h. The mixture was partitioned into a biphasic water-ethyl acetate mixture and the isolated organic layer was then washed with brine, dried over anhydrous magnesium sulfate, concentrated to a residue, and purified by flash chromatography: eluting the desired product from silica gel with a gradient of 10-35% ethyl acetate in hexanes. 13 g of a yellow oil was isolated. MS (ESI+): 479.4 (M+1).

c) 2-tert-Butyl-5-(2,4-dimethoxy-benzyl)-7-oxo-4,5,6,7-tetrahydro-thiazolo[4,5-c]pyridine-6-carboxylic acid ethyl ester A solution of 2-tert-butyl-4-{[(2,4-dimethoxy-benzyl)-ethoxycarbonylmethyl-amino]-methyl}-thiazole-5-carboxylic acid ethyl ester (12.8 g, 26.7 mmol) in 350 mL of anhydrous THF was cooled to 0° C. with an external ice bath and 53 mL of 1 N potassium tert-butoxide was added slowly. The reaction was stirred at 0° C. for 2 h and then allowed to warm to room temperature and stirred for 2 h. The reaction was diluted with ethyl acetate and washed with a solution of 200 mL saturated ammonium chloride and 50 mL 1 N HCl. The organic fraction was washed with brine, dried over anhydrous sodium sulfate and concentrated to 11.5 g of product. MS (ESI+): m/z 433.4 (M+1).

d) 2-tert-Butyl-7-hydroxy-thiazolo[4,5-c]pyridine-6-carboxylic acid ethyl ester

A solution of 2-tert-butyl-5-(2,4-dimethoxy-benzyl)-7-oxo-4,5,6,7-tetrahydro-thiazolo[4,5-c]pyridine-6-carboxylic acid ethyl ester (1 g, 2.3 mmol) in 23 mL of dichloromethane was cooled to 0° C. with an external ice bath and thionyl chloride (253 µL, 3.47 mmol) was added. The ice bath was removed and the reaction was allowed to stir at room temperature for 16 h. Pyridine (500 µL) was added and the mixture was stirred for 5 min before concentrating on silica gel under reduced pressure and purification by column chromatography. The desired product was eluted from silica gel with a gradient of 10-50% ethyl acetate in hexanes to give 363 mg of pale yellow solid. MS (ESI−): m/z 279.3 (M−1).

e) [(2-tert-Butyl-7-hydroxy-thiazolo[4,5-c]pyridine-6-carbonyl)-amino]-acetic acid A suspension of 2-tert-butyl-7-hydroxy-thiazolo[4,5-c]pyridine-6-carboxylic acid ethyl ester (103 mg, 0.37 mmol) and glycine (247 mg, 3.3 mmol) in 5.9 mL of 0.5 N NaOMe in methanol was heated to 120° C. for 15 min with microwave irradiation using a CEM Discovery microwave reactor. The resultant mixture was concentrated under reduced pressure and the residue was suspended in ethyl acetate and extracted three times with saturated aqueous sodium bicarbonate solution. The combined aqueous fractions were acidified with conc. HCl and extracted twice with ethyl acetate. The organic fractions were dried over anhydrous sodium sulfate and concentrated to a residue. The crude product was purified by reverse phase chromatography on a C-18 column, eluting the desired product with a gradient of 5-80% acetonitrile in water+0.1% formic acid. The lyophilized material fractions provided 10 mg of white solid. MS (ESI−): m/z 308.1 (M−1).

Example 167

[(2-tert-Butyl-7-hydroxy-4-methyl-thiazolo[4,5-c]pyridine-6-carbonyl)-amino]-acetic acid a) 4-Bromo-2-tert-butyl-7-hydroxy-thiazolo[4,5-c]pyridine-6-carboxylic acid ethyl ester A solution of 2-tert-butyl-7-hydroxy-thiazolo[4,5-c]pyridine-6-carboxylic acid ethyl ester (3.87 g, 13.8 mmol, example 166(d)), N-bromosuccinamide (2.67 g, 15 mmol), and benzoyl peroxide (315 mg, 1.3 mmol) in 46 mL of carbon tetrachloride was heated at reflux temperature for 4 h. The reaction mixture was concentrated under reduced pressure and purified by column chromatography, eluting the desired product from silica gel with a gradient of 0-30% ethyl acetate in hexanes to give 3.4 g of the title compound. MS (ESI−): 356.99, 358.98 e/z (M−1, $^{79}$Br/$^{81}$Br).

b) 2-tert-Butyl-7-hydroxy-4-methyl-thiazolo[4,5-c]pyridine-6-carboxylic acid ethyl ester A solution of 4-bromo-2-tert-butyl-7-hydroxy-thiazolo[4,5-c]pyridine-6-carboxylic acid ethyl ester (145 mg, 0.40 mmol), tetramethyl tin (220 µL, 1.6 mmol), dichlorobis(triphenylphosphine)-palladium II (30 mg, 0.04 mmol) in 2.5 mL anhydrous DMF was heated to 130° C. for 1 h. The reaction mixture was cooled, diluted with ethyl acetate, and washed successively with water, saturated sodium bicarbonate, and brine. The organic fraction was dried over anhydrous sodium sulfate, concentrated to a crude residue and purified by colc) [(2-tert-Butyl-7-hydroxy-4-methyl-thiazolo[4,5-c]
pyridine-6-carbonyl)-amino]-acetic acid The title compound was prepared from 2-tert-butyl-7-hydroxy-4-methyl-thiazolo[4,5-c]pyridine-6-carboxylic acid ethyl under conditions analogous to the experimental procedure found in example 166(e). MS (ESI+): m/z 266.9 (M+1).

Example 168

[(2-tert-Butyl-4-cyano-7-hydroxy-thiazolo[4,5-c]
pyridine-6-carbonyl)-amino]-acetic acid a) 2-tert-Butyl-4-cyano-7-hydroxy-thiazolo[4,5-c]
pyridine-6-carboxylic acid ethyl ester A solution of 4-bromo-2-tert-butyl-7-hydroxy-thiazolo[4,5-c]pyridine-6-carboxylic acid ethyl ester (100 mg, 0.28 mmol), tris(dibenzylideneacetone)dipalladium(0)(13 mg, 0.014 mmol), 1,1'-bis(diphenylphosphino) ferrocene (15 mg, 0.028 mmol), zinc dust (2 mg, 0.033 mmol), and zinc cyanide (20 mg, 0.168 mmol) in 0.56 mL of dimethylacetamide was heated at 115° C. for 5 h under a nitrogen atmosphere. The mixture was cooled, diluted with ethyl acetate and saturated aqueous ammonium chloride and filtered through a celite pad. The organic fraction was isolated and washed with brine, dried over anhydrous sodium sulfate, and concentrated to a crude residue. The crude material was purified by column chromatography, eluting the desired product from silica gel with a gradient of 10-60% ethyl acetate in hexanes to give 61 mg of the title compound. MS (ESI–): m/z 304.1 (M–1).

b) [(2-tert-Butyl-4-cyano-7-hydroxy-thiazolo[4,5-c]
pyridine-6-carbonyl)-amino]-acetic acid A suspension of 2-tert-butyl-4-cyano-7-hydroxy-thiazolo[4,5-c]pyridine-6-carboxylic acid ethyl ester (85 mg, 0.28 mmol) and glycine (188 mg, 2.5 mmol) in 4.4 mL of 0.5 N NaOMe in methanol was heated at reflux temperature for 25 h. The reaction mixture was diluted with water, acidified with 1 N HCl, and extracted with ethyl acetate. The organic fraction was concentrated to a residue and purified by reverse phase chromatography on a C-18 column, eluting the desired product with a gradient of 10-90% acetonitrile in water+0.1% formic acid. The lyophilized material fractions provided 50 mg of white solid. MS (ESI–): m/z 333.0 (M–1).

Example 169

[(4-Butyl-2-tert-butyl-7-hydroxy-thiazolo[4,5-c]pyridine-6-carbonyl)-amino]-acetic acid a) 4-Butyl-2-tert-butyl-7-hydroxy-thiazolo[4,5-c]
pyridine-6-carboxylic acid ethyl ester A solution of 4-bromo-2-tert-butyl-7-hydroxy-thiazolo[4,5-c]pyridine-6-carboxylic acid ethyl ester (244 mg, 0.68 mmol), tetrabutyl tin (573 μL, 1.74 mmol), dichlorobis(triphenylphosphine)-palladium II (49 mg, 0.07 mmol) in 4.6 mL anhydrous DMF was heated to 130° C. for 1 h. The reaction mixture was cooled, diluted with ethyl acetate, and washed successively with water and brine. The organic fraction was dried over anhydrous sodium sulfate, concentrated to a crude residue to give 184 mg of a white solid. MS (ESI+): m/z 337.3 (M+1).

b) [(4-Butyl-2-tert-butyl-7-hydroxy-thiazolo[4,5-c]
pyridine-6-carbonyl)-amino]-acetic acid The title compound was prepared from 4-butyl-2-tert-butyl-7-hydroxy-thiazolo[4,5-c]pyridine-6-carboxylic acid ethyl ester under conditions analogous to the experimental procedure found in example 168(b). MS (ESI–): m/z 363.9 (M–1).

Example 170

[(2-tert-butyl-7-hydroxy-4-((E)-styryl)-thiazolo[4,5-c]pyridine-6-carbonyl)-amino]-acetic acid a) 2-tert-butyl-7-hydroxy-4-styryl-thiazolo[4,5-c]
pyridine-6-carboxylic acid ethyl ester Under a nitrogen atmosphere 4-bromo-2-tert-butyl-7-hydroxy-thiazolo[4,5-c]pyridine-6-carboxylic acid ethyl ester (300 mg, 0.835 mmol), styreneboronic acid (185 mg, 1.25 mmol), cesium carbonate (675 mg, 2.08 mmol), and tetrakis(triphenylphosphine)palladium(0)(143 mg, 0.12 mmol) were suspended in 4 mL of anhydrous 1,4 dioxane. The reaction was heated at reflux temperature for 18 h, then cooled to room temperature and diluted with ethyl acetate. The organic mixture was successively washed with water, saturated sodium bicarbonate, and brine solutions. The organic fractions were dried over anhydrous sodium sulfate and concentrated to a crude solid residue, which was then purified by column chromatography, eluting the desired product from silica gel with a gradient of 10-90% ethyl acetate in hexanes: 180 mg of a yellow oil. MS: (+) m/z 382.9 (M+1).

b) [(2-tert-butyl-7-hydroxy-4-styryl-thiazolo[4,5-c]
pyridine-6-carbonyl)-amino]-acetic acid The title compound was prepared from 2-tert-butyl-7-hydroxy-4-styryl-thiazolo[4,5-c]pyridine-6-carboxylic acid ethyl ester under conditions analogous to the experimental procedure found in example 168(b) without further purification. MS (ESI+): m/z 412.0 (M+1).

Example 171

[(2-tert-butyl-7-hydroxy-4-phenyl-thiazolo[4,5-c]
pyridine-6-carbonyl)-amino]-acetic acid a) 2-tert-Butyl-7-hydroxy-4-phenyl-thiazolo[4,5-c]
pyridine-6-carboxylic acid ethyl ester The title compound was prepared from 4-bromo-2-tert-butyl-7-hydroxy-thiazolo[4,5-c]pyridine-6-carboxylic acid ethyl ester and tributylphenyl tin under conditions analogous to the experimental procedure found in example 169(a). MS (ESI+): m/z 412.0 (M+1).

b) [(2-tert-butyl-7-hydroxy-4-phenyl-thiazolo[4,5-c]
pyridine-6-carbonyl)-amino]-acetic acid The title compound was prepared from 2-tert-butyl-7-hydroxy-4-phenyl-thiazolo[4,5-c]pyridine-6-carboxylic acid ethyl ester under conditions analogous to the experimental procedure found in example 168(b) without further purification. MS (ESI+): m/z 412.0 (M+1).

Example 172

[(2-tert-butyl-7-hydroxy-4-phenethyl-thiazolo[4,5-c]pyridine-6-carbonyl)-amino]-acetic acid a) 2-tert-Butyl-7-hydroxy-4-phenethyl-thiazolo[4,5-c]pyridine-6-carboxylic acid ethyl ester A suspension of 2-tert-butyl-7-hydroxy-4-phenyl-thiazolo[4,5-c]pyridine-6-carboxylic acid ethyl ester (120 mg, 0.31 mmol) and 75 mg of 10% palladium on carbon in 6 mL of 1:10 Ethyl acetate:ethanol was placed under a hydrogen atmosphere at 20 PSI and shaken for 4 hours. The resultant mixture was filtered through a celite pad and concentrated under reduced pressure. The crude solid residue was purified by column chromatography, eluting the desired product from silica gel with a gradient of 0-30% ethyl acetate in hexanes: 75 mg of a white solid. MS (ESI+): m/z 385.0 (M+1).

b) [(2-tert-butyl-7-hydroxy-4-phenethyl-thiazolo[4,5-c]pyridine-6-carbonyl)-amino]-acetic acid The title compound was prepared from 2-tert-butyl-7-hydroxy-4-phenethyl-thiazolo[4,5-c]pyridine-6-carboxylic acid ethyl ester under conditions analogous to the experimental procedure found in example 168(b) without further purification. MS (ESI+): m/z 412.0 (M+1).

Example 173

[(2-tert-butyl-7-hydroxy-4-isopropylsulfanylmethyl-thiazolo[4,5-c]pyridine-6-carbonyl)-amino]-acetic acid a) 2-tert-butyl-7-(2,2-dimethyl-propionyloxy)-4-methyl-thiazolo[4,5-c]pyridine-6-carboxylic acid ethyl ester A solution of 2-tert-butyl-7-hydroxy-4-methyl-thiazolo[4,5-c]pyridine-6-carboxylic acid ethyl (200 mg, 0.68 mmol), trimethylacetylchloride (100 µL, 0.816 mmol), DMAP (7.3 mg, 0.06 mmol), and triethylamine (190 µL, 1.36 mmol) in 4.5 mL of dichloromethane was stirred under a nitrogen atmosphere for 4 h. The reaction mixture was diluted with ethyl acetate and washed with 0.10 N HCl and brine. The organic fraction was dried over anhydrous sodium sulfate and concentrated under reduced pressure to 262 mg of the title compound. MS (ESI+): m/z 378.9 (M+1).

b) 2-tert-butyl-7-(2,2-dimethyl-propionyloxy)-4-isopropylsulfanylmethyl-thiazolo[4,5-c]pyridine-6-carboxylic acid ethyl ester A solution of 2-tert-butyl-7-(2,2-dimethyl-propionyloxy)-4-methyl-thiazolo[4,5-c]pyridine-6-carboxylic acid ethyl ester (178 mg, 0.47 mmol), N-bromosuccinamide (92 mg, 0.52 mmol), and benzoyl peroxide (12 mg, 0.05 mmol) in 1.2 mL of carbon tetrachloride was heated at reflux temperature for 16 h. The reaction mixture was filtered through a celite pad and concentrated under reduced pressure to 206 mg of a yellow oil, which was used directly in the next step.

A suspension of the crude 4-bromomethyl-2-tert-butyl-7-(2,2-dimethyl-propionyloxy)-thiazolo[4,5-c]pyridine-6-carboxylic acid ethyl ester (above), 2-propanethiol (75 µL, 0.8 mmol), and cesium carbonate (130 mg, 0.4 mmol) in 0.8 mL of a 1:1 mixture of THF:ethanol was stirred for 22 h. The resultant reaction mixture was diluted with ethyl acetate, and washed with water and brine. The organic fractions were dried over anhydrous sodium sulfate and concentrated under reduced pressure to 160 mg of the title compound. MS (ESI+): m/z 452.95 (M+1).

c) 2-tert-butyl-7-hydroxy-4-isopropylsulfanylmethyl-thiazolo[4,5-c]pyridine-6-carboxylic acid ethyl ester A solution of 2-tert-butyl-7-(2,2-dimethyl-propionyloxy)-4-isopropylsulfanylmethyl-thiazolo[4,5-c]pyridine-6-carboxylic acid ethyl ester (150 mg, 0.33 mmol) and sodium ethoxide (215 mg of 21% sodium ethoxide in ethanol) in 0.6 mL of ethanol was heated at 90° C. for 2 h. The reaction mixture was diluted with ethyl acetate and washed with 1 N HCl and brine. The organic fraction was dried over sodium sulfate and concentrated under reduced pressure. The crude product was purified by column chromatography, eluting the desired product from silica gel with a gradient of 0-40% ethyl acetate in hexanes to give 80 mg of a clear oil. MS (ESI+): m/z 368.9 (M+1).

d) [(2-tert-butyl-7-hydroxy-4-isopropylsulfanylmethyl-thiazolo[4,5-c]pyridine-6-carbonyl)-amino]-acetic acid The title compound was prepared from 2-tert-butyl-7-hydroxy-4-isopropylsulfanylmethyl-thiazolo[4,5-c]pyridine-6-carboxylic acid ethyl ester under conditions analogous to the experimental procedure found in example 168(b) without further purification. MS (ESI+): m/z 397.9 (M+1).

Example 174

[(7-Hydroxy-2-methyl-4-phenyl-thiazolo[4,5-c]pyridine-6-carbonyl)-amino]-acetic acid a) 4-{[(2,4-Dimethoxy-benzyl)-ethoxycarbonylmethyl-amino]-methyl}-2-methyl-thiazole-5-carboxylic acid ethyl ester A solution of 2-Bromo-4-{[(2,4-dimethoxy-benzyl)-ethoxycarbonylmethyl-amino]-methyl}-thiazole-5-carboxylic acid ethyl ester (4 g, 8 mmol, example 81(b), tetramethyl tin (3.3 mL, 24 mmol), dichlorobis(triphenylphosphine)palladium II (460 mg, 0.66 mmol) in 50 mL anhydrous DMF was heated to 130° C. for 1 h. The reaction mixture was cooled, diluted with ethyl acetate, and washed successively with water, saturated sodium bicarbonate, and brine. The organic fraction was dried over anhydrous sodium sulfate, concentrated to a crude residue and purified by column chromatography (eluting from silica gel with a gradient of 15-60% ethyl acetate in hexanes) to give 3.13 mg of the title compound. MS (ESI+): m/z 436.8 (M+1).

b) 7-Hydroxy-2-methyl-thiazolo[4,5-c]pyridine-6-carboxylic acid ethyl ester

The title compound was prepared from 4-{[(2,4-Dimethoxy-benzyl)-ethoxycarbonylmethyl-amino]-methyl}-2-methyl-thiazole-5-carboxylic acid ethyl ester under conditions analogous to the experimental procedure found in examples 166(c)-(d). MS (ESI−): m/z 237.0 (M−1).

c) 4-Bromo-7-hydroxy-2-methyl-thiazolo[4,5-c]pyridine-6-carboxylic acid ethyl ester The title compound was prepared from 7-hydroxy-2-methyl-thiazolo[4,5-c]pyridine-6-carboxylic acid ethyl ester under conditions analogous to the experimental procedure found in example 167(a). MS (ESI+): m/z 316.8, 318.8 (M+1, $^{79}$Br/$^{81}$Br).

d) 7-Hydroxy-2-methyl-4-phenyl-thiazolo[4,5-c]pyridine-6-carboxylic acid ethyl ester The title compound was prepared from 4-Bromo-7-hydroxy-2-methyl-thiazolo[4,5-c]pyridine-6-carboxylic acid ethyl ester and tributylphenyl tin under conditions analogous to the experimental procedure found in example 169(a). MS (ESI+): m/z 315.1 (M+1).

e) [(7-hydroxy-2-methyl-4-phenyl-thiazolo[4,5-c]pyridine-6-carbonyl)-amino]-acetic acid The title compound was prepared from 7-Hydroxy-2-methyl-4-phenyl-thiazolo[4,5-c]pyridine-6-carboxylic acid ethyl ester under conditions analogous to the experimental procedure found in example 168(b) without further purification. MS (ESI+): m/z 343.96 (M+1).

Example 175

[(7-Hydroxy-2-methyl-thiazolo[4,5-c]pyridine-6-carbonyl)-amino]-acetic acid

The title compound was prepared from 7-hydroxy-2-methyl-thiazolo[4,5-c]pyridine-6-carboxylic acid ethyl ester under conditions analogous to the experimental procedure found in example 168(b) without further purification. MS (ESI+): m/z 267.9 (M+1).

Example 176

[(7-Hydroxy-2-naphthalen-2-yl-thiazolo[4,5-c]pyridine-6-carbonyl)-amino]-acetic acid a) 4-[(2,4-Dimethoxy-benzyl)-ethoxycarbonylmethyl-amino]-methyl-2-naphthalen-2-yl-thiazole-5-carboxylic acid ethyl ester Under a nitrogen atmosphere 2-Bromo-4-{[(2,4-dimethoxy-benzyl)-ethoxycarbonylmethyl-amino]-methyl}-thiazole-5-carboxylic acid ethyl ester (1 g, 2 mmol, example 96(b), 2-napthyleneboronic acid (688 mg, 4 mmol), cesium carbonate (1.43 g, 4.4 mmol), and tetrakis(triphenylphosphine)palladium(0)(347 mg, 0.3 mmol) were suspended in 10 mL of anhydrous 1,4 dioxane. The reaction was heated at reflux temperature for 18 h, then cooled to room temperature and diluted with ethyl acetate. The organic mixture was successively washed with water, saturated sodium bicarbonate, and brine solutions. The organic fractions were dried over anhydrous sodium sulfate and concentrated to a crude solid residue, which was then purified by column chromatography, eluting the desired product from silica gel with a gradient of 5-40% ethyl acetate in hexanes: 876 mg of the title compound. MS: (+) m/z 548.9 (M+1)

b) 5-(2,4-Dimethoxy-benzyl)-2-naphthalen-2-yl-7-oxo-4,5,6,7-tetrahydro-thiazolo[4,5-c]pyridine-6-carboxylic acid ethyl ester The title compound was prepared from 4-{[(2,4-Dimethoxy-benzyl)-ethoxycarbonylmethyl-amino]-methyl}-2-naphthalen-2-yl-thiazole-5-carboxylic acid ethyl ester under conditions analogous to the experimental procedure found in example 166(c). MS (ESI+): m/z 525.1 (M+23)

c) 7-Hydroxy-2-naphthalen-2-yl-thiazolo[4,5-c]pyridine-6-carboxylic acid ethyl ester The title compound was prepared from 5-(2,4-Dimethoxy-benzyl)-2-naphthalen-2-yl-7-oxo-4,5,6,7-tetrahydro-thiazolo[4,5-c]pyridine-6-carboxylic acid ethyl ester under conditions analogous to the experimental procedure found in example 166(d). MS (ESI+): m/z 351.1 (M+1)

d) [(7-Hydroxy-2-naphthalen-2-yl-thiazolo[4,5-c]pyridine-6-carbonyl)-amino]-acetic acid The title compound was prepared from 7-hydroxy-2-naphthalen-2-yl-thiazolo[4,5-c]pyridine-6-carboxylic acid ethyl ester under conditions analogous to the experimental procedure found in example 168(b) without further purification. MS (ESI+): m/z 379.9 (M+1)

Example 177

[(7-Hydroxy-2-thiophen-2-yl-thiazolo[4,5-c]pyridine-6-carbonyl)-amino]-acetic acid a) 3-(4-{[(2,4-Dimethoxy-benzyl)-ethoxycarbonylmethyl-amino]-methyl}-2-thiophen-2-yl-thiazol-5-yl)-3-oxo-propionic acid ethyl ester A solution of 2-Bromo-4-{[(2,4-dimethoxy-benzyl)-ethoxycarbonylmethyl-amino]-methyl}-thiazole-5-carboxylic acid ethyl ester (1 g, 2 mmol, example 96(b), 2-(tributylstannyl)thiophene (1.26 mL, 2 mmol), dichlorobis(triphenylphosphine)palladium II (140 mg, 0.2 mmol) in 13 mL anhydrous DMF was heated to 130° C. for 20 min. The reaction mixture was cooled, diluted with ethyl acetate, and washed successively with water, saturated sodium bicarbonate, and brine. The organic fraction was dried over anhydrous sodium sulfate, concentrated to a crude residue and purified by column chromatography (eluting from silica gel with a gradient of 15-70% ethyl acetate in hexanes) to give 867 mg of a yellow oil. MS (ESI+): m/z 527.2 (M+23)

b) 5-(2,4-Dimethoxy-benzyl)-7-oxo-2-thiophen-2-yl-4,5,6,7-tetrahydro-thiazolo[4,5-c]pyridine-6-carboxylic acid ethyl ester The title compound was prepared from 3-(4-{[(2,4-dimethoxy-benzyl)-ethoxycarbonylmethyl-amino]-methyl}-2-thiophen-2-yl-thiazol-5-yl)-3-oxo-propionic acid ethyl ester under conditions analogous to the experimental procedure found in example 166(c). MS (ESI+): m/z 458.7 (M+1)

c) 7-Hydroxy-2-thiophen-2-yl-thiazolo[4,5-c]pyridine-6-carboxylic acid ethyl ester The title compound was prepared from 5-(2,4-dimethoxy-benzyl)-7-oxo-2-thiophen-2-yl-4,5,6,7-tetrahydro-thiazolo[4,5-c]pyridine-6-carboxylic acid ethyl ester under conditions analogous to the experimental procedure found in example 166(d). MS (ESI+): m/z 306.9 (M+1)

d) [(7-Hydroxy-2-thiophen-2-yl-thiazolo[4,5-c]pyridine-6-carbonyl)-amino]-acetic acid The title compound was prepared from 7-hydroxy-2-thiophen-2-yl-thiazolo[4,5-c]pyridine-6-carboxylic acid ethyl ester under conditions analogous to the experimental procedure found in example 168(b) without further purification. MS (ESI+): m/z 335.9 (M+1)

Example 178

[(2-Furan-2-yl-7-hydroxy-thiazolo[4,5-c]pyridine-6-carbonyl)-amino]-acetic acid a) 3-(4-{[(2,4-Dimethoxy-benzyl)-ethoxycarbonylmethyl-amino]-methyl}-2-furan-2-yl-thiazol-5-yl)-3-oxo-propionic acid ethyl ester The title compound was prepared from 2-bromo-4-{[(2,4-dimethoxy-benzyl)-ethoxycarbonylmethyl-amino]-methyl}-thiazole-5-carboxylic acid ethyl ester under conditions analogous to the experimental procedure found in example 177(a). MS (ESI+): 511.1 m/z (M+23)

b) 5-(2,4-Dimethoxy-benzyl)-2-furan-2-yl-7-oxo-4,5,6,7-tetrahydro-thiazolo[4,5-c]pyridine-6-carboxylic acid ethyl ester The title compound was prepared from 3-(4-{[(2,4-dimethoxy-benzyl)-ethoxycarbonylmethyl-amino]-methyl}-2-furan-2-yl-thiazol-5-yl)-3-oxo-propionic acid ethyl ester under conditions analogous to the experimental procedure found in example 166(c). MS (ESI+): m/z 442.8 (M+1)

c) 2-Furan-2-yl-7-hydroxy-thiazolo[4,5-c]pyridine-6-carboxylic acid ethyl ester

The title compound was prepared from 5-(2,4-Dimethoxy-benzyl)-2-furan-2-yl-7-oxo-4,5,6,7-tetrahydro-thiazolo[4,5-c]pyridine-6-carboxylic acid ethyl ester under conditions analogous to the experimental procedure found in example 166(d). MS (ESI+): m/z 290.9 (M+1)

d) [(2-Furan-2-yl-7-hydroxy-thiazolo[4,5-c]pyridine-6-carbonyl)-amino]-acetic acid The title compound was prepared from 2-furan-2-yl-7-hydroxy-thiazolo[4,5-c]pyridine-6-carboxylic acid ethyl ester under conditions analogous to the experimental procedure found in example 168(b) without further purification. MS (ESI+): m/z 319.9 (M+1)

What is claimed is:
1. A compound of formula I:

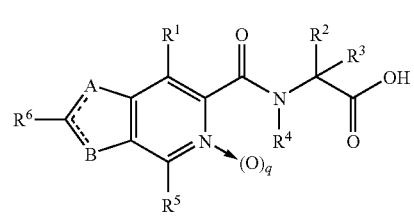

wherein:
q is 0 or 1;
A and B are independently selected from the group consisting =C($R^7$)—, —N($R^8$)—, =N—, and —S— with the proviso that at least one of the following is present:
A is =C($R^7$)— and B is —N($R^8$)—;
A is —S— and B is =N—;
A =N— and B is —S—; or
A is —N($R^8$)— and B is =C($R^7$)—;
one of -A═C($R^6$)— or —B═C($R^6$)— is a double bond and the other is a single bond;
$R^1$ is selected from the group consisting of hydroxyl, alkoxy, substituted alkoxy, acyloxy, cycloalkoxy, substituted cycloalkoxy, aryloxy, substituted aryloxy, heteroaryloxy, substituted heteroaryloxy, heterocyclyloxy, substituted heterocyclyloxy, mercapto, thioether, substituted alkylthio, arylsulfanyl, heteroarylsulfanyl, amino, substituted amino, acylamino, and aminoacyl;
$R^2$ is selected from the group consisting of hydrogen, deuterium, and methyl;
$R^3$ is selected from the group consisting of hydrogen, deuterium, alkyl, and substituted alkyl;
$R^4$ is selected from the group consisting of hydrogen, alkyl, and substituted alkyl;
$R^5$ is selected from the group consisting of hydrogen, halo, cyano, hydroxyl, alkyl, substituted alkyl, cycloalkyl, substituted cycloalkyl, alkenyl, substituted alkenyl, alkynyl, substituted alkynyl, alkoxy, substituted alkoxy, cycloalkoxy, substituted cycloalkoxy, aryl, substituted aryl, aryloxy, substituted aryloxy, heteroaryl, substituted heteroaryl, heterocyclyl, substituted heterocyclyl, heterocyclyloxy, substituted heterocyclyloxy, heteroaryloxy, substituted heteroaryloxy, acyl, aminoacyl, nitro, amino, substituted amino, acylamino, sulfanyl, sulfonyl, thioether, arylthio, and substituted arylthio;
$R^6$ and $R^7$ are each independently selected from the group consisting of hydrogen, halo, cyano, hydroxyl, alkyl, substituted alkyl, cycloalkyl, substituted cycloalkyl, alkenyl, substituted alkenyl, alkynyl, substituted alkynyl, alkoxy, substituted alkoxy, cycloalkoxy, substituted cycloalkoxy, aryl, substituted aryl, aryloxy, substituted aryloxy, heteroaryl, substituted heteroaryl, heterocyclyl, substituted heterocyclyl, heterocyclyloxy, substituted heterocyclyloxy, heteroaryloxy, substituted heteroaryloxy, acyl, aminoacyl, nitro, amino, substituted amino, acylamino, sulfanyl, sulfonyl, thioether, arylthio, and substituted arylthio;
or where when A or B is =C($R^7$)—, then $R^6$ and $R^7$ together with the carbon atoms bound thereto join to form a cycloalkenyl, substituted cycloalkenyl, aryl, substituted aryl, heteroaryl, or substituted heteroaryl; and
$R^8$ is selected from the group consisting of hydrogen, hydroxyl, alkyl, substituted alkyl, alkenyl, substituted alkenyl, alkynyl, substituted alkynyl, aryl, substituted aryl, heteroaryl, and substituted heteroaryl;

or a pharmaceutically acceptable salt, single stereoisomer, mixture of stereoisomers, or ester thereof.

2. The compound of claim 1 wherein q is 0.

3. The compound of claim 1 wherein $R^1$ is hydroxyl.

4. The compound of claim 1 wherein $R^1$ is hydroxyl and $R^2$, $R^3$, and $R^4$ are hydrogen.

5. The compound of claim 1 wherein $R^1$ is hydroxyl, $R^2$ is methyl and $R^3$ and $R^4$ are hydrogen.

6. The compound of claim 1 wherein $R^5$ is selected from the group consisting of hydrogen, alkyl, cyano, halo, and aryl.

7. The compound of claim 6 wherein $R^5$ is selected from hydrogen, cyano, methyl, ethyl, propyl, butyl, chloro, and phenyl.

8. The compound of claim 1 wherein $R^5$ is selected from the group consisting of hydrogen, cyano, alkyl, substituted alkyl, substituted alkenyl, alkynyl, aryl, substituted aryl, heteroaryl, heterocyclyl, and acyl.

9. The compound of claim 1 wherein $R^5$ is selected from the group consisting of hydrogen, cyano, acetyl, methyl, ethyl, propyl, butyl, benzyl, phenethyl, ethynyl, styryl, isopropyl-sulfonylmethyl, phenyl, 4-cyano-phenyl, furan-2-yl, thiazol-2-yl, and piperidin-1-yl.

10. The compound of claim 1 wherein $R^6$ is selected from the group consisting of hydrogen, halo, cyano, alkyl, aryl, substituted aryl, aryloxy, substituted amino, heteroaryl, and substituted heteroaryl.

11. The compound of claim 1 wherein $R^6$ is selected from the group consisting of hydrogen, chloro, bromo, cyano, methyl, propyl, t-butyl, phenyl, 4-chloro-phenyl, and 4-fluoro-phenyl.

12. The compound of claim 1 wherein $R^6$ is selected from the group consisting of methyl, tert-butyl, phenyl, 4-cyano-phenyl, 4-t-butyl-phenyl, trifluoromethyl-phenyl, 3-chloro-4-fluoro-phenyl, 4-chloro-phenyl, 4-fluoro-phenyl, 2-methoxy-phenyl, 3-methoxy-phenyl, 4-methoxy-phenyl, biphenyl-4-yl, 4-phenoxy-phenyl, phenoxy, naphthalene-2-yl, 2,3-dihydro-benzo[1,4]dioxin-6-yl, 2,3-dihydro-benzofuran-5-yl, dibenzofuran-4-yl, pyridin-2-yl, pyridin-3-yl, 6-chloro-pyridin-3-yl, 5-bromo-pyridin-3-yl, 6-butoxy-pyridin-3-yl, quinolin-3-yl, 6-phenylsulfanyl-pyridin-3-yl, pyrimidin-5-yl, thiophen-2-yl, benzo[b]thiophen-2-yl, benzo[b]thiophen-3-yl, furan-2-yl, benzofuran-2-yl, 1-benzyl-1H-pyrazol-4-yl, and 2-benzyl-2H-pyrazol-3-yl.

13. The compound of claim 1 wherein A is $=C(R^7)-$, and $R^7$ is selected from the group consisting of hydrogen, halo, cyano, alkyl, aryl, and substituted aryl.

14. The compound of claim 1 wherein A is $=C(R^7)-$, and $R^7$ is selected from the group consisting of hydrogen, chloro, bromo, cyano, methyl, propyl, t-butyl, and phenyl.

15. The compound of claim 1 wherein B is $-N(R^8)-$, and $R^8$ is selected from the group consisting of alkyl, substituted alkyl, aryl, and substituted aryl.

16. The compound of claim 1 wherein B is $-N(R^8)-$, and $R^8$ is selected from the group consisting of hydrogen, methyl, n-propyl, t-butyl, 3-methyl-butyl, 1-cyclohexylmethyl, phenethyl, (R)-1-phenyl-ethyl, (S)-1-phenyl-ethyl, phenyl, 4-methoxy-phenyl, 4-fluoro-phenyl, benzyl, 2-fluoro-benzyl, 3-fluoro-benzyl, 4-fluoro-benzyl, 3,4-difluoro-benzyl, 2-methoxy-benzyl, 3-methoxy-benzyl, 4-methoxy-benzyl, and benzo[1,3]-dioxol-5-ylmethyl.

17. The compound of claim 1 wherein A is $=C(R^7)-$, $R^6$ and $R^7$ together with the carbon atoms bound thereto join to form an aryl group.

18. The compound of claim 17 wherein the aryl group is phenyl.

19. The compound of claim 1 wherein

A is $=C(R^7)-$;
B is $-N(R^8)-$;
$R^1$ is hydroxyl;
$R^2$, $R^3$, and $R^4$ are hydrogen;
$R^5$ is selected from the group consisting of hydrogen, halo, cyano, alkyl, and aryl;
$R^6$ is selected from the group consisting of hydrogen, halo, cyano, alkyl, aryl, substituted aryl, aryloxy, substituted amino, heteroaryl, and substituted heteroaryl;
$R^7$ is selected from the group consisting of hydrogen, halo, cyano, alkyl, aryl, and substituted aryl; and
$R^8$ is selected from the group consisting of alkyl, substituted alkyl, aryl, and substituted aryl;

or a pharmaceutically acceptable salt, single stereoisomer, mixture of stereoisomers, or ester thereof.

20. The compound of claim 1 wherein

A is $=C(R^7)-$;
B is $-N(R^8)-$;
$R^1$ is hydroxyl;
$R^2$, $R^3$, and $R^4$ are hydrogen;
$R^5$ is selected from the group consisting of hydrogen, halo, cyano, alkyl, and aryl;
$R^8$ is alkyl, aryl, or substituted aryl; and
$R^6$ and $R^7$, together with the carbons to which they are attached, form an aryl or substituted aryl group;

or a pharmaceutically acceptable salt, single stereoisomer, mixture of stereoisomers, or ester thereof.

21. The compound of claim 20 wherein $R^5$ is hydrogen, cyano, methyl, or phenyl and $R^8$ is methyl or phenyl.

22. The compound of claim 1 wherein

A is $=C(R^7)-$;
B is $-N(R^8)-$;
$R^1$ is hydroxyl;
$R^2$, $R^3$, and $R^4$ are hydrogen;
$R^5$ is selected from the group consisting of hydrogen, chloro, cyano, methyl, ethyl, and phenyl;
$R^6$ is selected from the group consisting of hydrogen, chloro, bromo, cyano, methyl, propyl, t-butyl, phenyl, 4-chloro-phenyl, and 4-fluoro-phenyl;
$R^7$ is selected from the group consisting of hydrogen, chloro, bromo, cyano, methyl, propyl, t-butyl, and phenyl; and
$R^8$ is selected from the group consisting of hydrogen, methyl, 3-methyl-butyl, 1-cyclohexylmethyl, phenethyl, (R)-1-phenyl-ethyl, (S)-1-phenyl-ethyl, phenyl, 4-methoxy-phenyl, 4-fluoro-phenyl, benzyl, 2-fluoro-benzyl, 3-fluoro-benzyl, 4-fluoro-benzyl, 3,4-difluoro-benzyl, 2-methoxy-benzyl, 3-methoxy-benzyl, 4-methoxy-benzyl, and benzo[1,3]-dioxol-5-ylmethyl;

or a pharmaceutically acceptable salt, single stereoisomer, mixture of stereoisomers, or ester thereof.

23. The compound of claim 1 wherein

A is $=C(R^7)-$;
B is $-N(R^8)-$;
$R^1$ is hydroxyl;
$R^2$, $R^3$, and $R^4$ are hydrogen;
$R^5$ is cyano;
$R^6$ is selected from hydrogen, chloro, or bromo;
$R^7$ is selected from the group consisting of hydrogen, methyl, chloro, bromo, and phenyl; and
$R^8$ is selected from the group consisting of phenethyl, (R)-1-phenyl-ethyl, (S)-1-phenyl-ethyl, phenyl, 4-methoxy-phenyl, 4-fluoro-phenyl, benzyl, 2-fluoro-benzyl, 4-fluoro-benzyl, 2-methoxy-benzyl, and 4-methoxy-benzyl;

or a pharmaceutically acceptable salt, single stereoisomer, mixture of stereoisomers, or ester thereof.

24. The compound of claim 1 wherein
A is —S—;
B is =N—;
$R^1$ is hydroxyl;
$R^2$, $R^3$, and $R^4$ are hydrogen;
$R^5$ is selected from the group consisting of hydrogen, cyano, alkyl, substituted alkyl, substituted alkenyl, alkynyl, aryl, substituted aryl, heteroaryl, heterocyclyl, and acyl; and
$R^6$ is selected from the group consisting of hydrogen, alkyl, aryl, substituted aryl, aryloxy, substituted amino, heteroaryl, and substituted heteroaryl;
or a pharmaceutically acceptable salt, single stereoisomer, mixture of stereoisomers or ester thereof.

25. The compound of claim 1 wherein
A is —S—;
B is =N—;
$R^1$ is hydroxyl;
$R^2$, $R^3$, and $R^4$ are hydrogen or methyl;
$R^5$ is selected from the group consisting of hydrogen, cyano, acetyl, methyl, ethyl, propyl, butyl, phenethyl, ethynyl, styryl, isopropyl-sulfonylmethyl, phenyl, 4-cyano-phenyl, furan-2-yl, thiazol-2-yl, and piperidin-1-yl; and
$R^6$ is selected from the group consisting of methyl, tert-butyl, phenyl, 4-cyano-phenyl, 4-t-butyl-phenyl, trifluoromethyl-phenyl, 3-chloro-4-fluoro-phenyl, 4-chloro-phenyl, 4-fluoro-phenyl, 2-methoxy-phenyl, 3-methoxy-phenyl, 4-methoxy-phenyl, biphenyl-4-yl, 4-phenoxy-phenyl, phenoxy, naphthalene-2-yl, 2,3-dihydro-benzo [1, 4]dioxin-6-yl, 2,3-dihydro-benzofuran-5-yl, dibenzofuran-4-yl, pyridin-2-yl, pyridin-3-yl, 6-chloro-pyridin-3-yl, 5-bromo-pyridin-3-yl, 6-butoxy-pyridin-3-yl, quinolin-3-yl, 6-phenylsulfanyl-pyridin-3-yl, pyrimidin-5-yl, thiophen-2-yl, benzo[b]thiophen-2-yl, benzo[b]thiophen-3-yl, furan-2-yl, benzofuran-2-yl, 1-benzyl-1H-pyrazol-4-yl, and 2-benzyl-2H-pyrazol-3-yl;
or a pharmaceutically acceptable salt, single stereoisomer, mixture of stereoisomers, or ester thereof.

26. The compound of claim 1 wherein
A is —S—;
B is =N—;
$R^1$ is hydroxyl;
$R^2$, $R^3$, and $R^4$ are hydrogen;
$R^5$ is selected from the group consisting of hydrogen, methyl, ethyl, butyl, and phenyl; and
$R^6$ is phenyl;
or a pharmaceutically acceptable salt, single stereoisomer, mixture of stereoisomers, or ester thereof.

27. The compound of claim 1 wherein
A is =N—;
B is —S—;
$R^1$ is hydroxyl;
$R^2$, $R^3$, and $R^4$ are hydrogen;
$R^5$ is selected from the group consisting of hydrogen, alkyl, and aryl; and
$R^6$ is selected from hydrogen, alkyl, aryl, substituted aryl, aryloxy, substituted amino, heteroaryl, and substituted heteroaryl;
or a pharmaceutically acceptable salt, single stereoisomer, mixture of stereoisomers, or ester thereof.

28. The compound of claim 27 wherein $R^5$ is selected from the group consisting of hydrogen, methyl, benzyl, phenyl, and 4-morpholin-4-ylphenyl, and $R^6$ is phenyl.

29. The compound of claim 1 wherein
A is —N($R^8$)—;
B is =C($R^7$)—;
$R^1$ is hydroxyl;
$R^2$, $R^3$, and $R^4$ are hydrogen;
$R^5$ is selected from hydrogen, cyano, and alkyl;
$R^6$ and $R^7$ are selected from hydrogen or halogen;
or $R^6$ and $R^7$, together with the carbons to which they are attached, form an aryl or substituted aryl group; and
$R^8$ is selected from the group consisting of hydrogen, alkyl, substituted alky, and aryl;
or a pharmaceutically acceptable salt, single stereoisomer, mixture of stereoisomers, or ester thereof.

30. A compound selected from the group consisting of [(2-bromo-4-hydroxy-1-phenyl-1H-pyrrolo[2,3-c]pyridine-5-carbonyl)-amino]-acetic acid, [(4-hydroxy-1-phenyl-1H-pyrrolo[2,3-c]pyridine-5-carbonyl)-amino]-acetic acid, [(2,3-dibromo-4-hydroxy-1-phenyl-1H-pyrrolo[2,3-c]pyridine-5-carbonyl)-amino]-acetic acid, {[3-bromo-2-(4-fluoro-phenyl)-4-hydroxy-1-phenyl-1H-pyrrolo[2,3-c]pyridine-5-carbonyl]-amino}-acetic acid, [(1-benzyl-2,3-dibromo-4-hydroxy-1H-pyrrolo[2,3-c]pyridine-5-carbonyl]-amino}-acetic acid, {[2-(4-fluoro-phenyl)-4-hydroxy-1-phenyl-1H-pyrrolo[2,3-c]pyridine-5-carbonyl]-amino}-acetic acid, [(1-benzyl-4-hydroxy-1H-pyrrolo[2,3-c]pyridine-5-carbonyl)-amino]-acetic acid, {[3-bromo-1,2-bis-(4-fluoro-phenyl)-4-hydroxy-1H-pyrrolo[2,3-c]pyridine-5-carbonyl]-amino}-acetic acid, {[1,2-bis-(4-fluoro-phenyl)-4-hydroxy-1H-pyrrolo[2,3-c]pyridine-5-carbonyl]-amino}-acetic acid, {[3-chloro-1,2-bis-(4-fluoro-phenyl)-4-hydroxy-1H-pyrrolo[2,3-c]pyridine-5-carbonyl]-amino}-acetic acid, {[3-bromo-2-(4-fluoro-phenyl)-4-hydroxy-1-(4-methoxy-phenyl)-1H-pyrrolo[2,3-c]pyridine-5-carbonyl]-amino}-acetic acid, {[2-(4-fluoro-phenyl)-4-hydroxy-1-(4-methoxy-phenyl)-1H-pyrrolo[2,3-c]pyridine-5-carbonyl]-amino}-acetic acid, {[2-bromo-1-(4-fluoro-phenyl)-4-hydroxy-3-phenyl-1H-pyrrolo[2,3-c]pyridine-5-carbonyl]-amino}-acetic acid, {[1-(4-fluoro-phenyl)-4-hydroxy-3-phenyl-1H-pyrrolo[2,3-c]pyridine-5-carbonyl]-amino}-acetic acid, {[7-chloro-1-(4-fluoro-phenyl)-4-hydroxy-3-phenyl-1H-pyrrolo[2,3-c]pyridine-5-carbonyl]-amino}-acetic acid, {[7-methyl-1-(4-fluoro-phenyl)-4-hydroxy-3-phenyl-1H-pyrrolo[2,3-c]pyridine-5-carbonyl]-amino}-acetic acid, {[3-bromo-2-tert-butyl-1-(4-fluoro-phenyl)-4-hydroxy-1H-pyrrolo[2,3-c]pyridine-5-carbonyl]-amino}-acetic acid, {[2-tert-butyl-1-(4-fluoro-phenyl)-4-hydroxy-1H-pyrrolo[2,3-c]pyridine-5-carbonyl]-amino}-acetic acid, [(1-benzyl-4-hydroxy-2,3-dimethyl-1H-pyrrolo[2,3-c]pyridine-5-carbonyl)-amino]-acetic acid, [(2,3-dibromo-4-hydroxy-1-methyl-1H-pyrrolo[2,3-c]pyridine-5-carbonyl)-amino]-acetic acid, [(4-hydroxy-1,2,3-trimethyl-1H-pyrrolo[2,3-c]pyridine-5-carbonyl)-amino]-acetic acid, {[2-bromo-3-tert-butyl-1-(4-fluoro-phenyl)-4-hydroxy-1H-pyrrolo[2,3-c]pyridine-5-carbonyl]-amino}-acetic acid, {[3-tert-butyl-1-(4-fluoro-phenyl)-4-hydroxy-1H-pyrrolo[2,3-c]pyridine-5-carbonyl]-amino}-acetic acid, [(1-benzyl-4-hydroxy-2,3-dipropyl-1H-pyrrolo[2,3-c]pyridine-5-carbonyl)-amino]-acetic acid, [(1-benzyl-3,7-dichloro-4-hydroxy-1H-pyrrolo[2,3-c]pyridine-5-carbonyl)-amino]-acetic acid, [(4-hydroxy-9-phenyl-9h-beta-carboline-3-carbonyl)-amino]-acetic acid, [(4-hydroxy-1-methyl-9-phenyl-9h-beta-carboline-3-carbonyl)-amino]-acetic acid, [(4-hydroxy-1,9-diphenyl-9h-beta-carboline-3-carbonyl)-amino]-acetic acid, [(1-benzyl-3-chloro-4-hydroxy-7-methyl-1H-pyrrolo[2,3-c]pyridine-5-carbonyl)-amino]-acetic acid, [(1-benzyl-3-chloro-4-hydroxy-7-phenyl-1H-pyrrolo[2,3-c]pyridine-5-carbonyl)-amino]- acetic acid, [(1-benzyl-3-chloro-7-ethyl-4-hydroxy-1H-pyrrolo[2,3-c]pyridine-5-carbonyl)-amino]-acetic acid, {[2-(4-fluoro-phenyl)-4-hydroxy-1,3-diphenyl-1H-pyrrolo[2,3-c]pyridine-5-carbonyl]-amino}-acetic acid, [(3-chloro-4-hydroxy-1-phenyl-1H-pyrrolo[2,3-c]pyridine-5-carbonyl)-amino]-acetic acid, [(3-chloro-4-hydroxy-7-methyl-1-phenyl-1H-pyrrolo[2,3-c]pyridine-5-carbonyl)-amino]-acetic acid, {[1-(benzo[1,3]dioxol-5-ylmethyl)-3-bromo-2-(4-chloro-phenyl)-4-hydroxy-1H-pyrrolo[2,3-c]pyridine-5-carbonyl]-amino}-acetic acid, {[3-bromo-2-(4-chloro-phenyl)-4-hydroxy-1-phenyl-1H-pyrrolo[2,3-c]pyridine-5-carbonyl]-amino}-acetic acid, [(1-(benzo[1,3]dioxol-5-ylmethyl)-4-hydroxy-2-phenyl-1H-pyrrolo[2,3-c]pyridine-5-carbonyl)-amino]-acetic acid, {[1-(benzo[1,3]dioxol-5-ylmethyl)-2-(4-chloro-phenyl)-4-hydroxy-1H-pyrrolo[2,3-c]pyridine-5-carbonyl]-amino}-acetic acid, {[1-benzo[1,3]dioxol-5-ylmethyl-2-(4-chloro-phenyl)-4-hydroxy-3-methyl-1H-pyrrolo[2,3-c]pyridine-5-carbonyl]-amino}-acetic acid, [(4-hydroxy-1,2-diphenyl-1H-pyrrolo[2,3-c]pyridine-5-carbonyl)-amino]-acetic acid, {[2-(4-chloro-phenyl)-4-hydroxy-3-methyl-1-phenyl-1H-pyrrolo[2,3-c]pyridine-5-carbonyl]-amino}-acetic acid, [(7-hydroxy-2-phenyl-thiazolo[4,5-c]pyridine-6-carbonyl)-amino]-acetic acid, [(7-hydroxy-2,4-diphenyl-thiazolo[4,5-c]pyridine-6-carbonyl)-amino]-acetic acid, [(7-hydroxy-4-methyl-2-phenyl-thiazolo[4,5-c]pyridine-6-carbonyl)-amino]-acetic acid, (S)-2-[(7-hydroxy-4-methyl-2-phenyl-thiazolo[4,5-c]pyridine-6-carbonyl)-amino]-propionic acid, {[7-hydroxy-2-(4-trifluoromethyl-phenyl)-thiazolo[4,5-c]pyridine-6-carbonyl]-amino}-acetic acid, {[2-(4-chloro-phenyl)-7-hydroxy-thiazolo[4,5-c]pyridine-6-carbonyl]-amino}-acetic acid, {[7-hydroxy-2-(4-methoxy-phenyl)-thiazolo[4,5-c]pyridine-6-carbonyl]-amino}-acetic acid, {[2-(4-fluoro-phenyl)-7-hydroxy-thiazolo[4,5-c]pyridine-6-carbonyl]-amino}-acetic acid, [(4-ethyl-7-hydroxy-2-phenyl-thiazolo[4,5-c]pyridine-6-carbonyl)-amino]-acetic acid, [(7-hydroxy-2-phenoxy-thiazolo[4,5-c]pyridine-6-carbonyl)-amino]-acetic acid, {[7-hydroxy-2-(methyl-phenyl-amino)-thiazolo[4,5-c]pyridine-6-carbonyl]-amino}-acetic acid, {[7-hydroxy-2-(phenylamino)-thiazolo[4,5-c]pyridine-6-carbonyl]-amino}-acetic acid, [(7-hydroxy-2-phenyl-thiazolo[5,4-c]pyridine-6-carbonyl)-amino]-acetic acid, {[2-(5-bromo-pyridin-3-yl)-7-hydroxy-thiazolo[4,5-c]pyridine-6-carbonyl]-amino}-acetic acid, [(7-hydroxy-2-pyridin-3-yl-thiazolo[4,5-c]pyridine-6-carbonyl)-amino]-acetic acid, [(4-butyl-7-hydroxy-2-phenyl-thiazolo[4,5-c]pyridine-6-carbonyl)-amino]-acetic acid, [(7-hydroxy-2-pyridin-2-yl-thiazolo[4,5-c]pyridine-6-carbonyl)-amino]-acetic acid, {[2-(4-fluoro-phenyl)-7-hydroxy-4-methyl-thiazolo[4,5-c]pyridine-6-carbonyl]-amino}-acetic acid, [(7-hydroxy-2-phenyl-4-propyl-thiazolo[4,5-c]pyridine-6-carbonyl)-amino]-acetic acid, {[7-hydroxy-2-(4-phenoxy-phenyl)-thiazolo[4,5-c]pyridine-6-carbonyl]-amino}-acetic acid, [(4-cyano-7-hydroxy-2-phenyl-thiazolo[4,5-c]pyridine-6-carbonyl)-amino]-acetic acid, [(7-hydroxy-4-isobutyl-2-phenyl-thiazolo[4,5-c]pyridine-6-carbonyl)-amino]-acetic acid, {[7-hydroxy-2-(3-methoxy-phenyl)-thiazolo[4,5-c]pyridine-6-carbonyl]-amino}-acetic acid, [(4-furan-2-yl-7-hydroxy-2-phenyl-thiazolo[4,5-c]pyridine-6-carbonyl)-amino]-acetic acid, [(7-hydroxy-2-phenyl-4-thiazol-2-yl-thiazolo[4,5-c]pyridine-6-carbonyl)-amino]-acetic acid, {[7-hydroxy-2-(2-methoxy-phenyl)-thiazolo[4,5-c]pyridine-6-carbonyl]-amino}-acetic acid, [(7-hydroxy-4-methyl-2-phenyl-thiazolo[5,4-c]pyridine-6-carbonyl)-amino]-acetic acid, {[2-(4-cyano-phenyl)-7-hydroxy-thiazolo[4,5-c]pyridine-6-carbonyl]-amino}-acetic acid, [(7-hydroxy-2,4-diphenyl-thiazolo[5,4-c]pyridine-6-carbonyl)-amino]-acetic acid, {[2-(3-chloro-4-fluoro-phenyl)-7-hydroxy-thiazolo[4,5-c]pyridine-6-carbonyl]-amino}-acetic acid, [(4-benzyl-7-hydroxy-2-phenyl-thiazolo[5,4-c]pyridine-6-carbonyl)-amino]-acetic acid, {[7-hydroxy-4-(4-morpholin-4-yl-phenyl)-2-phenyl-thiazolo[5,4-c]pyridine-6-carbonyl]-amino}-acetic acid, {[4-(4-cyano-phenyl)-7-hydroxy-2-phenyl-thiazolo[4,5-c]pyridine-6-carbonyl]-amino}-acetic acid, {[4-cyano-2-(4-fluoro-phenyl)-7-hydroxy-thiazolo[4,5-c]pyridine-6-carbonyl]-amino}-acetic acid, {[4-cyano-7-hydroxy-2-(3-methoxy-phenyl)-thiazolo[4,5-c]pyridine-6-carbonyl]-amino}-acetic acid, [(4-cyano-7-hydroxy-2-phenyl-thiazolo[5,4-c]pyridine-6-carbonyl)-amino]-acetic acid, [(4-ethynyl-7-hydroxy-2-phenyl-thiazolo[4,5-c]pyridine-6-carbonyl)-amino]-acetic acid, [(4-acetyl-7-hydroxy-2-phenyl-thiazolo[4,5-c]pyridine-6-carbonyl)-amino]-acetic acid, [(7-hydroxy-2-phenyl-4-piperidin-1-yl-thiazolo[4,5-c]pyridine-6-carbonyl)-amino]-acetic acid, {[2-(4-tert-butyl-phenyl)-7-hydroxy-thiazolo[4,5-c]pyridine-6-carbony]-amino}-acetic acid, {[2-(2,3-dihydro-benzo[1,4]dioxin-6-yl)-7-hydroxy-thiazolo[4,5-c]pyridine-6-carbonyl]-amino}-acetic acid, {[2-benzo[b]thiophen-3-yl-7-hydroxy-thiazolo[4,5-c]pyridine-6-carbonyl]-amino}-acetic acid, [(2-biphenyl-4-yl-7-hydroxy-thiazolo[4,5-c]pyridine-6-carbonyl)-amino]-acetic acid, [(2-benzo[b]thiophen-2-yl-7-hydroxy-thiazolo[4,5-c]pyridine-6-carbonyl)-amino]-acetic acid, [(7-hydroxy-2-quinolin-3-yl-thiazolo[4,5-c]pyridine-6-carbonyl)-amino]-acetic acid, [(2-benzofuran-2-yl-7-hydroxy-thiazolo[4,5-c]pyridine-6-carbonyl)-amino]-acetic acid, [(2-dibenzofuran-4-yl-7-hydroxy-thiazolo[4,5-c]pyridine-6-carbonyl)-amino]-acetic acid, {[2-(2,3-dihydro-benzofuran-5-yl)-7-hydroxy-thiazolo[4,5-c]pyridine-6-carbonyl]-amino}-acetic acid, [(7-hydroxy-2-pyrimidin-5-yl-thiazolo[4,5-c]pyridine-6-carbonyl)-amino]-acetic acid, {[2-(1-benzyl-1H-pyrazol-4-yl)-7-hydroxy-thiazolo[4,5-c]pyridine-6-carbonyl]-amino}-acetic acid, {[2-(6-chloro-pyridin-3-yl)-7-hydroxy-thiazolo[4,5-c]pyridine-6-carbonyl]-amino}-acetic acid, {[2-(6-butoxy-pyridin-3-yl)-7-hydroxy-thiazolo[4,5-c]pyridine-6-carbonyl]-amino}-acetic acid, {[7-hydroxy-2-(6-phenylsulfanyl-pyridin-3-yl)-thiazolo[4,5-c]pyridine-6-carbonyl]-amino}-acetic acid, {[2-(1-benzyl-1H-pyrazol-4-yl)4-cyano-7-hydroxy-thiazolo[4,5-c]pyridine-6-carbonyl]-amino}-acetic acid, {[2,3-dichloro-cyano-4-hydroxy-1-(3-methyl-butyl)-1H-pyrrolo[2,3-c]pyridine-5-carbonyl]-amino}-acetic acid, {[7-cyano-4-hydroxy-1-(3-methyl-butyl)-1H-pyrrolo[2,3-c]pyridine-5-carbonyl]-amino}-acetic acid, {[3-chloro-7-cyano-4-hydroxy-1-(3-methyl-butyl)-1H-pyrrolo[2,3-c]pyridine-5-carbonyl]-amino}-acetic acid, {[2,3-dichloro-7-cyano-1-cyclohexylmethyl-4-hydroxy-1H-pyrrolo[2,3-c]pyridine-5-carbonyl]-amino}-acetic acid, {[7-cyano-4-hydroxy-1-cyclohexylmethyl-1H-pyrrolo[2,3-c]pyridine-5-carbonyl]-amino}-acetic acid, [(1-benzyl-3-chloro-4-hydroxy-1H-pyrrolo[2,3-c]pyridine-5-carbonyl)-amino]-acetic acid, [(4-hydroxy-9-methyl-9H-beta-carboline-3-carbonyl)-amino]-acetic acid, [(4-hydroxy-1,9-dimethyl-9H-beta-carboline-3-carbonyl)-amino]-acetic acid, [(4-hydroxy-9-methyl-1-phenyl-9H-beta-carboline-3-carbonyl)-amino]-acetic acid, [(1-cyano-4-hydroxy-9-methyl-9H-beta-carboline-3-carbonyl)-amino]-acetic acid, {[3-bromo-7-cyano-2-(4-fluoro-phenyl)-4-hydroxy-1-phenyl-1H-pyrrolo[2,3-c]pyridine-5-carbonyl]-amino}-acetic acid, {[7-cyano-2-(4-fluoro-phenyl)-4-hydroxy-1-phenyl-1H-pyrrolo[2,3-c]pyridine-5-carbonyl]-amino}-acetic acid, [(4-hydroxy-5-phenyl-5H-pyrido[4,3-b]indole-3-carbonyl)-amino]-acetic acid, [(1-cyano-4-hydroxy-5-phenyl-5H-pyrido[4,3-b]indole-3-carbonyl)-amino]-acetic acid, [(4-hydroxy-1-methyl-5-phenyl-5H-pyrido[4,3-b]indole-3-carbonyl)-amino]-acetic acid, [(1-benzyl-3-chloro-7-cyano-4-hydroxy-1H-pyrrolo[2,3-c]pyridine-5-carbonyl)-amino]-acetic acid, {[3-cyano-2-(4-fluoro-phenyl)-4-hydroxy-1-phenyl-1H-pyrrolo[2,3-c]pyridine-5-carbonyl]-amino}-acetic acid, {[3-cyano-2-(4-fluoro-phenyl)-4-hydroxy-7-methyl-1-phenyl-1H-pyrrolo[2,3-c]pyridine-5-carbonyl]-amino}-acetic acid, {[3,7- dicyano-2-(4-fluoro-phenyl)-4-hydroxy-1-phenyl-1H-pyrrolo[2,3-c]pyridine-5-carbonyl]-amino}-acetic acid, [(7-cyano-4-hydroxy-1-phenyl-1H-pyrrolo[2,3-c]pyridine-5-carbonyl)-amino]-acetic acid, [(3-chloro-7-cyano-4-hydroxy-1-phenyl-1H-pyrrolo[2,3-c]pyridine-5-carbonyl)-amino]-acetic acid, {[2,3-dibromo-1-(4-fluoro-benzyl)-4-hydroxy-1H-pyrrolo[2,3-c]pyridine-5-carbonyl]-amino}-acetic acid, [(4-hydroxy-1-phenethyl-1H-pyrrolo[2,3-c]pyridine-5-carbonyl)-amino]-acetic acid, {[2,3-dibromo-7-cyano-1-(4-fluoro-benzyl)-4-hydroxy-1H-pyrrolo[2,3-c]pyridine-5-carbonyl]-amino}-acetic acid, [(3-bromo-7-cyano-4-hydroxy-1-phenyl-1H-pyrrolo[2,3-c]pyridine-5-carbonyl)-amino]-acetic acid, {[7-cyano-1-(4-fluoro-benzyl)-4-hydroxy-1H-pyrrolo[2,3-c]pyridine-5-carbonyl]-amino}-acetic acid, [(3-chloro-7-cyano-4-hydroxy-1-phenethyl-1H-pyrrolo[2,3-c]pyridine-5-carbonyl)-amino]-acetic acid, {[2,3-dibromo-4-hydroxy-1-(1(S)-phenyl-ethyl)-1H-pyrrolo[2,3-c]pyridine-5-carbonyl]-amino}-acetic acid, {[3-chloro-7-cyano-1-(4-fluoro-benzyl)-4-hydroxy-1H-pyrrolo[2,3-c]pyridine-5-carbonyl]-amino}-acetic acid, [(1-benzyl-2,3-dichloro-7-cyano-4-hydroxy-1H-pyrrolo[2,3-c]pyridine-5-carbonyl)-amino]-acetic acid, {[4-hydroxy-1-(1S-phenyl-ethyl)-1H-pyrrolo[2,3-c]pyridine-5-carbonyl]-amino}-acetic acid, [(2,3-dichloro-7-cyano-4-hydroxy-1-phenyl-1H-pyrrolo[2,3-c]pyridine-5-carbonyl)-amino}-acetic acid, [(2,3-dichloro-7-cyano-4-hydroxy-1-phenethyl-1H-pyrrolo[2,3-c]pyridine-5-carbonyl)-amino]-acetic acid,{[(2,3-dichloro-7-cyano-4-hydroxy-1-(1S-phenyl-ethyl)-1H-pyrrolo[2,3-c]pyridine-5-carbonyl]-amino}-acetic acid, [(1-benzyl-3-bromo-7-cyano-4-hydroxy-1H-pyrrolo[2,3-c]pyridine-5-carbonyl)-amino]-acetic acid, {[4-hydroxy-1-(1R-phenyl-ethyl)-1H-pyrrolo[2,3-c]pyridine-5-carbonyl]-amino}-acetic acid, {[4-hydroxy-1-(4-methoxy-benzyl)-1H-pyrrolo[2,3-c]pyridine-5-carbonyl]-amino}-acetic acid, {[7-cyano-4-hydroxy-1-(4-methoxy-benzyl)-1H-pyrrolo[2,3-c]pyridine-5-carbonyl]-amino}-acetic acid, [(1-benzyl-7-cyano-4-hydroxy-3-methyl-1H-pyrrolo[2,3-c]pyridine-5-carbonyl)-amino]-acetic acid, {[2,3-dichloro-7-cyano-4-hydroxy-1-(4-methoxy-benzyl)-1H-pyrrolo[2,3-c]pyridine-5-carbonyl]-amino}-acetic acid, {[2,3-dichloro-7-cyano-4-hydroxy-1-(1R-phenyl-ethyl)-1H-pyrrolo[2,3-c]pyridine-5-carbonyl]-amino}-acetic acid, {[3-chloro-7-cyano-4-hydroxy-1-(4-methoxy-benzyl)-1H-pyrrolo[2,3-c]pyridine-5-carbonyl]-amino}-acetic acid, {[7-cyano-4-hydroxy-1-(4-methoxy-phenyl)-1H-pyrrolo[2,3-c]pyridine-5-carbonyl]-amino}-acetic acid, {[2,3-dichloro-7-cyano-4-hydroxy-1-(4-methoxy-phenyl)-1H-pyrrolo[2,3-c]pyridine-5-carbonyl]-amino}-acetic acid, {[3-chloro-7-cyano-4-hydroxy-1-(4-methoxy-phenyl)-1H-pyrrolo[2,3-c]pyridine-5-carbonyl]-amino}-acetic acid, {[1-(4-fluoro-benzyl)-4-hydroxy-2,3-dimethyl-1H-pyrrolo[2,3-c]pyridine-5-carbonyl]-amino}-acetic acid, {[7-cyano-1-(4-fluoro-phenyl)-4-hydroxy-1H-pyrrolo[2,3-c]pyridine-5-carbonyl]-amino}-acetic acid, {[2,3-dichloro-7-cyano-4-hydroxy-1-(4-fluoro-phenyl)-1H-pyrrolo[2,3-c]pyridine-5-carbonyl]-amino}-acetic acid, {[3-chloro-7-cyano-4-hydroxy-1-(4- fluoro-phenyl)-1H-pyrrolo[2,3-c]pyridine-5-carbonyl]-amino}-acetic acid, {[1-(4-fluoro-benzyl)-4-hydroxy-1H-pyrrolo[2,3-c]pyridine-5-carbonyl]-amino}-acetic acid, [(2-cyano-4-hydroxy-1-phenyl-1H-pyrrolo[2,3-c]pyridine-5-carbonyl)-amino]-acetic acid, {[1-(2-fluoro-benzyl)-4-hydroxy-1H-pyrrolo[2,3-c]pyridine-5-carbonyl]-amino}-acetic acid, {[4-hydroxy-1-(2-methoxy-benzyl)-1H-pyrrolo[2,3-c]pyridine-5-carbonyl]-amino}-acetic acid, {[4-hydroxy-1-(3-methoxy-benzyl)-1H-pyrrolo[2,3-c]pyridine-5-carbonyl]-amino}-acetic acid, {[7-cyano-1-(4-fluoro-phenyl)-4-hydroxy-3-phenyl-1H-pyrrolo[2,3-c]pyridine-5-carbonyl]-amino}-acetic acid, {[7-cyano-1-(2-fluoro-benzyl)-4-hydroxy-1H-pyrrolo[2,3-c]pyridine-5-carbonyl]-amino}-acetic acid, {[7-cyano-1-(2-methoxy-benzyl)-4-hydroxy-1H-pyrrolo[2,3-c]pyridine-5-carbonyl]-amino}-acetic acid, {[7-cyano-1-(3-methoxy-benzyl)-4-hydroxy-1H-pyrrolo[2,3-c]pyridine-5-carbonyl]-amino}-acetic acid, {[2-cyano-1-(3-fluoro-benzyl)-4-hydroxy-1H-pyrrolo[2,3-c]pyridine-5-carbonyl]-amino}-acetic acid, {[2,3-dichloro-7-cyano-1-(2-fluoro-benzyl)-4-hydroxy-1H-pyrrolo[2,3-c]pyridine-5-carbonyl]-amino}-acetic acid, {[1-(3-fluoro-benzyl)-4-hydroxy-1H-pyrrolo[2,3-c]pyridine-5-carbonyl]-amino}-acetic acid, {[3-chloro-7-cyano-1-(2-fluoro-benzyl)-4-hydroxy-1H-pyrrolo[2,3-c]pyridine-5-carbonyl]-amino}-acetic acid, {[3-chloro-7-cyano-4-hydroxy-1-(3-methoxy-benzyl)-1H-pyrrolo[2,3-c]pyridine-5-carbonyl]-amino}-acetic acid, {[7-cyano-1-(3-fluoro-benzyl)-4-hydroxy-1H-pyrrolo[2,3-c]pyridine-5-carbonyl]-amino}-acetic acid, {[7-cyano-1-(3,4-difluoro-benzyl)-4-hydroxy-1H-pyrrolo[2,3-c]pyridine-5-carbonyl]-amino}-acetic acid, {[3-chloro-7-cyano-1-(3,4-difluoro-benzyl)-4-hydroxy-1H-pyrrolo[2,3-c]pyridine-5-carbonyl]-amino}-acetic acid, {[2,3-dichloro-7-cyano-1-(3-fluoro-benzyl)-4-hydroxy-1H-pyrrolo[2,3-c]pyridine-5-carbonyl]-amino}-acetic acid, {[3-chloro-7-cyano-1-(3-fluoro-benzyl)-4-hydroxy-1H-pyrrolo[2,3-c]pyridine-5-carbonyl]-amino}-acetic acid, {[2,3-dichloro-7-cyano-1-(3,4-difluoro-benzyl)-4-hydroxy-1H-pyrrolo[2,3-c]pyridine-5-carbonyl]-amino}-acetic acid, [(1-benzyl-2,3-dichloro-7-hydroxy-1H-pyrrolo[3,2-c]pyridine-6-carbonyl)-amino]-acetic acid, [(2tert-butyl-7-hydroxy-thiazolo[4,5-c]pyridine-6-carbonyl]-amino]-acetic acid, [(2tert-butyl-7-hydroxy-4-methyl-thiazolo[4,5-c]pyridine-6-carbonyl)-amino]-acetic acid, [(2-tert-butyl-4-cyano-7-hydroxy-thiazolo[4,5- c]pyridine-6-carbonyl)-amino]-acetic acid, [(4-butyl-2-tert-butyl-7-hydroxy-thiazolo[4,5- c]pyridine-6-carbonyl)-amino]-acetic acid, [(2-tert-butyl-7-hydroxy-4-((E)-styryl)-thiazolo[4,5-c]pyridine-6-carbonyl)-amino]-acetic acid, [(2-tert-butyl-7-hydroxy-4-phenyl-thiazolo[4,5-c]pyridine-6-carbonyl)-amino]-acetic acid, [(2-tert-butyl-7-hydroxy-4-phenethyl-thiazolo[4,5- c]pyridine-6-carbonyl)-amino]-acetic acid, [(2-tert-butyl-7-hydroxy-4-isopropylsulfanylmethyl-thiazolo[4,5-c]pyridine-6-carbonyl)-amino]-acetic acid, [(7-hydroxy-2-methyl-4-phenyl-thiazolo[4,5-c]pyridine-6-carbonyl)-amino]-acetic acid, [(7-hydroxy-2-methyl-thiazolo[4,5-c]pyridine-6-carbonyl)-amino]-acetic acid, [(7-hydroxy-2-naphthalen-2-yl-thiazolo[4,5-c]pyridine-6-carbonyl)-amino]-acetic acid, [(7-hydroxy-2-thiophen-2-yl-thiazolo[4,5-c]pyridine-6-carbonyl)-amino]-acetic acid, and [(2-furan-2-yl-7-hydroxy-thiazolo[4,5-c]pyridine-6-carbonyl)-amino]-acetic acid or a pharmaceutically acceptable salt, single stereoisomer, mixture of stereoisomer, or ester thereof.

31. A pharmaceutical composition comprising a compound of claim 1 and a pharmaceutically acceptable excipient.

32. The composition of claim 31 further comprising at least one additional therapeutic agent selected from the group consisting of vitamin $B_{12}$, folic acid, ferrous sulfate, recombinant human erythropoietin, and an erythropoiesis stimulating agent (ESA).

* * * * *